US012211609B1

(12) United States Patent
Azizian et al.

(10) Patent No.: US 12,211,609 B1
(45) Date of Patent: Jan. 28, 2025

(54) ULTRASOUND IMAGE SYNTHESIS USING ONE OR MORE NEURAL NETWORKS

(71) Applicant: Nvidia Corporation, Santa Clara, CA (US)

(72) Inventors: Mahdi Azizian, San Jose, CA (US); Thomas Kierski, Durham, NC (US); Sean Huver, Mountain View, CA (US)

(73) Assignee: NVIDIA Corporation, Santa Clara, CA (US)

( * ) Notice: Subject to any disclaimer, the term of this patent is extended or adjusted under 35 U.S.C. 154(b) by 262 days.

(21) Appl. No.: 17/667,377

(22) Filed: Feb. 8, 2022

(51) Int. Cl.
*G06V 10/00* (2022.01)
*G06T 3/06* (2024.01)
*G06T 7/00* (2017.01)
*G06T 11/00* (2006.01)
*G16H 30/40* (2018.01)

(52) U.S. Cl.
CPC ............... *G16H 30/40* (2018.01); *G06T 3/06* (2024.01); *G06T 7/0012* (2013.01); *G06T 11/008* (2013.01); *G06T 2207/10136* (2013.01); *G06T 2207/20081* (2013.01); *G06T 2207/20084* (2013.01)

(58) Field of Classification Search
CPC ............ G06N 3/08; G06N 3/02; G06N 3/045; G06N 3/092; G06N 3/0475; G06N 3/042; G06N 3/082; G06N 3/0454; G06N 3/0464; G06N 3/049; G06T 2207/20081; G06T 2207/20084; G06T 2207/10136; G06T 7/0012; G06T 3/06; G16H 30/40
See application file for complete search history.

(56) References Cited

U.S. PATENT DOCUMENTS

| | | | |
|---|---|---|---|
| 7,627,386 B2 * | 12/2009 | Mo | G01S 7/5206 600/443 |
| 9,710,910 B2 * | 7/2017 | Kim | G06T 7/0012 |
| 9,743,911 B2 * | 8/2017 | Hedlund | A61B 6/487 |
| 9,995,647 B2 * | 6/2018 | Huseynov | G01M 3/24 |
| 10,517,568 B2 * | 12/2019 | Wasielewski | A61B 8/5223 |
| 10,635,943 B1 * | 4/2020 | Lebel | G06T 5/50 |
| 10,702,242 B2 * | 7/2020 | de Jonge | G06F 18/24133 |
| 11,875,507 B1 * | 1/2024 | Gardella | G06T 7/269 |
| 11,948,345 B2 * | 4/2024 | Wang | G06V 10/82 |
| 11,957,515 B2 * | 4/2024 | Swisher | G01S 7/52046 |
| 2005/0054955 A1 * | 3/2005 | Lidgren | A61B 34/20 601/2 |
| 2020/0286228 A1 * | 9/2020 | Guenther | G06T 7/0012 |

OTHER PUBLICATIONS

IEEE "IEEE Standard for Floating-Point Arithmetric", Microprocessor Standards Committee of the IEEE Computer Society, IEEE Std 754-2008, dated Jun. 12, 2008.
Jin et al., "Deep CT to MR Synthesis Using Paired and Unpaired Data," Sep. 3, 2018, 23 Pages.

* cited by examiner

*Primary Examiner* — Amir Alavi

(74) *Attorney, Agent, or Firm* — Davis Wright Tremaine LLP

(57) ABSTRACT

Apparatuses, systems, and techniques are presented to generate ultrasound images. In at least one embodiment, use one or more neural networks are used to generate one or more ultrasound images of one or more objects based, at least in part, upon one or more acoustic properties of the one or more objects.

30 Claims, 49 Drawing Sheets

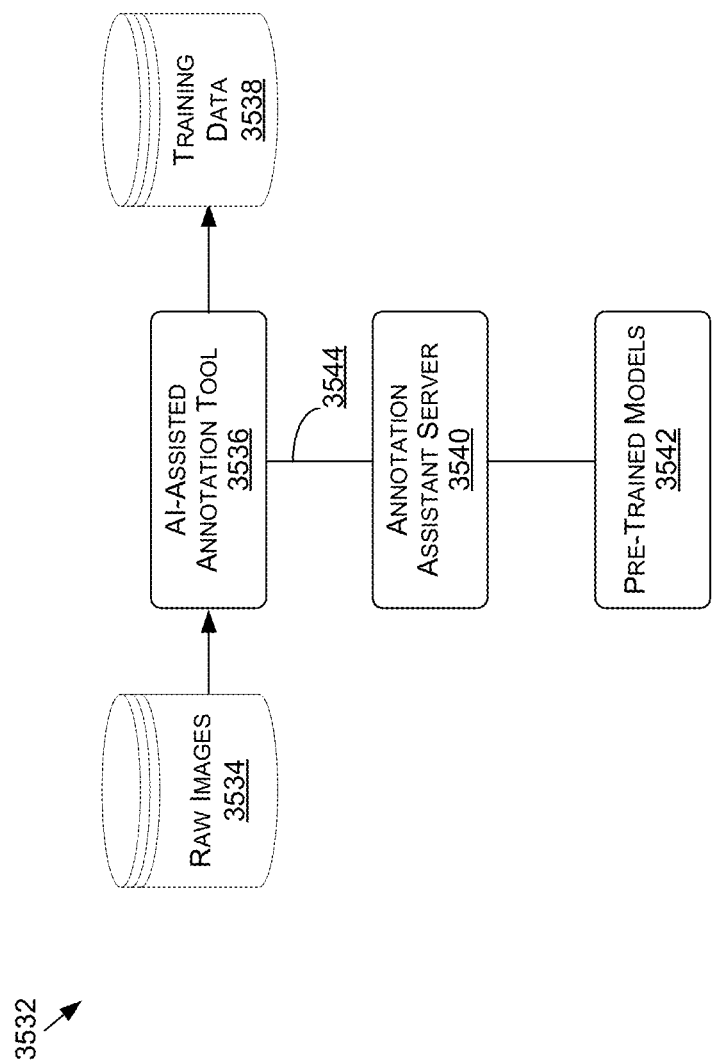

ULTRASOUND IMAGE SYNTHESIS USING ONE OR MORE NEURAL NETWORKS

FIELD

At least one embodiment pertains to processing resources used to perform and facilitate artificial intelligence. For example, at least one embodiment pertains to processors or computing systems used to train neural networks according to various novel techniques described herein.

BACKGROUND

Various diagnostic approaches, such as those that utilize machine learning, can benefit from the use of a large set of accurately labeled training data. For data relating to radiological healthcare data, such as ultrasound image data, such accurately labeled training data can be difficult and expensive to generate or obtain. Without a sufficient amount of valid training data, results of diagnostic approaches that rely upon this training data can be limited in accuracy.

BRIEF DESCRIPTION OF THE DRAWINGS

Various embodiments in accordance with the present disclosure will be described with reference to the drawings, in which:

FIG. 35B is an example illustration of a client-server architecture to enhance annotation tools with pre-trained annotation models, in accordance with at least one embodiment.

DETAILED DESCRIPTION

In at least one embodiment, an image can be received that includes a representation of at least one object. In at least one embodiment, this can include one or more representations of objects such as internal organs of a human patient, as may be included in an image (or set of image data) of magnetic resonance imaging (MRI), histopathology, or computed tomography (CT) data. In at least one embodiment, this image data may include three-dimensional (3D) data, such as may be utilized to generate a three-dimensional image or representation of one or more internal organs or other objects or regions of interest. In at least one embodiment, such a 3D representation can be used to generate one or more images, such as two-dimensional (2D) slices 100, or cross-sectional images of an organ (or other object) of interest, such as is illustrated in FIG. 1. In at least one embodiment, this can include CT data for a cross-section through an organ of interest. In at least one embodiment, locations and directions of a given cross section can be determined manually, randomly, or according to a selection algorithm. In at least one embodiment, a cross-section can be performed over an entire 3D image, or a portion of a 3D image.

Figures 1A, 1B:
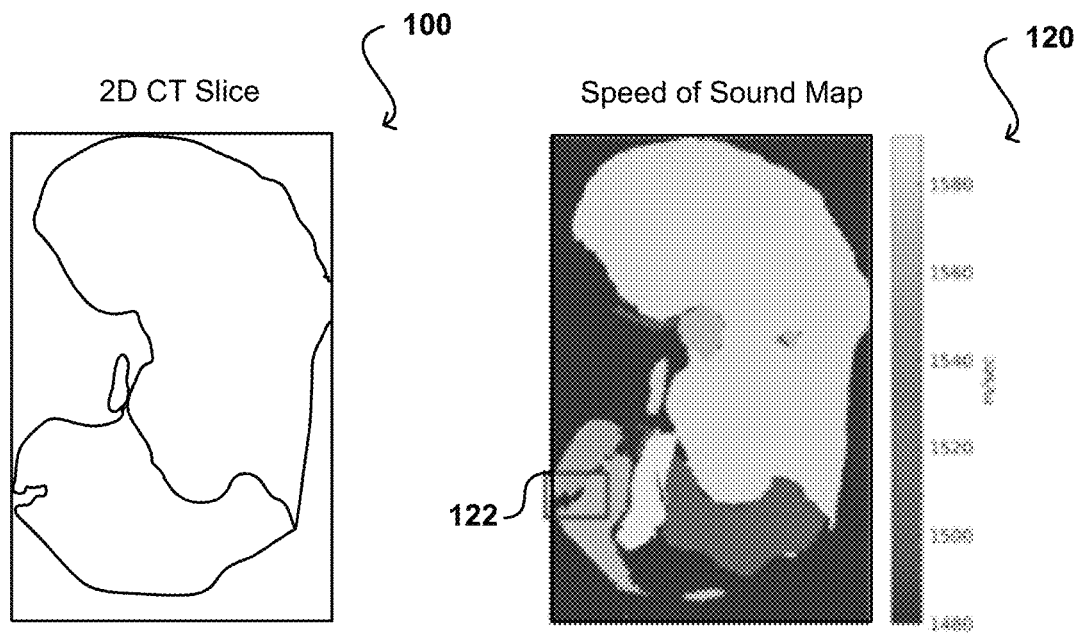
FIGS. 1A, 1B, 1C and 1D illustrate images from an ultrasound image synthesis process, according to at least one embodiment.

In at least one embodiment, such an image slice or cross-section image can be analyzed to determine one or more types of information. In at least one embodiment, an original 3D medical image can have had annotations applied, such that regions in these 2D slices will also have appropriate annotations. In at least one embodiment, these annotations of objects or regions in these 2D slices can be used to generate determine values, and generate maps, of various properties of one or more objects or regions represented in a given slice or image. In at least one embodiment, these annotations can be used to identify objects or regions that may correspond to different types of human tissue, bone, blood, skin, organs, and so on. In at least one embodiment, these annotations are "dense" annotations, or annotations that cover a majority of pixels of voxels in a 3D image volume, such that there are few if any regions that are unlabeled or do not have annotations applied. In at least one embodiment, each of these types of objects or regions can have different known acoustic properties, or properties with which a wave will propagate through an object or region of that type. In at least one embodiment, information about these types can then be used to generate one or more property maps one of these two-dimensional images, where regions of different types will have different acoustic properties indicated. In at least one embodiment, these annotated 2D image slices function as segmentation maps, with each segment having a different set of acoustic properties. In at least one embodiment, one or more property maps can be generated that may relate to properties such as attenuation, density, speed of sound, or non-linear coefficients of a wave equation. In at least one embodiment, these may correspond to coefficients of a wave equation, and their selection may depend at least in part upon terms included in a selected wave equation. In at least one embodiment, other wave equations may be used that include terms related to pressure or other such properties. In at least one embodiment, a property map can be generated for one of these acoustic properties, such as speed of sound map 120 that can be generated for 2D image 100 as illustrated in FIG. 1B. In at least one embodiment, this property map 120 can include regions of different color (according to a color scale illustrated) corresponding to different propagation speeds of sound typical in that type of tissue, object, or region. In at least one embodiment, one or more regions 122 of such a map can be selected for analyzing in more detail, as illustrated in image 104 of FIG. 1C. In at least one embodiment, this can be used to generate images with specific combinations of tissue or features, such as may be useful for training a neural network.

Figures 1C, 1D:
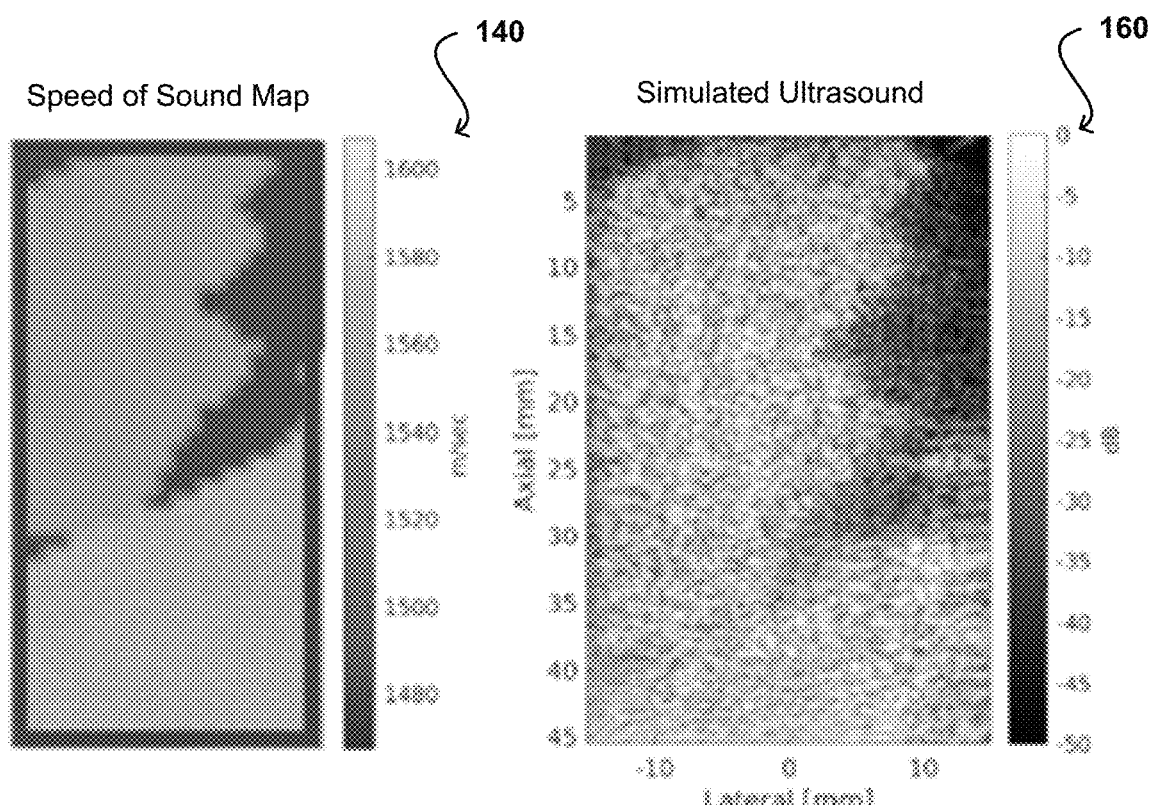

In at least one embodiment, a generated property map such as that illustrated in FIG. 1C can be fed as input to a neural network, such as a Fourier neural operator, that can then infer simulated, or "synthesized," image data from properties of one or more objects represented in one or more input property maps. In at least one embodiment, this can include generation of a simulated ultrasound image 160 as illustrated in FIG. 1D. In at least one embodiment, a network can infer appearance information from an ultrasound based on factors such as a propagation speed of sound at that location as illustrated in FIG. 1C. In at least one embodiment, such a neural network can take additional maps as input as well, which can help to improve an accuracy of such a simulated image. In at least one embodiment, this can include taking as input two or more of an attenuation map, a density map, a speed of sound map, or a non-linear coefficient map, among other such options. In at least one embodiment, such a neural network can take as input any map (or other two-or three-dimensional representation) of one or more properties that can help infer a type of output image, such as an ultrasound image or other medical (or non-medical) image. In at least one embodiment, a number of different 2D slices can be generated from a single 3D image, such as 3D CT scan data, and multiple regions selected from each 2D slice, which can be used to synthesize several different ultrasound images, which can each then be used as training data (or for other such purposes). In at least one embodiment, such a network can be trained using ground truth ultrasound images, as well as input property maps generated from, or for, such ultrasound images.

Figure 2:
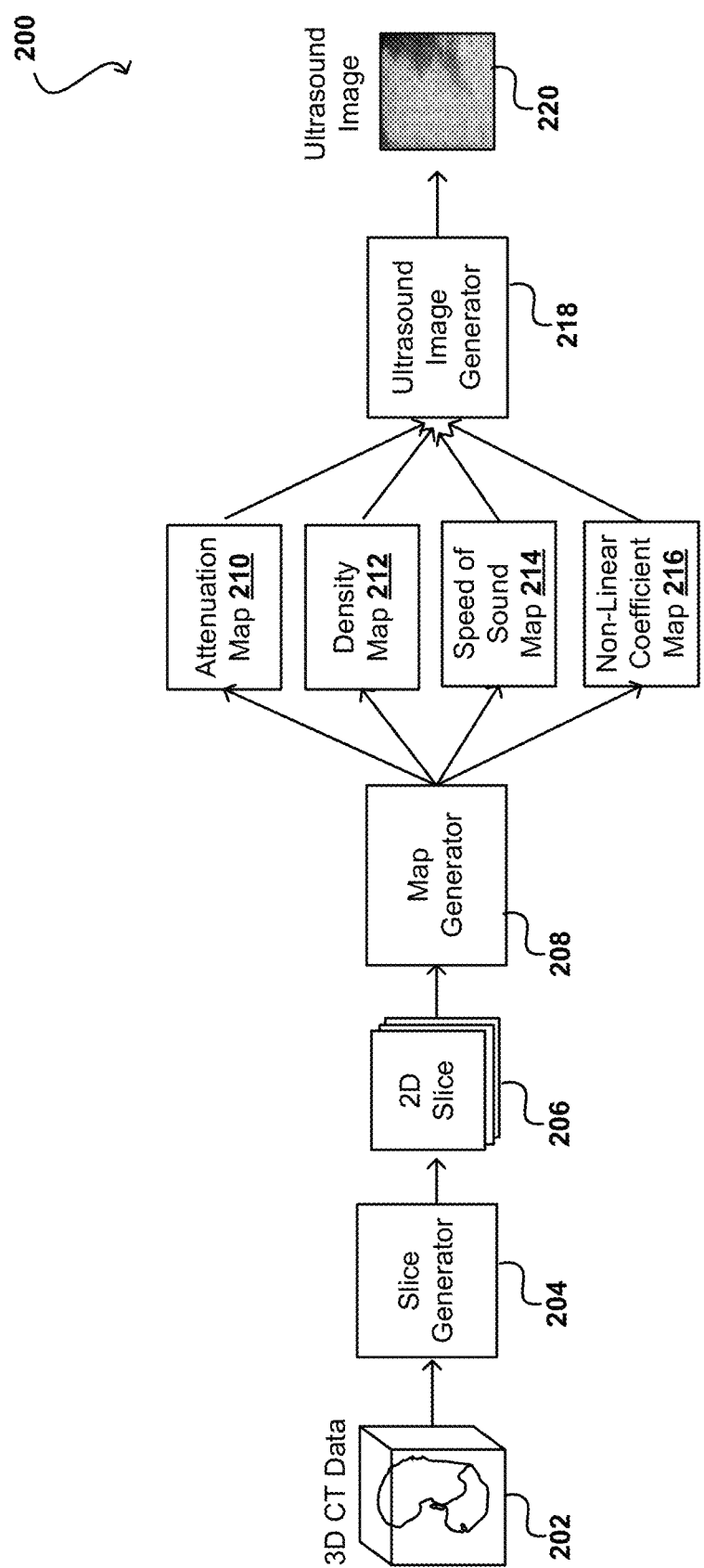
FIG. 2 illustrates a system for synthesizing one or more ultrasound images, according to at least one embodiment.

In at least one embodiment, a synthesis pipeline 200 can be utilized as illustrated in FIG. 2. In at least one embodiment, such a pipeline can receive or obtain 3D image or sensor data, such as 3D CT data, that can be provided as input to slice generator 204. In at least one embodiment, a slice generator may select a location and angle at which to take a slice or cross-section, and may also determine a portion or sub-region of this 3D image to slice, such as may include at least one object of interest. In at least one embodiment, multiple 2D slices 206 may be generated at different locations or at different angles. In at least one embodiment, annotations in this 3D data can then be carried over to regions of these 2D slices or cross-sections, which can then each serve as a type of semantic segmentation map.

In at least one embodiment, a generated 2D slice 206 can be provided as input to a map generator 208. In at least one embodiment, map generator 204 can be any type of generator process that can take a dictionary or set of known acoustic properties for different types of objects, and translate a 2D slice object segmentation map into a 2D property map. In at least one embodiment, this may involve taking a 2D image with three distinct regions, and then setting property values for each of those regions according to known property values for types of objects in those regions. In at least one embodiment, such a map generator can generate one or more types of maps, as may include values for different parameters or metrics that can be determined from this input data, including any annotations provided with, or determined for, this input data. In at least one embodiment, these annotations may identify regions of input image data that correspond to different types of tissue, different types of objects, or different regions within an object that may have different measurable properties, among other such options. In at least one embodiment, this can include generating one or more property maps for an input image slice, as may include an attenuation map 210, a density map 212, a speed of sound map 214, or a non-linear coefficient map 216, among other such options.

In at least one embodiment, one or more generated property maps can be provided as input to an ultrasound image generator 218. In at least one embodiment, generator 218 can include at least one neural network, such as a Fourier neural operator network or other generative network. In at least one embodiment, this network can be trained to take as input one or more acoustic property maps, and generate an ultrasound image 220 based at least in part upon that property data. In at least one embodiment, this network can be trained to predict wave behavior in different regions based upon acoustic properties identified through these input property maps. In at least one embodiment, this neural network can then output ultrasound image data that corresponds to this predicted wave behavior, indicating how sound waves would likely propagate through that object to be detected by a sensor in an actual ultrasound system. In at least one embodiment, this enables an ultrasound image to be generated for each 2D slice, and thus enables multiple ultrasound images to be synthesized based on different slices taken through a single annotated 3D medical (or other) image. In at least one embodiment, these synthetic ultrasound images can then be used as training data for training machine learning models that require annotated ultrasound ground truth data. In at least one embodiment, an ultrasound generation model can be trained with ground truth ultrasound data as well, such as may be utilized with a Fullwave or other simulation tool that can model physically realistic ultrasound propagation and a constructed b-mode image. In at least one embodiment, other images can be generated as well that may depend at least in part upon a propagation of waves (e.g., light or sound), as may include x-ray images or raw radio frequency (RF) data, among other such options.

Figure 3:
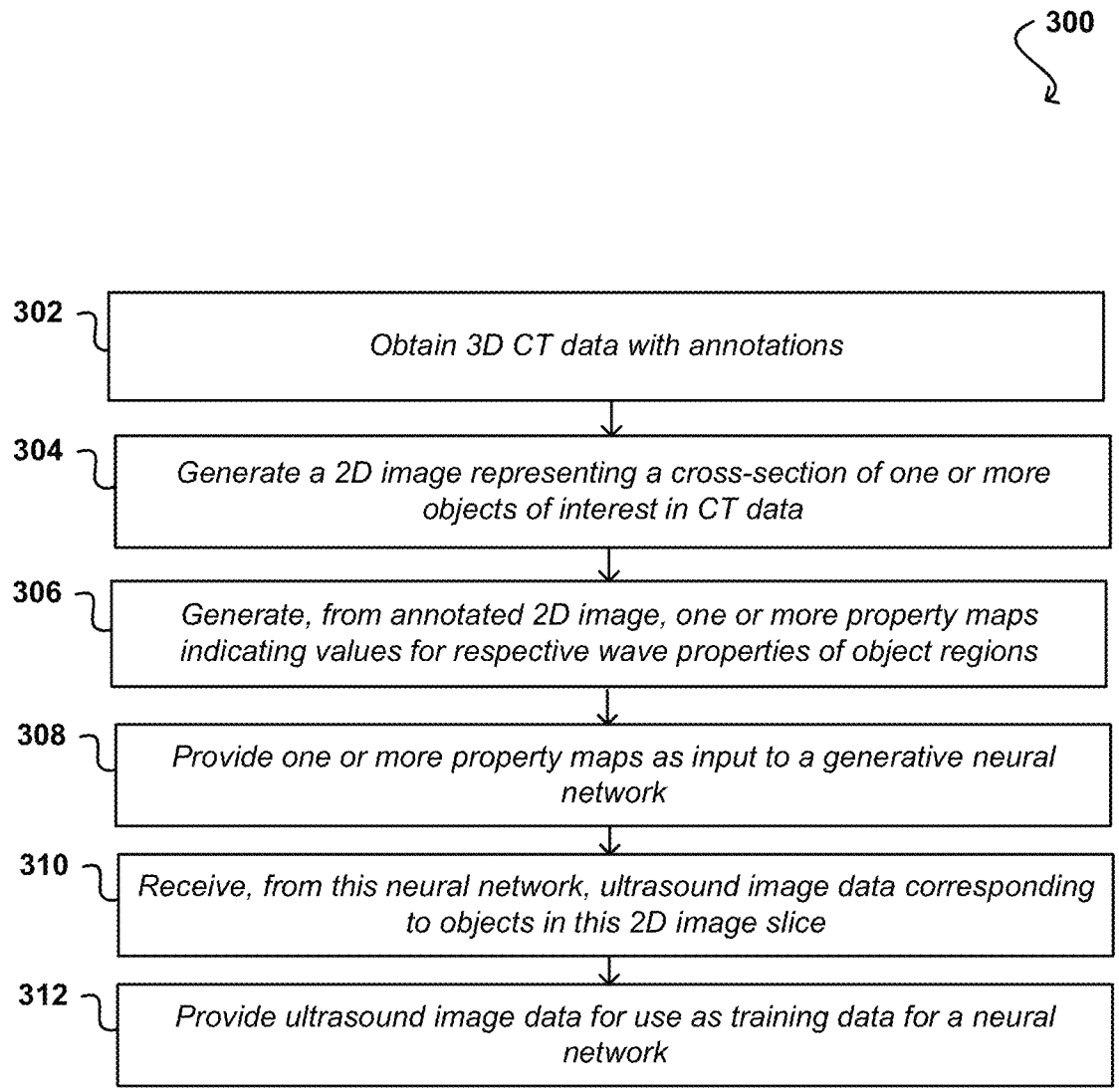
FIG. 3 illustrates a process for synthesizing an ultrasound image, according to at least one embodiment.

In at least one embodiment, a process 300 for synthesizing an ultrasound image can be performed as illustrated in FIG. 3. In at least one embodiment, 3D image data, such as annotated 3D CT data, can be obtained for a patient that includes at least one object or region of interest. In at least one embodiment, a 2D image can be generated from this 3D image data that represents a slice or cross section of one or more objects or regions of interest in this 3D data. In at least one embodiment, one or more property maps can be generated from this annotated 2D image. In at least one embodiment, dense annotation of this 3D CT data can result in an annotated 2D image with few, if any, pixels that do not belong to a labeled object, region, or segment. In at least one embodiment, each such property map can include regions with different values of a respective acoustic property determined based at least in part upon a type of object represented by that region. In at least one embodiment, these can include acoustic properties such as density, speed of sound, attenuation, or nonlinear coefficient, among other such options. In at least one embodiment, one or more of these property maps can then be provided 308 as input to a generative neural network, such as a Fourier neural operator. In at least one embodiment, four different property maps are provided as input that correspond to a same 2D image. In at least one embodiment, synthetic ultrasound image data can then be received 310 as output from this neural network, where pixel values of this ultrasound image are inferred based, at least in part, upon acoustic property values for that pixel location, as well as may be influenced by surrounding pixel locations. In at least one embodiment, this ultrasound image data can then be provided 312 for use as training data for a neural network, or can be provided for presentation or storage, among other such options.

Figure 4:
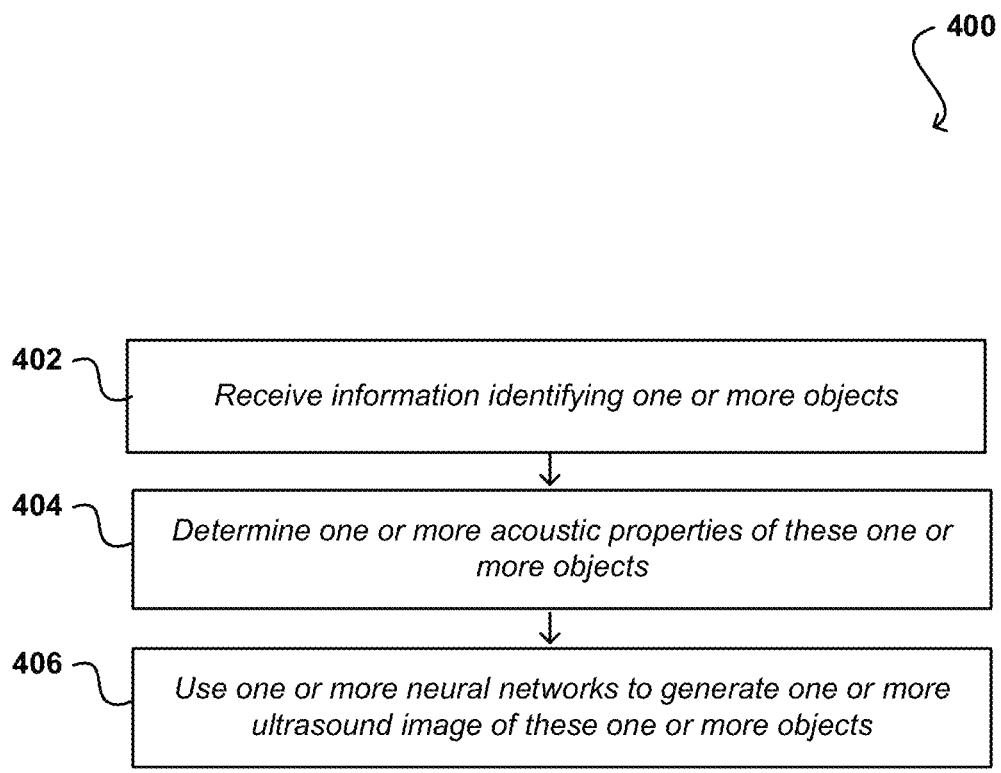
FIG. 4 illustrates a process for generating one or more ultrasound images, according to at least one embodiment.

In at least one embodiment, a process 400 for generating one or more ultrasound images can be performed as illustrated in FIG. 4. In at least one embodiment, information is received 402 identifying one or more objects. In at least one embodiment, this may include receiving a 2D cross-section or slice taken from an annotated 3D medical image. In at least one embodiment, one or more acoustic properties of these one or more objects can be determined 404, as may relate to a density, attenuation, speed of sound, nonlinear coefficient of a wave equation, or other such property. In at least one embodiment, one or more neural networks can be used 406 to generate one or more ultrasound images of these one or more objects based, at least in part, upon these one or more acoustic properties.

Figure 5:
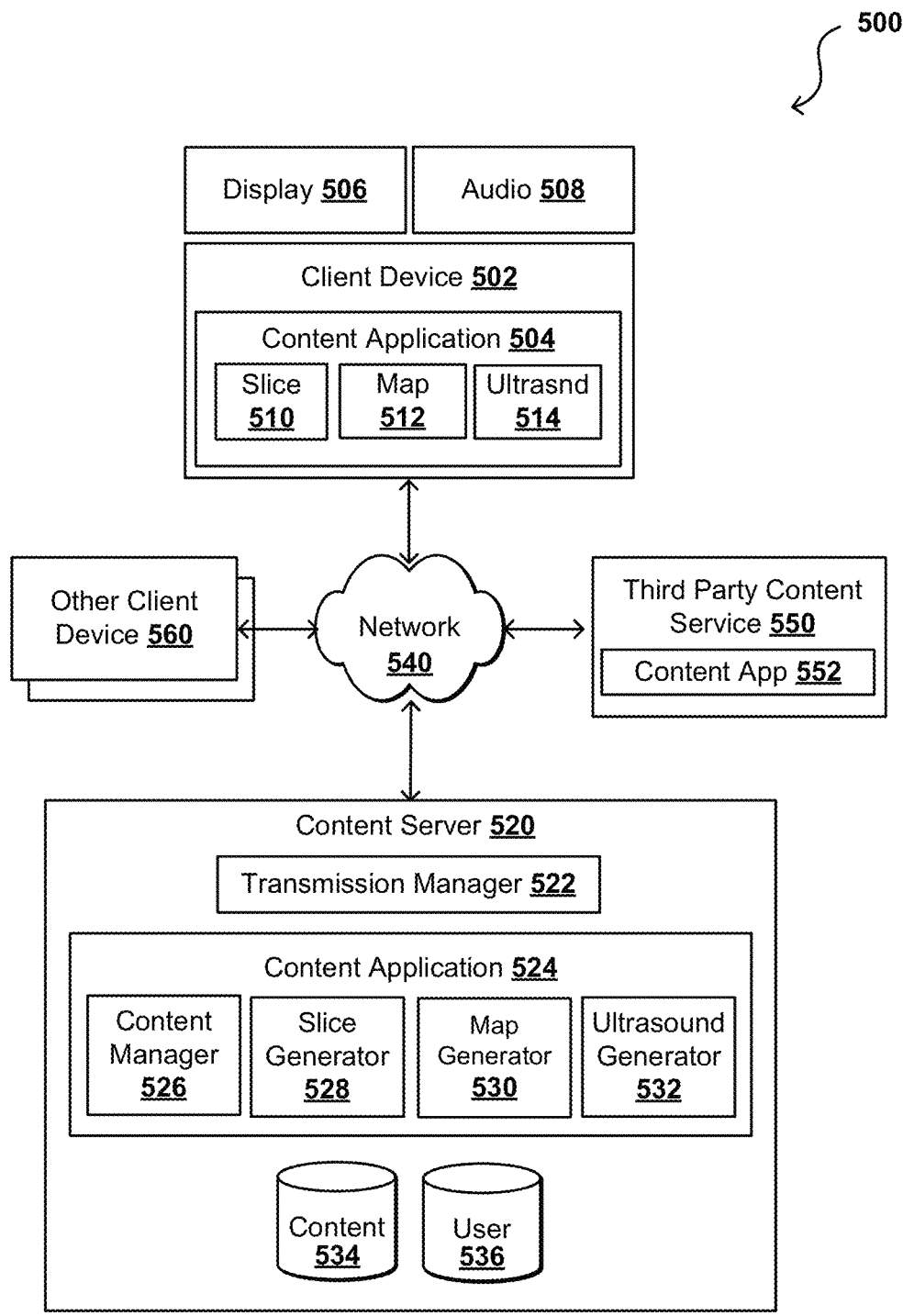
FIG. 5 illustrates an environment in which an ultrasound image can be synthesized, according to at least one embodiment.

In at least one embodiment, aspects of generating ultrasound or other such images as discussed herein can be performed on different devices or in different locations, such as may be local or obtained across a network or from a resource in a compute cloud. In at least one embodiment, a client device 502 can generate this content for a session, such as a medical diagnostic session or network training, using components of a content application 504 on client device 502 and data stored locally on that client device as illustrated in FIG. 5. In at least one embodiment, a content application 524 (e.g., a medical diagnostic application) executing on content server 520 may initiate a session associated with at least client device 502, as may utilize a session manager and user data stored in a user database 534, and can cause content 532 to be determined by a content manager 526 and transmitted to client device 502 using an appropriate transmission manager 522 to send by download, streaming, or another such transmission channel. In at least one embodiment, client device 502 receiving this content can provide this content to a corresponding content application 504, which may provide this content for presentation via client device 502, such as image content through a display 506 and audio, such as sounds and discussion audio, through at least one audio playback device 508, such as speakers or headphones. In at least one embodiment, at least some of this content may already be stored on, rendered on, or accessible to client device 502 such that transmission over network 540 is not required for at least that portion of content, such as where that content may have been previously downloaded or stored locally on a hard drive or optical disk. In at least one embodiment, a transmission mechanism such as data streaming can be used to transfer this content from server 520, or content database 534, to client device 502. In at least one embodiment, at least a portion of this content can be obtained or streamed from another source, such as a third party content service 550 that may also include a content application 552 for generating or providing content. In at least one embodiment, portions of this functionality can be performed using multiple computing devices, or multiple processors within one or more computing devices, such as may include a combination of CPUs and GPUs.

In at least one embodiment, content application 524 includes a content manager 526 that can determine or analyze content before this content is transmitted to client device 502. In at least one embodiment, content manager 526 can also include, or work with, other components that are able to generate, modify, or enhance content to be provided. In at least one embodiment, this can include a slice generator 528 for generating slices or cross-sectional images from input 3D (or 2D) image data. In at least one embodiment, a map generator component 530 can generate at least one property map for each such slice, as may be based upon types of objects or regions represented in that slice. In at least one embodiment, an ultrasound image generation: component 532, as may include at least one neural network, can use one or more such property maps to generate one or more ultrasound images, as discussed herein. In at least one embodiment, content manager 526 can then select an ultrasound image of an appropriate resolution or format to send to client device 502. In at least one embodiment, a content application 504 on client device 502 may also include components such as a slice generator 510, property map generator 512 and ultrasound image generator 514, such that any or all of this functionality can additionally, or alternatively, be performed on client device 502. In at least one embodiment, a content application 552 on a third party content service system 550 can also include such functionality. In at least one embodiment, locations where at least some of this functionality is performed may be configurable, or may depend upon factors such as a type of client device 502 or availability of a network connection with appropriate bandwidth, among other such factors. In at least one embodiment, a system for content generation can include any appropriate combination of hardware and software in one or more locations. In at least one embodiment, generated image or video content of one or more resolutions can also be provided, or made available, to other client devices 560, such as for download or streaming from a media source storing a copy of that image or video content. In at least one embodiment, this may include transmitting images of medical diagnostic content for a medical application, where different client devices may display that content at different resolutions, including one or more super-resolutions.

In at least one embodiment, such segmentation can be used with medical images. In at least one embodiment, this can include computerized tomography (CT) and/or magnetic resonance imaging (MRI) images, histopathologic images, as well as data from ultrasound scans or other such processes. In at least one embodiment, segmentation can be used for other types of images where specific types of objects, features, elements, or patterns are to be identified from input image or video data. In at least one embodiment, this can include identifying and parsing anatomical objects (e.g. organs, bones, or tumors) in 2D, 3D, or 4D medical images.

Inference and Training Logic

Figure 6A:
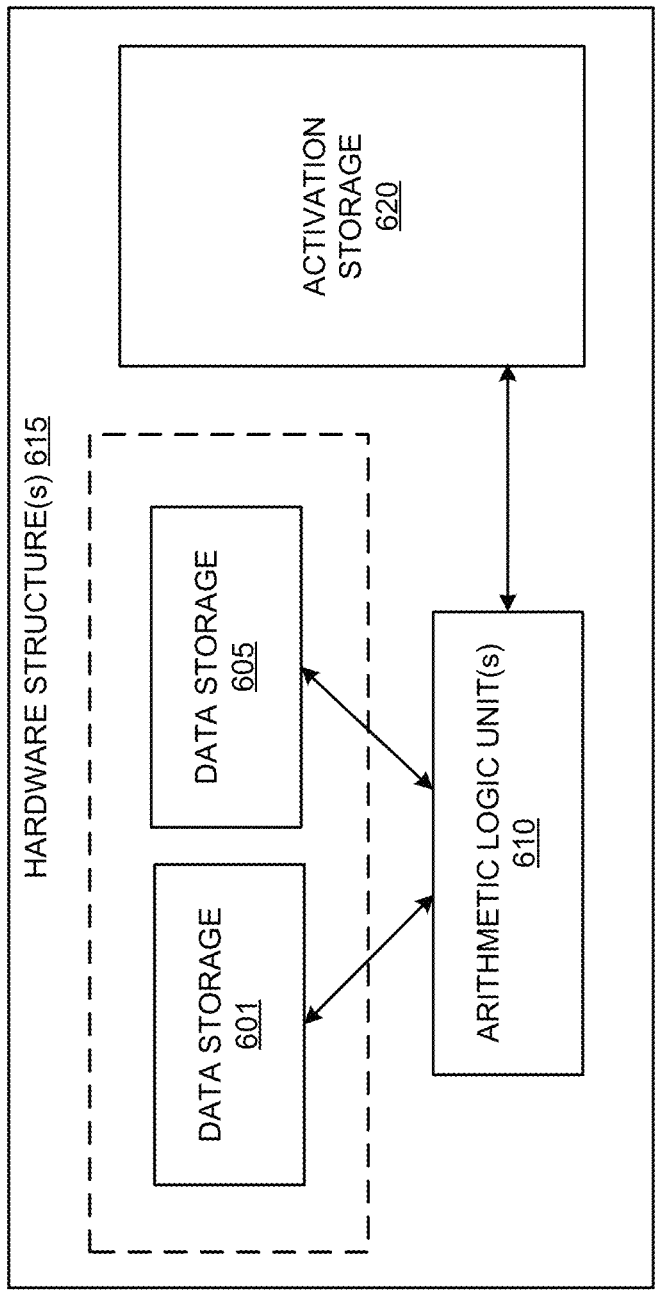
FIG. 6A illustrates inference and/or training logic, according to at least one embodiment.

FIG. 6A illustrates inference and/or training logic 615 used to perform inferencing and/or training operations associated with one or more embodiments. Details regarding inference and/or training logic 615 are provided below in conjunction with FIGS. 6A and/or 6B.

In at least one embodiment, inference and/or training logic 615 may include, without limitation, code and/or data storage 601 to store forward and/or output weight and/or input/output data, and/or other parameters to configure neurons or layers of a neural network trained and/or used for inferencing in aspects of one or more embodiments. In at least one embodiment, training logic 615 may include, or be coupled to code and/or data storage 601 to store graph code or other software to control timing and/or order, in which weight and/or other parameter information is to be loaded to configure, logic, including integer and/or floating point units (collectively, arithmetic logic units (ALUs). In at least one embodiment, code, such as graph code, loads weight or other parameter information into processor ALUs based on architecture of a neural network to which this code corresponds.

In at least one embodiment, code and/or data storage 601 stores weight parameters and/or input/output data of each layer of a neural network trained or used in conjunction with one or more embodiments during forward propagation of input/output data and/or weight parameters during training and/or inferencing using aspects of one or more embodiments. In at least one embodiment, any portion of code and/or data storage 601 may be included with other on-chip or off-chip data storage, including a processor's L1, L2, or L3 cache or system memory.

In at least one embodiment, any portion of code and/or data storage 601 may be internal or external to one or more processors or other hardware logic devices or circuits. In at least one embodiment, code and/or data storage 601 may be cache memory, dynamic randomly addressable memory ("DRAM"), static randomly addressable memory ("SRAM"), non-volatile memory (e.g., Flash memory), or other storage. In at least one embodiment, choice of whether code and/or data storage 601 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors.

In at least one embodiment, inference and/or training logic 615 may include, without limitation, a code and/or data storage 605 to store backward and/or output weight and/or input/output data corresponding to neurons or layers of a neural network trained and/or used for inferencing in aspects of one or more embodiments. In at least one embodiment, code and/or data storage 605 stores weight parameters and/or input/output data of each layer of a neural network trained or used in conjunction with one or more embodiments during backward propagation of input/output data and/or weight parameters during training and/or inferencing using aspects of one or more embodiments. In at least one embodiment, training logic 615 may include, or be coupled to code and/or data storage 605 to store graph code or other software to control timing and/or order, in which weight and/or other parameter information is to be loaded to configure, logic, including integer and/or floating point units (collectively, arithmetic logic units (ALUs). In at least one embodiment, code, such as graph code, loads weight or other parameter information into processor ALUs based on an architecture of a neural network to which this code corresponds. In at least one embodiment, any portion of code and/or data storage 605 may be included with other on-chip or off-chip data storage, including a processor's L1, L2, or L3 cache or system memory. In at least one embodiment, any portion of code and/or data storage 605 may be internal or external to on one or more processors or other hardware logic devices or circuits. In at least one embodiment, code and/or data storage 605 may be cache memory, DRAM, SRAM, non-volatile memory (e.g., Flash memory), or other storage. In at least one embodiment, choice of whether code and/or data storage 605 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors.

In at least one embodiment, code and/or data storage 601 and code and/or data storage 605 may be separate storage structures. In at least one embodiment, code and/or data storage 601 and code and/or data storage 605 may be same storage structure. In at least one embodiment, code and/or data storage 601 and code and/or data storage 605 may be partially same storage structure and partially separate storage structures. In at least one embodiment, any portion of code and/or data storage 601 and code and/or data storage 605 may be included with other on-chip or off-chip data storage, including a processor's L1, L2, or L3 cache or system memory.

In at least one embodiment, inference and/or training logic 615 may include, without limitation, one or more arithmetic logic unit(s) ("ALU(s)") 610, including integer and/or floating point units, to perform logical and/or mathematical operations based, at least in part on, or indicated by, training and/or inference code (e.g., graph code), a result of which may produce activations (e.g., output values from layers or neurons within a neural network) stored in an activation storage 620 that are functions of input/output and/or weight parameter data stored in code and/or data storage 601 and/or code and/or data storage 605. In at least one embodiment, activations stored in activation storage 620 are generated according to linear algebraic and or matrix-based mathematics performed by ALU(s) 610 in response to performing instructions or other code, wherein weight values stored in code and/or data storage 605 and/or code and/or data storage 601 are used as operands along with other values, such as bias values, gradient information, momentum values, or other parameters or hyperparameters, any or all of which may be stored in code and/or data storage 605 or code and/or data storage 601 or another storage on or off-chip.

In at least one embodiment, ALU(s) 610 are included within one or more processors or other hardware logic devices or circuits, whereas in another embodiment, ALU(s) 610 may be external to a processor or other hardware logic device or circuit that uses them (e.g., a co-processor). In at least one embodiment, ALUs 610 may be included within a processor's execution units or otherwise within a bank of ALUs accessible by a processor's execution units either within same processor or distributed between different processors of different types (e.g., central processing units, graphics processing units, fixed function units, etc.). In at least one embodiment, code and/or data storage 601, code and/or data storage 605, and activation storage 620 may be on same processor or other hardware logic device or circuit, whereas in another embodiment, they may be in different processors or other hardware logic devices or circuits, or some combination of same and different processors or other hardware logic devices or circuits. In at least one embodiment, any portion of activation storage 620 may be included with other on-chip or off-chip data storage, including a processor's L1, L2, or L3 cache or system memory. Furthermore, inferencing and/or training code may be stored with other code accessible to a processor or other hardware logic or circuit and fetched and/or processed using a processor's fetch, decode, scheduling, execution, retirement and/or other logical circuits.

In at least one embodiment, activation storage 620 may be cache memory, DRAM, SRAM, non-volatile memory (e.g., Flash memory), or other storage. In at least one embodiment, activation storage 620 may be completely or partially within or external to one or more processors or other logical circuits. In at least one embodiment, choice of whether activation storage 620 is internal or external to a processor, for example, or comprised of DRAM, SRAM, Flash or some other storage type may depend on available storage on-chip versus off-chip, latency requirements of training and/or inferencing functions being performed, batch size of data used in inferencing and/or training of a neural network, or some combination of these factors. In at least one embodiment, inference and/or training logic 615 illustrated in FIG. 6A may be used in conjunction with an application-specific integrated circuit ("ASIC"), such as Tensorflow® Processing Unit from Google, an inference processing unit (IPU) from Graphcore™, or a Nervana® (e.g., "Lake Crest") processor from Intel Corp. In at least one embodiment, inference and/or training logic 615 illustrated in FIG. 6A may be used in conjunction with central processing unit ("CPU") hardware, graphics processing unit ("GPU") hardware or other hardware, such as field programmable gate arrays ("FPGAs").

Figure 6B:
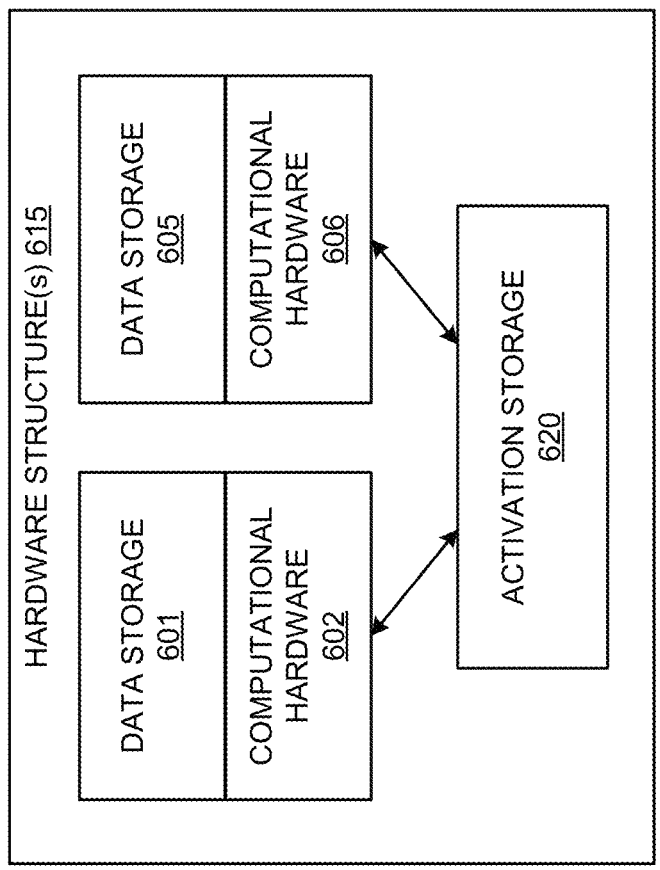
FIG. 6B illustrates inference and/or training logic, according to at least one embodiment.

FIG. 6B illustrates inference and/or training logic 615, according to at least one or more embodiments. In at least one embodiment, inference and/or training logic 615 may include, without limitation, hardware logic in which computational resources are dedicated or otherwise exclusively used in conjunction with weight values or other information corresponding to one or more layers of neurons within a neural network. In at least one embodiment, inference and/or training logic 615 illustrated in FIG. 6B may be used in conjunction with an application-specific integrated circuit (ASIC), such as Tensorflow® Processing Unit from Google, an inference processing unit (IPU) from Graphcore™, or a Nervana® (e.g., "Lake Crest") processor from Intel Corp. In at least one embodiment, inference and/or training logic 615 illustrated in FIG. 6B may be used in conjunction with central processing unit (CPU) hardware, graphics processing unit (GPU) hardware or other hardware, such as field programmable gate arrays (FPGAs). In at least one embodiment, inference and/or training logic 615 includes, without limitation, code and/or data storage 601 and code and/or data storage 605, which may be used to store code (e.g., graph code), weight values and/or other information, including bias values, gradient information, momentum values, and/or other parameter or hyperparameter information. In at least one embodiment illustrated in FIG. 6B, each of code and/or data storage 601 and code and/or data storage 605 is associated with a dedicated computational resource, such as computational hardware 602 and computational hardware 606, respectively. In at least one embodiment, each of computational hardware 602 and computational hardware 606 comprises one or more ALUs that perform mathematical functions, such as linear algebraic functions, only on information stored in code and/or data storage 601 and code and/or data storage 605, respectively, result of which is stored in activation storage 620.

In at least one embodiment, each of code and/or data storage 601 and 605 and corresponding computational hardware 602 and 606, respectively, correspond to different layers of a neural network, such that resulting activation from one "storage/computational pair 601/602" of code and/or data storage 601 and computational hardware 602 is provided as an input to "storage/computational pair 605/606" of code and/or data storage 605 and computational hardware 606, in order to mirror conceptual organization of a neural network. In at least one embodiment, each of storage/computational pairs 601/602 and 605/606 may correspond to more than one neural network layer. In at least one embodiment, additional storage/computation pairs (not shown) subsequent to or in parallel with storage computation pairs 601/602 and 605/606 may be included in inference and/or training logic 615.

Data Center

Figure 7:
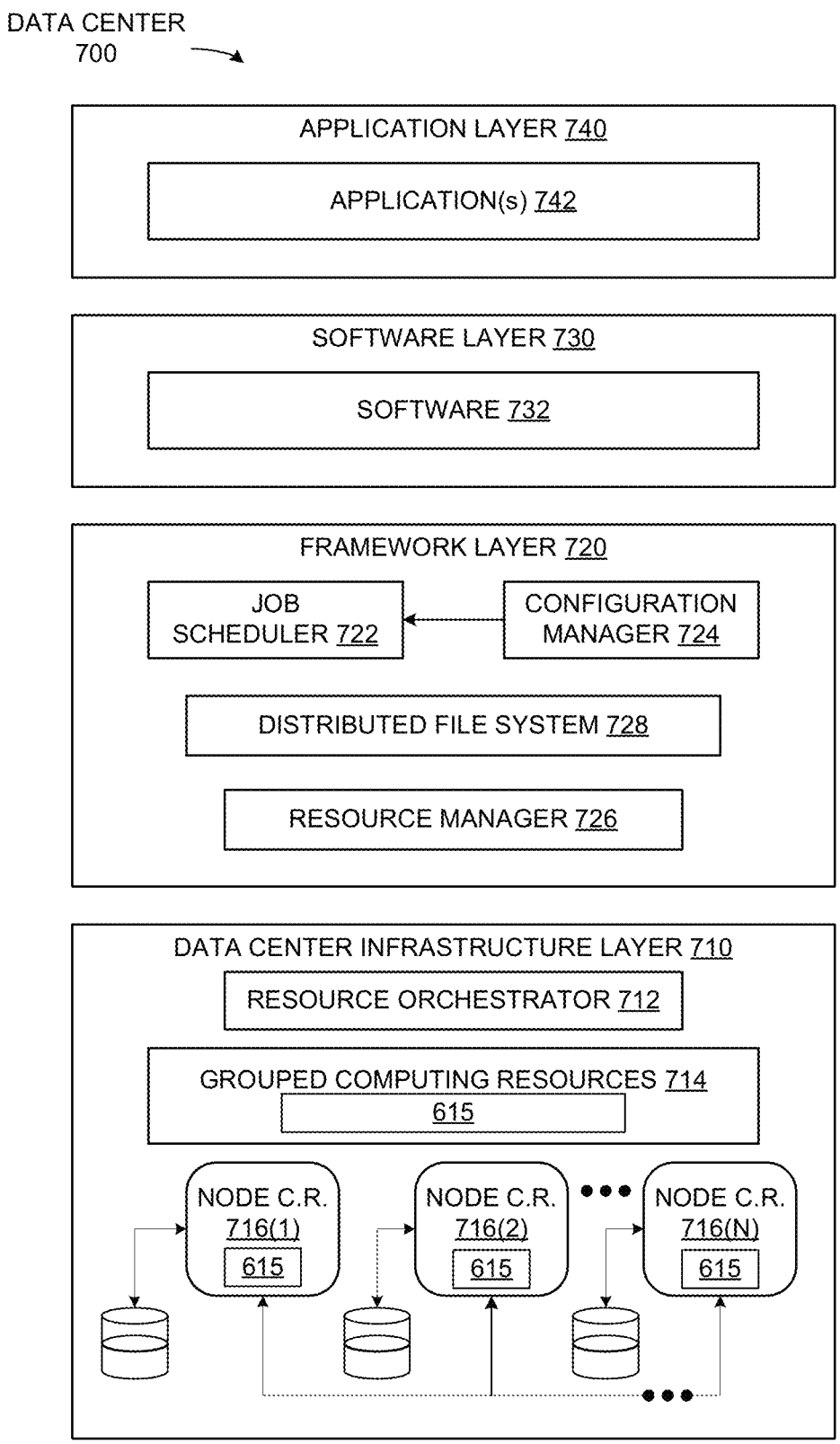
FIG. 7 illustrates an example data center system, according to at least one embodiment.

FIG. 7 illustrates an example data center 700, in which at least one embodiment may be used. In at least one embodiment, data center 700 includes a data center infrastructure layer 710, a framework layer 720, a software layer 730, and an application layer 740.

In at least one embodiment, as shown in FIG. 7, data center infrastructure layer 710 may include a resource orchestrator 712, grouped computing resources 714, and node computing resources ("node C.R.s") 716(1)-716(N), where "N" represents any whole, positive integer. In at least one embodiment, node C.R.s 716(1)-716(N) may include, but are not limited to, any number of central processing units ("CPUs") or other processors (including accelerators, field programmable gate arrays (FPGAs), graphics processors, etc.), memory devices (e.g., dynamic read-only memory), storage devices (e.g., solid state or disk drives), network input/output ("NW I/O") devices, network switches, virtual machines ("VMs"), power modules, and cooling modules, etc. In at least one embodiment, one or more node C.R.s from among node C.R.s 716(1)-716(N) may be a server having one or more of above-mentioned computing resources.

In at least one embodiment, grouped computing resources 714 may include separate groupings of node C.R.s housed within one or more racks (not shown), or many racks housed in data centers at various geographical locations (also not shown). Separate groupings of node C.R.s within grouped computing resources 714 may include grouped compute, network, memory or storage resources that may be configured or allocated to support one or more workloads. In at least one embodiment, several node C.R.s including CPUs or processors may grouped within one or more racks to provide compute resources to support one or more workloads. In at least one embodiment, one or more racks may also include any number of power modules, cooling modules, and network switches, in any combination.

In at least one embodiment, resource orchestrator 712 may configure or otherwise control one or more node C.R.s 716(1)-716(N) and/or grouped computing resources 714. In at least one embodiment, resource orchestrator 712 may include a software design infrastructure ("SDI") management entity for data center 700. In at least one embodiment, resource orchestrator may include hardware, software or some combination thereof.

In at least one embodiment, as shown in FIG. 7, framework layer 720 includes a job scheduler 722, a configuration manager 724, a resource manager 726 and a distributed file system 728. In at least one embodiment, framework layer 720 may include a framework to support software 732 of software layer 730 and/or one or more application(s) 742 of application layer 740. In at least one embodiment, software 732 or application(s) 742 may respectively include web-based service software or applications, such as those provided by Amazon Web Services, Google Cloud and Microsoft Azure. In at least one embodiment, framework layer 720 may be, but is not limited to, a type of free and open-source software web application framework such as Apache Spark™ (hereinafter "Spark") that may utilize distributed file system 728 for large-scale data processing (e.g., "big data"). In at least one embodiment, job scheduler 722 may include a Spark driver to facilitate scheduling of workloads supported by various layers of data center 700. In at least one embodiment, configuration manager 724 may be capable of configuring different layers such as software layer 730 and framework layer 720 including Spark and distributed file system 728 for supporting large-scale data processing. In at least one embodiment, resource manager 726 may be capable of managing clustered or grouped computing resources mapped to or allocated for support of distributed file system 728 and job scheduler 722. In at least one embodiment, clustered or grouped computing resources may include grouped computing resource 714 at data center infrastructure layer 710. In at least one embodiment, resource manager 726 may coordinate with resource orchestrator 712 to manage these mapped or allocated computing resources.

In at least one embodiment, software 732 included in software layer 730 may include software used by at least portions of node C.R.s 716(1)-716(N), grouped computing resources 714, and/or distributed file system 728 of framework layer 720. one or more types of software may include, but are not limited to, Internet web page search software, e-mail virus scan software, database software, and streaming video content software.

In at least one embodiment, application(s) 742 included in application layer 740 may include one or more types of applications used by at least portions of node C.R.s 716(1)-716(N), grouped computing resources 714, and/or distributed file system 728 of framework layer 720. One or more types of applications may include, but are not limited to, any number of a genomics application, a cognitive compute, and a machine learning application, including training or inferencing software, machine learning framework software (e.g., PyTorch, TensorFlow, Caffe, etc.) or other machine learning applications used in conjunction with one or more embodiments.

In at least one embodiment, any of configuration manager 724, resource manager 726, and resource orchestrator 712 may implement any number and type of self-modifying actions based on any amount and type of data acquired in any technically feasible fashion. In at least one embodiment, self-modifying actions may relieve a data center operator of data center 700 from making possibly bad configuration decisions and possibly avoiding underutilized and/or poor performing portions of a data center.

In at least one embodiment, data center 700 may include tools, services, software or other resources to train one or more machine learning models or predict or infer information using one or more machine learning models according to one or more embodiments described herein. For example, in at least one embodiment, a machine learning model may be trained by calculating weight parameters according to a neural network architecture using software and computing resources described above with respect to data center 700. In at least one embodiment, trained machine learning models corresponding to one or more neural networks may be used to infer or predict information using resources described above with respect to data center 700 by using weight parameters calculated through one or more training techniques described herein.

In at least one embodiment, data center may use CPUs, application-specific integrated circuits (ASICs), GPUs, FPGAs, or other hardware to perform training and/or inferencing using above-described resources. Moreover, one or more software and/or hardware resources described above may be configured as a service to allow users to train or performing inferencing of information, such as image recognition, speech recognition, or other artificial intelligence services.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 7 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Computer Systems

Figure 8:
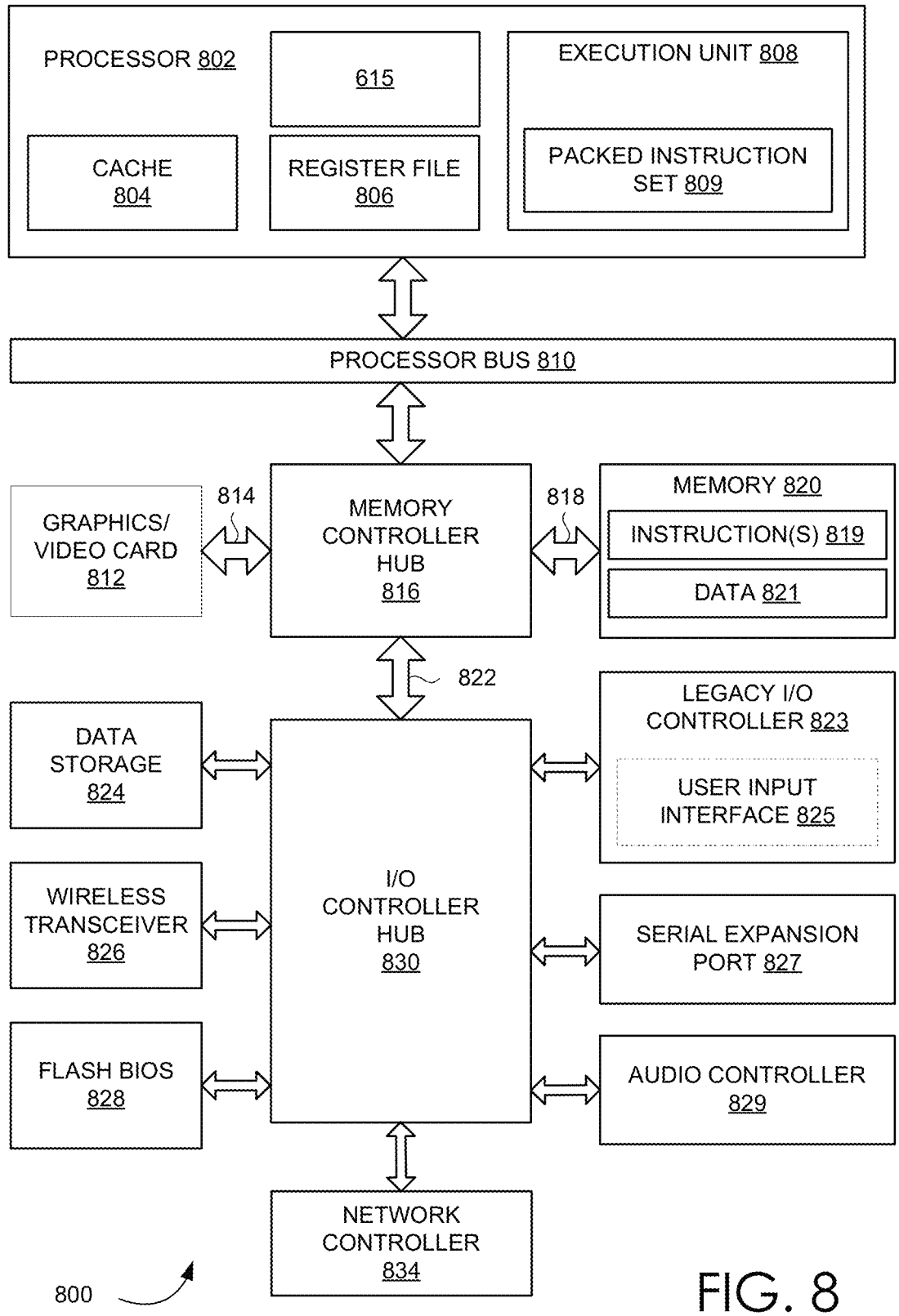
FIG. 8 illustrates a computer system, according to at least one embodiment.

FIG. 8 is a block diagram illustrating an exemplary computer system, which may be a system with interconnected devices and components, a system-on-a-chip (SOC) or some combination thereof 800 formed with a processor that may include execution units to execute an instruction, according to at least one embodiment. In at least one embodiment, computer system 800 may include, without limitation, a component, such as a processor 802 to employ execution units including logic to perform algorithms for process data, in accordance with present disclosure, such as in embodiment described herein. In at least one embodiment, computer system 800 may include processors, such as PENTIUM® Processor family, Xeon™, Itanium®, XScale™ and/or StrongARM™, Intel® Core™, or Intel® Nervana™ microprocessors available from Intel Corporation of Santa Clara, California, although other systems (including PCs having other microprocessors, engineering workstations, set-top boxes and like) may also be used. In at least one embodiment, computer system 800 may execute a version of WINDOWS' operating system available from Microsoft Corporation of Redmond, Wash., although other operating systems (UNIX and Linux for example), embedded software, and/or graphical user interfaces, may also be used.

Embodiments may be used in other devices such as handheld devices and embedded applications. Some examples of handheld devices include cellular phones, Internet Protocol devices, digital cameras, personal digital assistants ("PDAs"), and handheld PCs. In at least one embodiment, embedded applications may include a microcontroller, a digital signal processor ("DSP"), system on a chip, network computers ("NetPCs"), set-top boxes, network hubs, wide area network ("WAN") switches, or any other system that may perform one or more instructions in accordance with at least one embodiment.

In at least one embodiment, computer system 800 may include, without limitation, processor 802 that may include, without limitation, one or more execution units 808 to perform machine learning model training and/or inferencing according to techniques described herein. In at least one embodiment, computer system 800 is a single processor desktop or server system, but in another embodiment computer system 800 may be a multiprocessor system. In at least one embodiment, processor 802 may include, without limitation, a complex instruction set computer ("CISC") microprocessor, a reduced instruction set computing ("RISC") microprocessor, a very long instruction word ("VLIW") microprocessor, a processor implementing a combination of instruction sets, or any other processor device, such as a digital signal processor, for example. In at least one embodiment, processor 802 may be coupled to a processor bus 810 that may transmit data signals between processor 802 and other components in computer system 800.

In at least one embodiment, processor 802 may include, without limitation, a Level 1 ("L1") internal cache memory ("cache") 804. In at least one embodiment, processor 802 may have a single internal cache or multiple levels of internal cache. In at least one embodiment, cache memory may reside external to processor 802. Other embodiments may also include a combination of both internal and external caches depending on particular implementation and needs. In at least one embodiment, register file 806 may store different types of data in various registers including, without limitation, integer registers, floating point registers, status registers, and instruction pointer register.

In at least one embodiment, execution unit 808, including, without limitation, logic to perform integer and floating point operations, also resides in processor 802. In at least one embodiment, processor 802 may also include a microcode ("ucode") read only memory ("ROM") that stores microcode for certain macro instructions. In at least one embodiment, execution unit 808 may include logic to handle a packed instruction set 809. In at least one embodiment, by including packed instruction set 809 in an instruction set of a general-purpose processor 802, along with associated circuitry to execute instructions, operations used by many multimedia applications may be performed using packed data in a general-purpose processor 802. In one or more embodiments, many multimedia applications may be accelerated and executed more efficiently by using full width of a processor's data bus for performing operations on packed data, which may eliminate need to transfer smaller units of data across processor's data bus to perform one or more operations one data element at a time.

In at least one embodiment, execution unit 808 may also be used in microcontrollers, embedded processors, graphics devices, DSPs, and other types of logic circuits. In at least one embodiment, computer system 800 may include, without limitation, a memory 820. In at least one embodiment, memory 820 may be implemented as a Dynamic Random Access Memory ("DRAM") device, a Static Random Access Memory ("SRAM") device, flash memory device, or other memory device. In at least one embodiment, memory 820 may store instruction(s) 819 and/or data 821 represented by data signals that may be executed by processor 802.

In at least one embodiment, system logic chip may be coupled to processor bus 810 and memory 820. In at least one embodiment, system logic chip may include, without limitation, a memory controller hub ("MCH") 816, and processor 802 may communicate with MCH 816 via processor bus 810. In at least one embodiment, MCH 816 may provide a high bandwidth memory path 818 to memory 820 for instruction and data storage and for storage of graphics commands, data and textures. In at least one embodiment, MCH 816 may direct data signals between processor 802, memory 820, and other components in computer system 800 and to bridge data signals between processor bus 810, memory 820, and a system I/O 822. In at least one embodiment, system logic chip may provide a graphics port for coupling to a graphics controller. In at least one embodiment, MCH 816 may be coupled to memory 820 through a high bandwidth memory path 818 and graphics/video card 812 may be coupled to MCH 816 through an Accelerated Graphics Port ("AGP") interconnect 814.

In at least one embodiment, computer system 800 may use system I/O 822 that is a proprietary hub interface bus to couple MCH 816 to I/O controller hub ("ICH") 830. In at least one embodiment, ICH 830 may provide direct connections to some I/O devices via a local I/O bus. In at least one embodiment, local I/O bus may include, without limitation, a high-speed I/O bus for connecting peripherals to memory 820, chipset, and processor 802. Examples may include, without limitation, an audio controller 829, a firmware hub ("flash BIOS") 828, a wireless transceiver 826, a data storage 824, a legacy I/O controller 823 containing user input and keyboard interfaces 825, a serial expansion port 827, such as Universal Serial Bus ("USB"), and a network controller 834. data storage 824 may comprise a hard disk drive, a floppy disk drive, a CD-ROM device, a flash memory device, or other mass storage device.

In at least one embodiment, FIG. 8 illustrates a system, which includes interconnected hardware devices or "chips", whereas in other embodiments, FIG. 8 may illustrate an exemplary System on a Chip ("SoC"). In at least one embodiment, devices illustrated in FIG. cc may be interconnected with proprietary interconnects, standardized interconnects (e.g., PCIe) or some combination thereof. In at least one embodiment, one or more components of computer system 800 are interconnected using compute express link (CXL) interconnects.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 8 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 9:
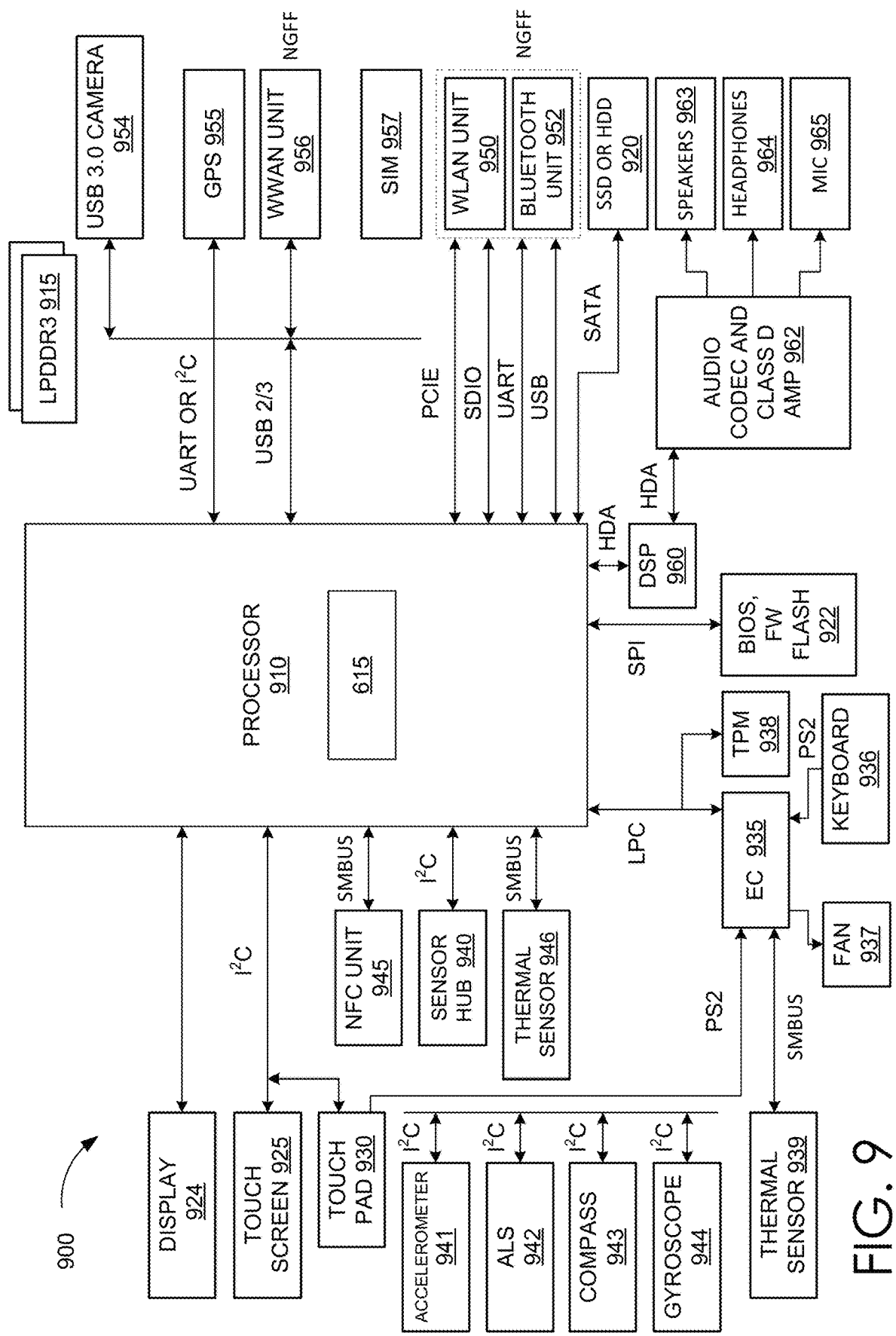
FIG. 9 illustrates a computer system, according to at least one embodiment.

FIG. 9 is a block diagram illustrating an electronic device 900 for utilizing a processor 910, according to at least one embodiment. In at least one embodiment, electronic device 900 may be, for example and without limitation, a notebook, a tower server, a rack server, a blade server, a laptop, a desktop, a tablet, a mobile device, a phone, an embedded computer, or any other suitable electronic device.

In at least one embodiment, system 900 may include, without limitation, processor 910 communicatively coupled to any suitable number or kind of components, peripherals, modules, or devices. In at least one embodiment, processor 910 coupled using a bus or interface, such as a 1° C. bus, a System Management Bus ("SMBus"), a Low Pin Count (LPC) bus, a Serial Peripheral Interface ("SPI"), a High Definition Audio ("HDA") bus, a Serial Advance Technology Attachment ("SATA") bus, a Universal Serial Bus ("USB") (versions 1, 2, 3), or a Universal Asynchronous Receiver/Transmitter ("UART") bus. In at least one embodiment, FIG. 9 illustrates a system, which includes interconnected hardware devices or "chips", whereas in other embodiments, FIG. 9 may illustrate an exemplary System on a Chip ("SoC"). In at least one embodiment, devices illustrated in FIG. 9 may be interconnected with proprietary interconnects, standardized interconnects (e.g., PCIe) or some combination thereof. In at least one embodiment, one or more components of FIG. 9 are interconnected using compute express link (CXL) interconnects.

In at least one embodiment, FIG. 9 may include a display 924, a touch screen 925, a touch pad 930, a Near Field Communications unit ("NFC") 945, a sensor hub 940, a thermal sensor 946, an Express Chipset ("EC") 935, a Trusted Platform Module ("TPM") 938, BIOS/firmware/flash memory ("BIOS, FW Flash") 922, a DSP 960, a drive 920 such as a Solid State Disk ("SSD") or a Hard Disk Drive ("HDD"), a wireless local area network unit ("WLAN") 950, a Bluetooth unit 952, a Wireless Wide Area Network unit ("WWAN") 956, a Global Positioning System (GPS) 955, a camera ("USB 3.0 camera") 954 such as a USB 3.0 camera, and/or a Low Power Double Data Rate ("LPDDR") memory unit ("LPDDR3") 915 implemented in, for example, LPDDR3 standard. These components may each be implemented in any suitable manner.

In at least one embodiment, other components may be communicatively coupled to processor 910 through components discussed above. In at least one embodiment, an accelerometer 941, Ambient Light Sensor ("ALS") 942, compass 943, and a gyroscope 944 may be communicatively coupled to sensor hub 940. In at least one embodiment, thermal sensor 939, a fan 937, a keyboard 946, and a touch pad 930 may be communicatively coupled to EC 935. In at least one embodiment, speaker 963, headphones 964, and microphone ("mic") 965 may be communicatively coupled to an audio unit ("audio codec and class d amp") 962, which may in turn be communicatively coupled to DSP 960. In at least one embodiment, audio unit 964 may include, for example and without limitation, an audio coder/decoder ("codec") and a class D amplifier. In at least one embodiment, SIM card ("SIM") 957 may be communicatively coupled to WWAN unit 956. In at least one embodiment, components such as WLAN unit 950 and Bluetooth unit 952, as well as WWAN unit 956 may be implemented in a Next Generation Form Factor ("NGFF").

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 9 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 10:
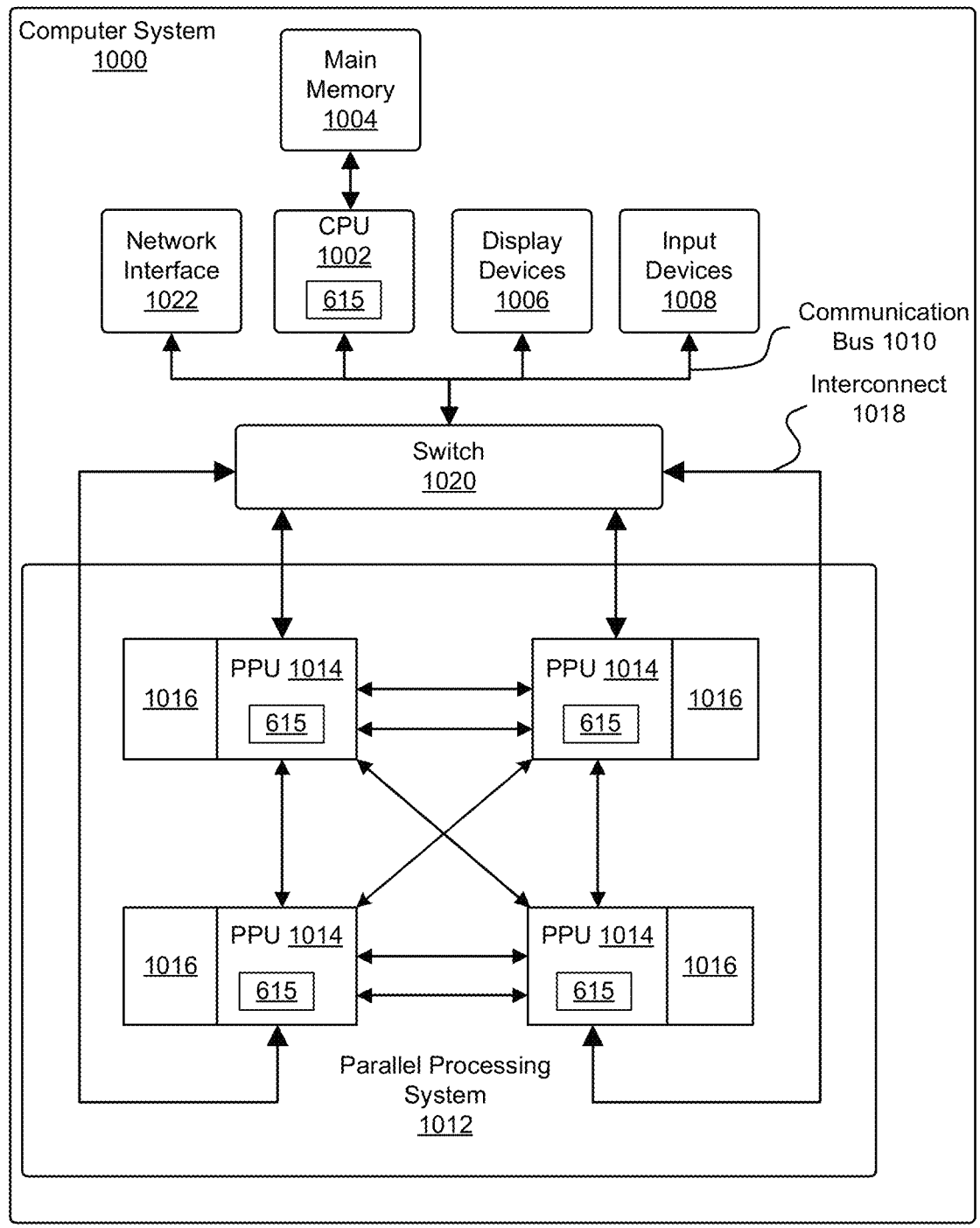
FIG. 10 illustrates a computer system, according to at least one embodiment.

FIG. 10 illustrates a computer system 1000, according to at least one embodiment. In at least one embodiment, computer system 1000 is configured to implement various processes and methods described throughout this disclosure.

In at least one embodiment, computer system 1000 comprises, without limitation, at least one central processing unit ("CPU") 1002 that is connected to a communication bus 1010 implemented using any suitable protocol, such as PCI ("Peripheral Component Interconnect"), peripheral component interconnect express ("PCI-Express"), AGP ("Accelerated Graphics Port"), HyperTransport, or any other bus or point-to-point communication protocol(s). In at least one embodiment, computer system 1000 includes, without limitation, a main memory 1004 and control logic (e.g., implemented as hardware, software, or a combination thereof) and data are stored in main memory 1004 which may take form of random access memory ("RAM"). In at least one embodiment, a network interface subsystem ("network interface") 1022 provides an interface to other computing devices and networks for receiving data from and transmitting data to other systems from computer system 1000.

In at least one embodiment, computer system 1000, in at least one embodiment, includes, without limitation, input devices 1008, parallel processing system 1012, and display devices 1006 which can be implemented using a conventional cathode ray tube ("CRT"), liquid crystal display ("LCD"), light emitting diode ("LED"), plasma display, or other suitable display technologies. In at least one embodiment, user input is received from input devices 1008 such as keyboard, mouse, touchpad, microphone, and more. In at least one embodiment, each of foregoing modules can be situated on a single semiconductor platform to form a processing system.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 10 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 11:
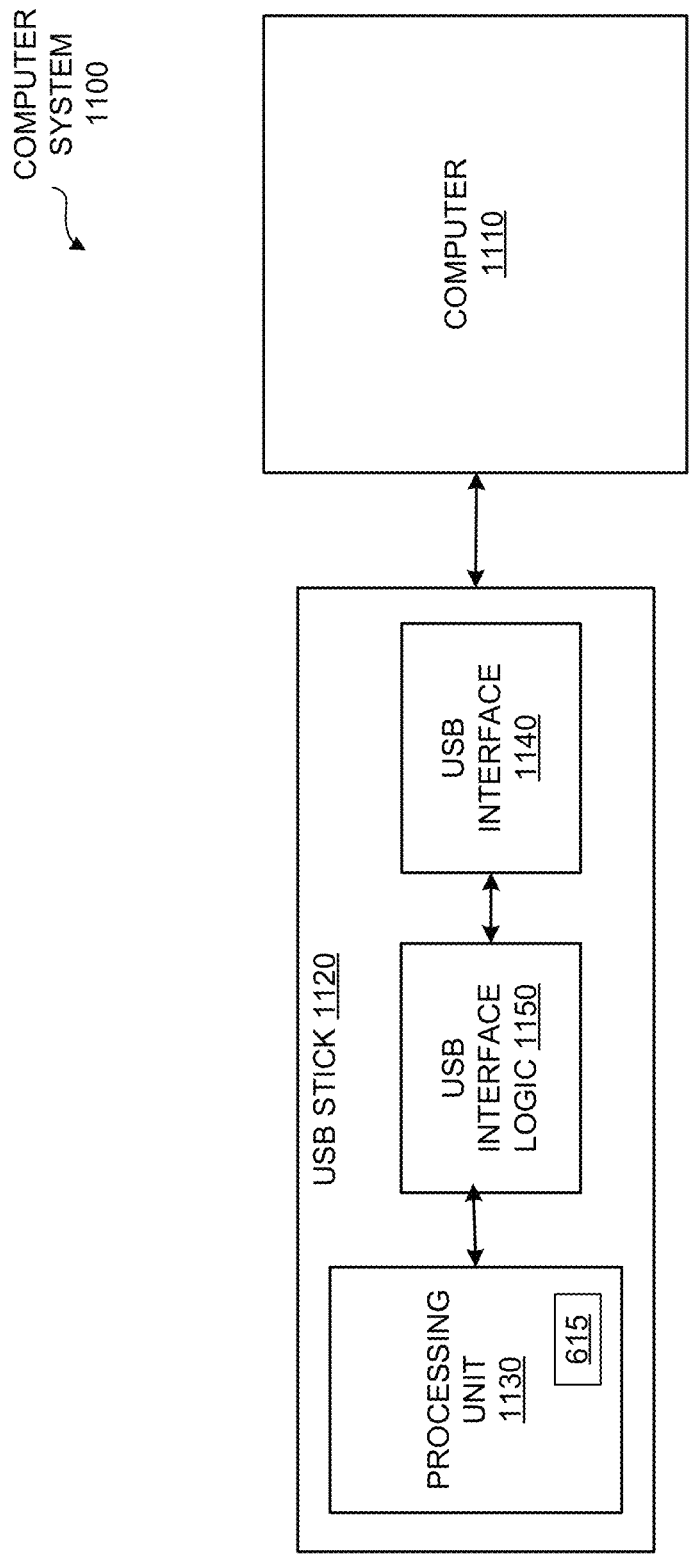
FIG. 11 illustrates a computer system, according at least one embodiment.

FIG. 11 illustrates a computer system 1100, according to at least one embodiment. In at least one embodiment, computer system 1100 includes, without limitation, a computer 1110 and a USB stick 1120. In at least one embodiment, computer 1110 may include, without limitation, any number and type of processor(s) (not shown) and a memory (not shown). In at least one embodiment, computer 1110 includes, without limitation, a server, a cloud instance, a laptop, and a desktop computer.

In at least one embodiment, USB stick 1120 includes, without limitation, a processing unit 1130, a USB interface 1140, and USB interface logic 1150. In at least one embodiment, processing unit 1130 may be any instruction execution system, apparatus, or device capable of executing instructions. In at least one embodiment, processing unit 1130 may include, without limitation, any number and type of processing cores (not shown). In at least one embodiment, processing core 1130 comprises an application specific integrated circuit ("ASIC") that is optimized to perform any amount and type of operations associated with machine learning. For instance, in at least one embodiment, processing core 1130 is a tensor processing unit ("TPC") that is optimized to perform machine learning inference operations. In at least one embodiment, processing core 1130 is a vision processing unit ("VPU") that is optimized to perform machine vision and machine learning inference operations.

In at least one embodiment, USB interface 1140 may be any type of USB connector or USB socket. For instance, in at least one embodiment, USB interface 1140 is a USB 3.0 Type-C socket for data and power. In at least one embodiment, USB interface 1140 is a USB 3.0 Type-A connector. In at least one embodiment, USB interface logic 1150 may include any amount and type of logic that enables processing unit 1130 to interface with or devices (e.g., computer 1110) via USB connector 1140.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 11 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 12A:
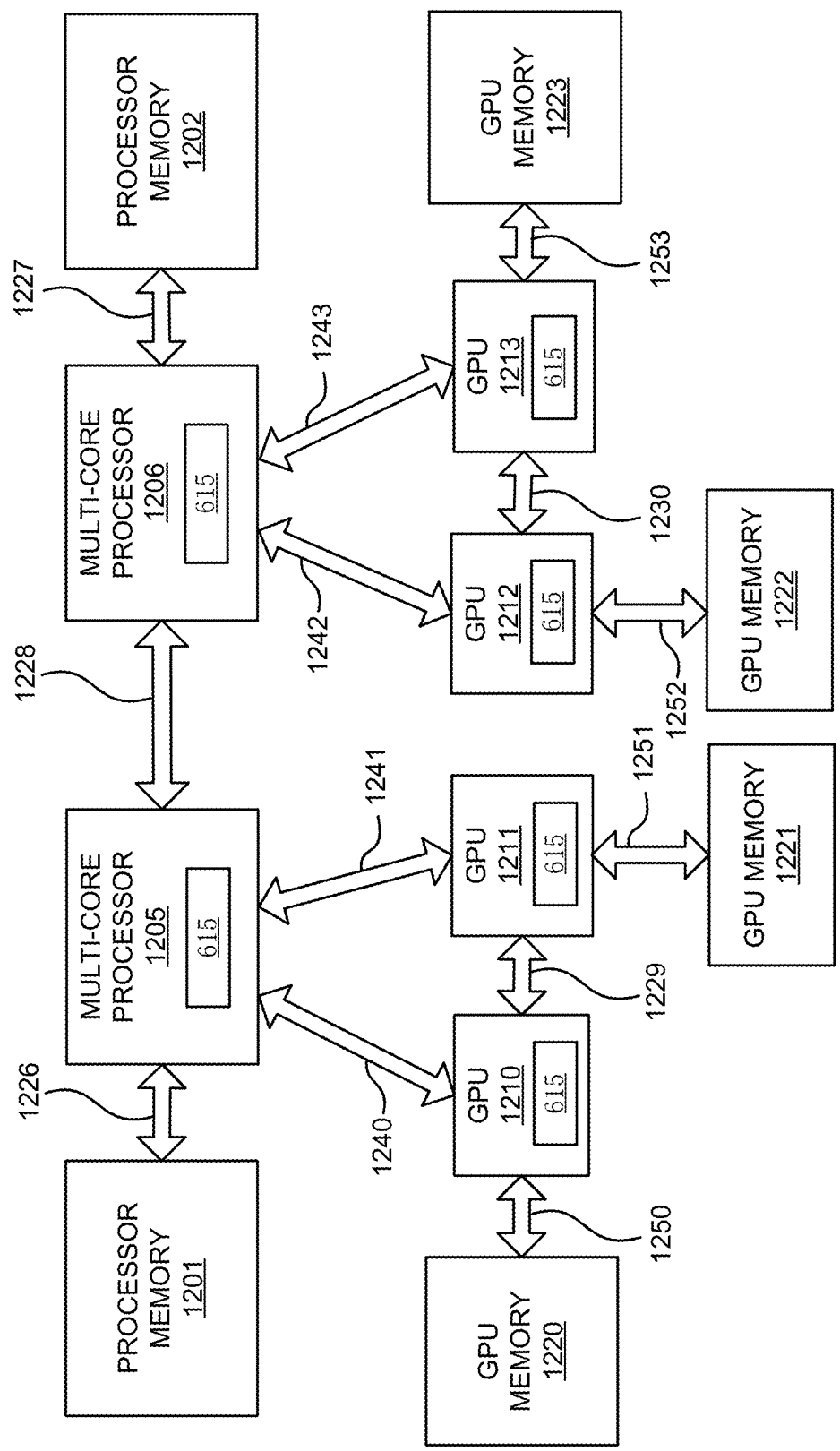
FIG. 12A illustrates a computer system, according to at least one embodiment.

FIG. 12A illustrates an exemplary architecture in which a plurality of GPUs 1210-1213 is communicatively coupled to a plurality of multi-core processors 1205-1206 over high-speed links 1240-1243 (e.g., buses, point-to-point interconnects, etc.). In one embodiment, high-speed links 1240-1243 support a communication throughput of 4 GB/s, 30 GB/s, 80 GB/s or higher. Various interconnect protocols may be used including, but not limited to, PCIe 4.0 or 5.0 and NVLink 2.0.

In addition, and in one embodiment, two or more of GPUs 1210-1213 are interconnected over high-speed links 1229-1230, which may be implemented using same or different protocols/links than those used for high-speed links 1240-1243. Similarly, two or more of multi-core processors 1205-1206 may be connected over high speed link 1228 which may be symmetric multi-processor (SMP) buses operating at 20 GB/s, 30 GB/s, 120 GB/s or higher. Alternatively, all communication between various system components shown in FIG. 12A may be accomplished using same protocols/links (e.g., over a common interconnection fabric).

In one embodiment, each multi-core processor 1205-1206 is communicatively coupled to a processor memory 1201-1202, via memory interconnects 1226-1227, respectively, and each GPU 1210-1213 is communicatively coupled to GPU memory 1220-1223 over GPU memory interconnects 1250-1253, respectively. Memory interconnects 1226-1227 and 1250-1253 may utilize same or different memory access technologies. By way of example, and not limitation, processor memories 1201-1202 and GPU memories 1220-1223 may be volatile memories such as dynamic random access memories (DRAMs) (including stacked DRAMs), Graphics DDR SDRAM (GDDR) (e.g., GDDR5, GDDR6), or High Bandwidth Memory (HBM) and/or may be non-volatile memories such as 3D XPoint or Nano-Ram. In one embodiment, some portion of processor memories 1201-1202 may be volatile memory and another portion may be non-volatile memory (e.g., using a two-level memory (2 LM) hierarchy).

As described below, although various processors 1205-1206 and GPUs 1210-1213 may be physically coupled to a particular memory 1201-1202, 1220-1223, respectively, a unified memory architecture may be implemented in which a same virtual system address space (also referred to as "effective address" space) is distributed among various physical memories. For example, processor memories 1201-1202 may each comprise 64 GB of system memory address space and GPU memories 1220-1223 may each comprise 32 GB of system memory address space (resulting in a total of 256 GB addressable memory in this example).

Figure 12B:
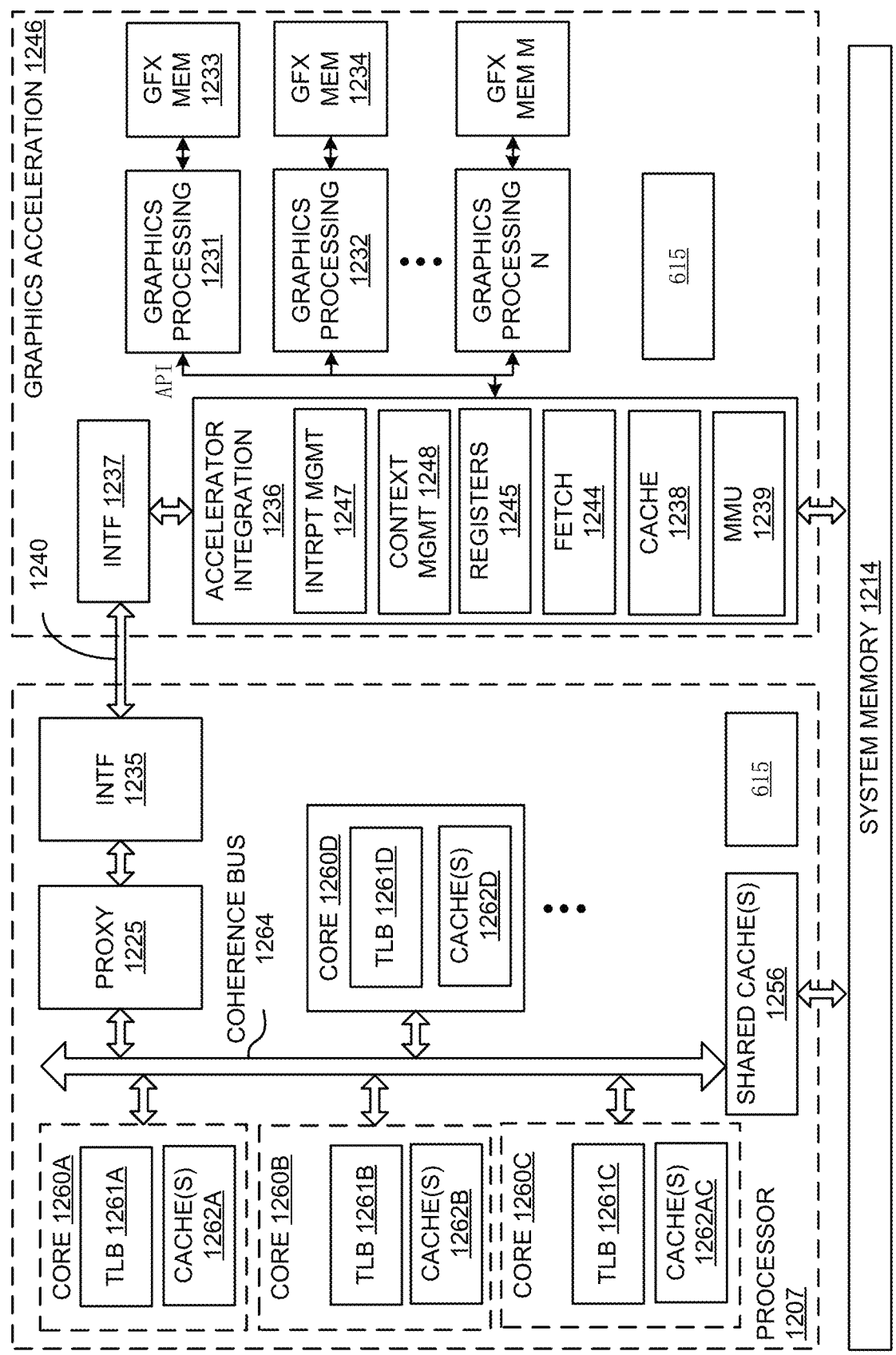
FIG. 12B illustrates a computer system, according to at least one embodiment.

FIG. 12B illustrates additional details for an interconnection between a multi-core processor 1207 and a graphics acceleration module 1246 in accordance with one exemplary embodiment. Graphics acceleration module 1246 may include one or more GPU chips integrated on a line card which is coupled to processor 1207 via high-speed link 1240. Alternatively, graphics acceleration module 1246 may be integrated on a same package or chip as processor 1207.

In at least one embodiment, illustrated processor 1207 includes a plurality of cores 1260A-1260D, each with a translation lookaside buffer 1261A-1261D and one or more caches 1262A-1262D. In at least one embodiment, cores 1260A-1260D may include various other components for executing instructions and processing data which are not illustrated. Caches 1262A-1262D may comprise level 1 (L1) and level 2 (L2) caches. In addition, one or more shared caches 1256 may be included in caches 1262A-1262D and shared by sets of cores 1260A-1260D. For example, one embodiment of processor 1207 includes 24 cores, each with its own L1 cache, twelve shared L2 caches, and twelve shared L3 caches. In this embodiment, one or more L2 and L3 caches are shared by two adjacent cores. Processor 1207 and graphics acceleration module 1246 connect with system memory 1214, which may include processor memories 1201-1202 of FIG. 12A.

Coherency is maintained for data and instructions stored in various caches 1262A-1262D, 1256 and system memory 1214 via inter-core communication over a coherence bus 1264. For example, each cache may have cache coherency logic/circuitry associated therewith to communicate to over coherence bus 1264 in response to detected reads or writes to particular cache lines. In one implementation, a cache snooping protocol is implemented over coherence bus 1264 to snoop cache accesses.

In one embodiment, a proxy circuit 1225 communicatively couples graphics acceleration module 1246 to coherence bus 1264, allowing graphics acceleration module 1246 to participate in a cache coherence protocol as a peer of cores 1260A-1260D. In particular, an interface 1235 provides connectivity to proxy circuit 1225 over high-speed link 1240 (e.g., a PCIe bus, NVLink, etc.) and an interface 1237 connects graphics acceleration module 1246 to link 1240.

In one implementation, an accelerator integration circuit 1236 provides cache management, memory access, context management, and interrupt management services on behalf of a plurality of graphics processing engines 1231, 1232, N of graphics acceleration module 1246. Graphics processing engines 1231, 1232, N may each comprise a separate graphics processing unit (GPU). Alternatively, graphics processing engines 1231, 1232, N may comprise different types of graphics processing engines within a GPU such as graphics execution units, media processing engines (e.g., video encoders/decoders), samplers, and blit engines. In at least one embodiment, graphics acceleration module 1246 may be a GPU with a plurality of graphics processing engines 1231-1232, N or graphics processing engines 1231-1232, N may be individual GPUs integrated on a common package, line card, or chip.

In one embodiment, accelerator integration circuit 1236 includes a memory management unit (MMU) 1239 for performing various memory management functions such as virtual-to-physical memory translations (also referred to as effective-to-real memory translations) and memory access protocols for accessing system memory 1214. MMU 1239 may also include a translation lookaside buffer (TLB) (not shown) for caching virtual/effective to physical/real address translations. In one implementation, a cache 1238 stores commands and data for efficient access by graphics processing engines 1231-1232, N. In one embodiment, data stored in cache 1238 and graphics memories 1233-1234, M is kept coherent with core caches 1262A-1262D, 1256, and system memory 1214. As mentioned above, this may be accomplished via proxy circuit 1225 on behalf of cache 1238 and memories 1233-1234, M (e.g., sending updates to cache 1238 related to modifications/accesses of cache lines on processor caches 1262A-1262D, 1256, and receiving updates from cache 1238).

A set of registers 1245 store context data for threads executed by graphics processing engines 1231-1232, N and a context management circuit 1248 manages thread contexts. For example, context management circuit 1248 may perform save and restore operations to save and restore contexts of various threads during contexts switches (e.g., where a first thread is saved and a second thread is stored so that a second thread can be executed by a graphics processing engine). For example, on a context switch, context management circuit 1248 may store current register values to a designated region in memory (e.g., identified by a context pointer). It may then restore register values when returning to a context. In one embodiment, an interrupt management circuit 1247 receives and processes interrupts received from system devices.

In one implementation, virtual/effective addresses from a graphics processing engine 1231 are translated to real/physical addresses in system memory 1214 by MMU 1239. One embodiment of accelerator integration circuit 1236 supports multiple (e.g., 4, 8, 16) graphics accelerator modules 1246 and/or other accelerator devices. Graphics accelerator module 1246 may be dedicated to a single application executed on processor 1207 or may be shared between multiple applications. In one embodiment, a virtualized graphics execution environment is presented in which resources of graphics processing engines 1231-1232, N are shared with multiple applications or virtual machines (VMs). In at least one embodiment, resources may be subdivided into "slices" which are allocated to different VMs and/or applications based on processing requirements and priorities associated with VMs and/or applications.

In at least one embodiment, accelerator integration circuit 1236 performs as a bridge to a system for graphics acceleration module 1246 and provides address translation and system memory cache services. In addition, accelerator integration circuit 1236 may provide virtualization facilities for a host processor to manage virtualization of graphics processing engines 1231-1232, N, interrupts, and memory management.

Because hardware resources of graphics processing engines 1231-1232, N are mapped explicitly to a real address space seen by host processor 1207, any host processor can address these resources directly using an effective address value. One function of accelerator integration circuit 1236, in one embodiment, is physical separation of graphics processing engines 1231-1232, N so that they appear to a system as independent units.

In at least one embodiment, one or more graphics memories 1233-1234, M are coupled to each of graphics processing engines 1231-1232, N, respectively. Graphics memories 1233-1234, M store instructions and data being processed by each of graphics processing engines 1231-1232, N. Graphics memories 1233-1234, M may be volatile memories such as DRAMs (including stacked DRAMs), GDDR memory (e.g., GDDR5, GDDR6), or HBM, and/or may be non-volatile memories such as 3D XPoint or Nano-Ram.

In one embodiment, to reduce data traffic over link 1240, biasing techniques are used to ensure that data stored in graphics memories 1233-1234, M is data which will be used most frequently by graphics processing engines 1231-1232, N and preferably not used by cores 1260A-1260D (at least not frequently). Similarly, a biasing mechanism attempts to keep data needed by cores (and preferably not graphics processing engines 1231-1232, N) within caches 1262A-1262D, 1256 of cores and system memory 1214.

Figure 12C:
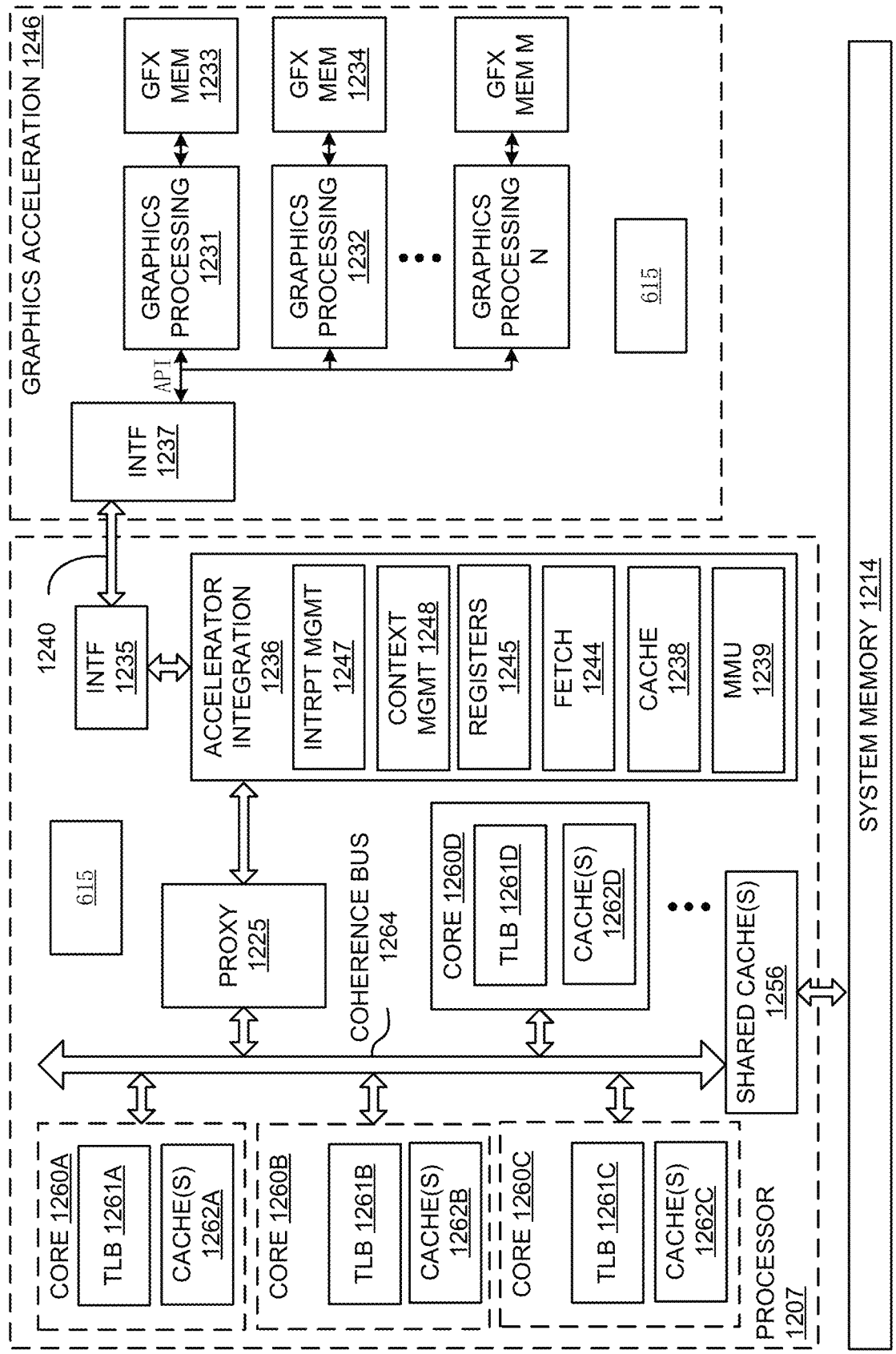
FIG. 12C illustrates a computer system, according to at least one embodiment.

FIG. 12C illustrates another exemplary embodiment in which accelerator integration circuit 1236 is integrated within processor 1207. In at least this embodiment, graphics processing engines 1231-1232, N communicate directly over high-speed link 1240 to accelerator integration circuit 1236 via interface 1237 and interface 1235 (which, again, may be utilize any form of bus or interface protocol). Accelerator integration circuit 1236 may perform same operations as those described with respect to FIG. 12B, but potentially at a higher throughput given its close proximity to coherence bus 1264 and caches 1262A-1262D, 1256. At least one embodiment supports different programming models including a dedicated-process programming model (no graphics acceleration module virtualization) and shared programming models (with virtualization), which may include programming models which are controlled by accelerator integration circuit 1236 and programming models which are controlled by graphics acceleration module 1246.

In at least one embodiment, graphics processing engines 1231-1232, N are dedicated to a single application or process under a single operating system. In at least one embodiment, a single application can funnel other application requests to graphics processing engines 1231-1232, N, providing virtualization within a VM/partition.

In at least one embodiment, graphics processing engines 1231-1232, N, may be shared by multiple VM/application partitions. In at least one embodiment, shared models may use a system hypervisor to virtualize graphics processing engines 1231-1232, N to allow access by each operating system. For single-partition systems without a hypervisor, graphics processing engines 1231-1232, N are owned by an operating system. In at least one embodiment, an operating system can virtualize graphics processing engines 1231-1232, N to provide access to each process or application.

In at least one embodiment, graphics acceleration module 1246 or an individual graphics processing engine 1231-1232, N selects a process element using a process handle. In at least one embodiment, process elements are stored in system memory 1214 and are addressable using an effective address to real address translation techniques described herein. In at least one embodiment, a process handle may be an implementation-specific value provided to a host process when registering its context with graphics processing engine 1231-1232, N (that is, calling system software to add a process element to a process element linked list). In at least one embodiment, a lower 16-bits of a process handle may be an offset of a process element within a process element linked list.

Figure 12D:
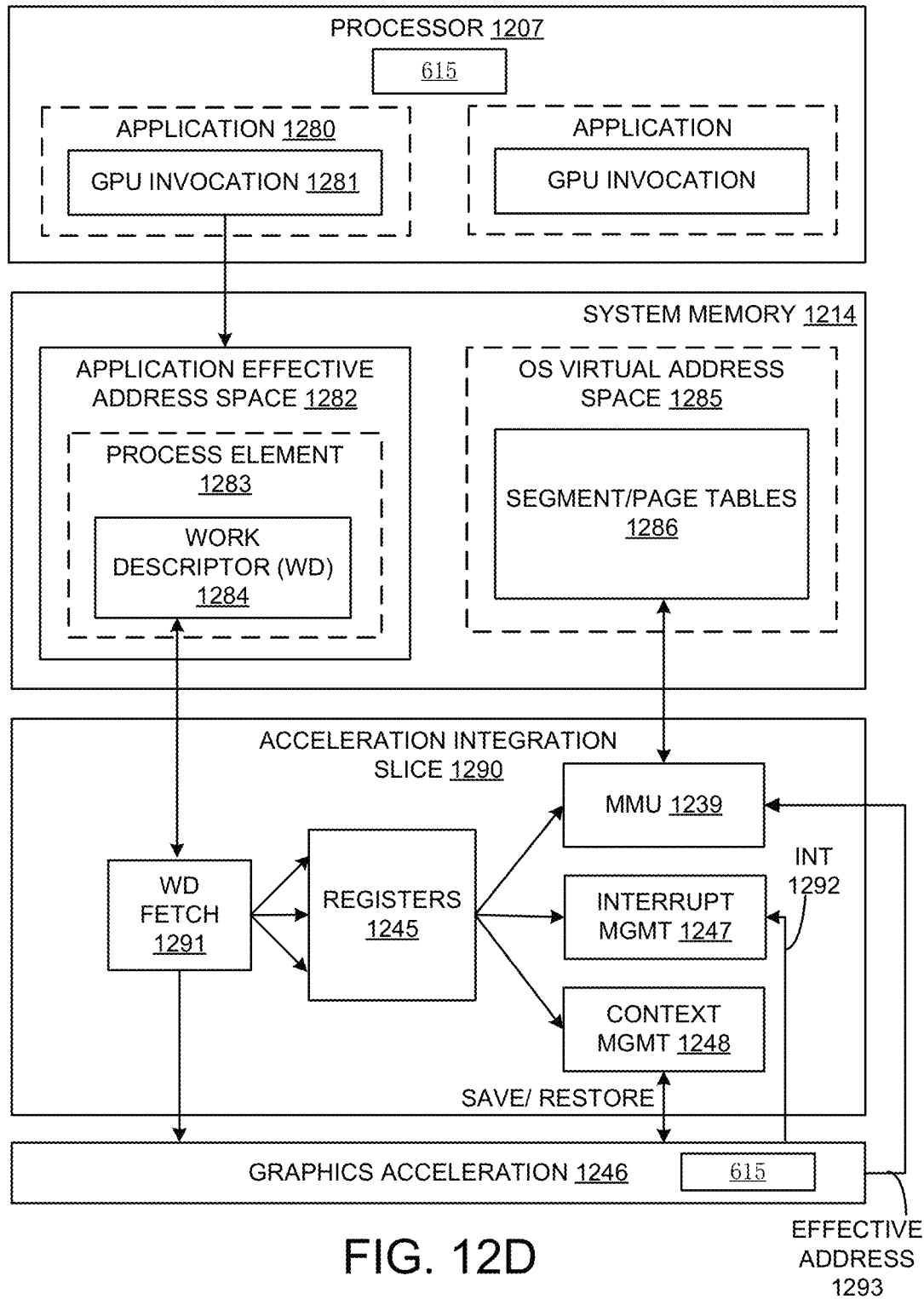
FIG. 12D illustrates a computer system, according to at least one embodiment.

FIG. 12D illustrates an exemplary accelerator integration slice 1290. As used herein, a "slice" comprises a specified portion of processing resources of accelerator integration circuit 1236. Application effective address space 1282 within system memory 1214 stores process elements 1283. In one embodiment, process elements 1283 are stored in response to GPU invocations 1281 from applications 1280 executed on processor 1207. A process element 1283 contains process state for corresponding application 1280. A work descriptor (WD) 1284 contained in process element 1283 can be a single job requested by an application or may contain a pointer to a queue of jobs. In at least one embodiment, WD 1284 is a pointer to a job request queue in an application's address space 1282.

Graphics acceleration module 1246 and/or individual graphics processing engines 1231-1232, N can be shared by all or a subset of processes in a system. In at least one embodiment, an infrastructure for setting up process state and sending a WD 1284 to a graphics acceleration module 1246 to start a job in a virtualized environment may be included.

In at least one embodiment, a dedicated-process programming model is implementation-specific. In this model, a single process owns graphics acceleration module 1246 or an individual graphics processing engine 1231. Because graphics acceleration module 1246 is owned by a single process, a hypervisor initializes accelerator integration circuit 1236 for an owning partition and an operating system initializes accelerator integration circuit 1236 for an owning process when graphics acceleration module 1246 is assigned.

In operation, a WD fetch unit 1291 in accelerator integration slice 1290 fetches next WD 1284 which includes an indication of work to be done by one or more graphics processing engines of graphics acceleration module 1246. Data from WD 1284 may be stored in registers 1245 and used by MMU 1239, interrupt management circuit 1247, and/or context management circuit 1248 as illustrated. For example, one embodiment of MMU 1239 includes segment/page walk circuitry for accessing segment/page tables 1286 within OS virtual address space 1285. Interrupt management circuit 1247 may process interrupt events 1292 received from graphics acceleration module 1246. When performing graphics operations, an effective address 1293 generated by a graphics processing engine 1231-1232, N is translated to a real address by MMU 1239.

In one embodiment, a same set of registers 1245 are duplicated for each graphics processing engine 1231-1232, N and/or graphics acceleration module 1246 and may be initialized by a hypervisor or operating system. Each of these duplicated registers may be included in an accelerator integration slice 1290. Exemplary registers that may be initialized by a hypervisor are shown in Table 1.

TABLE 1

| | Hypervisor Initialized Registers |
|---|---|
| 1 | Slice Control Register |
| 2 | Real Address (RA) Scheduled Processes Area Pointer |
| 3 | Authority Mask Override Register |
| 4 | Interrupt Vector Table Entry Offset |
| 5 | Interrupt Vector Table Entry Limit |
| 6 | State Register |
| 7 | Logical Partition ID |
| 8 | Real address (RA) Hypervisor Accelerator Utilization Record Pointer |
| 9 | Storage Description Register |

Exemplary registers that may be initialized by an operating system are shown in Table 2.

TABLE 2

| | Operating System Initialized Registers |
|---|---|
| 1 | Process and Thread Identification |
| 2 | Effective Address (EA) Context Save/Restore Pointer |
| 3 | Virtual Address (VA) Accelerator Utilization Record Pointer |
| 4 | Virtual Address (VA) Storage Segment Table Pointer |
| 5 | Authority Mask |
| 6 | Work descriptor |

In one embodiment, each WD 1284 is specific to a particular graphics acceleration module 1246 and/or graphics processing engines 1231-1232, N. It contains all information required by a graphics processing engine 1231-1232, N to do work or it can be a pointer to a memory location where an application has set up a command queue of work to be completed.

Figure 12E:
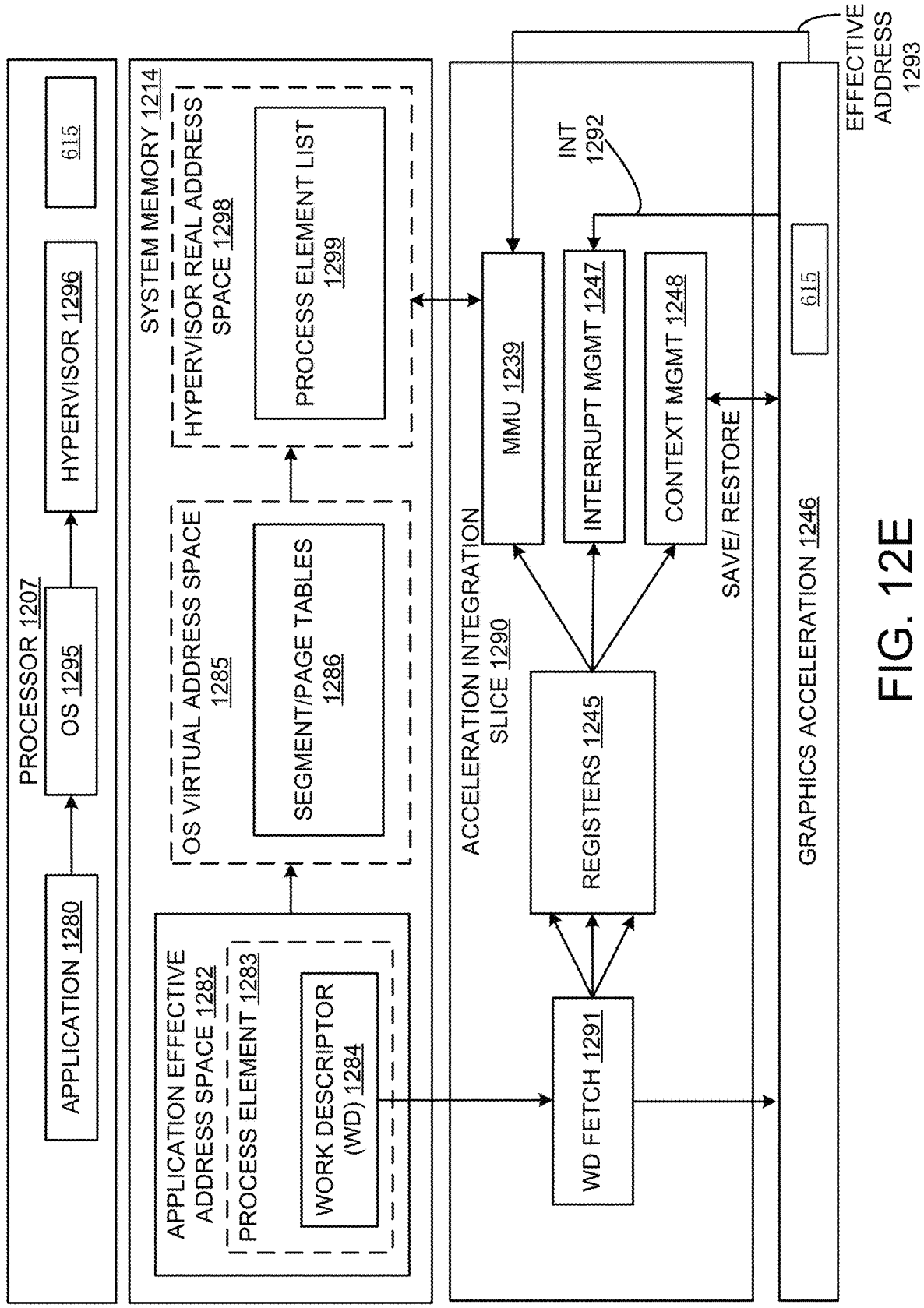
FIGS. 12E and 12F illustrate a shared programming model, according to at least one embodiment.

FIG. 12E illustrates additional details for one exemplary embodiment of a shared model. This embodiment includes a hypervisor real address space 1298 in which a process element list 1299 is stored. Hypervisor real address space 1298 is accessible via a hypervisor 1296 which virtualizes graphics acceleration module engines for operating system 1295.

In at least one embodiment, shared programming models allow for all or a subset of processes from all or a subset of partitions in a system to use a graphics acceleration module 1246. There are two programming models where graphics acceleration module 1246 is shared by multiple processes and partitions: time-sliced shared and graphics-directed shared.

In this model, system hypervisor 1296 owns graphics acceleration module 1246 and makes its function available to all operating systems 1295. For a graphics acceleration module 1246 to support virtualization by system hypervisor 1296, graphics acceleration module 1246 may adhere to the following: 1) An application's job request must be autonomous (that is, state does not need to be maintained between jobs), or graphics acceleration module 1246 must provide a context save and restore mechanism. 2) An application's job request is guaranteed by graphics acceleration module 1246 to complete in a specified amount of time, including any translation faults, or graphics acceleration module 1246 provides an ability to preempt processing of a job. 3) Graphics acceleration module 1246 must be guaranteed fairness between processes when operating in a directed shared programming model.

In at least one embodiment, application 1280 is required to make an operating system 1295 system call with a graphics acceleration module 1246 type, a work descriptor (WD), an authority mask register (AMR) value, and a context save/restore area pointer (CSRP). In at least one embodiment, graphics acceleration module 1246 type describes a targeted acceleration function for a system call. In at least one embodiment, graphics acceleration module 1246 type may be a system-specific value. In at least one embodiment, WD is formatted specifically for graphics acceleration module 1246 and can be in a form of a graphics acceleration module 1246 command, an effective address pointer to a user-defined structure, an effective address pointer to a queue of commands, or any other data structure to describe work to be done by graphics acceleration module 1246. In one embodiment, an AMR value is an AMR state to use for a current process. In at least one embodiment, a value passed to an operating system is similar to an application setting an AMR. If accelerator integration circuit 1236 and graphics acceleration module 1246 implementations do not support a User Authority Mask Override Register (UAMOR), an operating system may apply a current UAMOR value to an AMR value before passing an AMR in a hypervisor call. Hypervisor 1296 may optionally apply a current Authority Mask Override Register (AMOR) value before placing an AMR into process element 1283. In at least one embodiment, CSRP is one of registers 1245 containing an effective address of an area in an application's effective address space 1282 for graphics acceleration module 1246 to save and restore context state. This pointer is optional if no state is required to be saved between jobs or when a job is preempted. In at least one embodiment, context save/restore area may be pinned system memory.

Upon receiving a system call, operating system 1295 may verify that application 1280 has registered and been given authority to use graphics acceleration module 1246. Operating system 1295 then calls hypervisor 1296 with information shown in Table 3.

TABLE 3

OS to Hypervisor Call Parameters

| | |
|---|---|
| 1 | A work descriptor (WD) |
| 2 | An Authority Mask Register (AMR) value (potentially masked) |
| 3 | An effective address (EA) Context Save/Restore Area Pointer (CSRP) |
| 4 | A process ID (PID) and optional thread ID (TID) |
| 5 | A virtual address (VA) accelerator utilization record pointer (AURP) |
| 6 | Virtual address of storage segment table pointer (SSTP) |
| 7 | A logical interrupt service number (LISN) |

Upon receiving a hypervisor call, hypervisor 1296 verifies that operating system 1295 has registered and been given authority to use graphics acceleration module 1246. Hypervisor 1296 then puts process element 1283 into a process element linked list for a corresponding graphics acceleration module 1246 type. A process element may include information shown in Table 4.

TABLE 4

Process Element Information

| | |
|---|---|
| 1 | A work descriptor (WD) |
| 2 | An Authority Mask Register (AMR) value (potentially masked). |
| 3 | An effective address (EA) Context Save/Restore Area Pointer (CSRP) |
| 4 | A process ID (PID) and optional thread ID (TID) |
| 5 | A virtual address (VA) accelerator utilization record pointer (AURP) |
| 6 | Virtual address of storage segment table pointer (SSTP) |
| 7 | A logical interrupt service number (LISN) |
| 8 | Interrupt vector table, derived from hypervisor call parameters |
| 9 | A state register (SR) value |
| 10 | A logical partition ID (LPID) |
| 11 | A real address (RA) hypervisor accelerator utilization record pointer |
| 12 | Storage Descriptor Register (SDR) |

In at least one embodiment, hypervisor initializes a plurality of accelerator integration slice 1290 registers 1245.

Figure 12F:
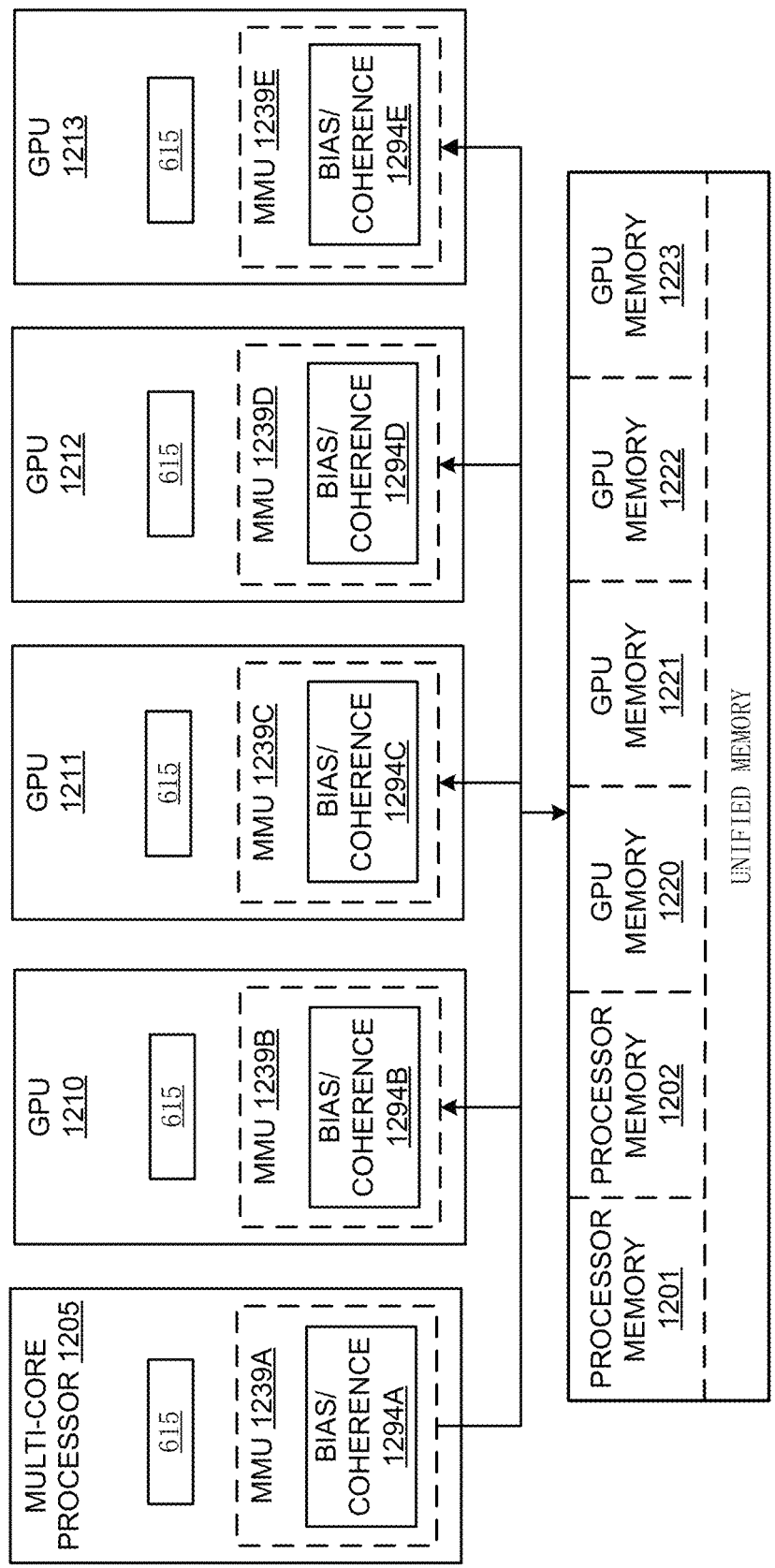

As illustrated in FIG. 12F, in at least one embodiment, a unified memory is used, addressable via a common virtual memory address space used to access physical processor memories 1201-1202 and GPU memories 1220-1223. In this implementation, operations executed on GPUs 1210-1213 utilize a same virtual/effective memory address space to access processor memories 1201-1202 and vice versa, thereby simplifying programmability. In one embodiment, a first portion of a virtual/effective address space is allocated to processor memory 1201, a second portion to second processor memory 1202, a third portion to GPU memory 1220, and so on. In at least one embodiment, an entire virtual/effective memory space (sometimes referred to as an effective address space) is thereby distributed across each of processor memories 1201-1202 and GPU memories 1220-1223, allowing any processor or GPU to access any physical memory with a virtual address mapped to that memory.

In one embodiment, bias/coherence management circuitry 1294A-1294E within one or more of MMUs 1239A-1239E ensures cache coherence between caches of one or more host processors (e.g., 1205) and GPUs 1210-1213 and implements biasing techniques indicating physical memories in which certain types of data should be stored. While multiple instances of bias/coherence management circuitry 1294A-1294E are illustrated in FIG. 12F, bias/coherence circuitry may be implemented within an MMU of one or more host processors 1205 and/or within accelerator integration circuit 1236.

One embodiment allows GPU-attached memory 1220-1223 to be mapped as part of system memory, and accessed using shared virtual memory (SVM) technology, but without suffering performance drawbacks associated with full system cache coherence. In at least one embodiment, an ability for GPU-attached memory 1220-1223 to be accessed as system memory without onerous cache coherence overhead provides a beneficial operating environment for GPU offload. This arrangement allows host processor 1205 software to setup operands and access computation results, without overhead of tradition I/O DMA data copies. Such traditional copies involve driver calls, interrupts and memory mapped I/O (MMIO) accesses that are all inefficient relative to simple memory accesses. In at least one embodiment, an ability to access GPU attached memory 1220-1223 without cache coherence overheads can be critical to execution time of an offloaded computation. In cases with substantial streaming write memory traffic, for example, cache coherence overhead can significantly reduce an effective write bandwidth seen by a GPU 1210-1213. In at least one embodiment, efficiency of operand setup, efficiency of results access, and efficiency of GPU computation may play a role in determining effectiveness of a GPU offload.

In at least one embodiment, selection of GPU bias and host processor bias is driven by a bias tracker data structure. A bias table may be used, for example, which may be a page-granular structure (i.e., controlled at a granularity of a memory page) that includes 1 or 2 bits per GPU-attached memory page. In at least one embodiment, a bias table may be implemented in a stolen memory range of one or more GPU-attached memories 1220-1223, with or without a bias cache in GPU 1210-1213 (e.g., to cache frequently/recently used entries of a bias table). Alternatively, an entire bias table may be maintained within a GPU.

In at least one embodiment, a bias table entry associated with each access to GPU-attached memory 1220-1223 is accessed prior to actual access to a GPU memory, causing the following operations. First, local requests from GPU 1210-1213 that find their page in GPU bias are forwarded directly to a corresponding GPU memory 1220-1223. Local requests from a GPU that find their page in host bias are forwarded to processor 1205 (e.g., over a high-speed link as discussed above). In one embodiment, requests from processor 1205 that find a requested page in host processor bias complete a request like a normal memory read. Alternatively, requests directed to a GPU-biased page may be forwarded to GPU 1210-1213. In at least one embodiment, a GPU may then transition a page to a host processor bias if it is not currently using a page. In at least one embodiment, bias state of a page can be changed either by a software-based mechanism, a hardware-assisted software-based mechanism, or, for a limited set of cases, a purely hardware-based mechanism.

One mechanism for changing bias state employs an API call (e.g., OpenCL), which, in turn, calls a GPU's device driver which, in turn, sends a message (or enqueues a command descriptor) to a GPU directing it to change a bias state and, for some transitions, perform a cache flushing operation in a host. In at least one embodiment, cache flushing operation is used for a transition from host processor 1205 bias to GPU bias, but is not for an opposite transition.

In one embodiment, cache coherency is maintained by temporarily rendering GPU-biased pages uncacheable by host processor 1205. To access these pages, processor 1205 may request access from GPU 1210 which may or may not grant access right away. Thus, to reduce communication between processor 1205 and GPU 1210 it is beneficial to ensure that GPU-biased pages are those which are required by a GPU but not host processor 1205 and vice versa.

Inference and/or training logic 615 are used to perform one or more embodiments. Details regarding the inference and/or training logic 615 are provided below in conjunction with FIGS. 6A and/or 6B.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 13:
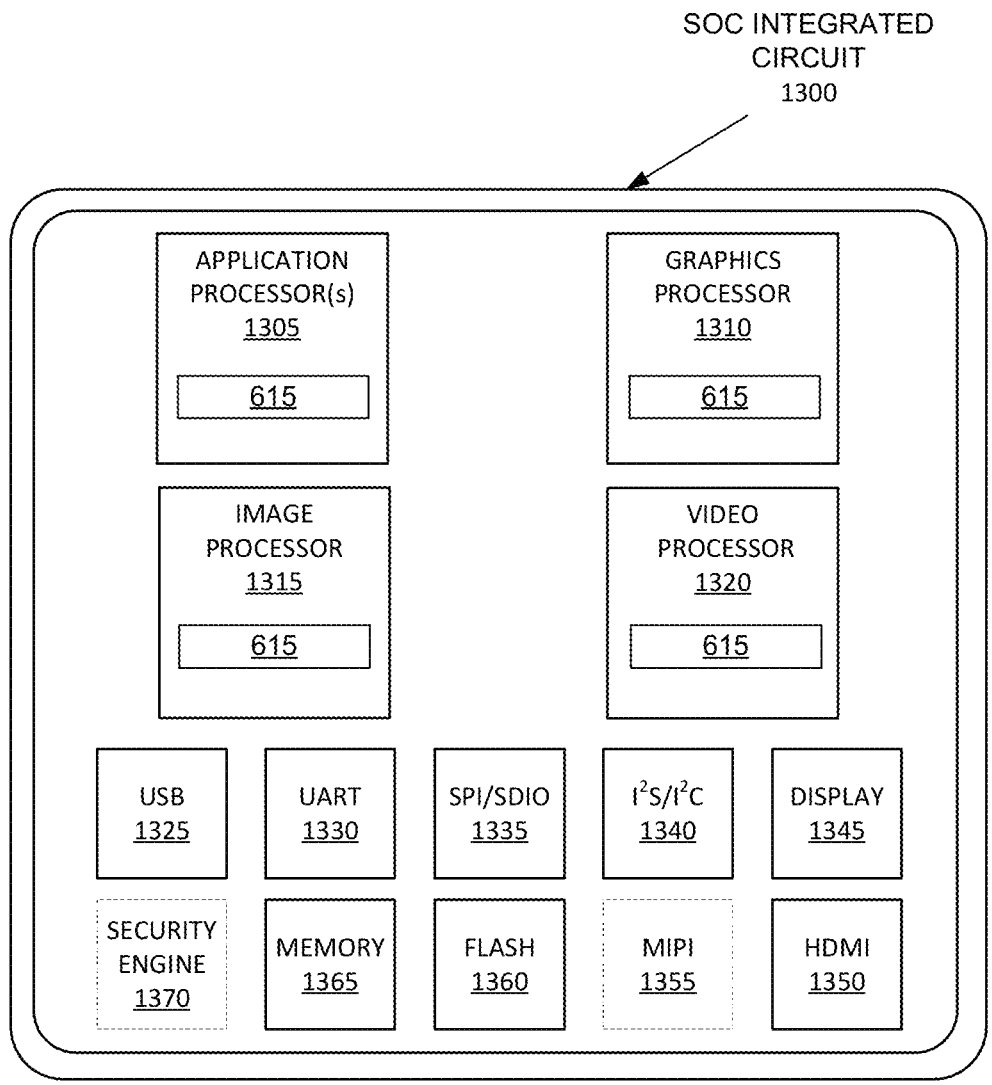
FIG. 13 illustrates exemplary integrated circuits and associated graphics processors, according to at least one embodiment.

FIG. 13 illustrates exemplary integrated circuits and associated graphics processors that may be fabricated using one or more IP cores, according to various embodiments described herein. In addition to what is illustrated, other logic and circuits may be included in at least one embodiment, including additional graphics processors/cores, peripheral interface controllers, or general-purpose processor cores.

FIG. 13 is a block diagram illustrating an exemplary system on a chip integrated circuit 1300 that may be fabricated using one or more IP cores, according to at least one embodiment. In at least one embodiment, integrated circuit 1300 includes one or more application processor(s) 1305 (e.g., CPUs), at least one graphics processor 1310, and may additionally include an image processor 1315 and/or a video processor 1320, any of which may be a modular IP core. In at least one embodiment, integrated circuit 1300 includes peripheral or bus logic including a USB controller 1325, UART controller 1330, an SPI/SDIO controller 1335, and an I²S/I²C controller 1340. In at least one embodiment, integrated circuit 1300 can include a display device 1345 coupled to one or more of a high-definition multimedia interface (HDMI) controller 1350 and a mobile industry processor interface (MIPI) display interface 1355. In at least one embodiment, storage may be provided by a flash memory subsystem 1360 including flash memory and a flash memory controller. In at least one embodiment, memory interface may be provided via a memory controller 1365 for access to SDRAM or SRAM memory devices. In at least one embodiment, some integrated circuits additionally include an embedded security engine 1370.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in integrated circuit 1300 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 14A:
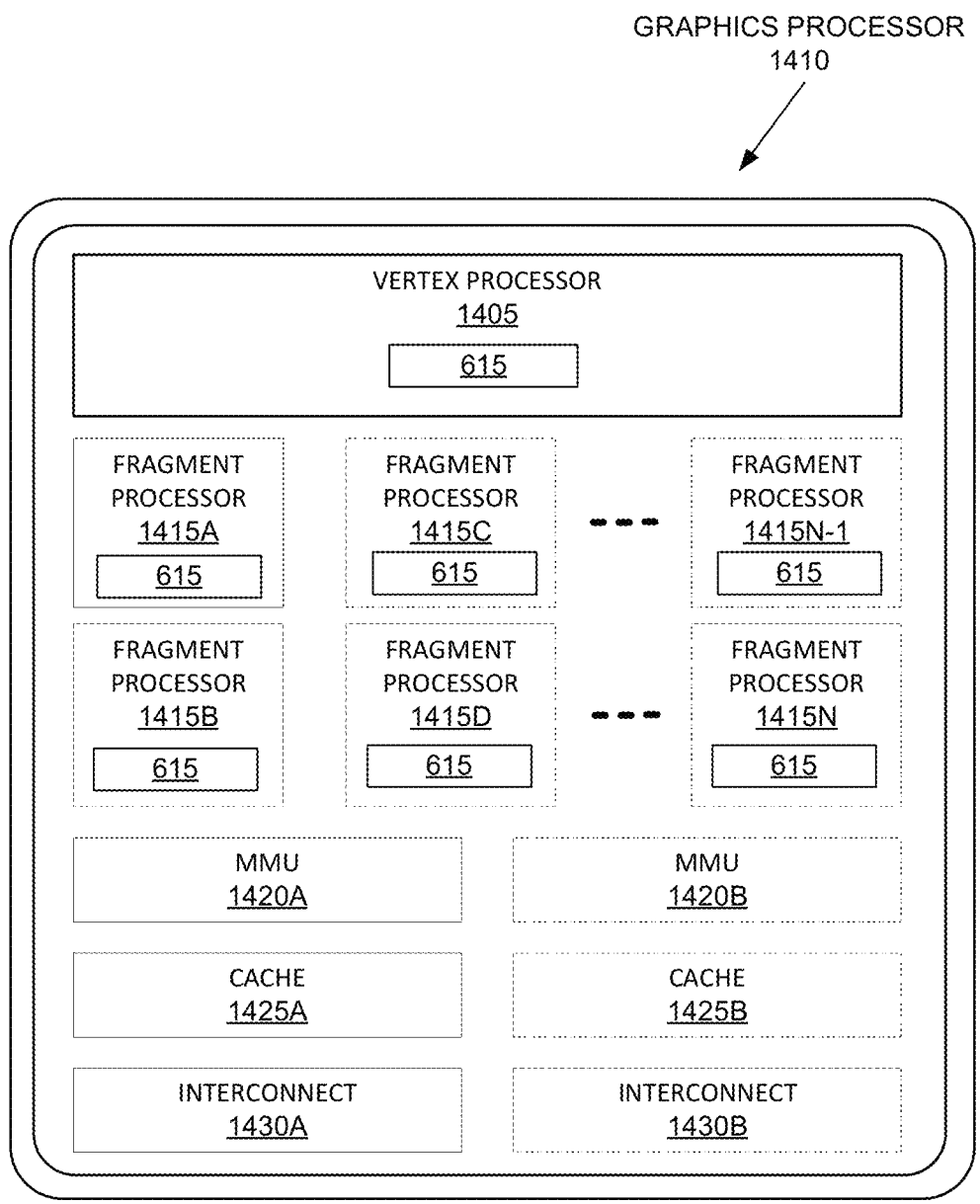
FIGS. 14A-14B illustrate exemplary integrated circuits and associated graphics processors, according to at least one embodiment.
Figure 14B:
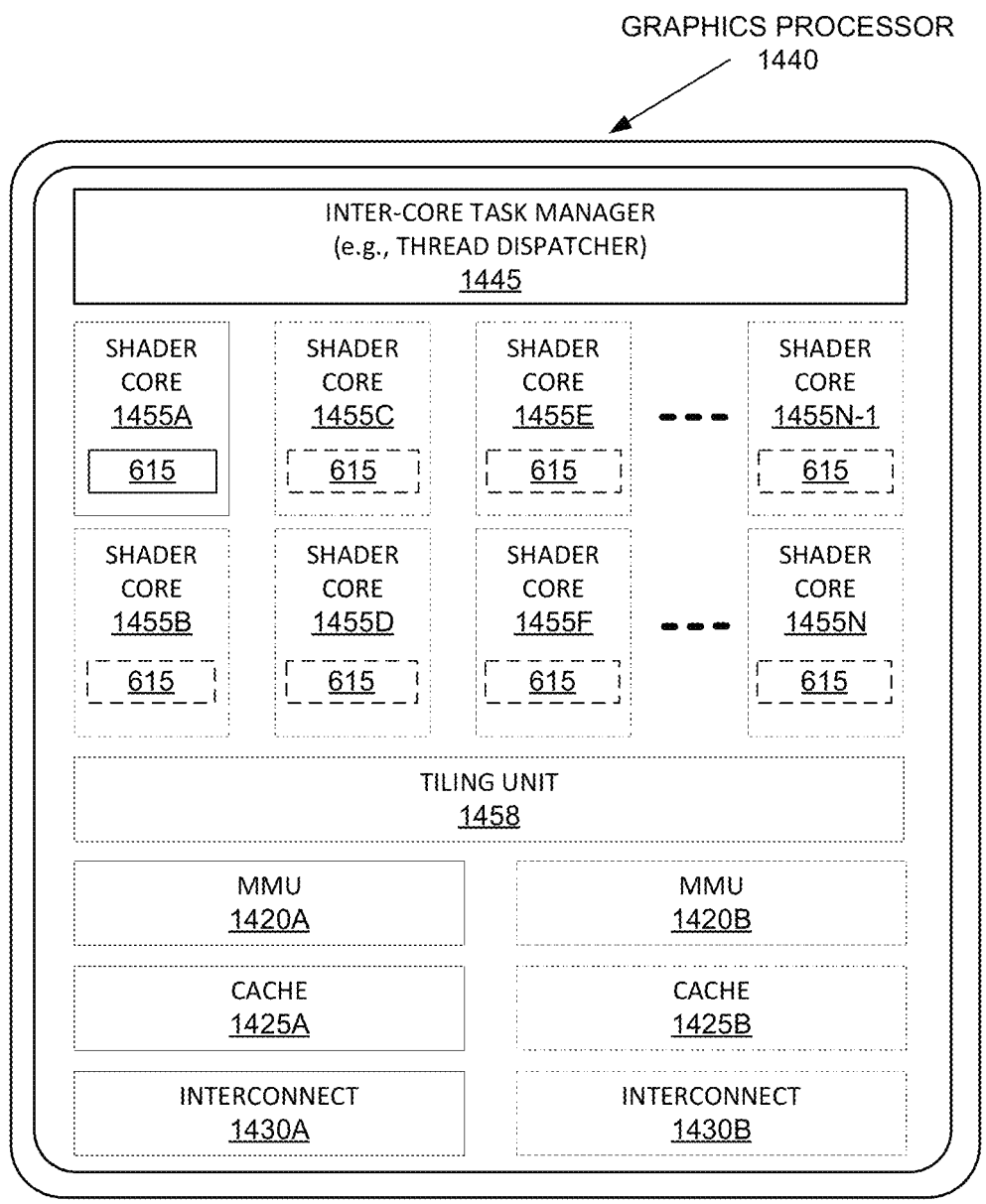

FIGS. 14A-14B illustrate exemplary integrated circuits and associated graphics processors that may be fabricated using one or more IP cores, according to various embodiments described herein. In addition to what is illustrated, other logic and circuits may be included in at least one embodiment, including additional graphics processors/cores, peripheral interface controllers, or general-purpose processor cores.

FIGS. 14A-14B are block diagrams illustrating exemplary graphics processors for use within an SoC, according to embodiments described herein. FIG. 14A illustrates an exemplary graphics processor 1410 of a system on a chip integrated circuit that may be fabricated using one or more IP cores, according to at least one embodiment. FIG. 14B illustrates an additional exemplary graphics processor 1440 of a system on a chip integrated circuit that may be fabricated using one or more IP cores, according to at least one embodiment. In at least one embodiment, graphics processor 1410 of FIG. 14A is a low power graphics processor core. In at least one embodiment, graphics processor 1440 of FIG. 14B is a higher performance graphics processor core. In at least one embodiment, each of graphics processors 1410, 1440 can be variants of graphics processor 1310 of FIG. 13.

In at least one embodiment, graphics processor 1410 includes a vertex processor 1405 and one or more fragment processor(s) 1415A-1415N (e.g., 1415A, 1415B, 1415C, 1415D, through 1415N-1, and 1415N). In at least one embodiment, graphics processor 1410 can execute different shader programs via separate logic, such that vertex processor 1405 is optimized to execute operations for vertex shader programs, while one or more fragment processor(s) 1415A-1415N execute fragment (e.g., pixel) shading operations for fragment or pixel shader programs. In at least one embodiment, vertex processor 1405 performs a vertex processing stage of a 3D graphics pipeline and generates primitives and vertex data. In at least one embodiment, fragment processor(s) 1415A-1415N use primitive and vertex data generated by vertex processor 1405 to produce a framebuffer that is displayed on a display device. In at least one embodiment, fragment processor(s) 1415A-1415N are optimized to execute fragment shader programs as provided for in an OpenGL API, which may be used to perform similar operations as a pixel shader program as provided for in a Direct 3D API In at least one embodiment, graphics processor 1410 additionally includes one or more memory management units (MMUs) 1420A-1420B, cache(s) 1425A-1425B, and circuit interconnect(s) 1430A-1430B. In at least one embodiment, one or more MMU(s) 1420A-1420B provide for virtual to physical address mapping for graphics processor 1410, including for vertex processor 1405 and/or fragment processor(s) 1415A-1415N, which may reference vertex or image/texture data stored in memory, in addition to vertex or image/texture data stored in one or more cache(s) 1425A-1425B. In at least one embodiment, one or more MMU(s) 1420A-1420B may be synchronized with other MMUs within system, including one or more MMUs associated with one or more application processor(s) 1305, image processors 1315, and/or video processors 1320 of FIG. 13, such that each processor 1305-1320 can participate in a shared or unified virtual memory system. In at least one embodiment, one or more circuit interconnect(s) 1430A-1430B enable graphics processor 1410 to interface with other IP cores within SoC, either via an internal bus of SoC or via a direct connection.

In at least one embodiment, graphics processor 1440 includes one or more MMU(s) 1420A-1420B, cache(s) 1425A-1425B, and circuit interconnect(s) 1430A-1430B of graphics processor 1410 of FIG. 14A. In at least one embodiment, graphics processor 1440 includes one or more shader core(s) 1455A-1455N (e.g., 1455A, 1455B, 1455C, 1455D, 1455E, 1455F, through 1455N-1, and 1455N), which provides for a unified shader core architecture in which a single core or type or core can execute all types of programmable shader code, including shader program code to implement vertex shaders, fragment shaders, and/or compute shaders. In at least one embodiment, a number of shader cores can vary. In at least one embodiment, graphics processor 1440 includes an inter-core task manager 1445, which acts as a thread dispatcher to dispatch execution threads to one or more shader cores 1455A-1455N and a tiling unit 1458 to accelerate tiling operations for tile-based rendering, in which rendering operations for a scene are subdivided in image space, for example to exploit local spatial coherence within a scene or to optimize use of internal caches.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in integrated circuit 14A and/or 14B for inferencing or predicting operations based, at least in part, on weight parameters calculated using neural network training operations, neural network functions and/or architectures, or neural network use cases described herein. Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 15A:
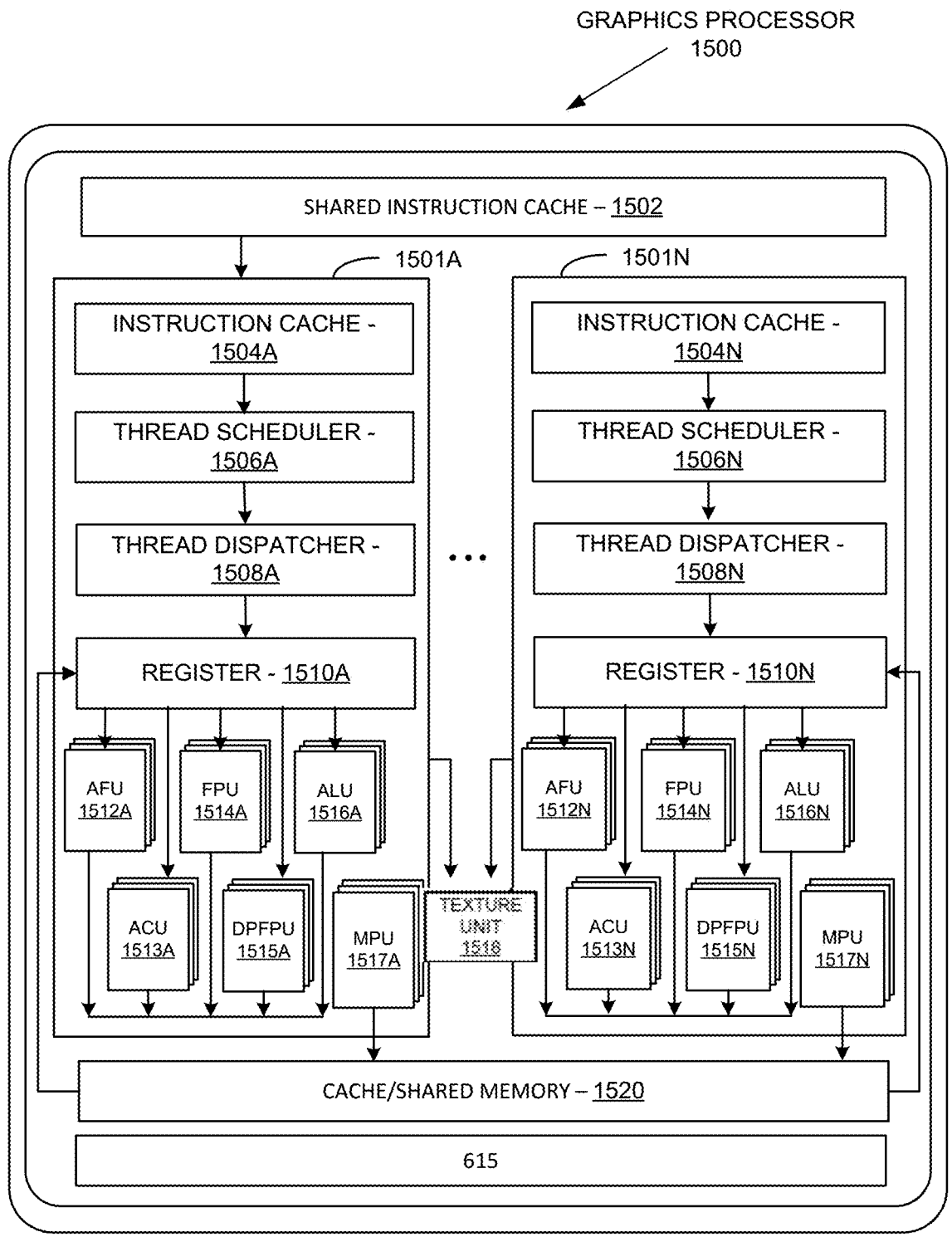
FIGS. 15A-15B illustrate additional exemplary graphics processor logic, according to at least one embodiment.
Figure 15B:
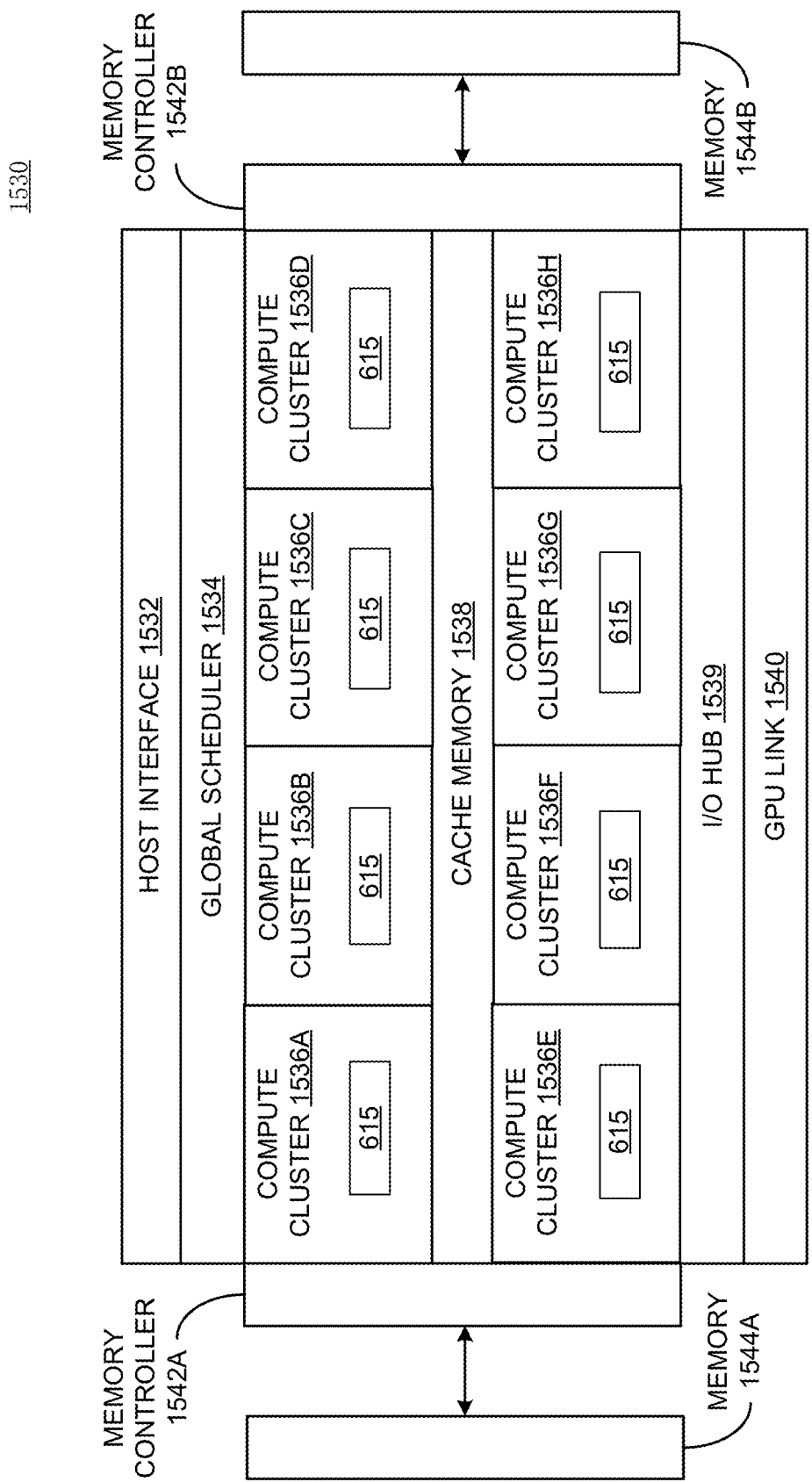

FIGS. 15A-15B illustrate additional exemplary graphics processor logic according to embodiments described herein. FIG. 15A illustrates a graphics core 1500 that may be included within graphics processor 1310 of FIG. 13, in at least one embodiment, and may be a unified shader core 1455A-1455N as in FIG. 14B in at least one embodiment. FIG. 15B illustrates a highly-parallel general-purpose graphics processing unit 1530 suitable for deployment on a multi-chip module in at least one embodiment.

In at least one embodiment, graphics core 1500 includes a shared instruction cache 1502, a texture unit 1518, and a cache/shared memory 1520 that are common to execution resources within graphics core 1500. In at least one embodiment, graphics core 1500 can include multiple slices 1501A-1501N or partition for each core, and a graphics processor can include multiple instances of graphics core 1500. Slices 1501A-1501N can include support logic including a local instruction cache 1504A-1504N, a thread scheduler 1506A-1506N, a thread dispatcher 1508A-1508N, and a set of registers 1510A-1510N. In at least one embodiment, slices 1501A-1501N can include a set of additional function units (AFUs 1512A-1512N), floating-point units (FPU 1514A-1514N), integer arithmetic logic units (ALUs 1516-1516N), address computational units (ACU 1513A-1513N), double-precision floating-point units (DPFPU 1515A-1515N), and matrix processing units (MPU 1517A-1517N).

In at least one embodiment, FPUs 1514A-1514N can perform single-precision (32-bit) and half-precision (16-bit) floating point operations, while DPFPUs 1515A-1515N perform double precision (64-bit) floating point operations. In at least one embodiment, ALUs 1516A-1516N can perform variable precision integer operations at 8-bit, 16-bit, and 32-bit precision, and can be configured for mixed precision operations. In at least one embodiment, MPUs 1517A-1517N can also be configured for mixed precision matrix operations, including half-precision floating point and 8-bit integer operations. In at least one embodiment, MPUs 1517A-1517N can perform a variety of matrix operations to accelerate machine learning application frameworks, including enabling support for accelerated general matrix to matrix multiplication (GEMM). In at least one embodiment, AFUs 1512A-1512N can perform additional logic operations not supported by floating-point or integer units, including trigonometric operations (e.g., Sine, Cosine, etc.).

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in graphics core 1500 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

FIG. 15B illustrates a general-purpose processing unit (GPGPU) 1530 that can be configured to enable highly-parallel compute operations to be performed by an array of graphics processing units, in at least one embodiment. In at least one embodiment, GPGPU 1530 can be linked directly to other instances of GPGPU 1530 to create a multi-GPU cluster to improve training speed for deep neural networks. In at least one embodiment, GPGPU 1530 includes a host interface 1532 to enable a connection with a host processor. In at least one embodiment, host interface 1532 is a PCI Express interface. In at least one embodiment, host interjace 1532 can be a vendor specific communications interface or communications fabric. In at least one embodiment, GPGPU 1530 receives commands from a host processor and uses a global scheduler 1534 to distribute execution threads associated with those commands to a set of compute clusters 1536A-1536H. In at least one embodiment, compute clusters 1536A-1536H share a cache memory 1538. In at least one embodiment, cache memory 1538 can serve as a higher-level cache for cache memories within compute clusters 1536A-1536H.

In at least one embodiment, GPGPU 1530 includes memory 1544A-1544B coupled with compute clusters 1536A-1536H via a set of memory controllers 1542A-1542B. In at least one embodiment, memory 1544A-1544B can include various types of memory devices including dynamic random access memory (DRAM) or graphics random access memory, such as synchronous graphics random access memory (SGRAM), including graphics double data rate (GDDR) memory.

In at least one embodiment, compute clusters 1536A-1536H each include a set of graphics cores, such as graphics core 1500 of FIG. 15A, which can include multiple types of integer and floating point logic units that can perform computational operations at a range of precisions including suited for machine learning computations. For example, in at least one embodiment, at least a subset of floating point units in each of compute clusters 1536A-1536H can be configured to perform 16-bit or 32-bit floating point operations, while a different subset of floating point units can be configured to perform 64-bit floating point operations.

In at least one embodiment, multiple instances of GPGPU 1530 can be configured to operate as a compute cluster. In at least one embodiment, communication used by compute clusters 1536A-1536H for synchronization and data exchange varies across embodiments. In at least one embodiment, multiple instances of GPGPU 1530 communicate over host interface 1532. In at least one embodiment, GPGPU 1530 includes an I/O hub 1539 that couples GPGPU 1530 with a GPU link 1540 that enables a direct connection to other instances of GPGPU 1530. In at least one embodiment, GPU link 1540 is coupled to a dedicated GPU-to-GPU bridge that enables communication and synchronization between multiple instances of GPGPU 1530. In at least one embodiment, GPU link 1540 couples with a high speed interconnect to transmit and receive data to other GPGPUs or parallel processors. In at least one embodiment, multiple instances of GPGPU 1530 are located in separate data processing systems and communicate via a network device that is accessible via host interface 1532. In at least one embodiment GPU, link 1540 can be configured to enable a connection to a host processor in addition to or as an alternative to host interface 1532.

In at least one embodiment, GPGPU 1530 can be configured to train neural networks. In at least one embodiment, GPGPU 1530 can be used within a inferencing platform. In at least one embodiment, in which GPGPU 1530 is used for inferencing, GPGPU may include fewer compute clusters 1536A-1536H relative to when GPGPU is used for training a neural network. In at least one embodiment, memory technology associated with memory 1544A-1544B may differ between inferencing and training configurations, with higher bandwidth memory technologies devoted to training configurations. In at least one embodiment, inferencing configuration of GPGPU 1530 can support inferencing specific instructions. For example, in at least one embodiment, an inferencing configuration can provide support for one or more 8-bit integer dot product instructions, which may be used during inferencing operations for deployed neural networks.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in GPGPU 1530 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 16:
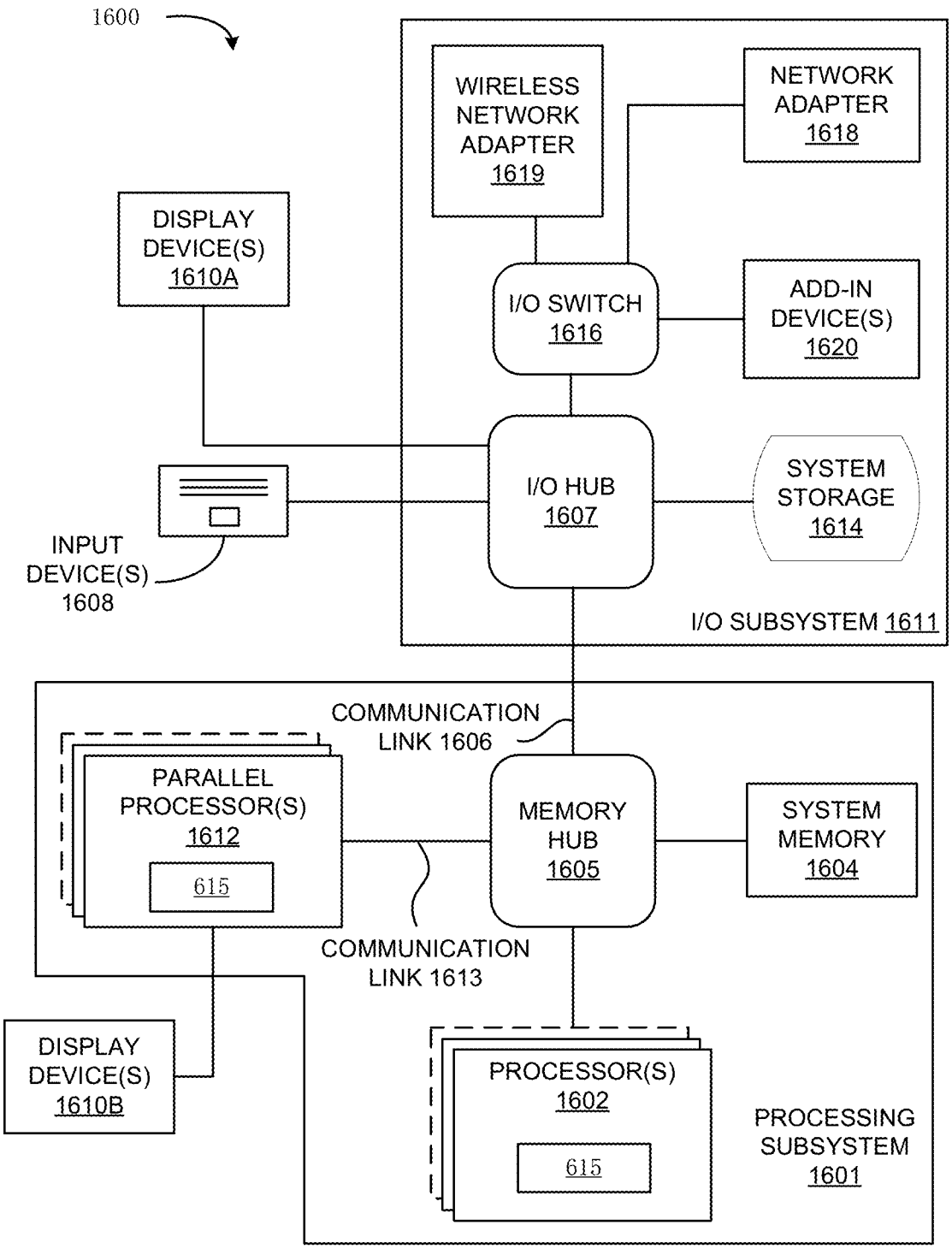
FIG. 16 illustrates a computer system, according to at least one embodiment.

FIG. 16 is a block diagram illustrating a computing system 1600 according to at least one embodiment. In at least one embodiment, computing system 1600 includes a processing subsystem 1601 having one or more processor(s) 1602 and a system memory 1604 communicating via an interconnection path that may include a memory hub 1605. In at least one embodiment, memory hub 1605 may be a separate component within a chipset component or may be integrated within one or more processor(s) 1602. In at least one embodiment, memory hub 1605 couples with an I/O subsystem 1611 via a communication link 1606. In at least one embodiment, I/O subsystem 1611 includes an I/O hub 1607 that can enable computing system 1600 to receive input from one or more input device(s) 1608. In at least one embodiment, I/O hub 1607 can enable a display controller, which may be included in one or more processor(s) 1602, to provide outputs to one or more display device(s) 1610A. In at least one embodiment, one or more display device(s) 1610A coupled with I/O hub 1607 can include a local, internal, or embedded display device.

In at least one embodiment, processing subsystem 1601 includes one or more parallel processor(s) 1612 coupled to memory hub 1605 via a bus or other communication link 1613. In at least one embodiment, communication link 1613 may be one of any number of standards based communication link technologies or protocols, such as, but not limited to PCI Express, or may be a vendor specific communications interface or communications fabric. In at least one embodiment, one or more parallel processor(s) 1612 form a computationally focused parallel or vector processing system that can include a large number of processing cores and/or processing clusters, such as a many integrated core (MIC) processor. In at least one embodiment, one or more parallel processor(s) 1612 form a graphics processing subsystem that can output pixels to one of one or more display device(s) 1610A coupled via I/O Hub 1607. In at least one embodiment, one or more parallel processor(s) 1612 can also include a display controller and display interface (not shown) to enable a direct connection to one or more display device(s) 1610B.

In at least one embodiment, a system storage unit 1614 can connect to I/O hub 1607 to provide a storage mechanism for computing system 1600. In at least one embodiment, an I/O switch 1616 can be used to provide an interface mechanism to enable connections between I/O hub 1607 and other components, such as a network adapter 1618 and/or wireless network adapter 1619 that may be integrated into a platform(s), and various other devices that can be added via one or more add-in device(s) 1620. In at least one embodiment, network adapter 1618 can be an Ethernet adapter or another wired network adapter. In at least one embodiment, wireless network adapter 1619 can include one or more of a Wi-Fi, Bluetooth, near field communication (NFC), or other network device that includes one or more wireless radios.

In at least one embodiment, computing system 1600 can include other components not explicitly shown, including USB or other port connections, optical storage drives, video capture devices, and like, may also be connected to I/O hub 1607. In at least one embodiment, communication paths interconnecting various components in FIG. 16 may be implemented using any suitable protocols, such as PCI (Peripheral Component Interconnect) based protocols (e.g., PCI-Express), or other bus or point-to-point communication interfaces and/or protocol(s), such as NV-Link high-speed interconnect, or interconnect protocols.

In at least one embodiment, one or more parallel processor(s) 1612 incorporate circuitry optimized for graphics and video processing, including, for example, video output circuitry, and constitutes a graphics processing unit (GPU). In at least one embodiment, one or more parallel processor(s) 1612 incorporate circuitry optimized for general purpose processing. In at least one embodiment, components of computing system 1600 may be integrated with one or more other system elements on a single integrated circuit. For example, in at least one embodiment, one or more parallel processor(s) 1612, memory hub 1605, processor(s) 1602, and I/O hub 1607 can be integrated into a system on chip (SoC) integrated circuit. In at least one embodiment, components of computing system 1600 can be integrated into a single package to form a system in package (SIP) configuration. In at least one embodiment, at least a portion of components of computing system 1600 can be integrated into a multi-chip module (MCM), which can be interconnected with other multi-chip modules into a modular computing system.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in system FIG. 1600 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Processors

Figure 17A:
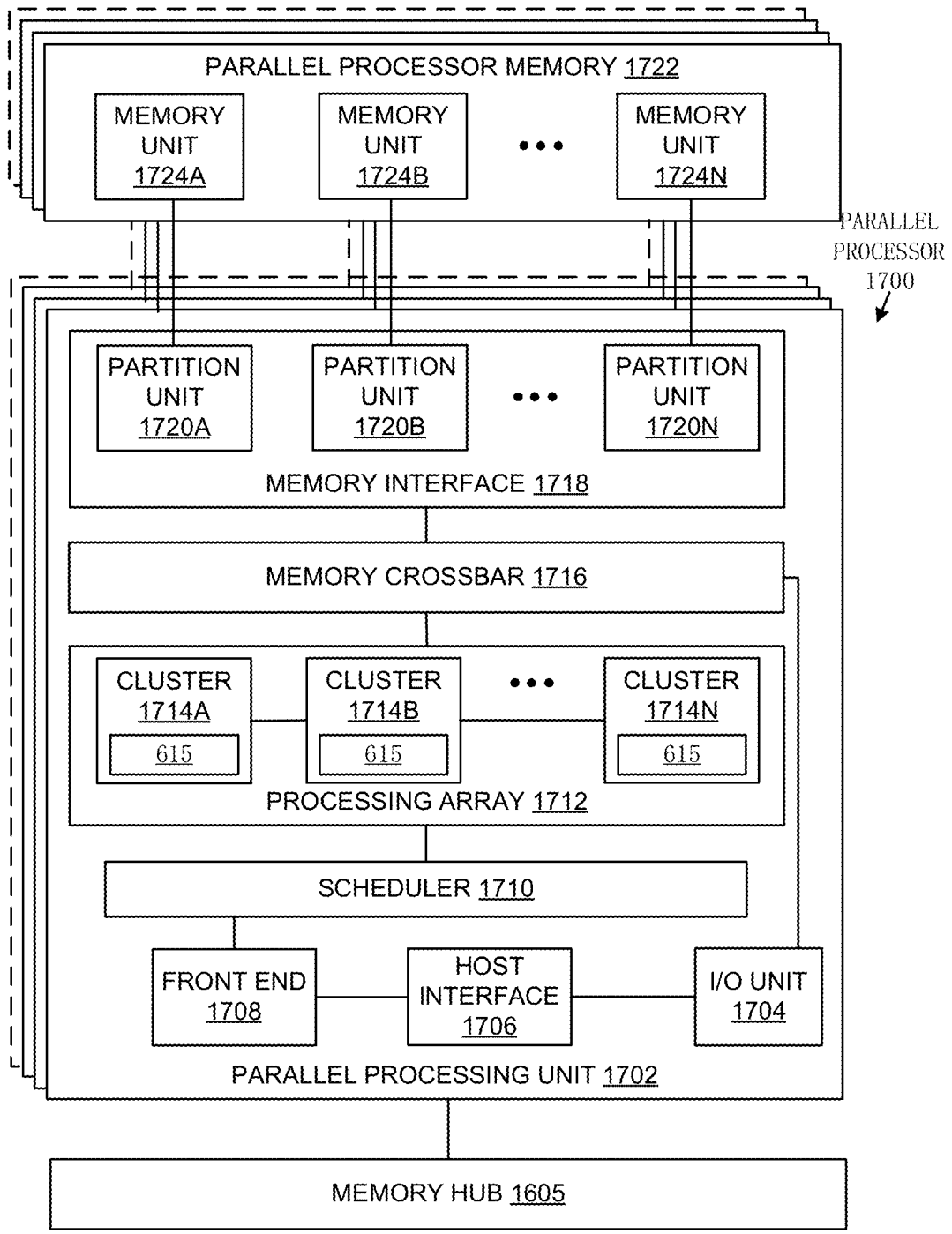
FIG. 17A illustrates a parallel processor, according to at least one embodiment.

FIG. 17A illustrates a parallel processor 1700 according to at least one embodiment. In at least one embodiment, various components of parallel processor 1700 may be implemented using one or more integrated circuit devices, such as programmable processors, application specific integrated circuits (ASICs), or field programmable gate arrays (FPGA). In at least one embodiment, illustrated parallel processor 1700 is a variant of one or more parallel processor(s) 1612 shown in FIG. 16 according to an exemplary embodiment.

In at least one embodiment, parallel processor 1700 includes a parallel processing unit 1702. In at least one embodiment, parallel processing unit 1702 includes an I/O unit 1704 that enables communication with other devices, including other instances of parallel processing unit 1702. In at least one embodiment, I/O unit 1704 may be directly connected to other devices. In at least one embodiment, I/O unit 1704 connects with other devices via use of a hub or switch interface, such as memory hub 1605. In at least one embodiment, connections between memory hub 1605 and I/O unit 1704 form a communication link 1613. In at least one embodiment, I/O unit 1704 connects with a host interface 1706 and a memory crossbar 1716, where host interface 1706 receives commands directed to performing processing operations and memory crossbar 1716 receives commands directed to performing memory operations.

In at least one embodiment, when host interface 1706 receives a command buffer via I/O unit 1704, host interface 1706 can direct work operations to perform those commands to a front end 1708. In at least one embodiment, front end 1708 couples with a scheduler 1710, which is configured to distribute commands or other work items to a processing cluster array 1712. In at least one embodiment, scheduler 1710 ensures that processing cluster array 1712 is properly configured and in a valid state before tasks are distributed to processing cluster array 1712. In at least one embodiment, scheduler 1710 is implemented via firmware logic executing on a microcontroller. In at least one embodiment, microcontroller implemented scheduler 1710 is configurable to perform complex scheduling and work distribution operations at coarse and fine granularity, enabling rapid preemption and context switching of threads executing on processing array 1712. In at least one embodiment, host software can prove workloads for scheduling on processing array 1712 via one of multiple graphics processing doorbells. In at least one embodiment, workloads can then be automatically distributed across processing array 1712 by scheduler 1710 logic within a microcontroller including scheduler 1710.

In at least one embodiment, processing cluster array 1712 can include up to "N" processing clusters (e.g., cluster 1714A, cluster 1714B, through cluster 1714N). In at least one embodiment, each cluster 1714A-1714N of processing cluster array 1712 can execute a large number of concurrent threads. In at least one embodiment, scheduler 1710 can allocate work to clusters 1714A-1714N of processing cluster array 1712 using various scheduling and/or work distribution algorithms, which may vary depending on workload arising for each type of program or computation. In at least one embodiment, scheduling can be handled dynamically by scheduler 1710, or can be assisted in part by compiler logic during compilation of program logic configured for execution by processing cluster array 1712. In at least one embodiment, different clusters 1714A-1714N of processing cluster array 1712 can be allocated for processing different types of programs or for performing different types of computations.

In at least one embodiment, processing cluster array 1712 can be configured to perform various types of parallel processing operations. In at least one embodiment, processing cluster array 1712 is configured to perform general-purpose parallel compute operations. For example, in at least one embodiment, processing cluster array 1712 can include logic to execute processing tasks including filtering of video and/or audio data, performing modeling operations, including physics operations, and performing data transformations.

In at least one embodiment, processing cluster array 1712 is configured to perform parallel graphics processing operations. In at least one embodiment, processing cluster array 1712 can include additional logic to support execution of such graphics processing operations, including, but not limited to texture sampling logic to perform texture operations, as well as tessellation logic and other vertex processing logic. In at least one embodiment, processing cluster array 1712 can be configured to execute graphics processing related shader programs such as, but not limited to vertex shaders, tessellation shaders, geometry shaders, and pixel shaders. In at least one embodiment, parallel processing unit 1702 can transfer data from system memory via I/O unit 1704 for processing. In at least one embodiment, during processing, transferred data can be stored to on-chip memory (e.g., parallel processor memory 1722) during processing, then written back to system memory.

In at least one embodiment, when parallel processing unit 1702 is used to perform graphics processing, scheduler 1710 can be configured to divide a processing workload into approximately equal sized tasks, to better enable distribution of graphics processing operations to multiple clusters 1714A-1714N of processing cluster array 1712. In at least one embodiment, portions of processing cluster array 1712 can be configured to perform different types of processing. For example, in at least one embodiment, a first portion may be configured to perform vertex shading and topology generation, a second portion may be configured to perform tessellation and geometry shading, and a third portion may be configured to perform pixel shading or other screen space operations, to produce a rendered image for display. In at least one embodiment, intermediate data produced by one or more of clusters 1714A-1714N may be stored in buffers to allow intermediate data to be transmitted between clusters 1714A-1714N for further processing.

In at least one embodiment, processing cluster array 1712 can receive processing tasks to be executed via scheduler 1710, which receives commands defining processing tasks from front end 1708. In at least one embodiment, processing tasks can include indices of data to be processed, e.g., surface (patch) data, primitive data, vertex data, and/or pixel data, as well as state parameters and commands defining how data is to be processed (e.g., what program is to be executed). In at least one embodiment, scheduler 1710 may be configured to fetch indices corresponding to tasks or may receive indices from front end 1708. In at least one embodiment, front end 1708 can be configured to ensure processing cluster array 1712 is configured to a valid state before a workload specified by incoming command buffers (e.g., batch-buffers, push buffers, etc.) is initiated.

In at least one embodiment, each of one or more instances of parallel processing unit 1702 can couple with parallel processor memory 1722. In at least one embodiment, parallel processor memory 1722 can be accessed via memory crossbar 1716, which can receive memory requests from processing cluster array 1712 as well as I/O unit 1704. In at least one embodiment, memory crossbar 1716 can access parallel processor memory 1722 via a memory interface 1718. In at least one embodiment, memory interface 1718 can include multiple partition units (e.g., partition unit 1720A, partition unit 1720B, through partition unit 1720N) that can each couple to a portion (e.g., memory unit) of parallel processor memory 1722. In at least one embodiment, a number of partition units 1720A-1720N is configured to be equal to a number of memory units, such that a first partition unit 1720A has a corresponding first memory unit 1724A, a second partition unit 1720B has a corresponding memory unit 1724B, and a Nth partition unit 1720N has a corresponding Nth memory unit 1724N. In at least one embodiment, a number of partition units 1720A-1720N may not be equal to a number of memory devices.

In at least one embodiment, memory units 1724A-1724N can include various types of memory devices, including dynamic random access memory (DRAM) or graphics random access memory, such as synchronous graphics random access memory (SGRAM), including graphics double data rate (GDDR) memory. In at least one embodiment, memory units 1724A-1724N may also include 3D stacked memory, including but not limited to high bandwidth memory (HBM). In at least one embodiment, render targets, such as frame buffers or texture maps may be stored across memory units 1724A-1724N, allowing partition units 1720A-1720N to write portions of each render target in parallel to efficiently use available bandwidth of parallel processor memory 1722. In at least one embodiment, a local instance of parallel processor memory 1722 may be excluded in favor of a unified memory design that utilizes system memory in conjunction with local cache memory.

In at least one embodiment, any one of clusters 1714A-1714N of processing cluster array 1712 can process data that will be written to any of memory units 1724A-1724N within parallel processor memory 1722. In at least one embodiment, memory crossbar 1716 can be configured to transfer an output of each cluster 1714A-1714N to any partition unit 1720A-1720N or to another cluster 1714A-1714N, which can perform additional processing operations on an output. In at least one embodiment, each cluster 1714A-1714N can communicate with memory interface 1718 through memory crossbar 1716 to read from or write to various external memory devices. In at least one embodiment, memory crossbar 1716 has a connection to memory interface 1718 to communicate with I/O unit 1704, as well as a connection to a local instance of parallel processor memory 1722, enabling processing units within different processing clusters 1714A-1714N to communicate with system memory or other memory that is not local to parallel processing unit 1702. In at least one embodiment, memory crossbar 1716 can use virtual channels to separate traffic streams between clusters 1714A-1714N and partition units 1720A-1720N.

In at least one embodiment, multiple instances of parallel processing unit 1702 can be provided on a single add-in card, or multiple add-in cards can be interconnected. In at least one embodiment, different instances of parallel processing unit 1702 can be configured to inter-operate even if different instances have different numbers of processing cores, different amounts of local parallel processor memory, and/or other configuration differences. For example, in at least one embodiment, some instances of parallel processing unit 1702 can include higher precision floating point units relative to other instances. In at least one embodiment, systems incorporating one or more instances of parallel processing unit 1702 or parallel processor 1700 can be implemented in a variety of configurations and form factors, including but not limited to desktop, laptop, or handheld personal computers, servers, workstations, game consoles, and/or embedded systems.

Figure 17B:
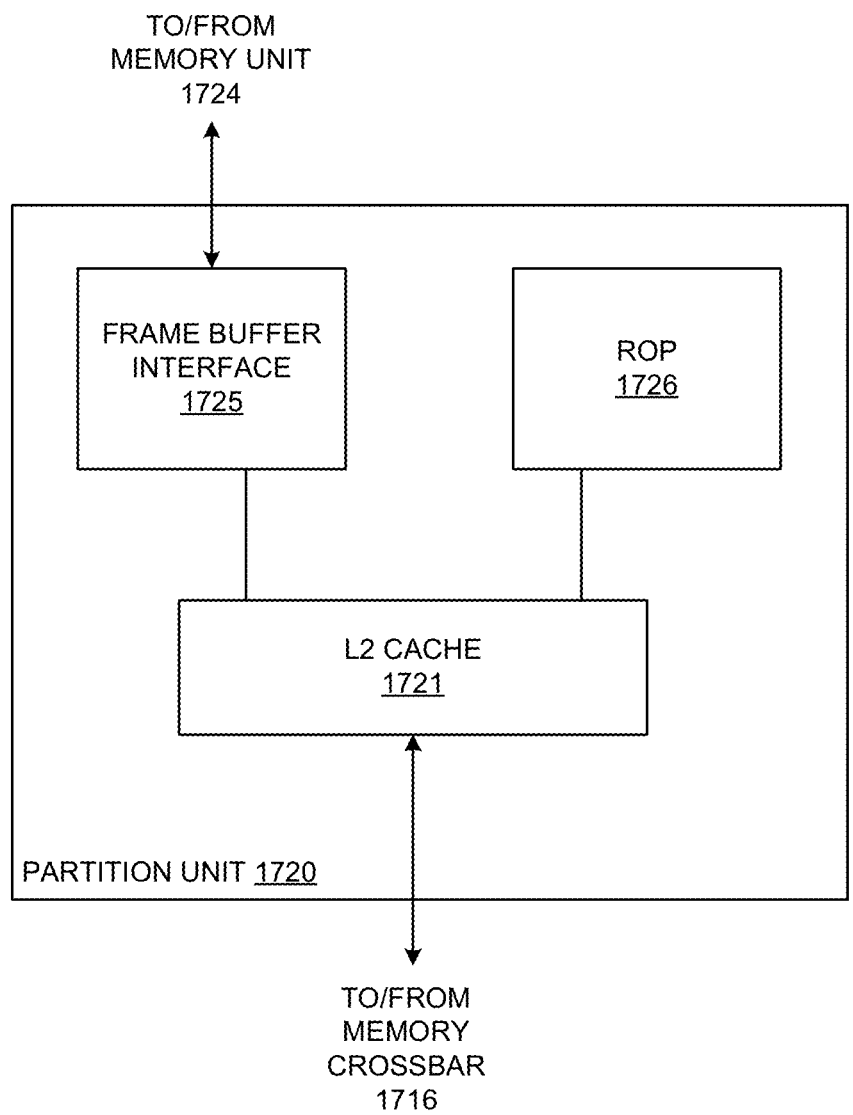
FIG. 17B illustrates a partition unit, according to at least one embodiment.

FIG. 17B is a block diagram of a partition unit 1720 according to at least one embodiment. In at least one embodiment, partition unit 1720 is an instance of one of partition units 1720A-1720N of FIG. 17A. In at least one embodiment, partition unit 1720 includes an L2 cache 1721, a frame buffer interface 1725, and a raster operations unit ("ROP") 1726. L2 cache 1721 is a read/write cache that is configured to perform load and store operations received from memory crossbar 1716 and ROP 1726. In at least one embodiment, read misses and urgent write-back requests are output by L2 cache 1721 to frame buffer interface 1725 for processing. In at least one embodiment, updates can also be sent to a frame buffer via frame buffer interface 1725 for processing. In at least one embodiment, frame buffer interface 1725 interfaces with one of memory units in parallel processor memory, such as memory units 1724A-1724N of FIG. 17 (e.g., within parallel processor memory 1722).

In at least one embodiment, ROP 1726 is a processing unit that performs raster operations such as stencil, z test, blending, and so forth. In at least one embodiment, ROP 1726 then outputs processed graphics data that is stored in graphics memory. In at least one embodiment, ROP 1726 includes compression logic to compress depth or color data that is written to memory and decompress depth or color data that is read from memory. In at least one embodiment, compression logic can be lossless compression logic that makes use of one or more of multiple compression algorithms. Compression logic that is performed by ROP 1726 can vary based on statistical characteristics of data to be compressed. For example, in at least one embodiment, delta color compression is performed on depth and color data on a per-tile basis.

In at least one embodiment, ROP 1726 is included within each processing cluster (e.g., cluster 1714A-1714N of FIG. 17A) instead of within partition unit 1720. In at least one embodiment, read and write requests for pixel data are transmitted over memory crossbar 1716 instead of pixel fragment data. In at least one embodiment, processed graphics data may be displayed on a display device, such as one of one or more display device(s) 1610 of FIG. 16, routed for further processing by processor(s) 1602, or routed for further processing by one of processing entities within parallel processor 1700 of FIG. 17A.

Figure 17C:
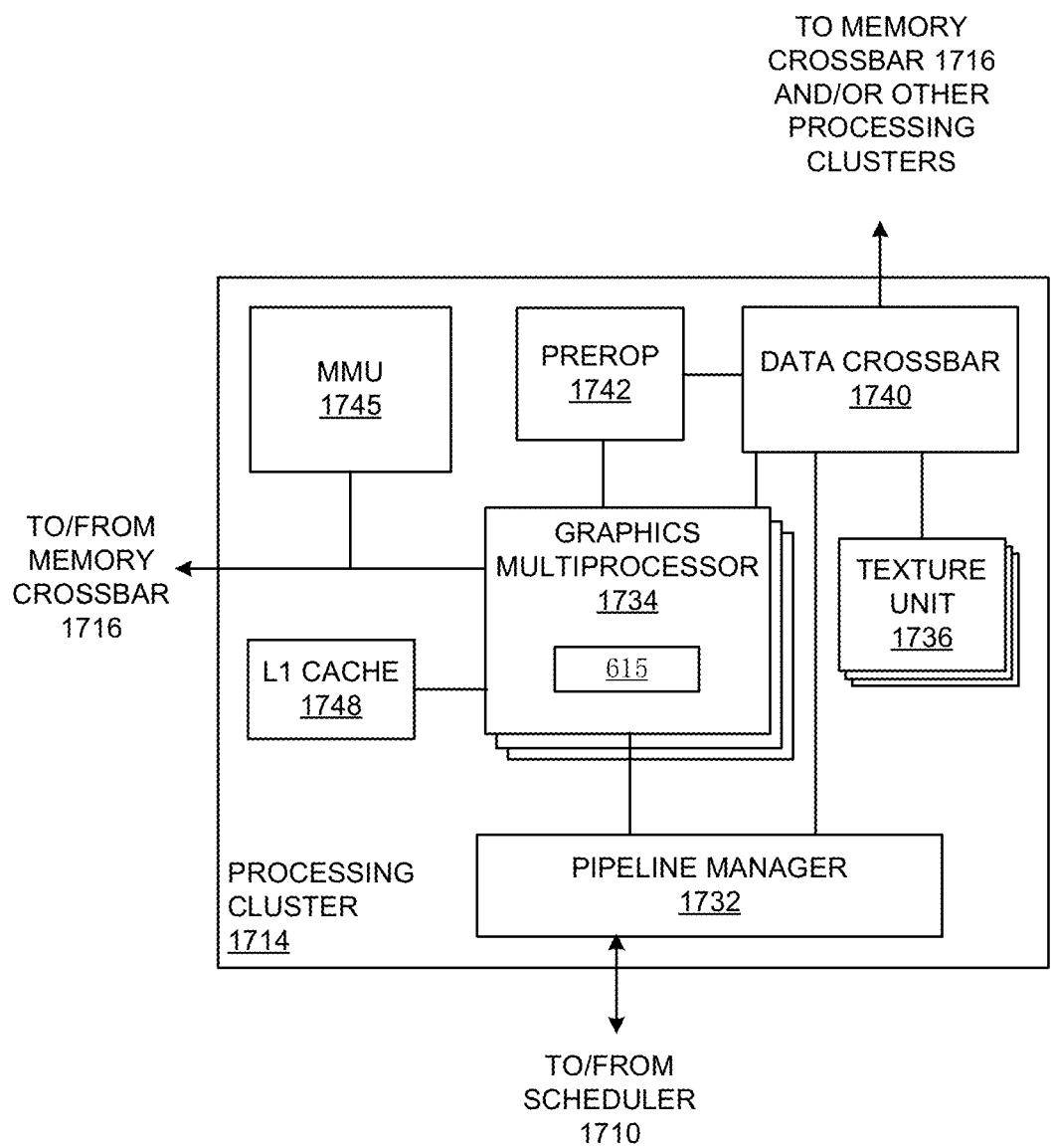
FIG. 17C illustrates a processing cluster, according to at least one embodiment.

FIG. 17C is a block diagram of a processing cluster 1714 within a parallel processing unit according to at least one embodiment. In at least one embodiment, a processing cluster is an instance of one of processing clusters 1714A-1714N of FIG. 17A. In at least one embodiment, one of more of processing cluster(s) 1714 can be configured to execute many threads in parallel, where "thread" refers to an instance of a particular program executing on a particular set of input data. In at least one embodiment, single-instruction, multiple-data (SIMD) instruction issue techniques are used to support parallel execution of a large number of threads without providing multiple independent instruction units. In at least one embodiment, single-instruction, multiple-thread (SIMT) techniques are used to support parallel execution of a large number of generally synchronized threads, using a common instruction unit configured to issue instructions to a set of processing engines within each one of processing clusters.

In at least one embodiment, operation of processing cluster 1714 can be controlled via a pipeline manager 1732 that distributes processing tasks to SIMT parallel processors. In at least one embodiment, pipeline manager 1732 receives instructions from scheduler 1710 of FIG. 17A and manages execution of those instructions via a graphics multiprocessor 1734 and/or a texture unit 1736. In at least one embodiment, graphics multiprocessor 1734 is an exemplary instance of a SIMT parallel processor. However, in at least one embodiment, various types of SIMT parallel processors of differing architectures may be included within processing cluster 1714. In at least one embodiment, one or more instances of graphics multiprocessor 1734 can be included within a processing cluster 1714. In at least one embodiment, graphics multiprocessor 1734 can process data and a data crossbar 1740 can be used to distribute processed data to one of multiple possible destinations, including other shader units. In at least one embodiment, pipeline manager 1732 can facilitate distribution of processed data by specifying destinations for processed data to be distributed vis data crossbar 1740.

In at least one embodiment, each graphics multiprocessor 1734 within processing cluster 1714 can include an identical set of functional execution logic (e.g., arithmetic logic units, load-store units, etc.). In at least one embodiment, functional execution logic can be configured in a pipelined manner in which new instructions can be issued before previous instructions are complete. In at least one embodiment, functional execution logic supports a variety of operations including integer and floating point arithmetic, comparison operations, Boolean operations, bit-shifting, and computation of various algebraic functions. In at least one embodiment, same functional-unit hardware can be leveraged to perform different operations and any combination of functional units may be present.

In at least one embodiment, instructions transmitted to processing cluster 1714 constitute a thread. In at least one embodiment, a set of threads executing across a set of parallel processing engines is a thread group. In at least one embodiment, thread group executes a program on different input data. In at least one embodiment, each thread within a thread group can be assigned to a different processing engine within a graphics multiprocessor 1734. In at least one embodiment, a thread group may include fewer threads than a number of processing engines within graphics multiprocessor 1734. In at least one embodiment, when a thread group includes fewer threads than a number of processing engines, one or more processing engines may be idle during cycles in which that thread group is being processed. In at least one embodiment, a thread group may also include more threads than a number of processing engines within graphics multiprocessor 1734. In at least one embodiment, when a thread group includes more threads than processing engines within graphics multiprocessor 1734, processing can be performed over consecutive clock cycles. In at least one embodiment, multiple thread groups can be executed concurrently on a graphics multiprocessor 1734.

In at least one embodiment, graphics multiprocessor 1734 includes an internal cache memory to perform load and store operations. In at least one embodiment, graphics multiprocessor 1734 can forego an internal cache and use a cache memory (e.g., L1 cache 1748) within processing cluster 1714. In at least one embodiment, each graphics multiprocessor 1734 also has access to L2 caches within partition units (e.g., partition units 1720A-1720N of FIG. 17A) that are shared among all processing clusters 1714 and may be used to transfer data between threads. In at least one embodiment, graphics multiprocessor 1734 may also access off-chip global memory, which can include one or more of local parallel processor memory and/or system memory. In at least one embodiment, any memory external to parallel processing unit 1702 may be used as global memory. In at least one embodiment, processing cluster 1714 includes multiple instances of graphics multiprocessor 1734 can share common instructions and data, which may be stored in L1 cache 1748.

In at least one embodiment, each processing cluster 1714 may include a memory management unit ("MMU") 1745 that is configured to map virtual addresses into physical addresses. In at least one embodiment, one or more instances of MMU 1745 may reside within memory interface 1718 of FIG. 17A. In at least one embodiment, MMU 1745 includes a set of page table entries (PTEs) used to map a virtual address to a physical address of a tile and optionally a cache line index. In at least one embodiment, MMU 1745 may include address translation lookaside buffers (TLB) or caches that may reside within graphics multiprocessor 1734 or L1 cache or processing cluster 1714. In at least one embodiment, physical address is processed to distribute surface data access locality to allow efficient request interleaving among partition units. In at least one embodiment, cache line index may be used to determine whether a request for a cache line is a hit or miss.

In at least one embodiment, a processing cluster 1714 may be configured such that each graphics multiprocessor 1734 is coupled to a texture unit 1736 for performing texture mapping operations, e.g., determining texture sample positions, reading texture data, and filtering texture data. In at least one embodiment, texture data is read from an internal texture L1 cache (not shown) or from an L1 cache within graphics multiprocessor 1734 and is fetched from an L2 cache, local parallel processor memory, or system memory, as needed. In at least one embodiment, each graphics multiprocessor 1734 outputs processed tasks to data crossbar 1740 to provide processed task(s) to another processing cluster 1714 for further processing or to store processed task(s) in an L2 cache, local parallel processor memory, or system memory via memory crossbar 1716. In at least one embodiment, preROP 1742 (pre-raster operations unit) is configured to receive data from graphics multiprocessor 1734, direct data to ROP units, which may be located with partition units as described herein (e.g., partition units 1720A-1720N of FIG. 17A). In at least one embodiment, PreROP 1742 unit can perform optimizations for color blending, organize pixel color data, and perform address translations.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in graphics processing cluster 1714 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 17D:
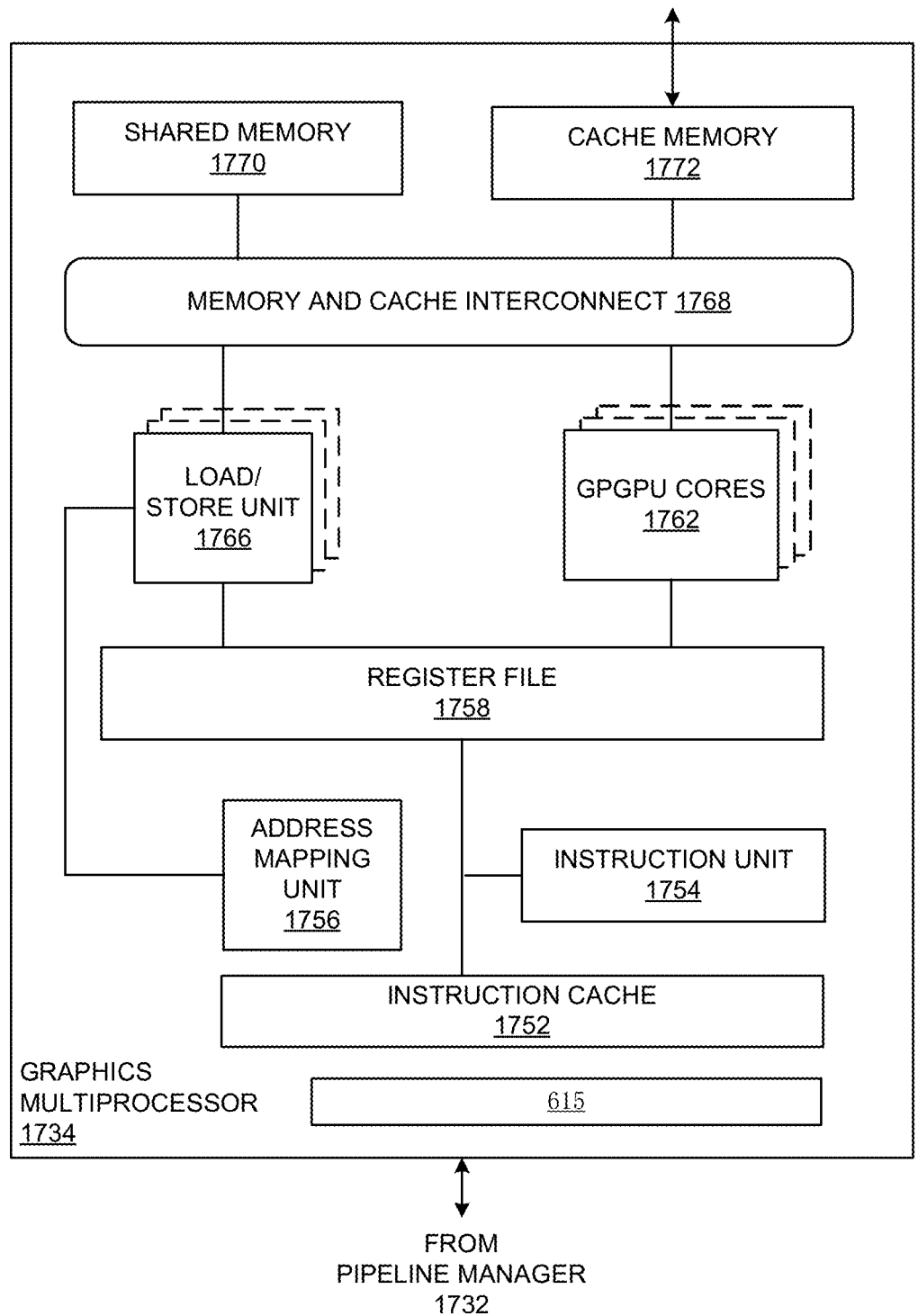
FIG. 17D illustrates a graphics multiprocessor, according to at least one embodiment.

FIG. 17D shows a graphics multiprocessor 1734 according to at least one embodiment. In at least one embodiment, graphics multiprocessor 1734 couples with pipeline manager 1732 of processing cluster 1714. In at least one embodiment, graphics multiprocessor 1734 has an execution pipeline including but not limited to an instruction cache 1752, an instruction unit 1754, an address mapping unit 1756, a register file 1758, one or more general purpose graphics processing unit (GPGPU) cores 1762, and one or more load/store units 1766. GPGPU core(s) 1762 and load/store unit(s) 1766 are coupled with cache memory 1772 and shared memory 1770 via a memory and cache interconnect 1768.

In at least one embodiment, instruction cache 1752 receives a stream of instructions to execute from pipeline manager 1732. In at least one embodiment, instructions are cached in instruction cache 1752 and dispatched for execution by instruction unit 1754. In at least one embodiment, instruction unit 1754 can dispatch instructions as thread groups (e.g., warps), with each thread group assigned to a different execution unit within GPGPU core(s) 1762. In at least one embodiment, an instruction can access any of a local, shared, or global address space by specifying an address within a unified address space. In at least one embodiment, address mapping unit 1756 can be used to translate addresses in a unified address space into a distinct memory address that can be accessed by load/store unit(s) 1766

In at least one embodiment, register file 1758 provides a set of registers for functional units of graphics multiprocessor 1734. In at least one embodiment, register file 1758 provides temporary storage for operands connected to data paths of functional units (e.g., GPGPU cores 1762, load/store units 1766) of graphics multiprocessor 1734. In at least one embodiment, register file 1758 is divided between each of functional units such that each functional unit is allocated a dedicated portion of register file 1758. In at least one embodiment, register file 1758 is divided between different warps being executed by graphics multiprocessor 1734.

In at least one embodiment, GPGPU cores 1762 can each include floating point units (FPUs) and/or integer arithmetic logic units (ALUs) that are used to execute instructions of graphics multiprocessor 1734. GPGPU cores 1762 can be similar in architecture or can differ in architecture. In at least one embodiment, a first portion of GPGPU cores 1762 include a single precision FPU and an integer ALU while a second portion of GPGPU cores include a double precision FPU. In at least one embodiment, FPUs can implement IEEE 754-2008 standard for floating point arithmetic or enable variable precision floating point arithmetic. In at least one embodiment, graphics multiprocessor 1734 can additionally include one or more fixed function or special function units to perform specific functions such as copy rectangle or pixel blending operations. In at least one embodiment one or more of GPGPU cores can also include fixed or special function logic.

In at least one embodiment, GPGPU cores 1762 include SIMD logic capable of performing a single instruction on multiple sets of data. In at least one embodiment GPGPU cores 1762 can physically execute SIMD4, SIMD8, and SIMD16 instructions and logically execute SIMD1, SIMD2, and SIMD32 instructions. In at least one embodiment, SIMD instructions for GPGPU cores can be generated at compile time by a shader compiler or automatically generated when executing programs written and compiled for single program multiple data (SPMD) or SIMT architectures. In at least one embodiment, multiple threads of a program configured for an SIMT execution model can executed via a single SIMD instruction. For example, in at least one embodiment, eight SIMT threads that perform same or similar operations can be executed in parallel via a single SIMD8 logic unit.

In at least one embodiment, memory and cache interconnect 1768 is an interconnect network that connects each functional unit of graphics multiprocessor 1734 to register file 1758 and to shared memory 1770. In at least one embodiment, memory and cache interconnect 1768 is a crossbar interconnect that allows load/store unit 1766 to implement load and store operations between shared memory 1770 and register file 1758. In at least one embodiment, register file 1758 can operate at a same frequency as GPGPU cores 1762, thus data transfer between GPGPU cores 1762 and register file 1758 is very low latency. In at least one embodiment, shared memory 1770 can be used to enable communication between threads that execute on functional units within graphics multiprocessor 1734. In at least one embodiment, cache memory 1772 can be used as a data cache for example, to cache texture data communicated between functional units and texture unit 1736. In at least one embodiment, shared memory 1770 can also be used as a program managed cache. In at least one embodiment, threads executing on GPGPU cores 1762 can programmatically store data within shared memory in addition to automatically cached data that is stored within cache memory 1772.

In at least one embodiment, a parallel processor or GPGPU as described herein is communicatively coupled to host/processor cores to accelerate graphics operations, machine-learning operations, pattern analysis operations, and various general purpose GPU (GPGPU) functions. In at least one embodiment, GPU may be communicatively coupled to host processor/cores over a bus or other interconnect (e.g., a high speed interconnect such as PCIe or NVLink). In at least one embodiment, GPU may be integrated on same package or chip as cores and communicatively coupled to cores over an internal processor bus/interconnect (i.e., internal to package or chip). In at least one embodiment, regardless of manner in which GPU is connected, processor cores may allocate work to GPU in form of sequences of commands/instructions contained in a work descriptor. In at least one embodiment, GPU then uses dedicated circuitry/logic for efficiently processing these commands/instructions.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in graphics multiprocessor 1734 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 18:
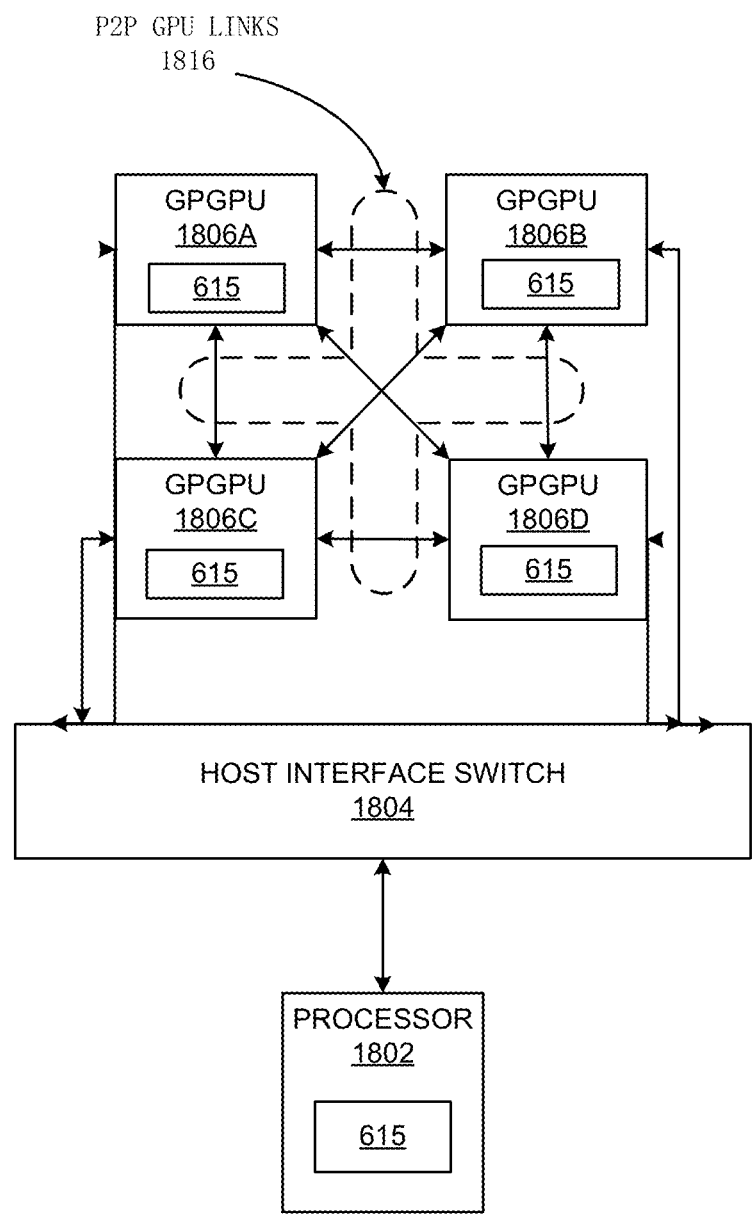
FIG. 18 illustrates a multi-graphics processing unit (GPU) system, according to at least one embodiment.

FIG. 18 illustrates a multi-GPU computing system 1800, according to at least one embodiment. In at least one embodiment, multi-GPU computing system 1800 can include a processor 1802 coupled to multiple general purpose graphics processing units (GPGPUs) 1806A-D via a host interface switch 1804. In at least one embodiment, host interface switch 1804 is a PCI express switch device that couples processor 1802 to a PCI express bus over which processor 1802 can communicate with GPGPUs 1806A-D. GPGPUs 1806A-D can interconnect via a set of high-speed point to point GPU to GPU links 1816. In at least one embodiment, GPU to GPU links 1816 connect to each of GPGPUs 1806A-D via a dedicated GPU link. In at least one embodiment, P2P GPU links 1816 enable direct communication between each of GPGPUs 1806A-D without requiring communication over host interface bus 1804 to which processor 1802 is connected. In at least one embodiment, with GPU-to-GPU traffic directed to P2P GPU links 1816, host interface bus 1804 remains available for system memory access or to communicate with other instances of multi-GPU computing system 1800, for example, via one or more network devices. While in at least one embodiment GPGPUs 1806A-D connect to processor 1802 via host interface switch 1804, in at least one embodiment processor 1802 includes direct support for P2P GPU links 1816 and can connect directly to GPGPUs 1806A-D.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in multi-GPU computing system 1800 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 19:
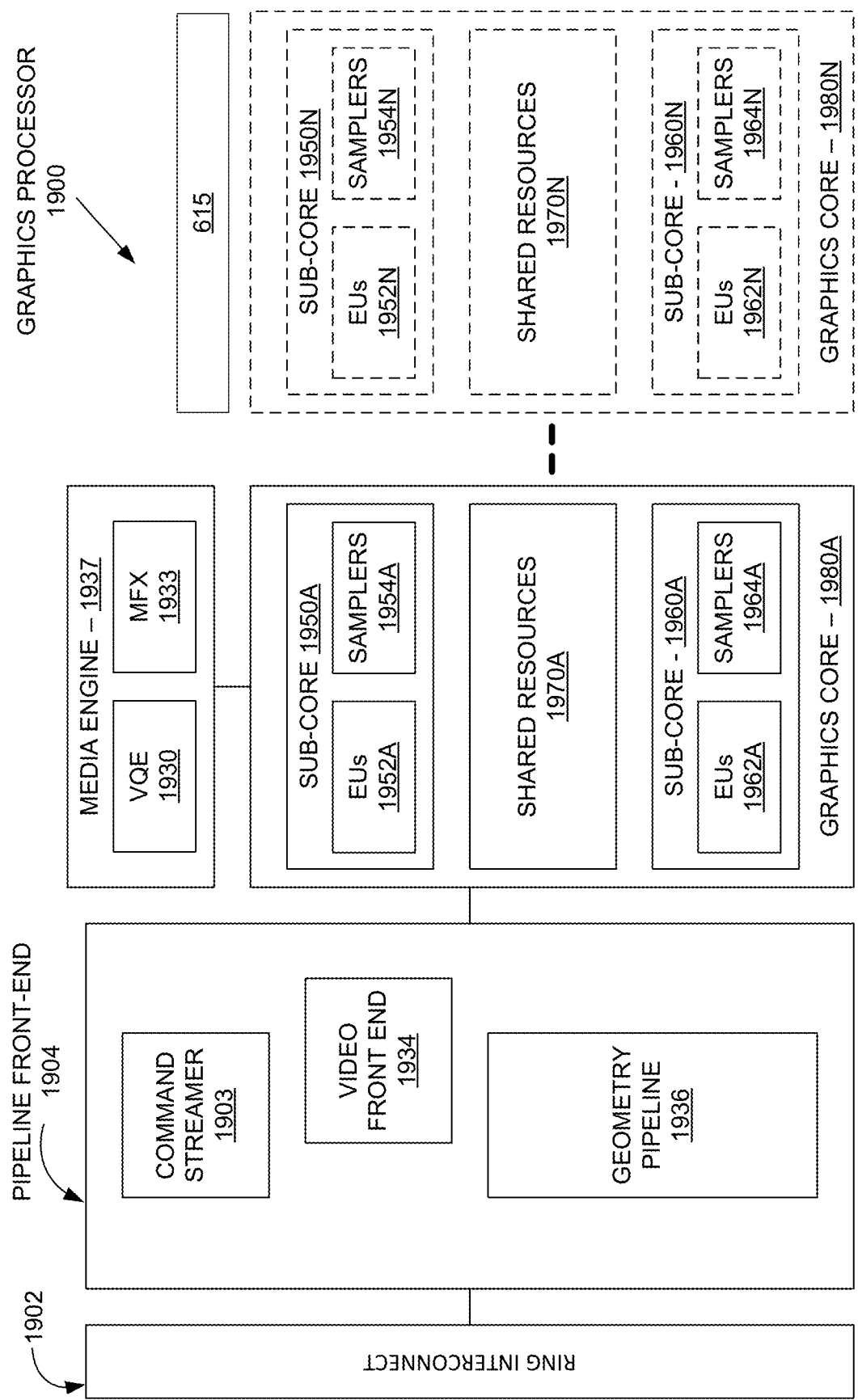
FIG. 19 illustrates a graphics processor, according to at least one embodiment.

FIG. 19 is a block diagram of a graphics processor 1900, according to at least one embodiment. In at least one embodiment, graphics processor 1900 includes a ring interconnect 1902, a pipeline front-end 1904, a media engine 1937, and graphics cores 1980A-1980N. In at least one embodiment, ring interconnect 1902 couples graphics processor 1900 to other processing units, including other graphics processors or one or more general-purpose processor cores. In at least one embodiment, graphics processor 1900 is one of many processors integrated within a multi-core processing system.

In at least one embodiment, graphics processor 1900 receives batches of commands via ring interconnect 1902. In at least one embodiment, incoming commands are interpreted by a command streamer 1903 in pipeline front-end 1904. In at least one embodiment, graphics processor 1900 includes scalable execution logic to perform 3D geometry processing and media processing via graphics core(s) 1980A-1980N. In at least one embodiment, for 3D geometry processing commands, command streamer 1903 supplies commands to geometry pipeline 1936. In at least one embodiment, for at least some media processing commands, command streamer 1903 supplies commands to a video front end 1934, which couples with a media engine 1937. In at least one embodiment, media engine 1937 includes a Video Quality Engine (VQE) 1930 for video and image post-processing and a multi-format encode/decode (MFX) 1933 engine to provide hardware-accelerated media data encode and decode. In at least one embodiment, geometry pipeline 1936 and media engine 1937 each generate execution threads for thread execution resources provided by at least one graphics core 1980A.

In at least one embodiment, graphics processor 1900 includes scalable thread execution resources featuring modular cores 1980A-1980N (sometimes referred to as core slices), each having multiple sub-cores 1950A-1950N, 1960A-1960N (sometimes referred to as core sub-slices). In at least one embodiment, graphics processor 1900 can have any number of graphics cores 1980A through 1980N. In at least one embodiment, graphics processor 1900 includes a graphics core 1980A having at least a first sub-core 1950A and a second sub-core 1960A. In at least one embodiment, graphics processor 1900 is a low power processor with a single sub-core (e.g., 1950A). In at least one embodiment, graphics processor 1900 includes multiple graphics cores 1980A-1980N, each including a set of first sub-cores 1950A-1950N and a set of second sub-cores 1960A-1960N. In at least one embodiment, each sub-core in first sub-cores 1950A-1950N includes at least a first set of execution units 1952A-1952N and media/texture samplers 1954A-1954N. In at least one embodiment, each sub-core in second sub-cores 1960A-1960N includes at least a second set of execution units 1962A-1962N and samplers 1964A-1964N. In at least one embodiment, each sub-core 1950A-1950N, 1960A-1960N shares a set of shared resources 1970A-1970N. In at least one embodiment, shared resources include shared cache memory and pixel operation logic.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, inference and/or training logic 615 may be used in graphics processor 1900 for inferencing or predicting operations based, at least in part, on weight parameters calculated using neural network training operations, neural network functions and/or architectures, or neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 20:
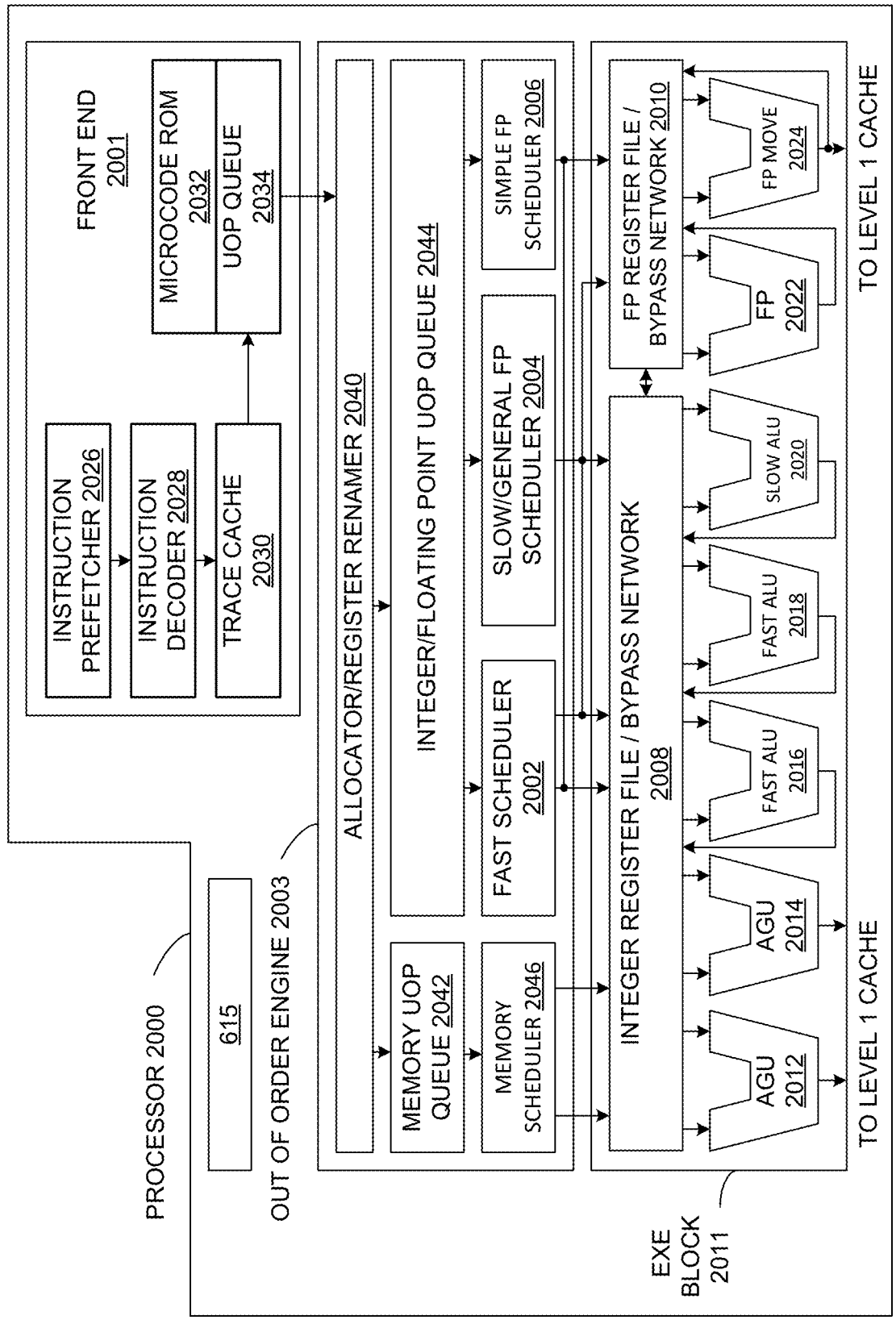
FIG. 20 illustrates a processor's micro-architecture, according to at least one embodiment.

FIG. 20 is a block diagram illustrating micro-architecture for a processor 2000 that may include logic circuits to perform instructions, according to at least one embodiment. In at least one embodiment, processor 2000 may perform instructions, including x86 instructions, ARM instructions, specialized instructions for application-specific integrated circuits (ASICs), etc. In at least one embodiment, processor 2000 may include registers to store packed data, such as 64-bit wide MMX™ registers in microprocessors enabled with MMX technology from Intel Corporation of Santa Clara, Calif. In at least one embodiment, MMX registers, available in both integer and floating point forms, may operate with packed data elements that accompany single instruction, multiple data ("SIMD") and streaming SIMD extensions ("SSE") instructions. In at least one embodiment, 128-bit wide XMM registers relating to SSE2, SSE3, SSE4, AVX, or beyond (referred to generically as "SSEx") technology may hold such packed data operands. In at least one embodiment, processor 2000 may perform instructions to accelerate machine learning or deep learning algorithms, training, or inferencing.

In at least one embodiment, processor 2000 includes an in-order front end ("front end") 2001 to fetch instructions to be executed and prepare instructions to be used later in processor pipeline. In at least one embodiment, front end 2001 may include several units. In at least one embodiment, an instruction prefetcher 2026 fetches instructions from memory and feeds instructions to an instruction decoder 2028 which in turn decodes or interprets instructions. For example, in at least one embodiment, instruction decoder 2028 decodes a received instruction into one or more operations called "micro-instructions" or "micro-operations" (also called "micro ops" or "uops") that machine may execute. In at least one embodiment, instruction decoder 2028 parses instruction into an opcode and corresponding data and control fields that may be used by micro-architecture to perform operations in accordance with at least one embodiment. In at least one embodiment, a trace cache 2030 may assemble decoded uops into program ordered sequences or traces in a uop queue 2034 for execution. In at least one embodiment, when trace cache 2030 encounters a complex instruction, a microcode ROM 2032 provides uops needed to complete operation.

In at least one embodiment, some instructions may be converted into a single micro-op, whereas others need several micro-ops to complete full operation. In at least one embodiment, if more than four micro-ops are needed to complete an instruction, instruction decoder 2028 may access microcode ROM 2032 to perform instruction. In at least one embodiment, an instruction may be decoded into a small number of micro-ops for processing at instruction decoder 2028. In at least one embodiment, an instruction may be stored within microcode ROM 2032 should a number of micro-ops be needed to accomplish operation. In at least one embodiment, trace cache 2030 refers to an entry point programmable logic array ("PLA") to determine a correct micro-instruction pointer for reading microcode sequences to complete one or more instructions from microcode ROM 2032 in accordance with at least one embodiment. In at least one embodiment, after microcode ROM 2032 finishes sequencing micro-ops for an instruction, front end 2001 of machine may resume fetching micro-ops from trace cache 2030.

In at least one embodiment, out-of-order execution engine ("out of order engine") 2003 may prepare instructions for execution. In at least one embodiment, out-of-order execution logic has a number of buffers to smooth out and re-order flow of instructions to optimize performance as they go down pipeline and get scheduled for execution. In at least one embodiment, out-of-order execution engine 2003 includes, without limitation, an allocator/register renamer 2040, a memory uop queue 2042, an integer/floating point uop queue 2044, a memory scheduler 2046, a fast scheduler 2002, a slow/general floating point scheduler ("slow/general FP scheduler") 2004, and a simple floating point scheduler ("simple FP scheduler") 2006. In at least one embodiment, fast schedule 2002, slow/general floating point scheduler 2004, and simple floating point scheduler 2006 are also collectively referred to herein as "uop schedulers 2002, 2004, 2006." In at least one embodiment, allocator/register renamer 2040 allocates machine buffers and resources that each uop needs in order to execute. In at least one embodiment, allocator/register renamer 2040 renames logic registers onto entries in a register file. In at least one embodiment, allocator/register renamer 2040 also allocates an entry for each uop in one of two uop queues, memory uop queue 2042 for memory operations and integer/floating point uop queue 2044 for non-memory operations, in front of memory scheduler 2046 and uop schedulers 2002, 2004, 2006. In at least one embodiment, uop schedulers 2002, 2004, 2006 determine when a uop is ready to execute based on readiness of their dependent input register operand sources and availability of execution resources uops need to complete their operation. In at least one embodiment, fast scheduler 2002 of at least one embodiment may schedule on each half of main clock cycle while slow/general floating point scheduler 2004 and simple floating point scheduler 2006 may schedule once per main processor clock cycle. In at least one embodiment, uop schedulers 2002, 2004, 2006 arbitrate for dispatch ports to schedule uops for execution.

In at least one embodiment, execution block 2011 includes, without limitation, an integer register file/bypass network 2008, a floating point register file/bypass network ("FP register file/bypass network") 2010, address generation units ("AGUs") 2012 and 2014, fast Arithmetic Logic Units (ALUs) ("fast ALUs") 2016 and 2018, a slow Arithmetic Logic Unit ("slow ALU") 2020, a floating point ALU ("FP") 2022, and a floating point move unit ("FP move") 2024. In at least one embodiment, integer register file/bypass network 2008 and floating point register file/bypass network 2010 are also referred to herein as "register files 2008, 2010." In at least one embodiment, AGUs 2012 and 2014, fast ALUs 2016 and 2018, slow ALU 2020, floating point ALU 2022, and floating point move unit 2024 are also referred to herein as "execution units 2012, 2014, 2016, 2018, 2020, 2022, and 2024." In at least one embodiment, execution block b11 may include, without limitation, any number (including zero) and type of register files, bypass networks, address generation units, and execution units, in any combination.

In at least one embodiment, register files 2008, 2010 may be arranged between uop schedulers 2002, 2004, 2006, and execution units 2012, 2014, 2016, 2018, 2020, 2022, and 2024. In at least one embodiment, integer register file/bypass network 2008 performs integer operations. In at least one embodiment, floating point register file/bypass network 2010 performs floating point operations. In at least one embodiment, each of register files 2008, 2010 may include, without limitation, a bypass network that may bypass or forward just completed results that have not yet been written into register file to new dependent uops. In at least one embodiment, register files 2008, 2010 may communicate data with each other. In at least one embodiment, integer register file/bypass network 2008 may include, without limitation, two separate register files, one register file for low-order thirty-two bits of data and a second register file for high order thirty-two bits of data. In at least one embodiment, floating point register file/bypass network 2010 may include, without limitation, 128-bit wide entries because floating point instructions typically have operands from 64 to 128 bits in width.

In at least one embodiment, execution units 2012, 2014, 2016, 2018, 2020, 2022, 2024 may execute instructions. In at least one embodiment, register files 2008, 2010 store integer and floating point data operand values that micro-instructions need to execute. In at least one embodiment, processor 2000 may include, without limitation, any number and combination of execution units 2012, 2014, 2016, 2018, 2020, 2022, 2024. In at least one embodiment, floating point ALU 2022 and floating point move unit 2024, may execute floating point, MMX, SIMD, AVX and SSE, or other operations, including specialized machine learning instructions. In at least one embodiment, floating point ALU 2022 may include, without limitation, a 64-bit by 64-bit floating point divider to execute divide, square root, and remainder micro ops. In at least one embodiment, instructions involving a floating point value may be handled with floating point hardware. In at least one embodiment, ALU operations may be passed to fast ALUs 2016, 2018. In at least one embodiment, fast ALUS 2016, 2018 may execute fast operations with an effective latency of half a clock cycle. In at least one embodiment, most complex integer operations go to slow ALU 2020 as slow ALU 2020 may include, without limitation, integer execution hardware for long-latency type of operations, such as a multiplier, shifts, flag logic, and branch processing. In at least one embodiment, memory load/store operations may be executed by AGUS 2012, 2014. In at least one embodiment, fast ALU 2016, fast ALU 2018, and slow ALU 2020 may perform integer operations on 64-bit data operands. In at least one embodiment, fast ALU 2016, fast ALU 2018, and slow ALU 2020 may be implemented to support a variety of data bit sizes including sixteen, thirty-two, 128, 256, etc. In at least one embodiment, floating point ALU 2022 and floating point move unit 2024 may be implemented to support a range of operands having bits of various widths. In at least one embodiment, floating point ALU 2022 and floating point move unit 2024 may operate on 128-bit wide packed data operands in conjunction with SIMD and multimedia instructions.

In at least one embodiment, uop schedulers 2002, 2004, 2006, dispatch dependent operations before parent load has finished executing. In at least one embodiment, as uops may be speculatively scheduled and executed in processor 2000, processor 2000 may also include logic to handle memory misses. In at least one embodiment, if a data load misses in data cache, there may be dependent operations in flight in pipeline that have left scheduler with temporarily incorrect data. In at least one embodiment, a replay mechanism tracks and re-executes instructions that use incorrect data. In at least one embodiment, dependent operations might need to be replayed and independent ones may be allowed to complete. In at least one embodiment, schedulers and replay mechanism of at least one embodiment of a processor may also be designed to catch instruction sequences for text string comparison operations.

In at least one embodiment, term "registers" may refer to on-board processor storage locations that may be used as part of instructions to identify operands. In at least one embodiment, registers may be those that may be usable from outside of processor (from a programmer's perspective). In at least one embodiment, registers might not be limited to a particular type of circuit. Rather, in at least one embodiment, a register may store data, provide data, and perform functions described herein. In at least one embodiment, registers described herein may be implemented by circuitry within a processor using any number of different techniques, such as dedicated physical registers, dynamically allocated physical registers using register renaming, combinations of dedicated and dynamically allocated physical registers, etc. In at least one embodiment, integer registers store 32-bit integer data. A register file of at least one embodiment also contains eight multimedia SIMD registers for packed data.

Inference and/or training logic 615 are used to perform inferencing and/or training operations associated with one or more embodiments. Details regarding inference and/or training logic 615 are provided below in conjunction with FIGS. 6A and/or 6B. In at least one embodiment portions or all of inference and/or training logic 615 may be incorporated into execution block 2011 and other memory or registers shown or not shown. For example, in at least one embodiment, training and/or inferencing techniques described herein may use one or more of ALUs illustrated in execution block 2011. Moreover, weight parameters may be stored in on-chip or off-chip memory and/or registers (shown or not shown) that configure ALUs of execution block 2011 to perform one or more machine learning algorithms, neural network architectures, use cases, or training techniques described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 21:
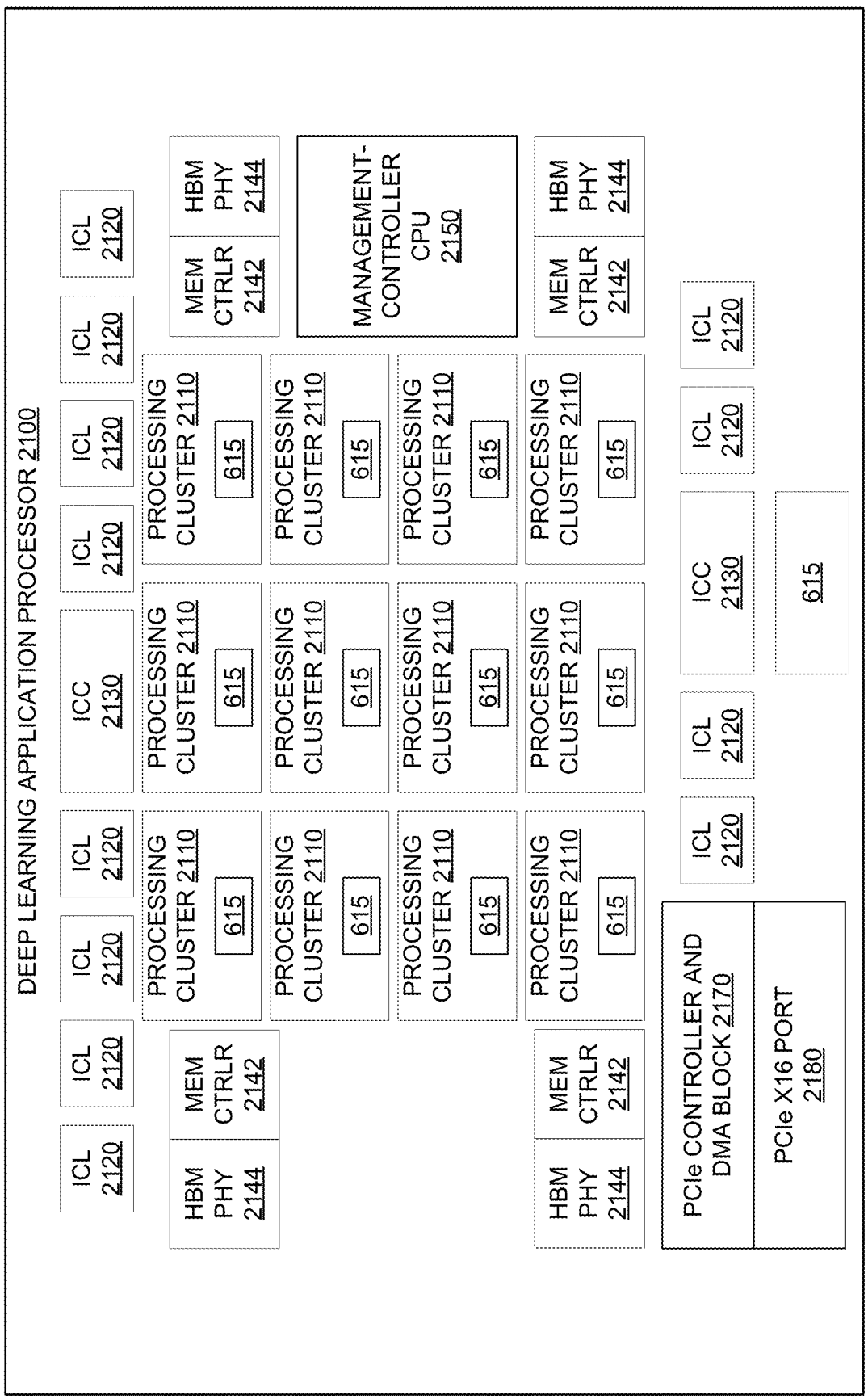
FIG. 21 illustrates a deep learning application processor, according to at least one embodiment.

FIG. 21 illustrates a deep learning application processor 2100, according to at least one embodiment. In at least one embodiment, deep learning application processor 2100 uses instructions that, if executed by deep learning application processor 2100, cause deep learning application processor 2100 to perform some or all of processes and techniques described throughout this disclosure. In at least one embodiment, deep learning application processor 2100 is an application-specific integrated circuit (ASIC). In at least one embodiment, application processor 2100 performs matrix multiply operations either "hard-wired" into hardware as a result of performing one or more instructions or both. In at least one embodiment, deep learning application processor 2100 includes, without limitation, processing clusters 2110(1)-2110(12), Inter-Chip Links ("ICLs") 2120(1)-2120(12), Inter-Chip Controllers ("ICCs") 2130(1)-2130(2), memory controllers ("Mem Ctrlrs") 2142(1)-2142(4), high bandwidth memory physical layer ("HBM PHY") 2144(1)-2144(4), a management-controller central processing unit ("management-controller CPU") 2150, a peripheral component interconnect express controller and direct memory access block ("PCIe Controller and DMA") 2170, and a sixteen-lane peripheral component interconnect express port ("PCI Express x 16") 2180.

In at least one embodiment, processing clusters 2110 may perform deep learning operations, including inference or prediction operations based on weight parameters calculated one or more training techniques, including those described herein. In at least one embodiment, each processing cluster 2110 may include, without limitation, any number and type of processors. In at least one embodiment, deep learning application processor 2100 may include any number and type of processing clusters 2100. In at least one embodiment, Inter-Chip Links 2120 are bi-directional. In at least one embodiment, Inter-Chip Links 2120 and Inter-Chip Controllers 2130 enable multiple deep learning application processors 2100 to exchange information, including activation information resulting from performing one or more machine learning algorithms embodied in one or more neural networks. In at least one embodiment, deep learning application processor 2100 may include any number (including zero) and type of ICLs 2120 and ICCs 2130.

In at least one embodiment, HBM2s 2140 provide a total of 32 Gigabytes (GB) of memory. HBM2 2140(i) is associated with both memory controller 2142(i) and HBM PHY 2144(i). In at least one embodiment, any number of HBM2s 2140 may provide any type and total amount of high bandwidth memory and may be associated with any number (including zero) and type of memory controllers 2142 and HBM PHYs 2144. In at least one embodiment, SPI, I2C, GPIO 2160, PCIe Controller and DMA 2170, and/or PCIe 2180 may be replaced with any number and type of blocks that enable any number and type of communication standards in any technically feasible fashion.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, deep learning application processor 2100 is used to train a machine learning model, such as a neural network, to predict or infer information provided to deep learning application processor 2100. In at least one embodiment, deep learning application processor 2100 is used to infer or predict information based on a trained machine learning model (e.g., neural network) that has been trained by another processor or system or by deep learning application processor 2100. In at least one embodiment, processor 2100 may be used to perform one or more neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 22:
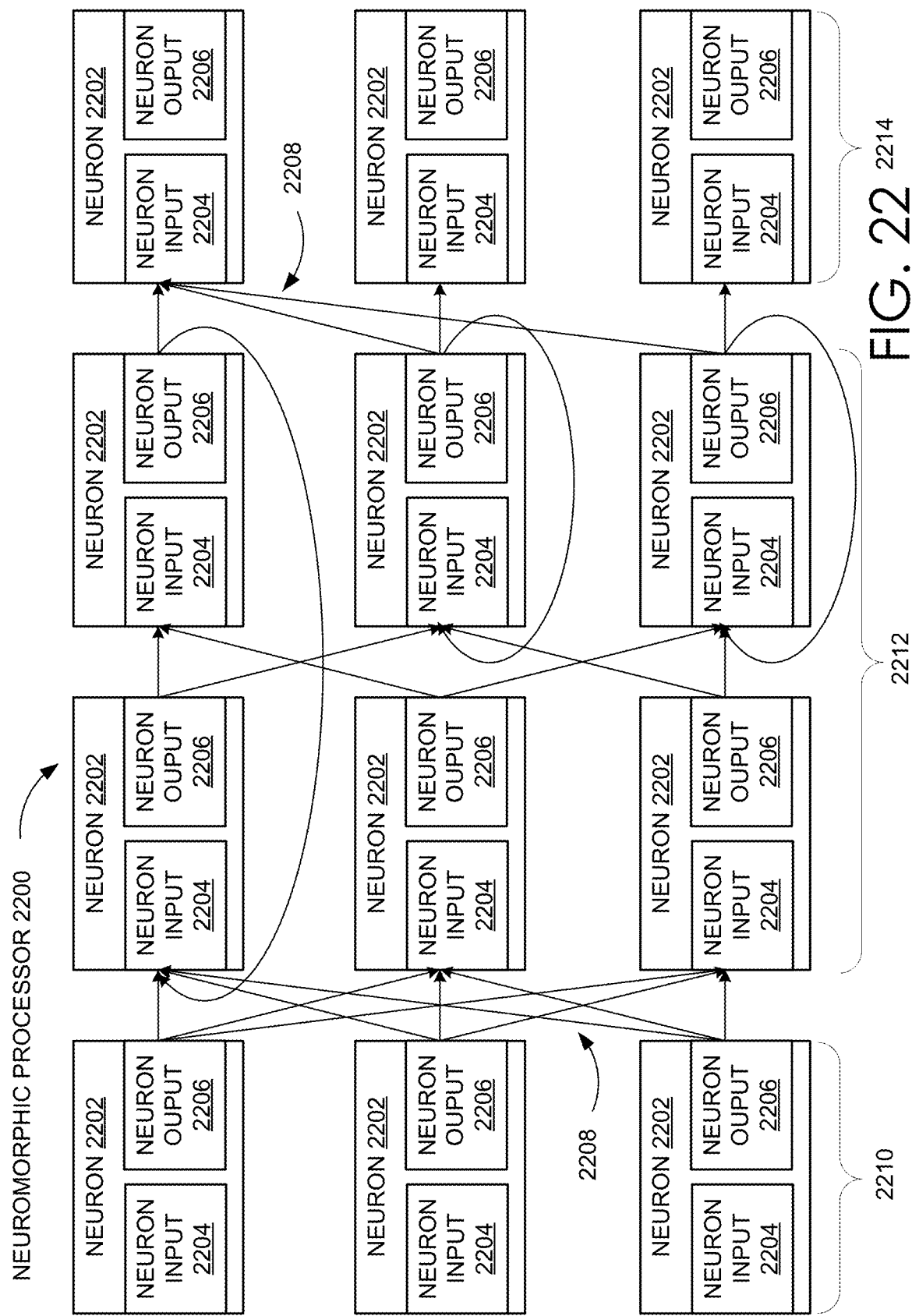
FIG. 22 illustrates an example neuromorphic processor, according to at least one embodiment.

FIG. 22 is a block diagram of a neuromorphic processor 2200, according to at least one embodiment. In at least one embodiment, neuromorphic processor 2200 may receive one or more inputs from sources external to neuromorphic processor 2200. In at least one embodiment, these inputs may be transmitted to one or more neurons 2202 within neuromorphic processor 2200. In at least one embodiment, neurons 2202 and components thereof may be implemented using circuitry or logic, including one or more arithmetic logic units (ALUs). In at least one embodiment, neuromorphic processor 2200 may include, without limitation, thousands or millions of instances of neurons 2202, but any suitable number of neurons 2202 may be used. In at least one embodiment, each instance of neuron 2202 may include a neuron input 2204 and a neuron output 2206. In at least one embodiment, neurons 2202 may generate outputs that may be transmitted to inputs of other instances of neurons 2202. For example, in at least one embodiment, neuron inputs 2204 and neuron outputs 2206 may be interconnected via synapses 2208.

In at least one embodiment, neurons 2202 and synapses 2208 may be interconnected such that neuromorphic processor 2200 operates to process or analyze information received by neuromorphic processor 2200. In at least one embodiment, neurons 2202 may transmit an output pulse (or "fire" or "spike") when inputs received through neuron input 2204 exceed a threshold. In at least one embodiment, neurons 2202 may sum or integrate signals received at neuron inputs 2204. For example, in at least one embodiment, neurons 2202 may be implemented as leaky integrate-and-fire neurons, wherein if a sum (referred to as a "membrane potential") exceeds a threshold value, neuron 2202 may generate an output (or "fire") using a transfer function such as a sigmoid or threshold function. In at least one embodiment, a leaky integrate-and-fire neuron may sum signals received at neuron inputs 2204 into a membrane potential and may also apply a decay factor (or leak) to reduce a membrane potential. In at least one embodiment, a leaky integrate-and-fire neuron may fire if multiple input signals are received at neuron inputs 2204 rapidly enough to exceed a threshold value (i.e., before a membrane potential decays too low to fire). In at least one embodiment, neurons 2202 may be implemented using circuits or logic that receive inputs, integrate inputs into a membrane potential, and decay a membrane potential. In at least one embodiment, inputs may be averaged, or any other suitable transfer function may be used. Furthermore, in at least one embodiment, neurons 2202 may include, without limitation, comparator circuits or logic that generate an output spike at neuron output 2206 when result of applying a transfer function to neuron input 2204 exceeds a threshold. In at least one embodiment, once neuron 2202 fires, it may disregard previously received input information by, for example, resetting a membrane potential to 0 or another suitable default value. In at least one embodiment, once membrane potential is reset to 0, neuron 2202 may resume normal operation after a suitable period of time (or refractory period).

In at least one embodiment, neurons 2202 may be interconnected through synapses 2208. In at least one embodiment, synapses 2208 may operate to transmit signals from an output of a first neuron 2202 to an input of a second neuron 2202. In at least one embodiment, neurons 2202 may transmit information over more than one instance of synapse 2208. In at least one embodiment, one or more instances of neuron output 2206 may be connected, via an instance of synapse 2208, to an instance of neuron input 2204 in same neuron 2202. In at least one embodiment, an instance of neuron 2202 generating an output to be transmitted over an instance of synapse 2208 may be referred to as a "pre-synaptic neuron" with respect to that instance of synapse 2208. In at least one embodiment, an instance of neuron 2202 receiving an input transmitted over an instance of synapse 2208 may be referred to as a "post-synaptic neuron" with respect to that instance of synapse 2208. Because an instance of neuron 2202 may receive inputs from one or more instances of synapse 2208, and may also transmit outputs over one or more instances of synapse 2208, a single instance of neuron 2202 may therefore be both a "pre-synaptic neuron" and "post-synaptic neuron," with respect to various instances of synapses 2208, in at least one embodiment.

In at least one embodiment, neurons 2202 may be organized into one or more layers. Each instance of neuron 2202 may have one neuron output 2206 that may fan out through one or more synapses 2208 to one or more neuron inputs 2204. In at least one embodiment, neuron outputs 2206 of neurons 2202 in a first layer 2210 may be connected to neuron inputs 2204 of neurons 2202 in a second layer 2212. In at least one embodiment, layer 2210 may be referred to as a "feed-forward layer." In at least one embodiment, each instance of neuron 2202 in an instance of first layer 2210 may fan out to each instance of neuron 2202 in second layer 2212. In at least one embodiment, first layer 2210 may be referred to as a "fully connected feed-forward layer." In at least one embodiment, each instance of neuron 2202 in an instance of second layer 2212 may fan out to fewer than all instances of neuron 2202 in a third layer 2214. In at least one embodiment, second layer 2212 may be referred to as a "sparsely connected feed-forward layer." In at least one embodiment, neurons 2202 in second layer 2212 may fan out to neurons 2202 in multiple other layers, including to neurons 2202 in (same) second layer 2212. In at least one embodiment, second layer 2212 may be referred to as a "recurrent layer." In at least one embodiment, neuromorphic processor 2200 may include, without limitation, any suitable combination of recurrent layers and feed-forward layers, including, without limitation, both sparsely connected feed-forward layers and fully connected feed-forward layers.

In at least one embodiment, neuromorphic processor 2200 may include, without limitation, a reconfigurable interconnect architecture or dedicated hard wired interconnects to connect synapse 2208 to neurons 2202. In at least one embodiment, neuromorphic processor 2200 may include, without limitation, circuitry or logic that allows synapses to be allocated to different neurons 2202 as needed based on neural network topology and neuron fan-in/out. For example, in at least one embodiment, synapses 2208 may be connected to neurons 2202 using an interconnect fabric, such as network-on-chip, or with dedicated connections. In at least one embodiment, synapse interconnections and components thereof may be implemented using circuitry or logic.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 23:
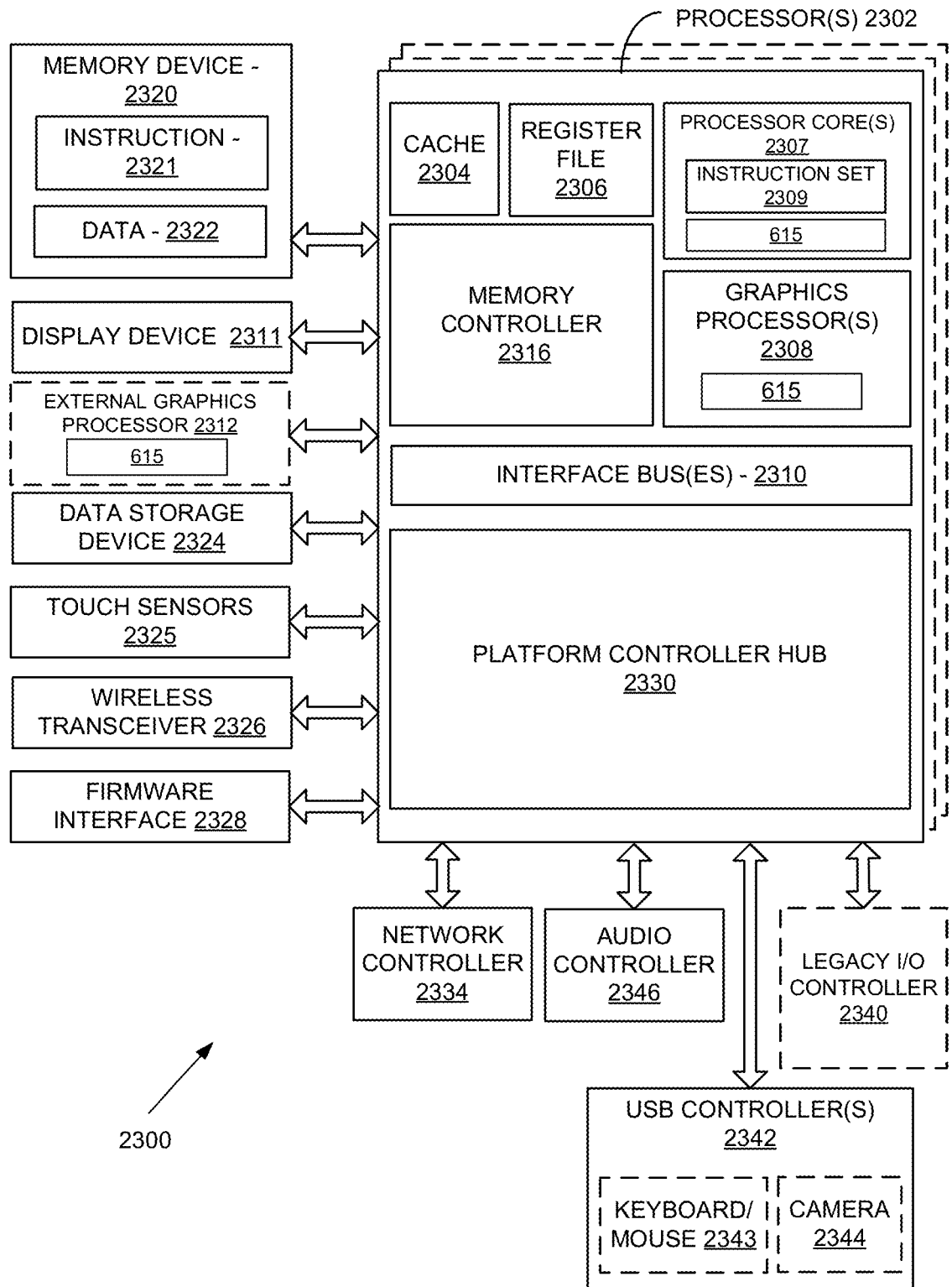
FIGS. 23 and 24 illustrate at least portions of a graphics processor, according to at least one embodiment.

FIG. 23 is a block diagram of a processing system, according to at least one embodiment. In at least one embodiment, system 2300 includes one or more processors 2302 and one or more graphics processors 2308, and may be a single processor desktop system, a multiprocessor workstation system, or a server system having a large number of processors 2302 or processor cores 2307. In at least one embodiment, system 2300 is a processing platform incorporated within a system-on-a-chip (SoC) integrated circuit for use in mobile, handheld, or embedded devices.

In at least one embodiment, system 2300 can include, or be incorporated within a server-based gaming platform, a game console, including a game and media console, a mobile gaming console, a handheld game console, or an online game console. In at least one embodiment, system 2300 is a mobile phone, smart phone, tablet computing device or mobile Internet device. In at least one embodiment, processing system 2300 can also include, couple with, or be integrated within a wearable device, such as a smart watch wearable device, smart eyewear device, augmented reality device, or virtual reality device. In at least one embodiment, processing system 2300 is a television or set top box device having one or more processors 2302 and a graphical interface generated by one or more graphics processors 2308.

In at least one embodiment, one or more processors 2302 each include one or more processor cores 2307 to process instructions which, when executed, perform operations for system and user software. In at least one embodiment, each of one or more processor cores 2307 is configured to process a specific instruction set 2309. In at least one embodiment, instruction set 2309 may facilitate Complex Instruction Set Computing (CISC), Reduced Instruction Set Computing (RISC), or computing via a Very Long Instruction Word (VLIW). In at least one embodiment, processor cores 2307 may each process a different instruction set 2309, which may include instructions to facilitate emulation of other instruction sets. In at least one embodiment, processor core 2307 may also include other processing devices, such a Digital Signal Processor (DSP).

In at least one embodiment, processor 2302 includes cache memory 2304. In at least one embodiment, processor 2302 can have a single internal cache or multiple levels of internal cache. In at least one embodiment, cache memory is shared among various components of processor 2302. In at least one embodiment, processor 2302 also uses an external cache (e.g., a Level-3 (L3) cache or Last Level Cache (LLC)) (not shown), which may be shared among processor cores 2307 using known cache coherency techniques. In at least one embodiment, register file 2306 is additionally included in processor 2302 which may include different types of registers for storing different types of data (e.g., integer registers, floating point registers, status registers, and an instruction pointer register). In at least one embodiment, register file 2306 may include general-purpose registers or other registers.

In at least one embodiment, one or more processor(s) 2302 are coupled with one or more interface bus(es) 2310 to transmit communication signals such as address, data, or control signals between processor 2302 and other components in system 2300. In at least one embodiment, interface bus 2310, in one embodiment, can be a processor bus, such as a version of a Direct Media Interface (DMI) bus. In at least one embodiment, interface 2310 is not limited to a DMI bus, and may include one or more Peripheral Component Interconnect buses (e.g., PCI, PCI Express), memory busses, or other types of interface busses. In at least one embodiment processor(s) 2302 include an integrated memory controller 2316 and a platform controller hub 2330. In at least one embodiment, memory controller 2316 facilitates communication between a memory device and other components of system 2300, while platform controller hub (PCH) 2330 provides connections to I/O devices via a local I/O bus.

In at least one embodiment, memory device 2320 can be a dynamic random access memory (DRAM) device, a static random access memory (SRAM) device, flash memory device, phase-change memory device, or some other memory device having suitable performance to serve as process memory. In at least one embodiment memory device 2320 can operate as system memory for system 2300, to store data 2322 and instructions 2321 for use when one or more processors 2302 executes an application or process. In at least one embodiment, memory controller 2316 also couples with an optional external graphics processor 2312, which may communicate with one or more graphics processors 2308 in processors 2302 to perform graphics and media operations. In at least one embodiment, a display device 2311 can connect to processor(s) 2302. In at least one embodiment display device 2311 can include one or more of an internal display device, as in a mobile electronic device or a laptop device or an external display device attached via a display interface (e.g., DisplayPort, etc.). In at least one embodiment, display device 2311 can include a head mounted display (HMD) such as a stereoscopic display device for use in virtual reality (VR) applications or augmented reality (AR) applications.

In at least one embodiment, platform controller hub 2330 enables peripherals to connect to memory device 2320 and processor 2302 via a high-speed I/O bus. In at least one embodiment, I/O peripherals include, but are not limited to, an audio controller 2346, a network controller 2334, a firmware interface 2328, a wireless transceiver 2326, touch sensors 2325, a data storage device 2324 (e.g., hard disk drive, flash memory, etc.). In at least one embodiment, data storage device 2324 can connect via a storage interface (e.g., SATA) or via a peripheral bus, such as a Peripheral Component Interconnect bus (e.g., PCI, PCI Express). In at least one embodiment, touch sensors 2325 can include touch screen sensors, pressure sensors, or fingerprint sensors. In at least one embodiment, wireless transceiver 2326 can be a Wi-Fi transceiver, a Bluetooth transceiver, or a mobile network transceiver such as a 3G, 4G, or Long Term Evolution (LTE) transceiver. In at least one embodiment, firmware interface 2328 enables communication with system firmware, and can be, for example, a unified extensible firmware interface (UEFI). In at least one embodiment, network controller 2334 can enable a network connection to a wired network. In at least one embodiment, a high-performance network controller (not shown) couples with interface bus 2310. In at least one embodiment, audio controller 2346 is a multi-channel high definition audio controller. In at least one embodiment, system 2300 includes an optional legacy I/O controller 2340 for coupling legacy (e.g., Personal System 2 (PS/2)) devices to system. In at least one embodiment, platform controller hub 2330 can also connect to one or more Universal Serial Bus (USB) controllers 2342 connect input devices, such as keyboard and mouse 2343 combinations, a camera 2344, or other USB input devices.

In at least one embodiment, an instance of memory controller 2316 and platform controller hub 2330 may be integrated into a discreet external graphics processor, such as external graphics processor 2312. In at least one embodiment, platform controller hub 2330 and/or memory controller 2316 may be external to one or more processor(s) 2302. For example, in at least one embodiment, system 2300 can include an external memory controller 2316 and platform controller hub 2330, which may be configured as a memory controller hub and peripheral controller hub within a system chipset that is in communication with processor(s) 2302.

Inference and/or training logic 615 are used to perform inferencing and/or training operations associated with one or more embodiments. Details regarding inference and/or training logic 615 are provided below in conjunction with FIGS. 6A and/or 6B. In at least one embodiment portions or all of inference and/or training logic 615 may be incorporated into graphics processor 2300. For example, in at least one embodiment, training and/or inferencing techniques described herein may use one or more of ALUs embodied in graphics processor 2312. Moreover, in at least one embodiment, inferencing and/or training operations described herein may be done using logic other than logic illustrated in FIG. 6A or 6B. In at least one embodiment, weight parameters may be stored in on-chip or off-chip memory and/or registers (shown or not shown) that configure ALUs of graphics processor 2300 to perform one or more machine learning algorithms, neural network architectures, use cases, or training techniques described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 24:
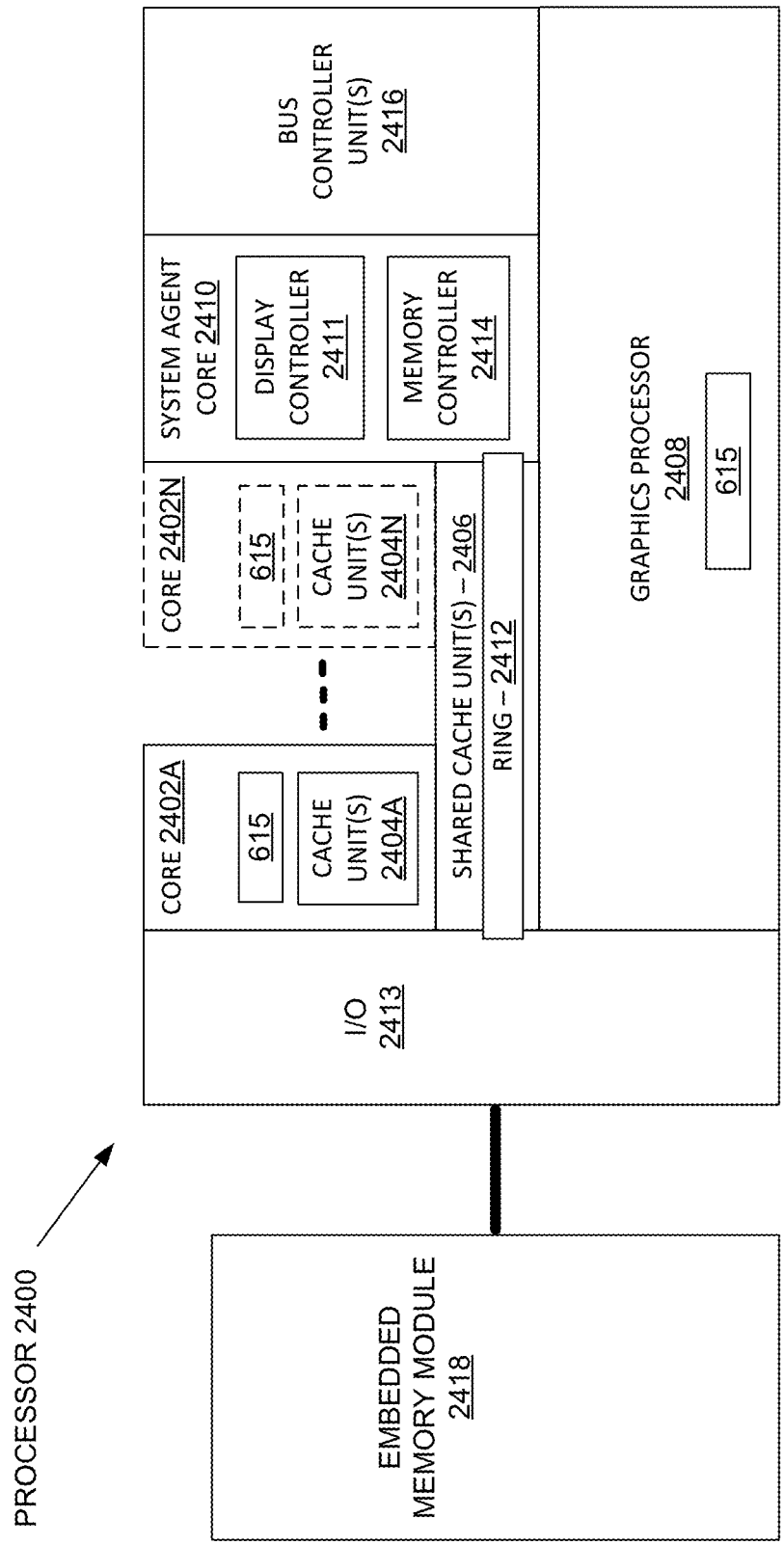

FIG. 24 is a block diagram of a processor 2400 having one or more processor cores 2402A-2402N, an integrated memory controller 2414, and an integrated graphics processor 2408, according to at least one embodiment. In at least one embodiment, processor 2400 can include additional cores up to and including additional core 2402N represented by dashed lined boxes. In at least one embodiment, each of processor cores 2402A-2402N includes one or more internal cache units 2404A-2404N. In at least one embodiment, each processor core also has access to one or more shared cached units 2406.

In at least one embodiment, internal cache units 2404A-2404N and shared cache units 2406 represent a cache memory hierarchy within processor 2400. In at least one embodiment, cache memory units 2404A-2404N may include at least one level of instruction and data cache within each processor core and one or more levels of shared mid-level cache, such as a Level 2 (L2), Level 3 (L3), Level 4 (L4), or other levels of cache, where a highest level of cache before external memory is classified as an LLC. In at least one embodiment, cache coherency logic maintains coherency between various cache units 2406 and 2404A-2404N.

In at least one embodiment, processor 2400 may also include a set of one or more bus controller units 2416 and a system agent core 2410. In at least one embodiment, one or more bus controller units 2416 manage a set of peripheral buses, such as one or more PCI or PCI express busses. In at least one embodiment, system agent core 2410 provides management functionality for various processor components. In at least one embodiment, system agent core 2410 includes one or more integrated memory controllers 2414 to manage access to various external memory devices (not shown).

In at least one embodiment, one or more of processor cores 2402A-2402N include support for simultaneous multi-threading. In at least one embodiment, system agent core 2410 includes components for coordinating and operating cores 2402A-2402N during multi-threaded processing. In at least one embodiment, system agent core 2410 may additionally include a power control unit (PCU), which includes logic and components to regulate one or more power states of processor cores 2402A-2402N and graphics processor 2408.

In at least one embodiment, processor 2400 additionally includes graphics processor 2408 to execute graphics processing operations. In at least one embodiment, graphics processor 2408 couples with shared cache units 2406, and system agent core 2410, including one or more integrated memory controllers 2414. In at least one embodiment, system agent core 2410 also includes a display controller 2411 to drive graphics processor output to one or more coupled displays. In at least one embodiment, display controller 2411 may also be a separate module coupled with graphics processor 2408 via at least one interconnect, or may be integrated within graphics processor 2408.

In at least one embodiment, a ring based interconnect unit 2412 is used to couple internal components of processor 2400. In at least one embodiment, an alternative interconnect unit may be used, such as a point-to-point interconnect, a switched interconnect, or other techniques. In at least one embodiment, graphics processor 2408 couples with ring interconnect 2412 via an I/O link 2413.

In at least one embodiment, I/O link 2413 represents at least one of multiple varieties of I/O interconnects, including an on package I/O interconnect which facilitates communication between various processor components and a high-performance embedded memory module 2418, such as an eDRAM module. In at least one embodiment, each of processor cores 2402A-2402N and graphics processor 2408 use embedded memory modules 2418 as a shared Last Level Cache.

In at least one embodiment, processor cores 2402A-2402N are homogenous cores executing a common instruction set architecture. In at least one embodiment, processor cores 2402A-2402N are heterogeneous in terms of instruction set architecture (ISA), where one or more of processor cores 2402A-2402N execute a common instruction set, while one or more other cores of processor cores 2402A-24-02N executes a subset of a common instruction set or a different instruction set. In at least one embodiment, processor cores 2402A-2402N are heterogeneous in terms of microarchitecture, where one or more cores having a relatively higher power consumption couple with one or more power cores having a lower power consumption. In at least one embodiment, processor 2400 can be implemented on one or more chips or as an SoC integrated circuit.

Inference and/or training logic 615 are used to perform inferencing and/or training operations associated with one or more embodiments. Details regarding inference and/or training logic 615 are provided below in conjunction with FIGS. 6A and/or 6B. In at least one embodiment portions or all of inference and/or training logic 615 may be incorporated into processor 2400. For example, in at least one embodiment, training and/or inferencing techniques described herein may use one or more of ALUs embodied in graphics processor 2312, graphics core(s) 2402A-2402N, or other components in FIG. 24. Moreover, in at least one embodiment, inferencing and/or training operations described herein may be done using logic other than logic illustrated in FIG. 6A or 6B. In at least one embodiment, weight parameters may be stored in on-chip or off-chip memory and/or registers (shown or not shown) that configure ALUs of graphics processor 2400 to perform one or more machine learning algorithms, neural network architectures, use cases, or training techniques described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 25:
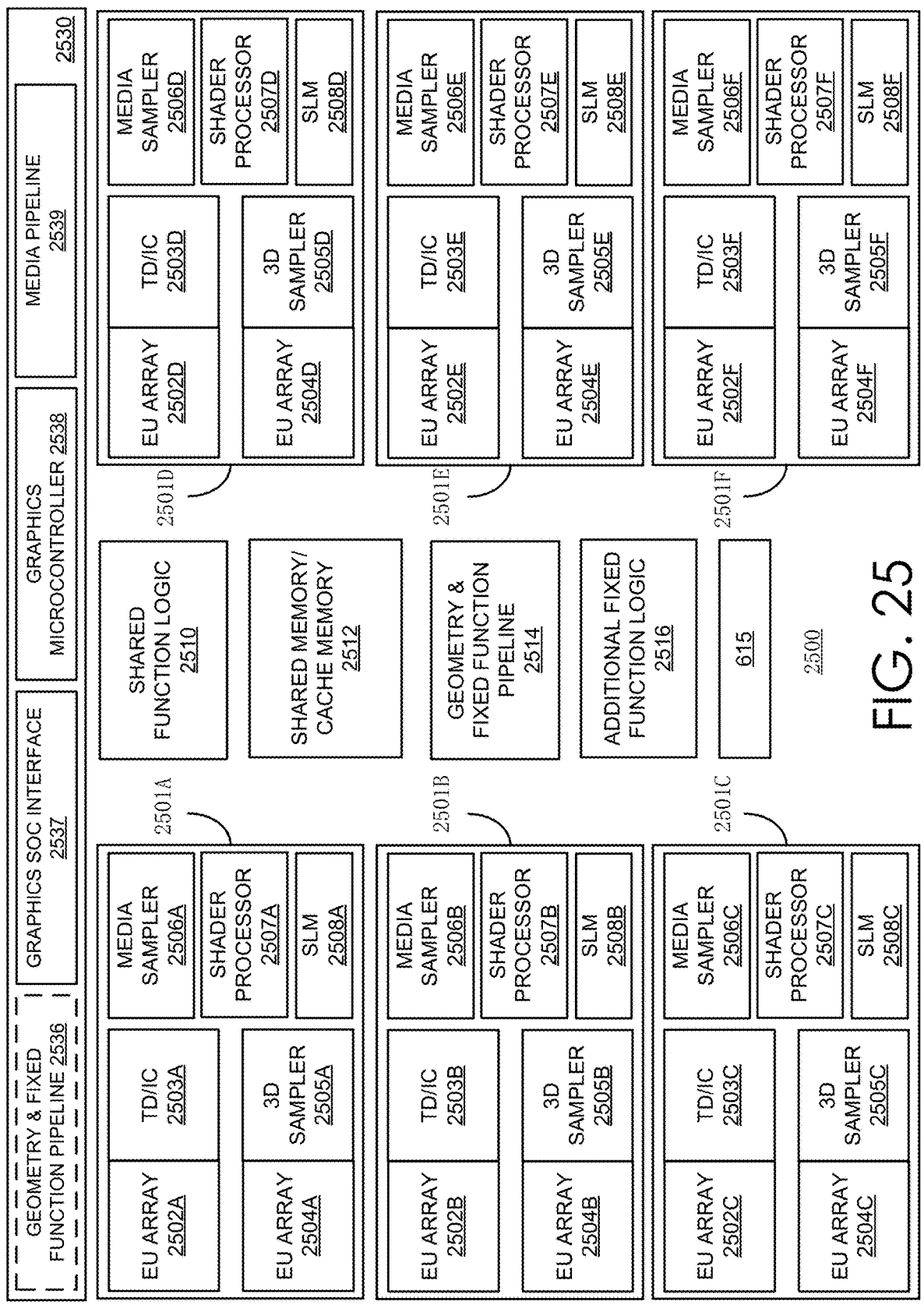
FIG. 25 illustrates at least portions of a graphics processor core, according to at least one embodiment.

FIG. 25 is a block diagram of hardware logic of a graphics processor core 2500, according to at least one embodiment described herein. In at least one embodiment, graphics processor core 2500 is included within a graphics core array. In at least one embodiment, graphics processor core 2500, sometimes referred to as a core slice, can be one or multiple graphics cores within a modular graphics processor. In at least one embodiment, graphics processor core 2500 is exemplary of one graphics core slice, and a graphics processor as described herein may include multiple graphics core slices based on target power and performance envelopes. In at least one embodiment, each graphics core 2500 can include a fixed function block 2530 coupled with multiple sub-cores 2501A-2501F, also referred to as sub-slices, that include modular blocks of general-purpose and fixed function logic.

In at least one embodiment, fixed function block 2530 includes a geometry/fixed function pipeline 2536 that can be shared by all sub-cores in graphics processor 2500, for example, in lower performance and/or lower power graphics processor implementations. In at least one embodiment, geometry/fixed function pipeline 2536 includes a 3D fixed function pipeline, a video front-end unit, a thread spawner and thread dispatcher, and a unified return buffer manager, which manages unified return buffers.

In at least one embodiment fixed, function block 2530 also includes a graphics SoC interface 2537, a graphics microcontroller 2538, and a media pipeline 2539. In at least one embodiment fixed, graphics SoC interface 2537 provides an interface between graphics core 2500 and other processor cores within a system on a chip integrated circuit. In at least one embodiment, graphics microcontroller 2538 is a programmable sub-processor that is configurable to manage various functions of graphics processor 2500, including thread dispatch, scheduling, and pre-emption. In at least one embodiment, media pipeline 2539 includes logic to facilitate decoding, encoding, pre-processing, and/or post-processing of multimedia data, including image and video data. In at least one embodiment, media pipeline 2539 implements media operations via requests to compute or sampling logic within sub-cores 2501-2501F.

In at least one embodiment, SoC interface 2537 enables graphics core 2500 to communicate with general-purpose application processor cores (e.g., CPUs) and/or other components within an SoC, including memory hierarchy elements such as a shared last level cache memory, system RAM, and/or embedded on-chip or on-package DRAM. In at least one embodiment, SoC interface 2537 can also enable communication with fixed function devices within an SoC, such as camera imaging pipelines, and enables use of and/or implements global memory atomics that may be shared between graphics core 2500 and CPUs within an SoC. In at least one embodiment, SoC interface 2537 can also implement power management controls for graphics core 2500 and enable an interface between a clock domain of graphic core 2500 and other clock domains within an SoC. In at least one embodiment, SoC interface 2537 enables receipt of command buffers from a command streamer and global thread dispatcher that are configured to provide commands and instructions to each of one or more graphics cores within a graphics processor. In at least one embodiment, commands and instructions can be dispatched to media pipeline 2539, when media operations are to be performed, or a geometry and fixed function pipeline (e.g., geometry and fixed function pipeline 2536, geometry and fixed function pipeline 2514) when graphics processing operations are to be performed.

In at least one embodiment, graphics microcontroller 2538 can be configured to perform various scheduling and management tasks for graphics core 2500. In at least one embodiment, graphics microcontroller 2538 can perform graphics and/or compute workload scheduling on various graphics parallel engines within execution unit (EU) arrays 2502A-2502F, 2504A-2504F within sub-cores 2501A-2501F. In at least one embodiment, host software executing on a CPU core of an SoC including graphics core 2500 can submit workloads one of multiple graphic processor doorbells, which invokes a scheduling operation on an appropriate graphics engine. In at least one embodiment, scheduling operations include determining which workload to run next, submitting a workload to a command streamer, pre-empting existing workloads running on an engine, monitoring progress of a workload, and notifying host software when a workload is complete. In at least one embodiment, graphics microcontroller 2538 can also facilitate low-power or idle states for graphics core 2500, providing graphics core 2500 with an ability to save and restore registers within graphics core 2500 across low-power state transitions independently from an operating system and/or graphics driver software on a system.

In at least one embodiment, graphics core 2500 may have greater than or fewer than illustrated sub-cores 2501A-2501F, up to N modular sub-cores. For each set of N sub-cores, in at least one embodiment, graphics core 2500 can also include shared function logic 2510, shared and/or cache memory 2512, a geometry/fixed function pipeline 2514, as well as additional fixed function logic 2516 to accelerate various graphics and compute processing operations. In at least one embodiment, shared function logic 2510 can include logic units (e.g., sampler, math, and/or inter-thread communication logic) that can be shared by each N sub-cores within graphics core 2500. In at least one embodiment fixed, shared and/or cache memory 2512 can be a last-level cache for N sub-cores 2501A-2501F within graphics core 2500 and can also serve as shared memory that is accessible by multiple sub-cores. In at least one embodiment, geometry/fixed function pipeline 2514 can be included instead of geometry/fixed function pipeline 2536 within fixed function block 2530 and can include same or similar logic units.

In at least one embodiment, graphics core 2500 includes additional fixed function logic 2516 that can include various fixed function acceleration logic for use by graphics core 2500. In at least one embodiment, additional fixed function logic 2516 includes an additional geometry pipeline for use in position only shading. In position-only shading, at least two geometry pipelines exist, whereas in a full geometry pipeline within geometry/fixed function pipeline 2516, 2536, and a cull pipeline, which is an additional geometry pipeline which may be included within additional fixed function logic 2516. In at least one embodiment, cull pipeline is a trimmed down version of a full geometry pipeline. In at least one embodiment, a full pipeline and a cull pipeline can execute different instances of an application, each instance having a separate context. In at least one embodiment, position only shading can hide long cull runs of discarded triangles, enabling shading to be completed earlier in some instances. For example, in at least one embodiment, cull pipeline logic within additional fixed function logic 2516 can execute position shaders in parallel with a main application and generally generates critical results faster than a full pipeline, as cull pipeline fetches and shades position attribute of vertices, without performing rasterization and rendering of pixels to a frame buffer. In at least one embodiment, cull pipeline can use generated critical results to compute visibility information for all triangles without regard to whether those triangles are culled. In at least one embodiment, full pipeline (which in this instance may be referred to as a replay pipeline) can consume visibility information to skip culled triangles to shade only visible triangles that are finally passed to a rasterization phase.

In at least one embodiment, additional fixed function logic 2516 can also include machine-learning acceleration logic, such as fixed function matrix multiplication logic, for implementations including optimizations for machine learning training or inferencing.

In at least one embodiment, within each graphics sub-core 2501A-2501F includes a set of execution resources that may be used to perform graphics, media, and compute operations in response to requests by graphics pipeline, media pipeline, or shader programs. In at least one embodiment, graphics sub-cores 2501A-2501F include multiple EU arrays 2502A-2502F, 2504A-2504F, thread dispatch and inter-thread communication (TD/IC) logic 2503A-2503F, a 3D (e.g., texture) sampler 2505A-2505F, a media sampler 2506A-2506F, a shader processor 2507A-2507F, and shared local memory (SLM) 2508A-2508F. EU arrays 2502A-2502F, 2504A-2504F each include multiple execution units, which are general-purpose graphics processing units capable of performing floating-point and integer/fixed-point logic operations in service of a graphics, media, or compute operation, including graphics, media, or compute shader programs. In at least one embodiment, TD/IC logic 2503A-2503F performs local thread dispatch and thread control operations for execution units within a sub-core and facilitate communication between threads executing on execution units of a sub-core. In at least one embodiment, 3D sampler 2505A-2505F can read texture or other 3D graphics related data into memory. In at least one embodiment, 3D sampler can read texture data differently based on a configured sample state and texture format associated with a given texture. In at least one embodiment, media sampler 2506A-2506F can perform similar read operations based on a type and format associated with media data. In at least one embodiment, each graphics sub-core 2501A-2501F can alternately include a unified 3D and media sampler. In at least one embodiment, threads executing on execution units within each of sub-cores 2501A-2501F can make use of shared local memory 2508A-2508F within each sub-core, to enable threads executing within a thread group to execute using a common pool of on-chip memory.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, portions or all of inference and/or training logic 615 may be incorporated into graphics processor 2510. For example, in at least one embodiment, training and/or inferencing techniques described herein may use one or more of ALUs embodied in graphics processor 2312, graphics microcontroller 2538, geometry & fixed function pipeline 2514 and 2536, or other logic in FIG. 24. Moreover, in at least one embodiment, inferencing and/or training operations described herein may be done using logic other than logic illustrated in FIG. 6A or 6B. In at least one embodiment, weight parameters may be stored in on-chip or off-chip memory and/or registers (shown or not shown) that configure ALUs of graphics processor 2500 to perform one or more machine learning algorithms, neural network architectures, use cases, or training techniques described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 26A:
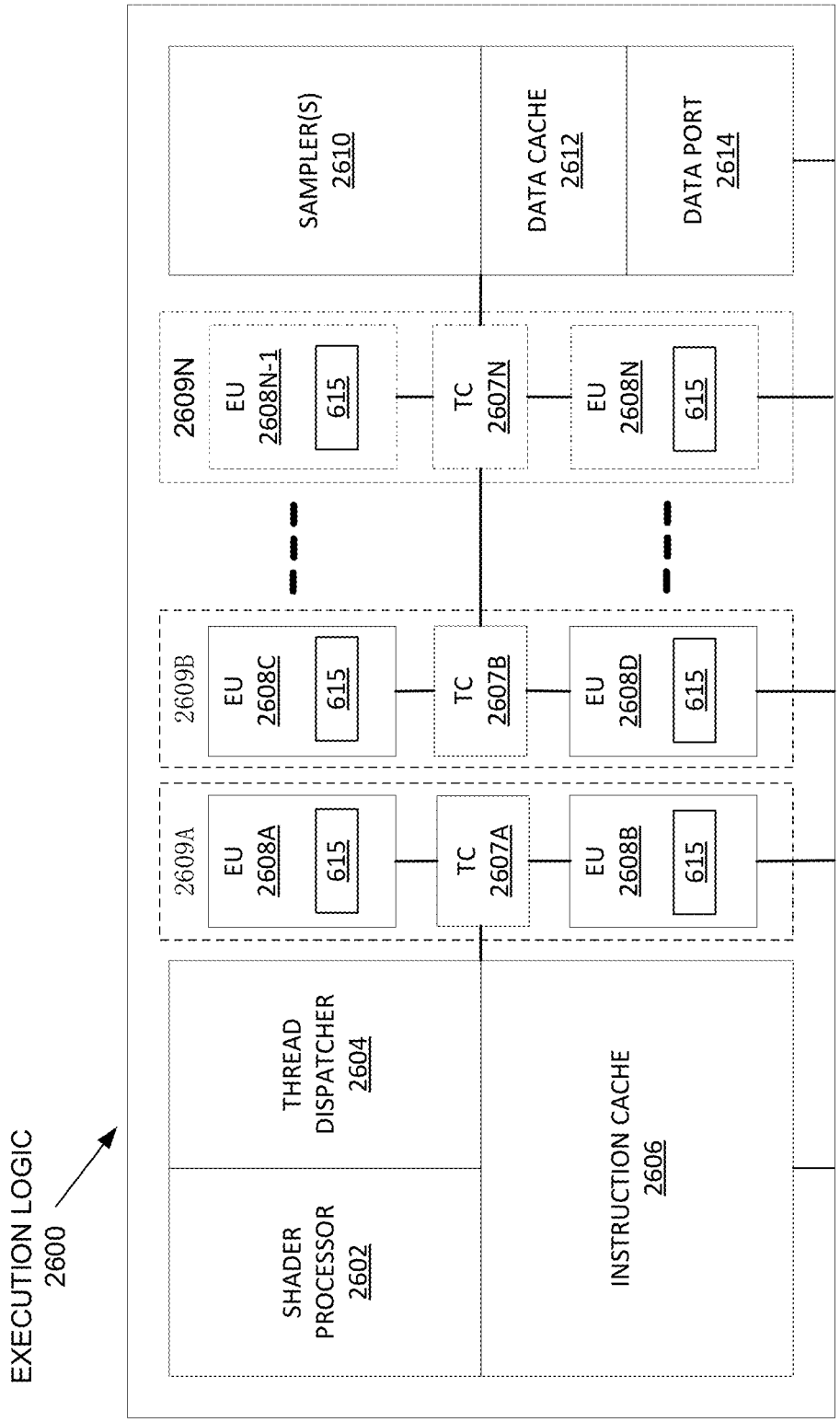
FIGS. 26A-26B illustrate at least portions of a graphics processor core, according to at least one embodiment.
Figure 26B:
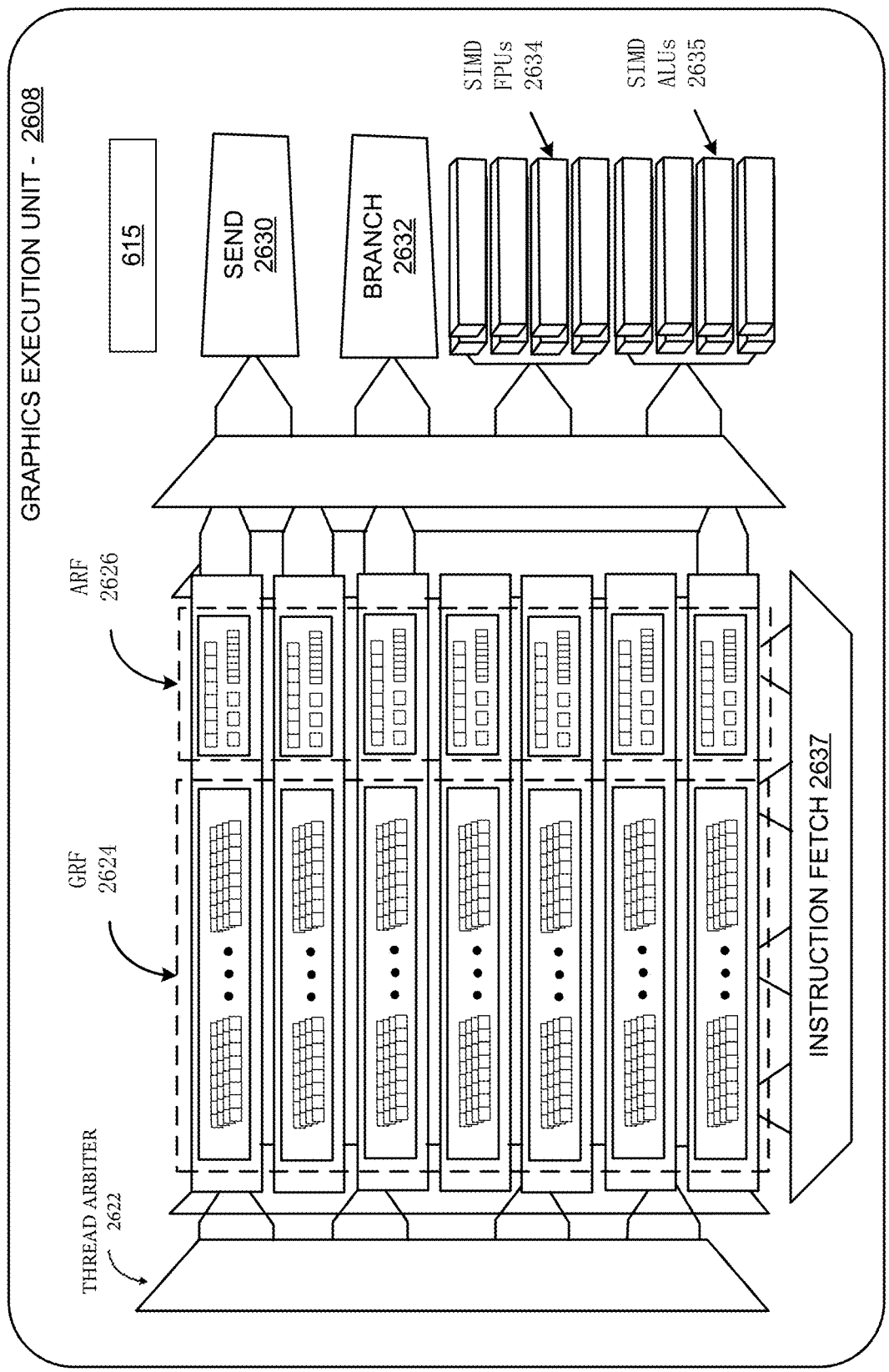

FIGS. 26A-26B illustrate thread execution logic 2600 including an array of processing elements of a graphics processor core according to at least one embodiment. FIG. 26A illustrates at least one embodiment, in which thread execution logic 2600 is used. FIG. 26B illustrates exemplary internal details of an execution unit, according to at least one embodiment.

As illustrated in FIG. 26A, in at least one embodiment, thread execution logic 2600 includes a shader processor 2602, a thread dispatcher 2604, instruction cache 2606, a scalable execution unit array including a plurality of execution units 2608A-2608N, sampler(s) 2610, a data cache 2612, and a data port 2614. In at least one embodiment a scalable execution unit array can dynamically scale by enabling or disabling one or more execution units (e.g., any of execution unit 2608A, 2608B, 2608C, 2608D, through 2608N-1 and 2608N) based on computational requirements of a workload, for example. In at least one embodiment, scalable execution units are interconnected via an interconnect fabric that links to each of execution unit. In at least one embodiment, thread execution logic 2600 includes one or more connections to memory, such as system memory or cache memory, through one or more of instruction cache 2606, data port 2614, sampler 2610, and execution units 2608A-2608N. In at least one embodiment, each execution unit (e.g., 2608A) is a stand-alone programmable general-purpose computational unit that is capable of executing multiple simultaneous hardware threads while processing multiple data elements in parallel for each thread. In at least one embodiment, array of execution units 2608A-2608N is scalable to include any number individual execution units.

In at least one embodiment, execution units 2608A-2608N are primarily used to execute shader programs. In at least one embodiment, shader processor 2602 can process various shader programs and dispatch execution threads associated with shader programs via a thread dispatcher 2604. In at least one embodiment, thread dispatcher 2604 includes logic to arbitrate thread initiation requests from graphics and media pipelines and instantiate requested threads on one or more execution units in execution units 2608A-2608N. For example, in at least one embodiment, a geometry pipeline can dispatch vertex, tessellation, or geometry shaders to thread execution logic for processing. In at least one embodiment, thread dispatcher 2604 can also process runtime thread spawning requests from executing shader programs.

In at least one embodiment, execution units 2608A-2608N support an instruction set that includes native support for many standard 3D graphics shader instructions, such that shader programs from graphics libraries (e.g., Direct 3D and OpenGL) are executed with a minimal translation. In at least one embodiment, execution units support vertex and geometry processing (e.g., vertex programs, geometry programs, vertex shaders), pixel processing (e.g., pixel shaders, fragment shaders) and general-purpose processing (e.g., compute and media shaders). In at least one embodiment, each of execution units 2608A-2608N, which include one or more arithmetic logic units (ALUs), is capable of multi-issue single instruction multiple data (SIMD) execution and multi-threaded operation enables an efficient execution environment despite higher latency memory accesses. In at least one embodiment, each hardware thread within each execution unit has a dedicated high-bandwidth register file and associated independent thread-state. In at least one embodiment, execution is multi-issue per clock to pipelines capable of integer, single and double precision floating point operations, SIMD branch capability, logical operations, transcendental operations, and other miscellaneous operations. In at least one embodiment, while waiting for data from memory or one of shared functions, dependency logic within execution units 2608A-2608N causes a waiting thread to sleep until requested data has been returned. In at least one embodiment, while a waiting thread is sleeping, hardware resources may be devoted to processing other threads. For example, in at least one embodiment, during a delay associated with a vertex shader operation, an execution unit can perform operations for a pixel shader, fragment shader, or another type of shader program, including a different vertex shader.

In at least one embodiment, each execution unit in execution units 2608A-2608N operates on arrays of data elements. In at least one embodiment, a number of data elements is "execution size," or number of channels for an instruction. In at least one embodiment, an execution channel is a logical unit of execution for data element access, masking, and flow control within instructions. In at least one embodiment, a number of channels may be independent of a number of physical Arithmetic Logic Units (ALUs) or Floating Point Units (FPUs) for a particular graphics processor. In at least one embodiment, execution units 2608A-2608N support integer and floating-point data types.

In at least one embodiment, an execution unit instruction set includes SIMD instructions. In at least one embodiment, various data elements can be stored as a packed data type in a register and execution unit will process various elements based on data size of elements. For example, in at least one embodiment, when operating on a 256-bit wide vector, 256 bits of a vector are stored in a register and an execution unit operates on a vector as four separate 64-bit packed data elements (Quad-Word (QW) size data elements), eight separate 32-bit packed data elements (Double Word (DW) size data elements), sixteen separate 16-bit packed data elements (Word (W) size data elements), or thirty-two separate 8-bit data elements (byte (B) size data elements). However, in at least one embodiment, different vector widths and register sizes are possible.

In at least one embodiment, one or more execution units can be combined into a fused execution unit 2609A-2609N having thread control logic (2607A-2607N) that is common to fused EUs. In at least one embodiment, multiple EUs can be fused into an EU group. In at least one embodiment, each EU in fused EU group can be configured to execute a separate SIMD hardware thread. Number of EUs in a fused EU group can vary according to various embodiments. In at least one embodiment, various SIMD widths can be performed per-EU, including but not limited to SIMD8, SIMD16, and SIMD32. In at least one embodiment, each fused graphics execution unit 2609A-2609N includes at least two execution units. For example, in at least one embodiment, fused execution unit 2609A includes a first EU 2608A, second EU 2608B, and thread control logic 2607A that is common to first EU 2608A and second EU 2608B. In at least one embodiment, thread control logic 2607A controls threads executed on fused graphics execution unit 2609A, allowing each EU within fused execution units 2609A-2609N to execute using a common instruction pointer register.

In at least one embodiment, one or more internal instruction caches (e.g., 2606) are included in thread execution logic 2600 to cache thread instructions for execution units. In at least one embodiment, one or more data caches (e.g., 2612) are included to cache thread data during thread execution. In at least one embodiment, a sampler 2610 is included to provide texture sampling for 3D operations and media sampling for media operations. In at least one embodiment, sampler 2610 includes specialized texture or media sampling functionality to process texture or media data during a sampling process before providing sampled data to an execution unit.

During execution, in at least one embodiment, graphics and media pipelines send thread initiation requests to thread execution logic 2600 via thread spawning and dispatch logic. In at least one embodiment, once a group of geometric objects has been processed and rasterized into pixel data, pixel processor logic (e.g., pixel shader logic, fragment shader logic, etc.) within shader processor 2602 is invoked to further compute output information and cause results to be written to output surfaces (e.g., color buffers, depth buffers, stencil buffers, etc.). In at least one embodiment, a pixel shader or fragment shader calculates values of various vertex attributes that are to be interpolated across a rasterized object. In at least one embodiment, pixel processor logic within shader processor 2602 then executes an application programming interface (API)-supplied pixel or fragment shader program. In at least one embodiment, to execute a shader program, shader processor 2602 dispatches threads to an execution unit (e.g., 2608A) via thread dispatcher 2604. In at least one embodiment, shader processor 2602 uses texture sampling logic in sampler 2610 to access texture data in texture maps stored in memory. In at least one embodiment, arithmetic operations on texture data and input geometry data compute pixel color data for each geometric fragment, or discards one or more pixels from further processing.

In at least one embodiment, data port 2614 provides a memory access mechanism for thread execution logic 2600 to output processed data to memory for further processing on a graphics processor output pipeline. In at least one embodiment, data port 2614 includes or couples to one or more cache memories (e.g., data cache 2612) to cache data for memory access via a data port.

As illustrated in FIG. 26B, in at least one embodiment, a graphics execution unit 2608 can include an instruction fetch unit 2637, a general register file array (GRF) 2624, an architectural register file array (ARF) 2626, a thread arbiter 2622, a send unit 2630, a branch unit 2632, a set of SIMD floating point units (FPUs) 2634, and, in at least one embodiment, a set of dedicated integer SIMD ALUs 2635. In at least one embodiment, GRF 2624 and ARF 2626 includes a set of general register files and architecture register files associated with each simultaneous hardware thread that may be active in graphics execution unit 2608. In at least one embodiment, per thread architectural state is maintained in ARF 2626, while data used during thread execution is stored in GRF 2624. In at least one embodiment, execution state of each thread, including instruction pointers for each thread, can be held in thread-specific registers in ARF 2626.

In at least one embodiment, graphics execution unit 2608 has an architecture that is a combination of Simultaneous Multi-Threading (SMT) and fine-grained Interleaved Multi-Threading (IMT). In at least one embodiment, architecture has a modular configuration that can be fine-tuned at design time based on a target number of simultaneous threads and number of registers per execution unit, where execution unit resources are divided across logic used to execute multiple simultaneous threads.

In at least one embodiment, graphics execution unit 2608 can co-issue multiple instructions, which may each be different instructions. In at least one embodiment, thread arbiter 2622 of graphics execution unit thread 2608 can dispatch instructions to one of send unit 2630, branch unit 2642, or SIMD FPU(s) 2634 for execution. In at least one embodiment, each execution thread can access 128 general-purpose registers within GRF 2624, where each register can store 32 bytes, accessible as a SIMD 8-element vector of 32-bit data elements. In at least one embodiment, each execution unit thread has access to 4 Kbytes within GRF 2624, although embodiments are not so limited, and greater or fewer register resources may be provided in other embodiments. In at least one embodiment, up to seven threads can execute simultaneously, although a number of threads per execution unit can also vary according to embodiments. In at least one embodiment, in which seven threads may access 4 Kbytes, GRF 2624 can store a total of 28 Kbytes. In at least one embodiment, flexible addressing modes can permit registers to be addressed together to build effectively wider registers or to represent strided rectangular block data structures.

In at least one embodiment, memory operations, sampler operations, and other longer-latency system communications are dispatched via "send" instructions that are executed by message passing send unit 2630. In at least one embodiment, branch instructions are dispatched to a dedicated branch unit 2632 to facilitate SIMD divergence and eventual convergence.

In at least one embodiment graphics execution unit 2608 includes one or more SIMD floating point units (FPU(s)) 2634 to perform floating-point operations. In at least one embodiment, FPU(s) 2634 also support integer computation. In at least one embodiment FPU(s) 2634 can SIMD execute up to M number of 32-bit floating-point (or integer) operations, or SIMD execute up to 2M 16-bit integer or 16-bit floating-point operations. In at least one embodiment, at least one of FPU(s) provides extended math capability to support high-throughput transcendental math functions and double precision 64-bit floating-point. In at least one embodiment, a set of 8-bit integer SIMD ALUs 2635 are also present, and may be specifically optimized to perform operations associated with machine learning computations.

In at least one embodiment, arrays of multiple instances of graphics execution unit 2608 can be instantiated in a graphics sub-core grouping (e.g., a sub-slice). In at least one embodiment, execution unit 2608 can execute instructions across a plurality of execution channels. In at least one embodiment, each thread executed on graphics execution unit 2608 is executed on a different channel.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, portions or all of inference and/or training logic 615 may be incorporated into execution logic 2600. Moreover, in at least one embodiment, inferencing and/or training operations described herein may be done using logic other than logic illustrated in FIG. 6A or 6B. In at least one embodiment, weight parameters may be stored in on-chip or off-chip memory and/or registers (shown or not shown) that configure ALUs of execution logic 2600 to perform one or more machine learning algorithms, neural network architectures, use cases, or training techniques described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 27:
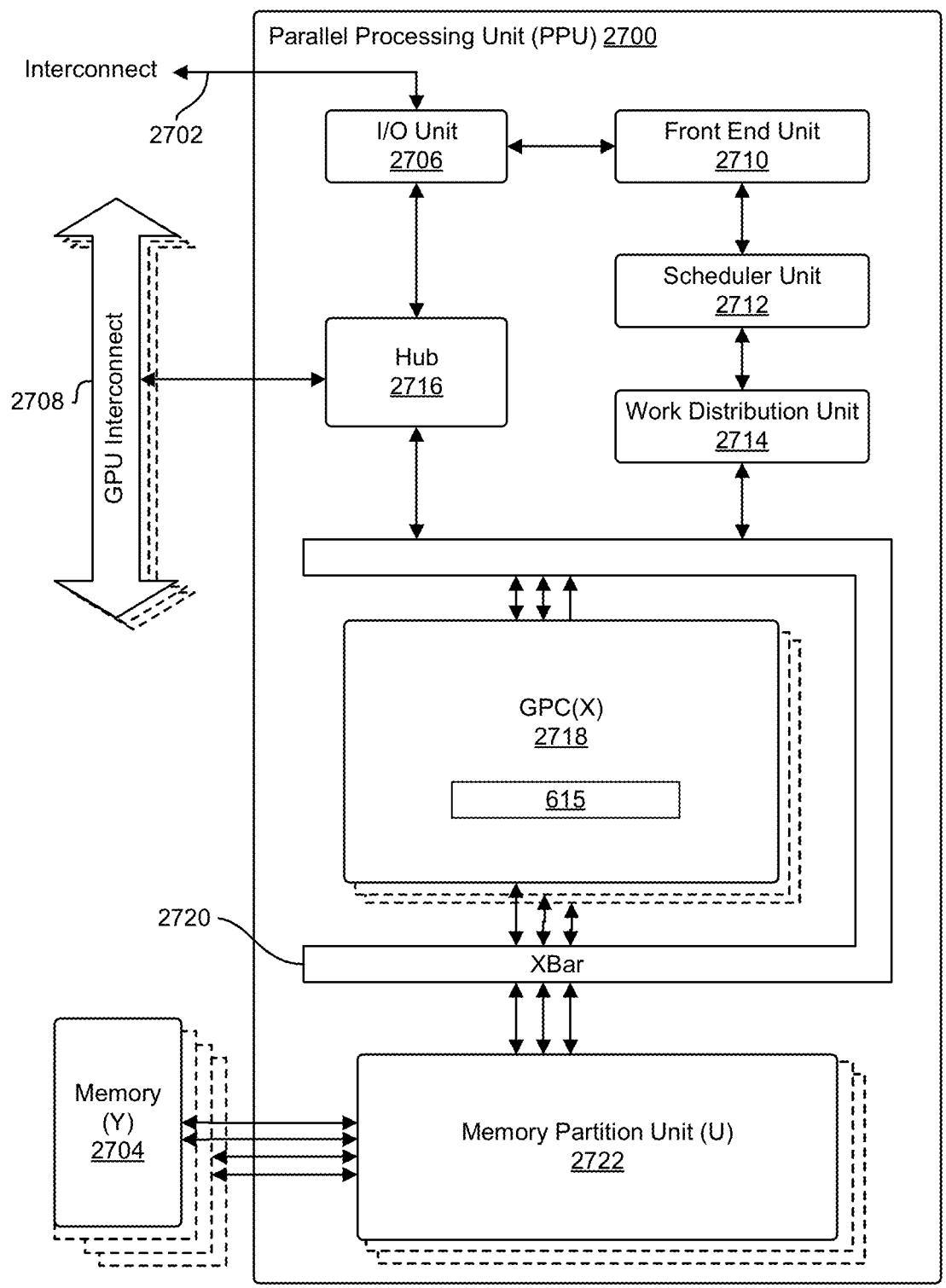
FIG. 27 illustrates a parallel processing unit ("PPU"), according to at least one embodiment.

FIG. 27 illustrates a parallel processing unit ("PPU") 2700, according to at least one embodiment. In at least one embodiment, PPU 2700 is configured with machine-readable code that, if executed by PPU 2700, causes PPU 2700 to perform some or all of processes and techniques described throughout this disclosure. In at least one embodiment, PPU 2700 is a multi-threaded processor that is implemented on one or more integrated circuit devices and that utilizes multithreading as a latency-hiding technique designed to process computer-readable instructions (also referred to as machine-readable instructions or simply instructions) on multiple threads in parallel. In at least one embodiment, a thread refers to a thread of execution and is an instantiation of a set of instructions configured to be executed by PPU 2700. In at least one embodiment, PPU 2700 is a graphics processing unit ("GPU") configured to implement a graphics rendering pipeline for processing three-dimensional ("3D") graphics data in order to generate two-dimensional ("2D") image data for display on a display device such as a liquid crystal display ("LCD") device. In at least one embodiment, PPU 2700 is utilized to perform computations such as linear algebra operations and machine-learning operations. FIG. 27 illustrates an example parallel processor for illustrative purposes only and should be construed as a non-limiting example of processor architectures contemplated within scope of this disclosure and that any suitable processor may be employed to supplement and/or substitute for same.

In at least one embodiment, one or more PPUs 2700 are configured to accelerate High Performance Computing ("HPC"), data center, and machine learning applications. In at least one embodiment, PPU 2700 is configured to accelerate deep learning systems and applications including following non-limiting examples: autonomous vehicle platforms, deep learning, high-accuracy speech, image, text recognition systems, intelligent video analytics, molecular simulations, drug discovery, disease diagnosis, weather forecasting, big data analytics, astronomy, molecular dynamics simulation, financial modeling, robotics, factory automation, real-time language translation, online search optimizations, and personalized user recommendations, and more.

In at least one embodiment, PPU 2700 includes, without limitation, an Input/Output ("I/O") unit 2706, a front-end unit 2710, a scheduler unit 2712, a work distribution unit 2714, a hub 2716, a crossbar ("Xbar") 2720, one or more general processing clusters ("GPCs") 2718, and one or more partition units ("memory partition units") 2722. In at least one embodiment, PPU 2700 is connected to a host processor or other PPUs 2700 via one or more high-speed GPU interconnects ("GPU interconnects") 2708. In at least one embodiment, PPU 2700 is connected to a host processor or other peripheral devices via an interconnect 2702. In at least one embodiment, PPU 2700 is connected to a local memory comprising one or more memory devices ("memory") 2704. In at least one embodiment, memory devices 2704 include, without limitation, one or more dynamic random access memory ("DRAM") devices. In at least one embodiment, one or more DRAM devices are configured and/or configurable as high-bandwidth memory ("HBM") subsystems, with multiple DRAM dies stacked within each device.

In at least one embodiment, high-speed GPU interconnect 2708 may refer to a wire-based multi-lane communications link that is used by systems to scale and include one or more PPUs 2700 combined with one or more central processing units ("CPUs"), supports cache coherence between PPUs 2700 and CPUs, and CPU mastering. In at least one embodiment, data and/or commands are transmitted by high-speed GPU interconnect 2708 through hub 2716 to/from other units of PPU 2700 such as one or more copy engines, video encoders, video decoders, power management units, and other components which may not be explicitly illustrated in FIG. 27.

In at least one embodiment, I/O unit 2706 is configured to transmit and receive communications (e.g., commands, data) from a host processor (not illustrated in FIG. 27) over system bus 2702. In at least one embodiment, I/O unit 2706 communicates with host processor directly via system bus 2702 or through one or more intermediate devices such as a memory bridge. In at least one embodiment, I/O unit 2706 may communicate with one or more other processors, such as one or more of PPUs 2700 via system bus 2702. In at least one embodiment, I/O unit 2706 implements a Peripheral Component Interconnect Express ("PCIe") interface for communications over a PCIe bus. In at least one embodiment, I/O unit 2706 implements interfaces for communicating with external devices.

In at least one embodiment, I/O unit 2706 decodes packets received via system bus 2702. In at least one embodiment, at least some packets represent commands configured to cause PPU 2700 to perform various operations. In at least one embodiment, I/O unit 2706 transmits decoded commands to various other units of PPU 2700 as specified by commands. In at least one embodiment, commands are transmitted to front-end unit 2710 and/or transmitted to hub 2716 or other units of PPU 2700 such as one or more copy engines, a video encoder, a video decoder, a power management unit, etc. (not explicitly illustrated in FIG. 27). In at least one embodiment, I/O unit 2706 is configured to route communications between and among various logical units of PPU 2700.

In at least one embodiment, a program executed by host processor encodes a command stream in a buffer that provides workloads to PPU 2700 for processing. In at least one embodiment, a workload comprises instructions and data to be processed by those instructions. In at least one embodiment, buffer is a region in a memory that is accessible (e.g., read/write) by both host processor and PPU 2700-a host interface unit may be configured to access buffer in a system memory connected to system bus 2702 via memory requests transmitted over system bus 2702 by I/O unit 2706. In at least one embodiment, host processor writes command stream to buffer and then transmits a pointer to start of command stream to PPU 2700 such that front-end unit 2710 receives pointers to one or more command streams and manages one or more command streams, reading commands from command streams and forwarding commands to various units of PPU 2700.

In at least one embodiment, front-end unit 2710 is coupled to scheduler unit 2712 that configures various GPCs 2718 to process tasks defined by one or more command streams. In at least one embodiment, scheduler unit 2712 is configured to track state information related to various tasks managed by scheduler unit 2712 where state information may indicate which of GPCs 2718 a task is assigned to, whether task is active or inactive, a priority level associated with task, and so forth. In at least one embodiment, scheduler unit 2712 manages execution of a plurality of tasks on one or more of GPCs 2718.

In at least one embodiment, scheduler unit 2712 is coupled to work distribution unit 2714 that is configured to dispatch tasks for execution on GPCs 2718. In at least one embodiment, work distribution unit 2714 tracks a number of scheduled tasks received from scheduler unit 2712 and work distribution unit 2714 manages a pending task pool and an active task pool for each of GPCs 2718. In at least one embodiment, pending task pool comprises a number of slots (e.g., 32 slots) that contain tasks assigned to be processed by a particular GPC 2718; active task pool may comprise a number of slots (e.g., 4 slots) for tasks that are actively being processed by GPCs 2718 such that as one of GPCs 2718 completes execution of a task, that task is evicted from active task pool for GPC 2718 and one of other tasks from pending task pool is selected and scheduled for execution on GPC 2718. In at least one embodiment, if an active task is idle on GPC 2718, such as while waiting for a data dependency to be resolved, then active task is evicted from GPC 2718 and returned to pending task pool while another task in pending task pool is selected and scheduled for execution on GPC 2718.

In at least one embodiment, work distribution unit 2714 communicates with one or more GPCs 2718 via XBar 2720. In at least one embodiment, XBar 2720 is an interconnect network that couples many of units of PPU 2700 to other units of PPU 2700 and can be configured to couple work distribution unit 2714 to a particular GPC 2718. In at least one embodiment, one or more other units of PPU 2700 may also be connected to XBar 2720 via hub 2716.

In at least one embodiment, tasks are managed by scheduler unit 2712 and dispatched to one of GPCs 2718 by work distribution unit 2714. GPC 2718 is configured to process task and generate results. In at least one embodiment, results may be consumed by other tasks within GPC 2718, routed to a different GPC 2718 via XBar 2720, or stored in memory 2704. In at least one embodiment, results can be written to memory 2704 via partition units 2722, which implement a memory interface for reading and writing data to/from memory 2704. In at least one embodiment, results can be transmitted to another PPU 2704 or CPU via high-speed GPU interconnect 2708. In at least one embodiment, PPU 2700 includes, without limitation, a number U of partition units 2722 that is equal to number of separate and distinct memory devices 2704 coupled to PPU 2700. In at least one embodiment, partition unit 2722 will be described in more detail below in conjunction with FIG. 29.

In at least one embodiment, a host processor executes a driver kernel that implements an application programming interface ("API") that enables one or more applications executing on host processor to schedule operations for execution on PPU 2700. In at least one embodiment, multiple compute applications are simultaneously executed by PPU 2700 and PPU 2700 provides isolation, quality of service ("QoS"), and independent address spaces for multiple compute applications. In at least one embodiment, an application generates instructions (e.g., in form of API calls) that cause driver kernel to generate one or more tasks for execution by PPU 2700 and driver kernel outputs tasks to one or more streams being processed by PPU 2700. In at least one embodiment, each task comprises one or more groups of related threads, which may be referred to as a warp. In at least one embodiment, a warp comprises a plurality of related threads (e.g., 32 threads) that can be executed in parallel. In at least one embodiment, cooperating threads can refer to a plurality of threads including instructions to perform task and that exchange data through shared memory. In at least one embodiment, threads and cooperating threads are described in more detail, in accordance with at least one embodiment, in conjunction with FIG. 29.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, deep learning application processor is used to train a machine learning model, such as a neural network, to predict or infer information provided to PPU 2700. In at least one embodiment, PPU 2700 is used to infer or predict information based on a trained machine learning model (e.g., neural network) that has been trained by another processor or system or by PPU 2700. In at least one embodiment, PPU 2700 may be used to perform one or more neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 28:
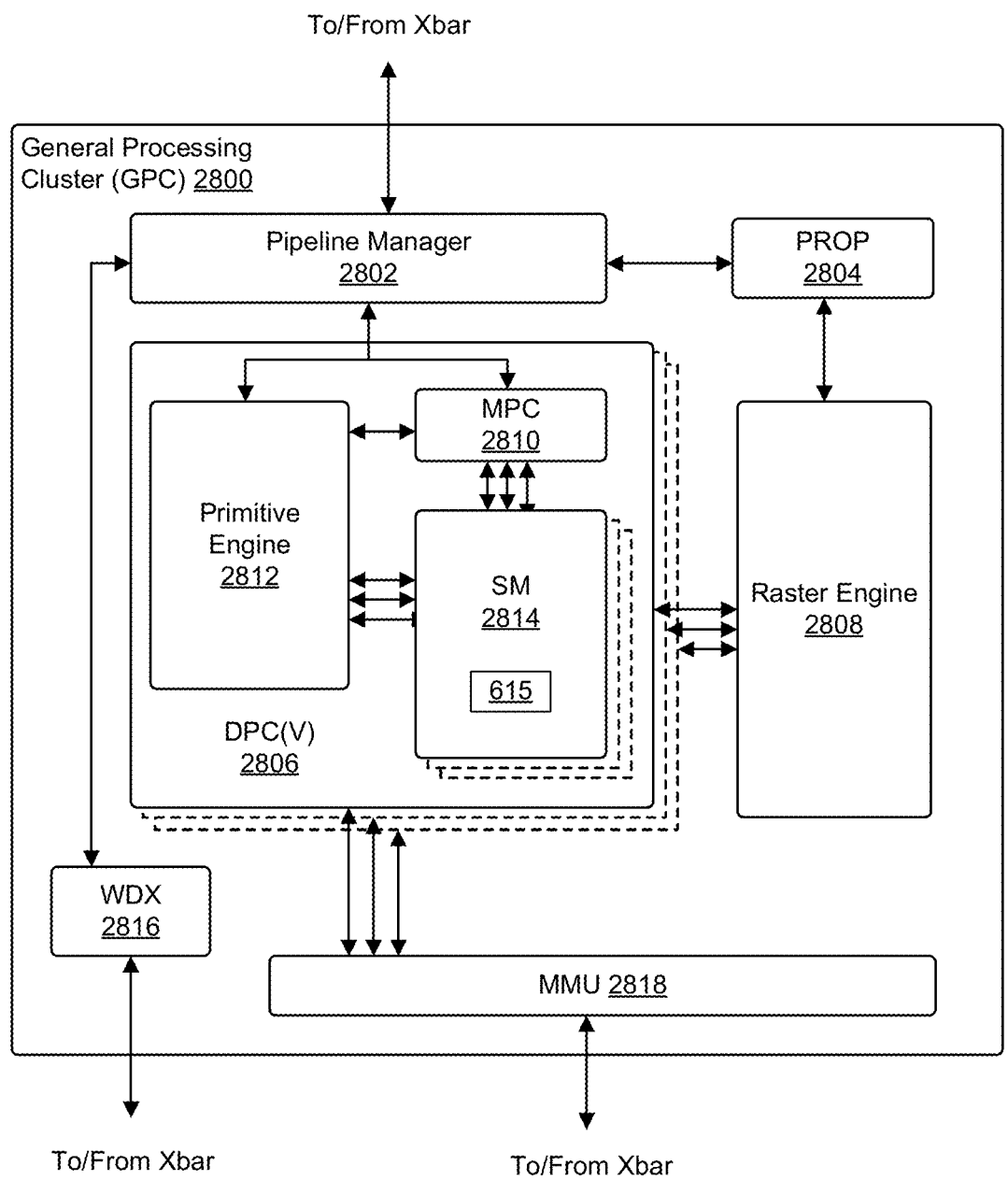
FIG. 28 illustrates a general processing cluster ("GPC"), according to at least one embodiment.

FIG. 28 illustrates a general processing cluster ("GPC") 2800, according to at least one embodiment. In at least one embodiment, GPC 2800 is GPC 2718 of FIG. 27. In at least one embodiment, each GPC 2800 includes, without limitation, a number of hardware units for processing tasks and each GPC 2800 includes, without limitation, a pipeline manager 2802, a pre-raster operations unit ("PROP") 2804, a raster engine 2808, a work distribution crossbar ("WDX") 2816, a memory management unit ("MMU") 2818, one or more Data Processing Clusters ("DPCs") 2806, and any suitable combination of parts.

In at least one embodiment, operation of GPC 2800 is controlled by pipeline manager 2802. In at least one embodiment, pipeline manager 2802 manages configuration of one or more DPCs 2806 for processing tasks allocated to GPC 2800. In at least one embodiment, pipeline manager 2802 configures at least one of one or more DPCs 2806 to implement at least a portion of a graphics rendering pipeline. In at least one embodiment, DPC 2806 is configured to execute a vertex shader program on a programmable streaming multi-processor ("SM") 2814. In at least one embodiment, pipeline manager 2802 is configured to route packets received from a work distribution unit to appropriate logical units within GPC 2800, in at least one embodiment, and some packets may be routed to fixed function hardware units in PROP 2804 and/or raster engine 2808 while other packets may be routed to DPCs 2806 for processing by a primitive engine 2812 or SM 2814. In at least one embodiment, pipeline manager 2802 configures at least one of DPCs 2806 to implement a neural network model and/or a computing pipeline.

In at least one embodiment, PROP unit 2804 is configured, in at least one embodiment, to route data generated by raster engine 2808 and DPCs 2806 to a Raster Operations ("ROP") unit in partition unit 2722, described in more detail above in conjunction with FIG. 27. In at least one embodiment, PROP unit 2804 is configured to perform optimizations for color blending, organize pixel data, perform address translations, and more. In at least one embodiment, raster engine 2808 includes, without limitation, a number of fixed function hardware units configured to perform various raster operations, in at least one embodiment, and raster engine 2808 includes, without limitation, a setup engine, a coarse raster engine, a culling engine, a clipping engine, a fine raster engine, a tile coalescing engine, and any suitable combination thereof. In at least one embodiment, setup engine receives transformed vertices and generates plane equations associated with geometric primitive defined by vertices; plane equations are transmitted to coarse raster engine to generate coverage information (e.g., an x, y coverage mask for a tile) for primitive; output of coarse raster engine is transmitted to culling engine where fragments associated with primitive that fail a z-test are culled, and transmitted to a clipping engine where fragments lying outside a viewing frustum are clipped. In at least one embodiment, fragments that survive clipping and culling are passed to fine raster engine to generate attributes for pixel fragments based on plane equations generated by setup engine. In at least one embodiment, output of raster engine 2808 comprises fragments to be processed by any suitable entity such as by a fragment shader implemented within DPC 2806.

In at least one embodiment, each DPC 2806 included in GPC 2800 comprise, without limitation, an M-Pipe Controller ("MPC") 2810; primitive engine 2812; one or more SMs 2814; and any suitable combination thereof. In at least one embodiment, MPC 2810 controls operation of DPC 2806, routing packets received from pipeline manager 2802 to appropriate units in DPC 2806. In at least one embodiment, packets associated with a vertex are routed to primitive engine 2812, which is configured to fetch vertex attributes associated with vertex from memory; in contrast, packets associated with a shader program may be transmitted to SM 2814.

In at least one embodiment, SM 2814 comprises, without limitation, a programmable streaming processor that is configured to process tasks represented by a number of threads. In at least one embodiment, SM 2814 is multi-threaded and configured to execute a plurality of threads (e.g., 32 threads) from a particular group of threads concurrently and implements a Single-Instruction, Multiple-Data ("SIMD") architecture where each thread in a group of threads (e.g., a warp) is configured to process a different set of data based on same set of instructions. In at least one embodiment, all threads in group of threads execute same instructions. In at least one embodiment, SM 2814 implements a Single-Instruction, Multiple Thread ("SIMT") architecture wherein each thread in a group of threads is configured to process a different set of data based on same set of instructions, but where individual threads in group of threads are allowed to diverge during execution. In at least one embodiment, a program counter, call stack, and execution state is maintained for each warp, enabling concurrency between warps and serial execution within warps when threads within warp diverge. In another embodiment, a program counter, call stack, and execution state is maintained for each individual thread, enabling equal concurrency between all threads, within and between warps. In at least one embodiment, execution state is maintained for each individual thread and threads executing same instructions may be converged and executed in parallel for better efficiency. At least one embodiment of SM 2814 are described in more detail below.

In at least one embodiment, MMU 2818 provides an interface between GPC 2800 and memory partition unit (e.g., partition unit 2722 of FIG. 27) and MMU 2818 provides translation of virtual addresses into physical addresses, memory protection, and arbitration of memory requests. In at least one embodiment, MMU 2818 provides one or more translation lookaside buffers ("TLBs") for performing translation of virtual addresses into physical addresses in memory.

Inference and/or training logic 615 are used to perform inferencing and/or training operations associated with one or more embodiments. Details regarding inference and/or training logic 615 are provided below in conjunction with FIGS.

6A and/or 6B. In at least one embodiment, deep learning application processor is used to train a machine learning model, such as a neural network, to predict or infer information provided to GPC 2800. In at least one embodiment, GPC 2800 is used to infer or predict information based on a trained machine learning model (e.g., neural network) that has been trained by another processor or system or by GPC 2800. In at least one embodiment, GPC 2800 may be used to perform one or more neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Figure 29:
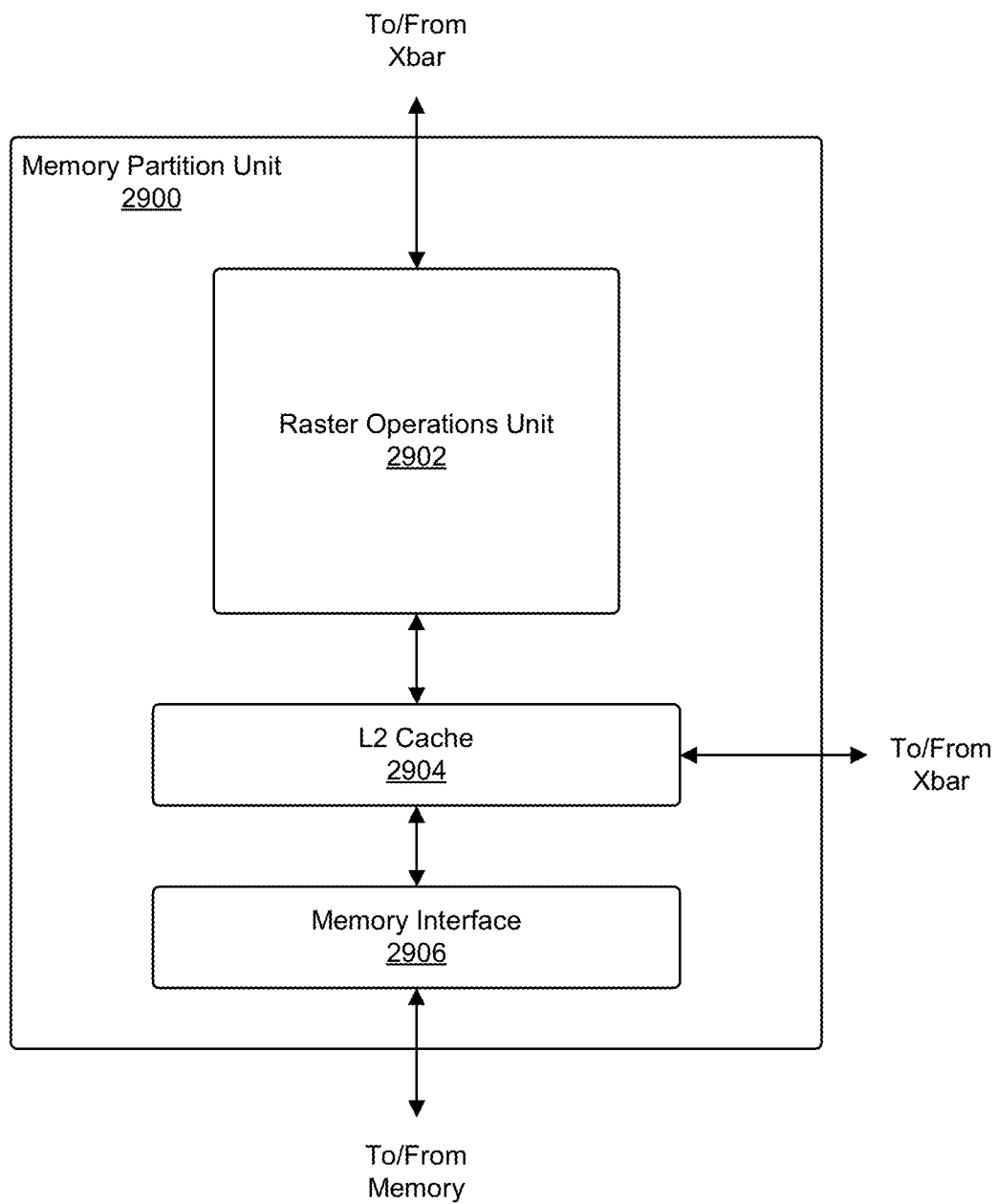
FIG. 29 illustrates a memory partition unit of a parallel processing unit ("PPU"), according to at least one embodiment.

FIG. 29 illustrates a memory partition unit 2900 of a parallel processing unit ("PPU"), in accordance with at least one embodiment. In at least one embodiment, memory partition unit 2900 includes, without limitation, a Raster Operations ("ROP") unit 2902; a level two ("L2") cache 2904; a memory interface 2906; and any suitable combination thereof. In at least one embodiment, memory interface 2906 is coupled to memory. In at least one embodiment, memory interface 2906 may implement 32, 64, 128, 1024-bit data buses, or similar implementations, for high-speed data transfer. In at least one embodiment, PPU incorporates U memory interfaces 2906, one memory interface 2906 per pair of partition units 2900, where each pair of partition units 2900 is connected to a corresponding memory device. For example, in at least one embodiment, PPU may be connected to up to Y memory devices, such as high bandwidth memory stacks or graphics double-data-rate, version 5, synchronous dynamic random a29ess memory ("GDDR5 SDRAM").

In at least one embodiment, memory interface 2906 implements a high bandwidth memory second generation ("HBM2") memory interface and Y equals half U. In at least one embodiment, HBM2 memory stacks are located on same physical package as PPU, providing substantial power and area savings compared with conventional GDDR5 SDRAM systems. In at least one embodiment, each HBM2 stack includes, without limitation, four memory dies and Y equals 4, with each HBM2 stack including two 128-bit channels per die for a total of 8 channels and a data bus width of 1024 bits. In at least one embodiment, memory supports Single-Error Correcting Double-Error Detecting ("SECDED") Error Correction Code ("ECC") to protect data. In at least one embodiment, ECC provides higher reliability for compute applications that are sensitive to data corruption.

In at least one embodiment, PPU implements a multi-level memory hierarchy. In at least one embodiment, memory partition unit 2900 supports a unified memory to provide a single unified virtual address space for central processing unit ("CPU") and PPU memory, enabling data sharing between virtual memory systems. In at least one embodiment, frequency of accesses by a PPU to memory located on other processors is traced to ensure that memory pages are moved to physical memory of PPU that is accessing pages more frequently. In at least one embodiment, high-speed GPU interconnect 2708 supports address translation services allowing PPU to directly access a CPU's page tables and providing full access to CPU memory by PPU.

In at least one embodiment, copy engines transfer data between multiple PPUs or between PPUs and CPUs. In at least one embodiment, copy engines can generate page faults for addresses that are not mapped into page tables and memory partition unit 2900 then services page faults, mapping addresses into page table, after which copy engine performs transfer. In at least one embodiment, memory is pinned (i.e., non-pageable) for multiple copy engine operations between multiple processors, substantially reducing available memory. In at least one embodiment, with hardware page faulting, addresses can be passed to copy engines without regard as to whether memory pages are resident, and copy process is transparent.

Data from memory 2704 of FIG. 27 or other system memory is fetched by memory partition unit 2900 and stored in L2 cache 2904, which is located on-chip and is shared between various GPCs, in accordance with at least one embodiment. Each memory partition unit 2900, in at least one embodiment, includes, without limitation, at least a portion of L2 cache associated with a corresponding memory device. In at least one embodiment, lower level caches are implemented in various units within GPCs. In at least one embodiment, each of SMs 2814 may implement a level one ("L1") cache wherein L1 cache is private memory that is dedicated to a particular SM 2814 and data from L2 cache 2904 is fetched and stored in each of L1 caches for processing in functional units of SMs 2814. In at least one embodiment, L2 cache 2904 is coupled to memory interface 2906 and XBar 2720.

ROP unit 2902 performs graphics raster operations related to pixel color, such as color compression, pixel blending, and more, in at least one embodiment. ROP unit 2902, in at least one embodiment, implements depth testing in conjunction with raster engine 2808, receiving a depth for a sample location associated with a pixel fragment from culling engine of raster engine 2808. In at least one embodiment, depth is tested against a corresponding depth in a depth buffer for a sample location associated with fragment. In at least one embodiment, if fragment passes depth test for sample location, then ROP unit 2902 updates depth buffer and transmits a result of depth test to raster engine 2808. It will be appreciated that number of partition units 2900 may be different than number of GPCs and, therefore, each ROP unit 2902 can, in at least one embodiment, be coupled to each of GPCs. In at least one embodiment, ROP unit 2902 tracks packets received from different GPCs and determines which that a result generated by ROP unit 2902 is routed to through XBar 2720.

Figure 30:
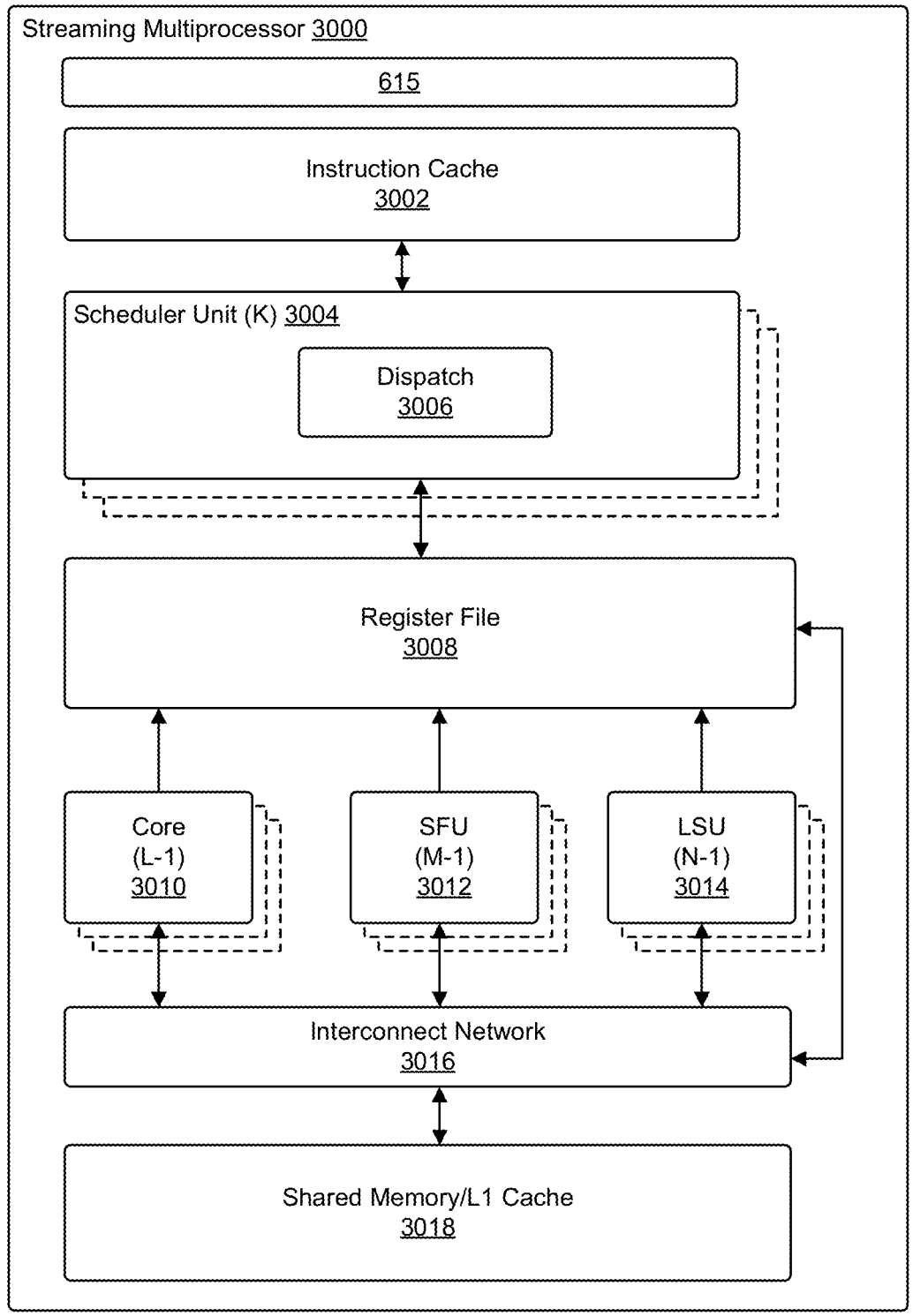
FIG. 30 illustrates a streaming multi-processor, according to at least one embodiment.

FIG. 30 illustrates a streaming multi-processor ("SM") 3000, according to at least one embodiment. In at least one embodiment, SM 3000 is SM 2814 of FIG. 28. In at least one embodiment, SM 3000 includes, without limitation, an instruction cache 3002; one or more scheduler units 3004; a register file 3008; one or more processing cores ("cores") 3010; one or more special function units ("SFUs") 3012; one or more load/store units ("LSUs") 3014; an interconnect network 3016; a shared memory/level one ("L1") cache 3018; and any suitable combination thereof. In at least one embodiment, a work distribution unit dispatches tasks for execution on general processing clusters ("GPCs") of parallel processing units ("PPUs") and each task is allocated to a particular Data Processing Cluster ("DPC") within a GPC and, if task is associated with a shader program, task is allocated to one of SMs 3000. In at least one embodiment, scheduler unit 3004 receives tasks from work distribution unit and manages instruction scheduling for one or more thread blocks assigned to SM 3000. In at least one embodiment, scheduler unit 3004 schedules thread blocks for execution as warps of parallel threads, wherein each thread block is allocated at least one warp. In at least one embodiment, each warp executes threads. In at least one embodiment, scheduler unit 3004 manages a plurality of different thread blocks, allocating warps to different thread blocks and then dispatching instructions from plurality of different cooperative groups to various functional units (e.g., processing cores 3010, SFUs 3012, and LSUs 3014) during each clock cycle.

In at least one embodiment, Cooperative Groups may refer to a programming model for organizing groups of communicating threads that allows developers to express granularity at which threads are communicating, enabling expression of richer, more efficient parallel decompositions. In at least one embodiment, cooperative launch APIs support synchronization amongst thread blocks for execution of parallel algorithms. In at least one embodiment, applications of conventional programming models provide a single, simple construct for synchronizing cooperating threads: a barrier across all threads of a thread block (e.g., syncthreads ( ) function). However, In at least one embodiment, programmers may define groups of threads at smaller than thread block granularities and synchronize within defined groups to enable greater performance, design flexibility, and software reuse in form of collective group-wide function interfaces. In at least one embodiment, Cooperative Groups enables programmers to define groups of threads explicitly at sub-block (i.e., as small as a single thread) and multi-block granularities, and to perform collective operations such as synchronization on threads in a cooperative group. In at least one embodiment, programming model supports clean composition across software boundaries, so that libraries and utility functions can synchronize safely within their local context without having to make assumptions about convergence. In at least one embodiment, Cooperative Groups primitives enable new patterns of cooperative parallelism, including, without limitation, producer-consumer parallelism, opportunistic parallelism, and global synchronization across an entire grid of thread blocks.

In at least one embodiment, a dispatch unit 3006 is configured to transmit instructions to one or more of functional units and scheduler unit 3004 includes, without limitation, two dispatch units 3006 that enable two different instructions from same warp to be dispatched during each clock cycle. In at least one embodiment, each scheduler unit 3004 includes a single dispatch unit 3006 or additional dispatch units 3006.

In at least one embodiment, each SM 3000, in at least one embodiment, includes, without limitation, register file 3008 that provides a set of registers for functional units of SM 3000. In at least one embodiment, register file 3008 is divided between each of functional units such that each functional unit is allocated a dedicated portion of register file 3008. In at least one embodiment, register file 3008 is divided between different warps being executed by SM 3000 and register file 3008 provides temporary storage for operands connected to data paths of functional units. In at least one embodiment, each SM 3000 comprises, without limitation, a plurality of L processing cores 3010. In at least one embodiment, SM 3000 includes, without limitation, a large number (e.g., 128 or more) of distinct processing cores 3010. In at least one embodiment, each processing core 3010, in at least one embodiment, includes, without limitation, a fully-pipelined, single-precision, double-precision, and/or mixed precision processing unit that includes, without limitation, a floating point arithmetic logic unit and an integer arithmetic logic unit. In at least one embodiment, floating point arithmetic logic units implement IEEE 754-2008 standard for floating point arithmetic. In at least one embodiment, processing cores 3010 include, without limitation, 64 single-precision (32-bit) floating point cores, 64 integer cores, 32 double-precision (64-bit) floating point cores, and 8 tensor cores.

Tensor cores are configured to perform matrix operations in accordance with at least one embodiment. In at least one embodiment, one or more tensor cores are included in processing cores 3010. In at least one embodiment, tensor cores are configured to perform deep learning matrix arithmetic, such as convolution operations for neural network training and inferencing. In at least one embodiment, each tensor core operates on a 4×4 matrix and performs a matrix multiply and accumulate operation $D=A\times B+C$, where A, B, C, and D are 4×4 matrices.

In at least one embodiment, matrix multiply inputs A and B are 16-bit floating point matrices and accumulation matrices C and D are 16-bit floating point or 32-bit floating point matrices. In at least one embodiment, tensor cores operate on 16-bit floating point input data with 32-bit floating point accumulation. In at least one embodiment, 16-bit floating point multiply uses 64 operations and results in a full precision product that is then accumulated using 32-bit floating point addition with other intermediate products for a 4×4×4 matrix multiply. Tensor cores are used to perform much larger two-dimensional or higher dimensional matrix operations, built up from these smaller elements, in at least one embodiment. In at least one embodiment, an API, such as CUDA 9 C++ API, exposes specialized matrix load, matrix multiply and accumulate, and matrix store operations to efficiently use tensor cores from a CUDA-C++ program. In at least one embodiment, at CUDA level, warp-level interface assumes 16×16 size matrices spanning all 32 threads of warp.

In at least one embodiment, each SM 3000 comprises, without limitation, M SFUs 3012 that perform special functions (e.g., attribute evaluation, reciprocal square root, etc.). In at least one embodiment, SFUs 3012 include, without limitation, a tree traversal unit configured to traverse a hierarchical tree data structure. In at least one embodiment, SFUs 3012 include, without limitation, a texture unit configured to perform texture map filtering operations. In at least one embodiment, texture units are configured to load texture maps (e.g., a 2D array of texels) from memory and sample texture maps to produce sampled texture values for use in shader programs executed by SM 3000. In at least one embodiment, texture maps are stored in shared memory/L1 cache 3018. In at least one embodiment, texture units implement texture operations such as filtering operations using mip-maps (e.g., texture maps of varying levels of detail), in accordance with at least one embodiment. In at least one embodiment, each SM 3000 includes, without limitation, two texture units.

Each SM 3000 comprises, without limitation, N LSUs 3014 that implement load and store operations between shared memory/L1 cache 3018 and register file 3008, in at least one embodiment. Each SM 3000 includes, without limitation, interconnect network 3016 that connects each of functional units to register file 3008 and LSU 3014 to register file 3008 and shared memory/L1 cache 3018 in at least one embodiment. In at least one embodiment, interconnect network 3016 is a crossbar that can be configured to connect any of functional units to any of registers in register file 3008 and connect LSUs 3014 to register file 3008 and memory locations in shared memory/L1 cache 3018.

In at least one embodiment, shared memory/L1 cache 3018 is an array of on-chip memory that allows for data storage and communication between SM 3000 and primitive engine and between threads in SM 3000, in at least one embodiment. In at least one embodiment, shared memory/L1 cache 3018 comprises, without limitation, 128 KB of storage capacity and is in path from SM 3000 to partition unit. In at least one embodiment, shared memory/L1 cache 3018, in at least one embodiment, is used to cache reads and writes. In at least one embodiment, one or more of shared memory/L1 cache 3018, L2 cache, and memory are backing stores.

Combining data cache and shared memory functionality into a single memory block provides improved performance for both types of memory accesses, in at least one embodiment. In at least one embodiment, capacity is used or is usable as a cache by programs that do not use shared memory, such as if shared memory is configured to use half of capacity, texture and load/store operations can use remaining capacity. Integration within shared memory/L1 cache 3018 enables shared memory/L1 cache 3018 to function as a high-throughput conduit for streaming data while simultaneously providing high-bandwidth and low-latency access to frequently reused data, in accordance with at least one embodiment. In at least one embodiment, when configured for general purpose parallel computation, a simpler configuration can be used compared with graphics processing. In at least one embodiment, fixed function graphics processing units are bypassed, creating a much simpler programming model. In general purpose parallel computation configuration, work distribution unit assigns and distributes blocks of threads directly to DPCs, in at least one embodiment. In at least one embodiment, threads in a block execute same program, using a unique thread ID in calculation to ensure each thread generates unique results, using SM 3000 to execute program and perform calculations, shared memory/L1 cache 3018 to communicate between threads, and LSU 3014 to read and write global memory through shared memory/L1 cache 3018 and memory partition unit. In at least one embodiment, when configured for general purpose parallel computation, SM 3000 writes commands that scheduler unit 3004 can use to launch new work on DPCs.

In at least one embodiment, PPU is included in or coupled to a desktop computer, a laptop computer, a tablet computer, servers, supercomputers, a smart-phone (e.g., a wireless, hand-held device), personal digital assistant ("PDA"), a digital camera, a vehicle, a head mounted display, a hand-held electronic device, and more. In at least one embodiment, PPU is embodied on a single semiconductor substrate. In at least one embodiment, PPU is included in a system-on-a-chip ("SoC") along with one or more other devices such as additional PPUs, memory, a reduced instruction set computer ("RISC") CPU, a memory management unit ("MMU"), a digital-to-analog converter ("DAC"), and like.

In at least one embodiment, PPU may be included on a graphics card that includes one or more memory devices. A graphics card may be configured to interface with a PCIe slot on a motherboard of a desktop computer. In at least one embodiment, PPU may be an integrated graphics processing unit ("iGPU") included in chipset of motherboard.

Inference and/or training logic 615 are used to perform inferencing and/or training operations associated with one or more embodiments. Details regarding inference and/or training logic 615 are provided below in conjunction with FIGS. 6A and/or 6B. In at least one embodiment, deep learning application processor is used to train a machine learning model, such as a neural network, to predict or infer information provided to SM 3000. In at least one embodiment, SM 3000 is used to infer or predict information based on a trained machine learning model (e.g., neural network) that has been trained by another processor or system or by SM 3000. In at least one embodiment, SM 3000 may be used to perform one or more neural network use cases described herein.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

At least one embodiment of the disclosure can be described in view of the following clauses:

1. A processor, comprising:
   one or more circuits to use one or more neural networks to generate one or more ultrasound images of one or more objects based at least in part upon one or more acoustic properties of the one or more objects.

2. The processor of claim 1, wherein the one or more circuits are further to generate, based at least in part upon an annotated two-dimensional image of the one or more objects, one or more acoustic property maps of the one or more acoustic properties to be provided as input to the one or more neural networks.

3. The processor of claim 2, wherein the one or more circuits are further to generate the two-dimensional image based at least in part upon a cross-section taken from an annotated three-dimensional medical image.

4. The processor of claim 3, wherein the one or more circuits are to generate multiple two-dimensional images from different cross-sections of the annotated three-dimensional image and generate corresponding ultrasound images.

5. The processor of claim 2, wherein the one or more acoustic property maps indicate regions of different acoustic property values determined based at least in part upon types of the one or more objects represented in the two-dimensional image.

6. The processor of claim 1, wherein the one or more acoustic properties include at least one of attenuation, density, speed of sound, and non-linear coefficients of a wave equation.

7. A system comprising:
   one or more processors to use one or more neural networks to generate one or more ultrasound images of one or more objects based at least in part upon one or more acoustic properties of the one or more objects.

8 The system of claim 7, wherein the one or more processors are further to generate, based at least in part upon an annotated two-dimensional image of the one or more objects, one or more acoustic property maps of the one or more acoustic properties to be provided as input to the one or more neural networks.

9. The system of claim 8, wherein the one or more processors are further to generate the two-dimensional image based at least in part upon a cross-section taken from an annotated three-dimensional medical image.

10. The system of claim 9, wherein the one or more processors are further to generate multiple two-dimensional images from different cross-sections of the annotated three-dimensional image and generate corresponding ultrasound images.

11. The system of claim 8, wherein the one or more acoustic property maps indicate regions of different acoustic property values determined based at least in part upon types of the one or more objects represented in the two-dimensional image.

12. The system of claim 7, wherein the one or more acoustic properties include at least one of attenuation, density, speed of sound, and non-linear coefficients of a wave equation.

13. A method comprising:
using one or more neural networks to generate one or more ultrasound images of one or more objects based at least in part upon one or more acoustic properties of the one or more objects.

14. The method of claim 13, further comprising:
generating, based at least in part upon an annotated two-dimensional image of the one or more objects, one or more acoustic property maps of the one or more acoustic properties to be provided as input to the one or more neural networks.

15. The method of claim 14, further comprising:
generating the two-dimensional image based at least in part upon a cross-section taken from an annotated three-dimensional medical image er.

16. The method of claim 15, further comprising:
generating multiple two-dimensional images from different cross-sections of the annotated three-dimensional image and generate corresponding ultrasound images.

17. The method of claim 14, wherein the one or more acoustic property maps indicate regions of different acoustic property values determined based at least in part upon types of the one or more objects represented in the two-dimensional image.

18. The method of claim 13, wherein the one or more acoustic properties include at least one of attenuation, density, speed of sound, and non-linear coefficients of a wave equation.

19. A machine-readable medium having stored thereon a set of instructions, which if performed by one or more processors, cause the one or more processors to at least:
use one or more neural networks to generate one or more ultrasound images of one or more objects based at least in part upon one or more acoustic properties of the one or more objects.

20. The machine-readable medium of claim 19, wherein instructions if performed further cause the one or more processors to:
generate, based at least in part upon an annotated two-dimensional image of the one or more objects, one or more acoustic property maps of the one or more acoustic properties to be provided as input to the one or more neural networks.

21. The machine-readable medium of claim 20, wherein the one or more processors are further to generate the two-dimensional image based at least in part upon a cross-section taken from an annotated three-dimensional medical image.

22. The machine-readable medium of claim 21, wherein the one or more processors are further to generate multiple two-dimensional images from different cross-sections of the annotated three-dimensional image and generate corresponding ultrasound images.

23. The machine-readable medium of claim 20, wherein the one or more acoustic property maps indicate regions of different acoustic property values determined based at least in part upon types of the one or more objects represented in the two-dimensional image.

24. The machine-readable medium of claim 19, wherein the one or more acoustic properties include at least one of attenuation, density, speed of sound, and non-linear coefficients of a wave equation.

25. An ultrasound image generation system, comprising:
one or more processors to use one or more neural networks to generate one or more ultrasound images of one or more objects based at least in part upon one or more acoustic properties of the one or more objects; and memory for storing network parameters for the one or more neural networks.

26. The ultrasound image generation system of claim 25, wherein the one or more processors are further to generate, based at least in part upon an annotated two-dimensional image of the one or more objects, one or more acoustic property maps of the one or more acoustic properties to be provided as input to the one or more neural networks.

27. The ultrasound image generation system of claim 26, wherein the one or more processors are further to generate the two-dimensional image based at least in part upon a cross-section taken from an annotated three-dimensional medical image.

28. The ultrasound image generation system of claim 27, wherein the one or more processors are further to generate multiple two-dimensional images from different cross-sections of the annotated three-dimensional image and generate corresponding ultrasound images.

29. The ultrasound image generation system of claim 26, wherein the one or more acoustic property maps indicate regions of different acoustic property values determined based at least in part upon types of the one or more objects represented in the two-dimensional image.

30. The ultrasound image generation system of claim 25, wherein the one or more acoustic properties include at least one of attenuation, density, speed of sound, and non-linear coefficients of a wave equation.

In at least one embodiment, a single semiconductor platform may refer to a sole unitary semiconductor-based integrated circuit or chip. In at least one embodiment, multi-chip modules may be used with increased connectivity which simulate on-chip operation, and make substantial improvements over utilizing a conventional central processing unit ("CPU") and bus implementation. In at least one embodiment, various modules may also be situated separately or in various combinations of semiconductor platforms per desires of user.

In at least one embodiment, computer programs in form of machine-readable executable code or computer control logic algorithms are stored in main memory 1004 and/or secondary storage. Computer programs, if executed by one or more processors, enable system 1000 to perform various functions in accordance with at least one embodiment. In at least one embodiment, memory 1004, storage, and/or any other storage are possible examples of computer-readable media. In at least one embodiment, secondary storage may refer to any suitable storage device or system such as a hard disk drive and/or a removable storage drive, representing a floppy disk drive, a magnetic tape drive, a compact disk drive, digital versatile disk ("DVD") drive, recording device, universal serial bus ("USB") flash memory, etc. In at least one embodiment, architecture and/or functionality of various previous figures are implemented in context of CPU 1002; parallel processing system 1012; an integrated circuit capable of at least a portion of capabilities of both CPU 1002; parallel processing system 1012; a chipset (e.g., a group of integrated circuits designed to work and sold as a unit for performing related functions, etc.); and any suitable combination of integrated circuit(s).

In at least one embodiment, architecture and/or functionality of various previous figures are implemented in context of a general computer system, a circuit board system, a game console system dedicated for entertainment purposes, an application-specific system, and more. In at least one embodiment, computer system 1000 may take form of a desktop computer, a laptop computer, a tablet computer, servers, supercomputers, a smart-phone (e.g., a wireless, hand-held device), personal digital assistant ("PDA"), a digital camera, a vehicle, a head mounted display, a handheld electronic device, a mobile phone device, a television, workstation, game consoles, embedded system, and/or any other type of logic.

In at least one embodiment, parallel processing system 1012 includes, without limitation, a plurality of parallel processing units ("PPUs") 1014 and associated memories 1016. In at least one embodiment, PPUs 1014 are connected to a host processor or other peripheral devices via an interconnect 1018 and a switch 1020 or multiplexer. In at least one embodiment, parallel processing system 1012 distributes computational tasks across PPUs 1014 which can be parallelizable—for example, as part of distribution of computational tasks across multiple graphics processing unit ("GPU") thread blocks. In at least one embodiment, memory is shared and accessible (e.g., for read and/or write access) across some or all of PPUs 1014, although such shared memory may incur performance penalties relative to use of local memory and registers resident to a PPU 1014. In at least one embodiment, operation of PPUs 1014 is synchronized through use of a command such as syncthreads ( ) wherein all threads in a block (e.g., executed across multiple PPUs 1014) to reach a certain point of execution of code before proceeding.

Virtualized Computing Platform

Embodiments are disclosed related a virtualized computing platform for advanced computing, such as image inferencing and image processing in medical applications. Without limitation, embodiments may include radiography, magnetic resonance imaging (MRI), nuclear medicine, ultrasound, sonography, elastography, photoacoustic imaging, tomography, echocardiography, functional near-infrared spectroscopy, and magnetic particle imaging, or a combination thereof. In at least one embodiment, a virtualized computing platform and associated processes described herein may additionally or alternatively be used, without limitation, in forensic science analysis, sub-surface detection and imaging (e.g., oil exploration, archaeology, paleontology, etc.), topography, oceanography, geology, osteology, meteorology, intelligent area or object tracking and monitoring, sensor data processing (e.g., RADAR, SONAR, LIDAR, etc.), and/or genomics and gene sequencing.

Figure 31:
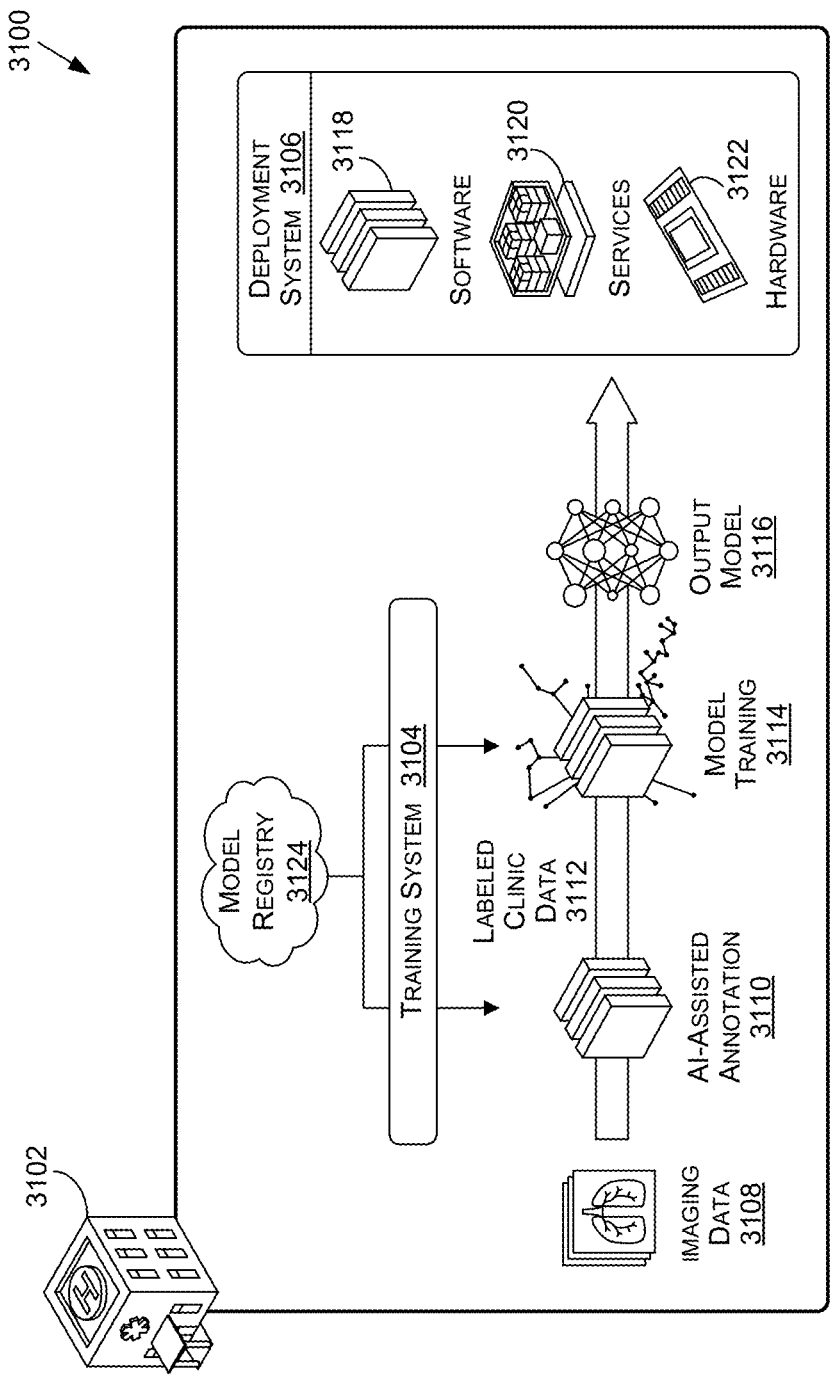
FIG. 31 is an example data flow diagram for an advanced computing pipeline, in accordance with at least one embodiment.

With reference to FIG. 31 is an example data flow diagram for a process 3100 of generating and deploying an image processing and inferencing pipeline, in accordance with at least one embodiment. In at least one embodiment, process 3100 may be deployed for use with imaging devices, processing devices, genomics devices, gene sequencing devices, radiology devices, and/or other device types at one or more facilities 3102, such as medical facilities, hospitals, healthcare institutes, clinics, research or diagnostic labs, etc. In at least one embodiment, process 3100 may be deployed to perform genomics analysis and inferencing on sequencing data. Examples of genomic analyses that may be performed using systems and processes described herein include, without limitation, variant calling, mutation detection, and gene expression quantification. Process 3100 may be executed within a training system 3104 and/or a deployment system 3106. In at least one embodiment, training system 3104 may be used to perform training, deployment, and implementation of machine learning models (e.g., neural networks, object detection algorithms, computer vision algorithms, etc.) for use in deployment system 3106. In at least one embodiment, deployment system 3106 may be configured to offload processing and compute resources among a distributed computing environment to reduce infrastructure requirements at facility 3102. In at least one embodiment, deployment system 3106 may provide a streamlined platform for selecting, customizing, and implementing virtual instruments for use with imaging devices (e.g., MRI, CT Scan, X-Ray, Ultrasound, etc.) or sequencing devices at facility 3102. In at least one embodiment, virtual instruments may include software-defined applications for performing one or more processing operations with respect to imaging data generated by imaging devices, sequencing devices, radiology devices, and/or other device types. In at least one embodiment, one or more applications in a pipeline may use or call upon services (e.g., inference, visualization, compute, AI, etc.) of deployment system 3106 during execution of applications.

In at least one embodiment, some of applications used in advanced processing and inferencing pipelines may use machine learning models or other AI to perform one or more processing steps. In at least one embodiment, machine learning models may be trained at facility 3102 using data 3108 (such as imaging data) generated at facility 3102 (and stored on one or more picture archiving and communication system (PACS) servers at facility 3102), may be trained using imaging or sequencing data 3108 from another facility(ies) (e.g., a different hospital, lab, clinic, etc.), or a combination thereof. In at least one embodiment, training system 3104 may be used to provide applications, services, and/or other resources for generating working, deployable machine learning models for deployment system 3106.

In at least one embodiment, model registry 3124 may be backed by object storage that may support versioning and object metadata. In at least one embodiment, object storage may be accessible through, for example, a cloud storage (e.g., cloud 3226 of FIG. 32) compatible application programming interface (API) from within a cloud platform. In at least one embodiment, machine learning models within model registry 3124 may uploaded, listed, modified, or deleted by developers or partners of a system interacting with an API. In at least one embodiment, an API may provide access to methods that allow users with appropriate credentials to associate models with applications, such that models may be executed as part of execution of containerized instantiations of applications.

In at least one embodiment, training pipeline 3204 (FIG. 32) may include a scenario where facility 3102 is training their own machine learning model, or has an existing machine learning model that needs to be optimized or updated. In at least one embodiment, imaging data 3108 generated by imaging device(s), sequencing devices, and/or other device types may be received. In at least one embodiment, once imaging data 3108 is received, AI-assisted annotation 3110 may be used to aid in generating annotations corresponding to imaging data 3108 to be used as ground truth data for a machine learning model. In at least one embodiment, AI-assisted annotation 3110 may include one or more machine learning models (e.g., convolutional neural networks (CNNs)) that may be trained to generate annotations corresponding to certain types of imaging data 3108 (e.g., from certain devices) and/or certain types of anomalies in imaging data 3108. In at least one embodiment, AI-assisted annotations 3110 may then be used directly, or may be adjusted or fine-tuned using an annotation tool (e.g., by a researcher, a clinician, a doctor, a scientist, etc.), to generate ground truth data. In at least one embodiment, in some examples, labeled clinic data 3112 (e.g., annotations provided by a clinician, doctor, scientist, technician, etc.) may be used as ground truth data for training a machine learning model. In at least one embodiment, AI-assisted annotations 3110, labeled clinic data 3112, or a combination thereof may be used as ground truth data for training a machine learning model. In at least one embodiment, a trained machine learning model may be referred to as output model 3116, and may be used by deployment system 3106, as described herein.

In at least one embodiment, training pipeline 3204 (FIG. 32) may include a scenario where facility 3102 needs a machine learning model for use in performing one or more processing tasks for one or more applications in deployment system 3106, but facility 3102 may not currently have such a machine learning model (or may not have a model that is optimized, efficient, or effective for such purposes). In at least one embodiment, an existing machine learning model may be selected from a model registry 3124. In at least one embodiment, model registry 3124 may include machine learning models trained to perform a variety of different inference tasks on imaging data. In at least one embodiment, machine learning models in model registry 3124 may have been trained on imaging data from different facilities than facility 3102 (e.g., facilities remotely located). In at least one embodiment, machine learning models may have been trained on imaging data from one location, two locations, or any number of locations. In at least one embodiment, when being trained on imaging data from a specific location, training may take place at that location, or at least in a manner that protects confidentiality of imaging data or restricts imaging data from being transferred off-premises (e.g., to comply with HIPAA regulations, privacy regulations, etc.). In at least one embodiment, once a model is trained-or partially trained—at one location, a machine learning model may be added to model registry 3124. In at least one embodiment, a machine learning model may then be retrained, or updated, at any number of other facilities, and a retrained or updated model may be made available in model registry 3124. In at least one embodiment, a machine learning model may then be selected from model registry 3124—and referred to as output model 3116—and may be used in deployment system 3106 to perform one or more processing tasks for one or more applications of a deployment system.

In at least one embodiment, training pipeline 3204 (FIG. 32), a scenario may include facility 3102 requiring a machine learning model for use in performing one or more processing tasks for one or more applications in deployment system 3106, but facility 3102 may not currently have such a machine learning model (or may not have a model that is optimized, efficient, or effective for such purposes). In at least one embodiment, a machine learning model selected from model registry 3124 may not be fine-tuned or optimized for imaging data 3108 generated at facility 3102 because of differences in populations, genetic variations, robustness of training data used to train a machine learning model, diversity in anomalies of training data, and/or other issues with training data. In at least one embodiment, AI-assisted annotation 3110 may be used to aid in generating annotations corresponding to imaging data 3108 to be used as ground truth data for retraining or updating a machine learning model. In at least one embodiment, labeled clinic data 3112 (e.g., annotations provided by a clinician, doctor, scientist, etc.) may be used as ground truth data for training a machine learning model. In at least one embodiment, retraining or updating a machine learning model may be referred to as model training 3114. In at least one embodiment, model training 3114—e.g., AI-assisted annotations 3110, labeled clinic data 3112, or a combination thereof—may be used as ground truth data for retraining or updating a machine learning model. In at least one embodiment, a trained machine learning model may be referred to as output model 3116, and may be used by deployment system 3106, as described herein.

In at least one embodiment, deployment system 3106 may include software 3118, services 3120, hardware 3122, and/or other components, features, and functionality. In at least one embodiment, deployment system 3106 may include a software "stack," such that software 3118 may be built on top of services 3120 and may use services 3120 to perform some or all of processing tasks, and services 3120 and software 3118 may be built on top of hardware 3122 and use hardware 3122 to execute processing, storage, and/or other compute tasks of deployment system 3106. In at least one embodiment, software 3118 may include any number of different containers, where each container may execute an instantiation of an application. In at least one embodiment, each application may perform one or more processing tasks in an advanced processing and inferencing pipeline (e.g., inferencing, object detection, feature detection, segmentation, image enhancement, calibration, etc.). In at least one embodiment, for each type of imaging device (e.g., CT, MRI, X-Ray, ultrasound, sonography, echocardiography, etc.), sequencing device, radiology device, genomics device, etc., there may be any number of containers that may perform a data processing task with respect to imaging data 3108 (or other data types, such as those described herein) generated by a device. In at least one embodiment, an advanced processing and inferencing pipeline may be defined based on selections of different containers that are desired or required for processing imaging data 3108, in addition to containers that receive and configure imaging data for use by each container and/or for use by facility 3102 after processing through a pipeline (e.g., to convert outputs back to a usable data type, such as digital imaging and communications in medicine (DICOM) data, radiology information system (RIS) data, clinical information system (CIS) data, remote procedure call (RPC) data, data substantially compliant with a representation state transfer (REST) interface, data substantially compliant with a file-based interface, and/or raw data, for storage and display at facility 3102). In at least one embodiment, a combination of containers within software 3118 (e.g., that make up a pipeline) may be referred to as a virtual instrument (as described in more detail herein), and a virtual instrument may leverage services 3120 and hardware 3122 to execute some or all processing tasks of applications instantiated in containers.

In at least one embodiment, a data processing pipeline may receive input data (e.g., imaging data 3108) in a DICOM, RIS, CIS, REST compliant, RPC, raw, and/or other format in response to an inference request (e.g., a request from a user of deployment system 3106, such as a clinician, a doctor, a radiologist, etc.). In at least one embodiment, input data may be representative of one or more images, video, and/or other data representations generated by one or more imaging devices, sequencing devices, radiology devices, genomics devices, and/or other device types. In at least one embodiment, data may undergo pre-processing as part of data processing pipeline to prepare data for processing by one or more applications. In at least one embodiment, post-processing may be performed on an output of one or more inferencing tasks or other processing tasks of a pipeline to prepare an output data for a next application and/or to prepare output data for transmission and/or use by a user (e.g., as a response to an inference request). In at least one embodiment, inferencing tasks may be performed by one or more machine learning models, such as trained or deployed neural networks, which may include output models 3116 of training system 3104.

In at least one embodiment, tasks of data processing pipeline may be encapsulated in a container(s) that each represent a discrete, fully functional instantiation of an application and virtualized computing environment that is able to reference machine learning models. In at least one embodiment, containers or applications may be published into a private (e.g., limited access) area of a container registry (described in more detail herein), and trained or deployed models may be stored in model registry 3124 and associated with one or more applications. In at least one embodiment, images of applications (e.g., container images) may be available in a container registry, and once selected by a user from a container registry for deployment in a pipeline, an image may be used to generate a container for an instantiation of an application for use by a user's system.

In at least one embodiment, developers (e.g., software developers, clinicians, doctors, etc.) may develop, publish, and store applications (e.g., as containers) for performing image processing and/or inferencing on supplied data. In at least one embodiment, development, publishing, and/or storing may be performed using a software development kit (SDK) associated with a system (e.g., to ensure that an application and/or container developed is compliant with or compatible with a system). In at least one embodiment, an application that is developed may be tested locally (e.g., at a first facility, on data from a first facility) with an SDK which may support at least some of services 3120 as a system (e.g., system 3200 of FIG. 32). In at least one embodiment, because DICOM objects may contain anywhere from one to hundreds of images or other data types, and due to a variation in data, a developer may be responsible for managing (e.g., setting constructs for, building pre-processing into an application, etc.) extraction and preparation of incoming DICOM data. In at least one embodiment, once validated by system 3200 (e.g., for accuracy, safety, patient privacy, etc.), an application may be available in a container registry for selection and/or implementation by a user (e.g., a hospital, clinic, lab, healthcare provider, etc.) to perform one or more processing tasks with respect to data at a facility (e.g., a second facility) of a user.

Figure 32:
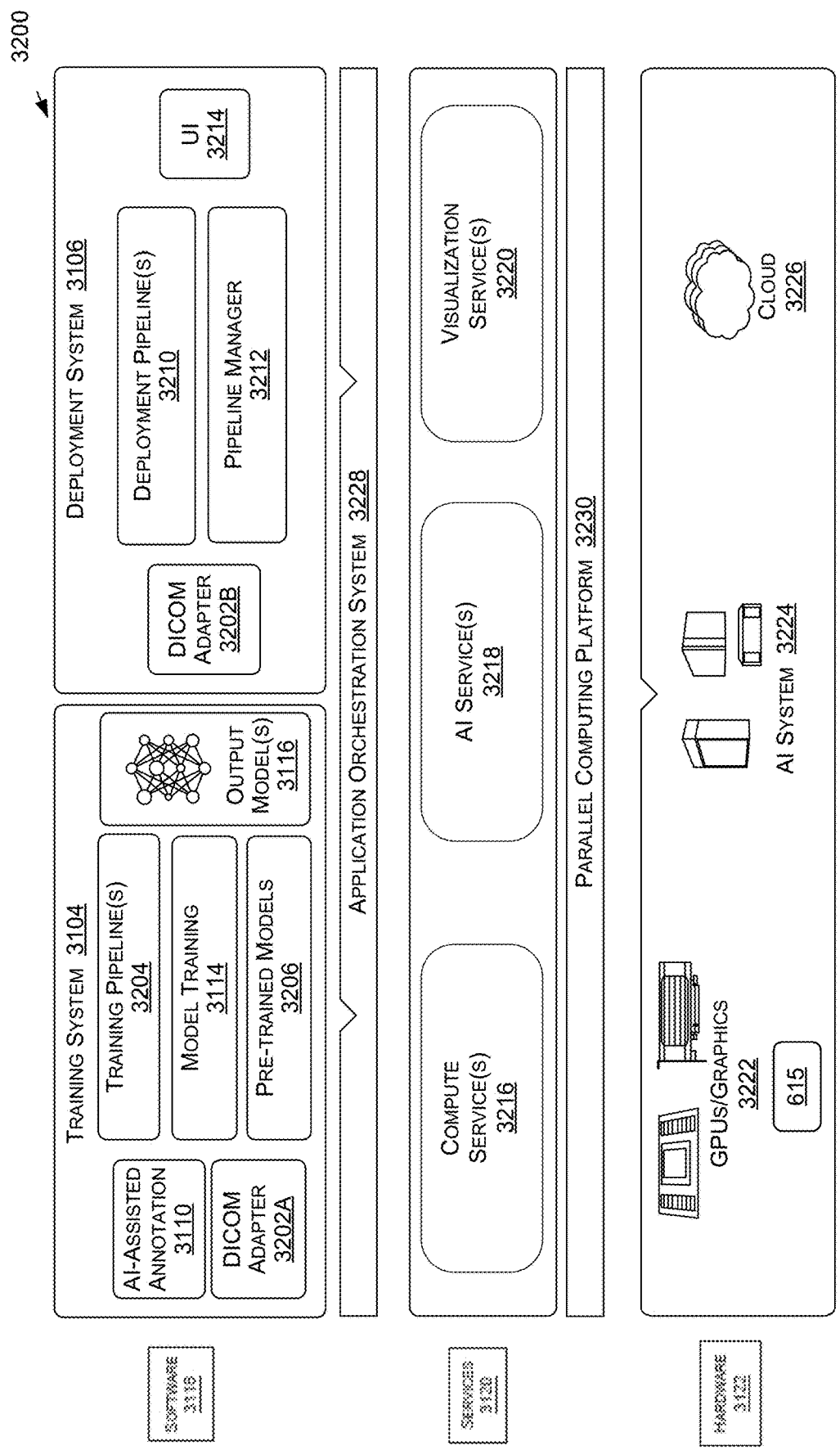
FIG. 32 is a system diagram for an example system for training, adapting, instantiating and deploying machine learning models in an advanced computing pipeline, in accordance with at least one embodiment.

In at least one embodiment, developers may then share applications or containers through a network for access and use by users of a system (e.g., system 3200 of FIG. 32). In at least one embodiment, completed and validated applications or containers may be stored in a container registry and associated machine learning models may be stored in model registry 3124. In at least one embodiment, a requesting entity (e.g., a user at a medical facility)-who provides an inference or image processing request—may browse a container registry and/or model registry 3124 for an application, container, dataset, machine learning model, etc., select a desired combination of elements for inclusion in data processing pipeline, and submit an imaging processing request. In at least one embodiment, a request may include input data (and associated patient data, in some examples) that is necessary to perform a request, and/or may include a selection of application(s) and/or machine learning models to be executed in processing a request. In at least one embodiment, a request may then be passed to one or more components of deployment system 3106 (e.g., a cloud) to perform processing of data processing pipeline. In at least one embodiment, processing by deployment system 3106 may include referencing selected elements (e.g., applications, containers, models, etc.) from a container registry and/or model registry 3124. In at least one embodiment, once results are generated by a pipeline, results may be returned to a user for reference (e.g., for viewing in a viewing application suite executing on a local, on-premises workstation or terminal). In at least one embodiment, a radiologist may receive results from an data processing pipeline including any number of application and/or containers, where results may include anomaly detection in X-rays, CT scans, MRIs, etc.

In at least one embodiment, to aid in processing or execution of applications or containers in pipelines, services 3120 may be leveraged. In at least one embodiment, services 3120 may include compute services, artificial intelligence (AI) services, visualization services, and/or other service types. In at least one embodiment, services 3120 may provide functionality that is common to one or more applications in software 3118, so functionality may be abstracted to a service that may be called upon or leveraged by applications. In at least one embodiment, functionality provided by services 3120 may run dynamically and more efficiently, while also scaling well by allowing applications to process data in parallel (e.g., using a parallel computing platform 3230 (FIG. 32)). In at least one embodiment, rather than each application that shares a same functionality offered by a service 3120 being required to have a respective instance of service 3120, service 3120 may be shared between and among various applications. In at least one embodiment, services may include an inference server or engine that may be used for executing detection or segmentation tasks, as non-limiting examples. In at least one embodiment, a model training service may be included that may provide machine learning model training and/or retraining capabilities. In at least one embodiment, a data augmentation service may further be included that may provide GPU accelerated data (e.g., DICOM, RIS, CIS, REST compliant, RPC, raw, etc.) extraction, resizing, scaling, and/or other augmentation. In at least one embodiment, a visualization service may be used that may add image rendering effects-such as ray-tracing, rasterization, denoising, sharpening, etc.—to add realism to two-dimensional (2D) and/or three-dimensional (3D) models. In at least one embodiment, virtual instrument services may be included that provide for beam-forming, segmentation, inferencing, imaging, and/or support for other applications within pipelines of virtual instruments.

In at least one embodiment, where a service 3120 includes an AI service (e.g., an inference service), one or more machine learning models associated with an application for anomaly detection (e.g., tumors, growth abnormalities, scarring, etc.) may be executed by calling upon (e.g., as an API call) an inference service (e.g., an inference server) to execute machine learning model(s), or processing thereof, as part of application execution. In at least one embodiment, where another application includes one or more machine learning models for segmentation tasks, an application may call upon an inference service to execute machine learning models for performing one or more of processing operations associated with segmentation tasks. In at least one embodiment, software 3118 implementing advanced processing and inferencing pipeline that includes segmentation application and anomaly detection application may be streamlined because each application may call upon a same inference service to perform one or more inferencing tasks.

In at least one embodiment, hardware 3122 may include GPUs, CPUs, graphics cards, an AI/deep learning system (e.g., an AI supercomputer, such as NVIDIA's DGX), a cloud platform, or a combination thereof. In at least one embodiment, different types of hardware 3122 may be used to provide efficient, purpose-built support for software 3118 and services 3120 in deployment system 3106. In at least one embodiment, use of GPU processing may be implemented for processing locally (e.g., at facility 3102), within an AI/deep learning system, in a cloud system, and/or in other processing components of deployment system 3106 to improve efficiency, accuracy, and efficacy of image processing, image reconstruction, segmentation, MRI exams, stroke or heart attack detection (e.g., in real-time), image quality in rendering, etc. In at least one embodiment, a facility may include imaging devices, genomics devices, sequencing devices, and/or other device types on-premises that may leverage GPUs to generate imaging data representative of a subject's anatomy. In at least one embodiment, software 3118 and/or services 3120 may be optimized for GPU processing with respect to deep learning, machine learning, and/or high-performance computing, as non-limiting examples. In at least one embodiment, at least some of computing environment of deployment system 3106 and/or training system 3104 may be executed in a datacenter one or more supercomputers or high performance computing systems, with GPU optimized software (e.g., hardware and software combination of NVIDIA's DGX System). In at least one embodiment, datacenters may be compliant with provisions of HIPAA, such that receipt, processing, and transmission of imaging data and/or other patient data is securely handled with respect to privacy of patient data. In at least one embodiment, hardware 3122 may include any number of GPUs that may be called upon to perform processing of data in parallel, as described herein. In at least one embodiment, cloud platform may further include GPU processing for GPU-optimized execution of deep learning tasks, machine learning tasks, or other computing tasks. In at least one embodiment, cloud platform (e.g., NVIDIA's NGC) may be executed using an AI/deep learning supercomputer(s) and/or GPU-optimized software (e.g., as provided on NVIDIA's DGX Systems) as a hardware abstraction and scaling platform. In at least one embodiment, cloud platform may integrate an application container clustering system or orchestration system (e.g., KUBERNETES) on multiple GPUs to enable seamless scaling and load balancing.

FIG. 32 is a system diagram for an example system 3200 for generating and deploying an imaging deployment pipeline, in accordance with at least one embodiment. In at least one embodiment, system 3200 may be used to implement process 3100 of FIG. 31 and/or other processes including advanced processing and inferencing pipelines. In at least one embodiment, system 3200 may include training system 3104 and deployment system 3106. In at least one embodiment, training system 3104 and deployment system 3106 may be implemented using software 3118, services 3120, and/or hardware 3122, as described herein.

In at least one embodiment, system 3200 (e.g., training system 3104 and/or deployment system 3106) may implemented in a cloud computing environment (e.g., using cloud 3226). In at least one embodiment, system 3200 may be implemented locally with respect to a healthcare services facility, or as a combination of both cloud and local computing resources. In at least one embodiment, in embodiments where cloud computing is implemented, patient data may be separated from, or unprocessed by, by one or more components of system 3200 that would render processing non-compliant with HIPAA and/or other data handling and privacy regulations or laws. In at least one embodiment, access to APIs in cloud 3226 may be restricted to authorized users through enacted security measures or protocols. In at least one embodiment, a security protocol may include web tokens that may be signed by an authentication (e.g., AuthN, AuthZ, Gluecon, etc.) service and may carry appropriate authorization. In at least one embodiment, APIs of virtual instruments (described herein), or other instantiations of system 3200, may be restricted to a set of public IPs that have been vetted or authorized for interaction.

In at least one embodiment, various components of system 3200 may communicate between and among one another using any of a variety of different network types, including but not limited to local area networks (LANs) and/or wide area networks (WANs) via wired and/or wireless communication protocols. In at least one embodiment, communication between facilities and components of system 3200 (e.g., for transmitting inference requests, for receiving results of inference requests, etc.) may be communicated over data bus(ses), wireless data protocols (Wi-Fi), wired data protocols (e.g., Ethernet), etc.

In at least one embodiment, training system 3104 may execute training pipelines 3204, similar to those described herein with respect to FIG. 31. In at least one embodiment, where one or more machine learning models are to be used in deployment pipelines 3210 by deployment system 3106, training pipelines 3204 may be used to train or retrain one or more (e.g. pre-trained) models, and/or implement one or more of pre-trained models 3206 (e.g., without a need for retraining or updating). In at least one embodiment, as a result of training pipelines 3204, output model(s) 3116 may be generated. In at least one embodiment, training pipelines 3204 may include any number of processing steps, such as but not limited to imaging data (or other input data) conversion or adaption (e.g., using DICOM adapter 3202A to convert DICOM images to another format suitable for processing by respective machine learning models, such as Neuroimaging Informatics Technology Initiative (NIfTI) format), AI-assisted annotation 3110, labeling or annotating of imaging data 3108 to generate labeled clinic data 3112, model selection from a model registry, model training 3114, training, retraining, or updating models, and/or other processing steps. In at least one embodiment, for different machine learning models used by deployment system 3106, different training pipelines 3204 may be used. In at least one embodiment, training pipeline 3204 similar to a first example described with respect to FIG. 31 may be used for a first machine learning model, training pipeline 3204 similar to a second example described with respect to FIG. 31 may be used for a second machine learning model, and training pipeline 3204 similar to a third example described with respect to FIG. 31 may be used for a third machine learning model. In at least one embodiment, any combination of tasks within training system 3104 may be used depending on what is required for each respective machine learning model. In at least one embodiment, one or more of machine learning models may already be trained and ready for deployment so machine learning models may not undergo any processing by training system 3104, and may be implemented by deployment system 3106.

In at least one embodiment, output model(s) 3116 and/or pre-trained model(s) 3206 may include any types of machine learning models depending on implementation or embodiment. In at least one embodiment, and without limitation, machine learning models used by system 3200 may include machine learning model(s) using linear regression, logistic regression, decision trees, support vector machines (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, Long/Short Term Memory (LSTM), Hopfield, Boltzmann, deep belief, deconvolutional, generative adversarial, liquid state machine, etc.), and/or other types of machine learning models.

In at least one embodiment, training pipelines 3204 may include AI-assisted annotation, as described in more detail herein with respect to at least FIG. 35B. In at least one embodiment, labeled clinic data 3112 (e.g., traditional annotation) may be generated by any number of techniques. In at least one embodiment, labels or other annotations may be generated within a drawing program (e.g., an annotation program), a computer aided design (CAD) program, a labeling program, another type of program suitable for generating annotations or labels for ground truth, and/or may be hand drawn, in some examples. In at least one embodiment, ground truth data may be synthetically produced (e.g., generated from computer models or renderings), real produced (e.g., designed and produced from real-world data), machine-automated (e.g., using feature analysis and learning to extract features from data and then generate labels), human annotated (e.g., labeler, or annotation expert, defines location of labels), and/or a combination thereof. In at least one embodiment, for each instance of imaging data 3108 (or other data type used by machine learning models), there may be corresponding ground truth data generated by training system 3104. In at least one embodiment, AI-assisted annotation may be performed as part of deployment pipelines 3210; either in addition to, or in lieu of AI-assisted annotation included in training pipelines 3204. In at least one embodiment, system 3200 may include a multi-layer platform that may include a software layer (e.g., software 3118) of diagnostic applications (or other application types) that may perform one or more medical imaging and diagnostic functions. In at least one embodiment, system 3200 may be communicatively coupled to (e.g., via encrypted links) PACS server networks of one or more facilities. In at least one embodiment, system 3200 may be configured to access and referenced data (e.g., DICOM data, RIS data, raw data, CIS data, REST compliant data, RPC data, raw data, etc.) from PACS servers (e.g., via a DICOM adapter 3202, or another data type adapter such as RIS, CIS, REST compliant, RPC, raw, etc.) to perform operations, such as training machine learning models, deploying machine learning models, image processing, inferencing, and/or other operations.

In at least one embodiment, a software layer may be implemented as a secure, encrypted, and/or authenticated API through which applications or containers may be invoked (e.g., called) from an external environment(s) (e.g., facility 3102). In at least one embodiment, applications may then call or execute one or more services 3120 for performing compute, AI, or visualization tasks associated with respective applications, and software 3118 and/or services 3120 may leverage hardware 3122 to perform processing tasks in an effective and efficient manner.

In at least one embodiment, deployment system 3106 may execute deployment pipelines 3210. In at least one embodiment, deployment pipelines 3210 may include any number of applications that may be sequentially, non-sequentially, or otherwise applied to imaging data (and/or other data types) generated by imaging devices, sequencing devices, genomics devices, etc.—including AI-assisted annotation, as described above. In at least one embodiment, as described herein, a deployment pipeline 3210 for an individual device may be referred to as a virtual instrument for a device (e.g., a virtual ultrasound instrument, a virtual CT scan instrument, a virtual sequencing instrument, etc.). In at least one embodiment, for a single device, there may be more than one deployment pipeline 3210 depending on information desired from data generated by a device. In at least one embodiment, where detections of anomalies are desired from an MRI machine, there may be a first deployment pipeline 3210, and where image enhancement is desired from output of an MRI machine, there may be a second deployment pipeline 3210.

In at least one embodiment, applications available for deployment pipelines 3210 may include any application that may be used for performing processing tasks on imaging data or other data from devices. In at least one embodiment, different applications may be responsible for image enhancement, segmentation, reconstruction, anomaly detection, object detection, feature detection, treatment planning, dosimetry, beam planning (or other radiation treatment procedures), and/or other analysis, image processing, or inferencing tasks. In at least one embodiment, deployment system 3106 may define constructs for each of applications, such that users of deployment system 3106 (e.g., medical facilities, labs, clinics, etc.) may understand constructs and adapt applications for implementation within their respective facility. In at least one embodiment, an application for image reconstruction may be selected for inclusion in deployment pipeline 3210, but data type generated by an imaging device may be different from a data type used within an application. In at least one embodiment, DICOM adapter 3202B (and/or a DICOM reader) or another data type adapter or reader (e.g., RIS, CIS, REST compliant, RPC, raw, etc.) may be used within deployment pipeline 3210 to convert data to a form useable by an application within deployment system 3106. In at least one embodiment, access to DICOM, RIS, CIS, REST compliant, RPC, raw, and/or other data type libraries may be accumulated and pre-processed, including decoding, extracting, and/or performing any convolutions, color corrections, sharpness, gamma, and/or other augmentations to data. In at least one embodiment, DICOM, RIS, CIS, REST compliant, RPC, and/or raw data may be unordered and a pre-pass may be executed to organize or sort collected data. In at least one embodiment, because various applications may share common image operations, in some embodiments, a data augmentation library (e.g., as one of services 3120) may be used to accelerate these operations. In at least one embodiment, to avoid bottlenecks of conventional processing approaches that rely on CPU processing, parallel computing platform 3230 may be used for GPU acceleration of these processing tasks.

In at least one embodiment, an image reconstruction application may include a processing task that includes use of a machine learning model. In at least one embodiment, a user may desire to use their own machine learning model, or to select a machine learning model from model registry 3124. In at least one embodiment, a user may implement their own machine learning model or select a machine learning model for inclusion in an application for performing a processing task. In at least one embodiment, applications may be selectable and customizable, and by defining constructs of applications, deployment and implementation of applications for a particular user are presented as a more seamless user experience. In at least one embodiment, by leveraging other features of system 3200—such as services 3120 and hardware 3122—deployment pipelines 3210 may be even more user friendly, provide for easier integration, and produce more accurate, efficient, and timely results.

In at least one embodiment, deployment system 3106 may include a user interface 3214 (e.g., a graphical user interface, a web interface, etc.) that may be used to select applications for inclusion in deployment pipeline(s) 3210, arrange applications, modify or change applications or parameters or constructs thereof, use and interact with deployment pipeline(s) 3210 during set-up and/or deployment, and/or to otherwise interact with deployment system 3106. In at least one embodiment, although not illustrated with respect to training system 3104, user interface 3214 (or a different user interface) may be used for selecting models for use in deployment system 3106, for selecting models for training, or retraining, in training system 3104, and/or for otherwise interacting with training system 3104.

Figure 33:
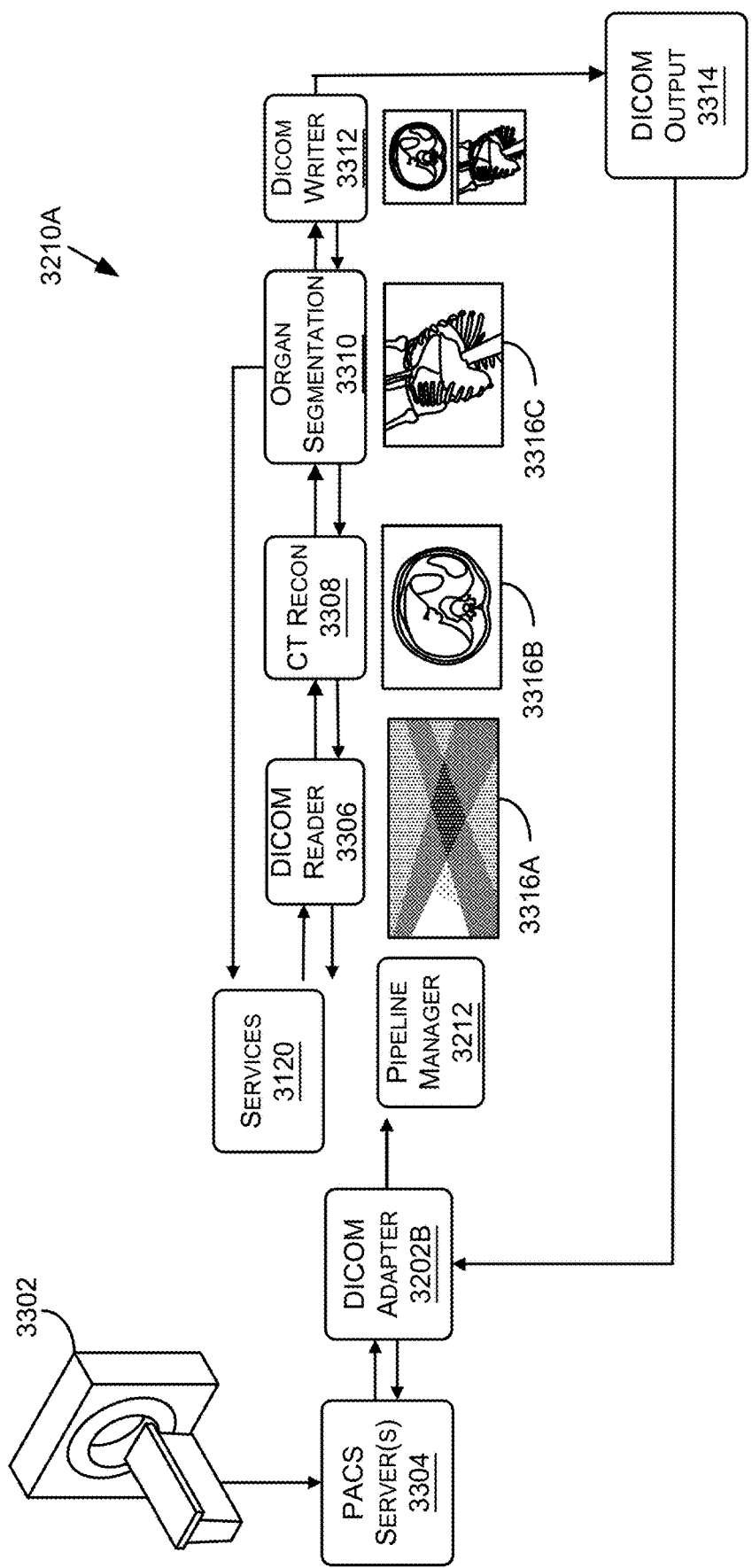
FIG. 33 includes an example illustration of an advanced computing pipeline 3210A for processing imaging data, in accordance with at least one embodiment.

In at least one embodiment, pipeline manager 3212 may be used, in addition to an application orchestration system 3228, to manage interaction between applications or containers of deployment pipeline(s) 3210 and services 3120 and/or hardware 3122. In at least one embodiment, pipeline manager 3212 may be configured to facilitate interactions from application to application, from application to service 3120, and/or from application or service to hardware 3122. In at least one embodiment, although illustrated as included in software 3118, this is not intended to be limiting, and in some examples (e.g., as illustrated in FIG. 33) pipeline manager 3212 may be included in services 3120. In at least one embodiment, application orchestration system 3228 (e.g., Kubernetes, DOCKER, etc.) may include a container orchestration system that may group applications into containers as logical units for coordination, management, scaling, and deployment. In at least one embodiment, by associating applications from deployment pipeline(s) 3210 (e.g., a reconstruction application, a segmentation application, etc.) with individual containers, each application may execute in a self-contained environment (e.g., at a kernel level) to increase speed and efficiency.

In at least one embodiment, each application and/or container (or image thereof) may be individually developed, modified, and deployed (e.g., a first user or developer may develop, modify, and deploy a first application and a second user or developer may develop, modify, and deploy a second application separate from a first user or developer), which may allow for focus on, and attention to, a task of a single application and/or container(s) without being hindered by tasks of another application(s) or container(s). In at least one embodiment, communication, and cooperation between different containers or applications may be aided by pipeline manager 3212 and application orchestration system 3228. In at least one embodiment, so long as an expected input and/or output of each container or application is known by a system (e.g., based on constructs of applications or containers), application orchestration system 3228 and/or pipeline manager 3212 may facilitate communication among and between, and sharing of resources among and between, each of applications or containers. In at least one embodiment, because one or more of applications or containers in deployment pipeline(s) 3210 may share same services and resources, application orchestration system 3228 may orchestrate, load balance, and determine sharing of services or resources between and among various applications or containers. In at least one embodiment, a scheduler may be used to track resource requirements of applications or containers, current usage or planned usage of these resources, and resource availability. In at least one embodiment, a scheduler may thus allocate resources to different applications and distribute resources between and among applications in view of requirements and availability of a system. In some examples, a scheduler (and/or other component of application orchestration system 3228) may determine resource availability and distribution based on constraints imposed on a system (e.g., user constraints), such as quality of service (QoS), urgency of need for data outputs (e.g., to determine whether to execute real-time processing or delayed processing), etc.

In at least one embodiment, services 3120 leveraged by and shared by applications or containers in deployment system 3106 may include compute services 3216, AI services 3218, visualization services 3220, and/or other service types. In at least one embodiment, applications may call (e.g., execute) one or more of services 3120 to perform processing operations for an application. In at least one embodiment, compute services 3216 may be leveraged by applications to perform super-computing or other high-performance computing (HPC) tasks. In at least one embodiment, compute service(s) 3216 may be leveraged to perform parallel processing (e.g., using a parallel computing platform 3230) for processing data through one or more of applications and/or one or more tasks of a single application, substantially simultaneously. In at least one embodiment, parallel computing platform 3230 (e.g., NVIDIA's CUDA) may enable general purpose computing on GPUs (GPGPU) (e.g., GPUs 3222). In at least one embodiment, a software layer of parallel computing platform 3230 may provide access to virtual instruction sets and parallel computational elements of GPUs, for execution of compute kernels. In at least one embodiment, parallel computing platform 3230 may include memory and, in some embodiments, a memory may be shared between and among multiple containers, and/or between and among different processing tasks within a single container. In at least one embodiment, inter-process communication (IPC) calls may be generated for multiple containers and/or for multiple processes within a container to use same data from a shared segment of memory of parallel computing platform 3230 (e.g., where multiple different stages of an application or multiple applications are processing same information). In at least one embodiment, rather than making a copy of data and moving data to different locations in memory (e.g., a read/write operation), same data in same location of a memory may be used for any number of processing tasks (e.g., at a same time, at different times, etc.). In at least one embodiment, as data is used to generate new data as a result of processing, this information of a new location of data may be stored and shared between various applications. In at least one embodiment, location of data and a location of updated or modified data may be part of a definition of how a payload is understood within containers.

In at least one embodiment, AI services 3218 may be leveraged to perform inferencing services for executing machine learning model(s) associated with applications (e.g., tasked with performing one or more processing tasks of an application). In at least one embodiment, AI services 3218 may leverage AI system 3224 to execute machine learning model(s) (e.g., neural networks, such as CNNs) for segmentation, reconstruction, object detection, feature detection, classification, and/or other inferencing tasks. In at least one embodiment, applications of deployment pipeline(s) 3210 may use one or more of output models 3116 from training system 3104 and/or other models of applications to perform inference on imaging data (e.g., DICOM data, RIS data, CIS data, REST compliant data, RPC data, raw data, etc.). In at least one embodiment, two or more examples of inferencing using application orchestration system 3228 (e.g., a scheduler) may be available. In at least one embodiment, a first category may include a high priority/low latency path that may achieve higher service level agreements, such as for performing inference on urgent requests during an emergency, or for a radiologist during diagnosis. In at least one embodiment, a second category may include a standard priority path that may be used for requests that may be non-urgent or where analysis may be performed at a later time. In at least one embodiment, application orchestration system 3228 may distribute resources (e.g., services 3120 and/or hardware 3122) based on priority paths for different inferencing tasks of AI services 3218.

In at least one embodiment, shared storage may be mounted to AI services 3218 within system 3200. In at least one embodiment, shared storage may operate as a cache (or other storage device type) and may be used to process inference requests from applications. In at least one embodiment, when an inference request is submitted, a request may be received by a set of API instances of deployment system 3106, and one or more instances may be selected (e.g., for best fit, for load balancing, etc.) to process a request. In at least one embodiment, to process a request, a request may be entered into a database, a machine learning model may be located from model registry 3124 if not already in a cache, a validation step may ensure appropriate machine learning model is loaded into a cache (e.g., shared storage), and/or a copy of a model may be saved to a cache. In at least one embodiment, a scheduler (e.g., of pipeline manager 3212) may be used to launch an application that is referenced in a request if an application is not already running or if there are not enough instances of an application. In at least one embodiment, if an inference server is not already launched to execute a model, an inference server may be launched. Any number of inference servers may be launched per model. In at least one embodiment, in a pull model, in which inference servers are clustered, models may be cached whenever load balancing is advantageous. In at least one embodiment, inference servers may be statically loaded in corresponding, distributed servers.

In at least one embodiment, inferencing may be performed using an inference server that runs in a container. In at least one embodiment, an instance of an inference server may be associated with a model (and optionally a plurality of versions of a model). In at least one embodiment, if an instance of an inference server does not exist when a request to perform inference on a model is received, a new instance may be loaded. In at least one embodiment, when starting an inference server, a model may be passed to an inference server such that a same container may be used to serve different models so long as inference server is running as a different instance.

In at least one embodiment, during application execution, an inference request for a given application may be received, and a container (e.g., hosting an instance of an inference server) may be loaded (if not already), and a start procedure may be called. In at least one embodiment, pre-processing logic in a container may load, decode, and/or perform any additional pre-processing on incoming data (e.g., using a CPU(s) and/or GPU(s)). In at least one embodiment, once data is prepared for inference, a container may perform inference as necessary on data. In at least one embodiment, this may include a single inference call on one image (e.g., a hand X-ray), or may require inference on hundreds of images (e.g., a chest CT). In at least one embodiment, an application may summarize results before completing, which may include, without limitation, a single confidence score, pixel level-segmentation, voxel-level segmentation, generating a visualization, or generating text to summarize findings. In at least one embodiment, different models or applications may be assigned different priorities. For example, some models may have a real-time (TAT<1 min) priority while others may have lower priority (e.g., TAT<10 min). In at least one embodiment, model execution times may be measured from requesting institution or entity and may include partner network traversal time, as well as execution on an inference service.

In at least one embodiment, transfer of requests between services 3120 and inference applications may be hidden behind a software development kit (SDK), and robust transport may be provide through a queue. In at least one embodiment, a request will be placed in a queue via an API for an individual application/tenant ID combination and an SDK will pull a request from a queue and give a request to an application. In at least one embodiment, a name of a queue may be provided in an environment from where an SDK will pick it up. In at least one embodiment, asynchronous communication through a queue may be useful as it may allow any instance of an application to pick up work as it becomes available. Results may be transferred back through a queue, to ensure no data is lost. In at least one embodiment, queues may also provide an ability to segment work, as highest priority work may go to a queue with most instances of an application connected to it, while lowest priority work may go to a queue with a single instance connected to it that processes tasks in an order received. In at least one embodiment, an application may run on a GPU-accelerated instance generated in cloud 3226, and an inference service may perform inferencing on a GPU.

In at least one embodiment, visualization services 3220 may be leveraged to generate visualizations for viewing outputs of applications and/or deployment pipeline(s) 3210. In at least one embodiment, GPUs 3222 may be leveraged by visualization services 3220 to generate visualizations. In at least one embodiment, rendering effects, such as ray-tracing, may be implemented by visualization services 3220 to generate higher quality visualizations. In at least one embodiment, visualizations may include, without limitation, 2D image renderings, 3D volume renderings, 3D volume reconstruction, 2D tomographic slices, virtual reality displays, augmented reality displays, etc. In at least one embodiment, virtualized environments may be used to generate a virtual interactive display or environment (e.g., a virtual environment) for interaction by users of a system (e.g., doctors, nurses, radiologists, etc.). In at least one embodiment, visualization services 3220 may include an internal visualizer, cinematics, and/or other rendering or image processing capabilities or functionality (e.g., ray tracing, rasterization, internal optics, etc.).

In at least one embodiment, hardware 3122 may include GPUs 3222, AI system 3224, cloud 3226, and/or any other hardware used for executing training system 3104 and/or deployment system 3106. In at least one embodiment, GPUs 3222 (e.g., NVIDIA's TESLA and/or QUADRO GPUs) may include any number of GPUs that may be used for executing processing tasks of compute services 3216, AI services 3218, visualization services 3220, other services, and/or any of features or functionality of software 3118. For example, with respect to AI services 3218, GPUs 3222 may be used to perform pre-processing on imaging data (or other data types used by machine learning models), post-processing on outputs of machine learning models, and/or to perform inferencing (e.g., to execute machine learning models). In at least one embodiment, cloud 3226, AI system 3224, and/or other components of system 3200 may use GPUs 3222. In at least one embodiment, cloud 3226 may include a GPU-optimized platform for deep learning tasks. In at least one embodiment, AI system 3224 may use GPUs, and cloud 3226—or at least a portion tasked with deep learning or inferencing—may be executed using one or more AI systems 3224. As such, although hardware 3122 is illustrated as discrete components, this is not intended to be limiting, and any components of hardware 3122 may be combined with, or leveraged by, any other components of hardware 3122.

In at least one embodiment, AI system 3224 may include a purpose-built computing system (e.g., a super-computer or an HPC) configured for inferencing, deep learning, machine learning, and/or other artificial intelligence tasks. In at least one embodiment, AI system 3224 (e.g., NVIDIA's DGX) may include GPU-optimized software (e.g., a software stack) that may be executed using a plurality of GPUs 3222, in addition to CPUs, RAM, storage, and/or other components, features, or functionality. In at least one embodiment, one or more AI systems 3224 may be implemented in cloud 3226 (e.g., in a data center) for performing some or all of AI-based processing tasks of system 3200.

In at least one embodiment, cloud 3226 may include a GPU-accelerated infrastructure (e.g., NVIDIA's NGC) that may provide a GPU-optimized platform for executing processing tasks of system 3200. In at least one embodiment, cloud 3226 may include an AI system(s) 3224 for performing one or more of AI-based tasks of system 3200 (e.g., as a hardware abstraction and scaling platform). In at least one embodiment, cloud 3226 may integrate with application orchestration system 3228 leveraging multiple GPUs to enable seamless scaling and load balancing between and among applications and services 3120. In at least one embodiment, cloud 3226 may tasked with executing at least some of services 3120 of system 3200, including compute services 3216, AI services 3218, and/or visualization services 3220, as described herein. In at least one embodiment, cloud 3226 may perform small and large batch inference (e.g., executing NVIDIA's TENSOR RT), provide an accelerated parallel computing API and platform 3230 (e.g., NVIDIA's CUDA), execute application orchestration system 3228 (e.g., KUBERNETES), provide a graphics rendering API and platform (e.g., for ray-tracing, 2D graphics, 3D graphics, and/or other rendering techniques to produce higher quality cinematics), and/or may provide other functionality for system 3200.

In at least one embodiment, in an effort to preserve patient confidentiality (e.g., where patient data or records are to be used off-premises), cloud 3226 may include a registry-such as a deep learning container registry. In at least one embodiment, a registry may store containers for instantiations of applications that may perform pre-processing, post-processing, or other processing tasks on patient data. In at least one embodiment, cloud 3226 may receive data that includes patient data as well as sensor data in containers, perform requested processing for just sensor data in those containers, and then forward a resultant output and/or visualizations to appropriate parties and/or devices (e.g., on-premises medical devices used for visualization or diagnoses), all without having to extract, store, or otherwise access patient data. In at least one embodiment, confidentiality of patient data is preserved in compliance with HIPAA and/or other data regulations.

FIG. 33 include an example illustration of a deployment pipeline 3210A for processing imaging data, in accordance with at least one embodiment. In at least one embodiment, system 3200—and specifically deployment system 3106—may be used to customize, update, and/or integrate deployment pipeline(s) 3210A into one or more production environments. In at least one embodiment, deployment pipeline 3210A of FIG. 33 includes a non-limiting example of a deployment pipeline 3210A that may be custom defined by a particular user (or team of users) at a facility (e.g., at a hospital, clinic, lab, research environment, etc.). Fo In at least one embodiment, to define deployment pipelines 3210A for a CT scanner 3302, user may select—from a container registry, for example—one or more applications that perform specific functions or tasks with respect to imaging data generated by CT scanner 3302. In at least one embodiment, applications may be applied to deployment pipeline 3210A as containers that may leverage services 3120 and/or hardware 3122 of system 3200. In addition, deployment pipeline 3210A may include additional processing tasks or applications that may be implemented to prepare data for use by applications (e.g., DICOM adapter 3202B and DICOM reader 3306 may be used in deployment pipeline 3210A to prepare data for use by CT reconstruction 3308, organ segmentation 3310, etc.). In at least one embodiment, deployment pipeline 3210A may be customized or selected for consistent deployment, one time use, or for another frequency or interval. In at least one embodiment, a user may desire to have CT reconstruction 3308 and organ segmentation 3310 for several subjects over a specific interval, and thus may deploy pipeline 3210A for that period of time. In at least one embodiment, a user may select, for each request from system 3200, applications that a user wants to perform processing on that data for that request. In at least one embodiment, deployment pipeline 3210A may be adjusted at any interval and, because of adaptability and scalability of a container structure within system 3200, this may be a seamless process.

In at least one embodiment, deployment pipeline 3210A of FIG. 33 may include CT scanner 3302 generating imaging data of a patient or subject. In at least one embodiment, imaging data from CT scanner 3302 may be stored on a PACS server(s) 3304 associated with a facility housing CT scanner 3302. PACS server(s) 3304 may include software and/or hardware components that may directly interface with imaging modalities (e.g., CT scanner 3302) at a facility. In at least one embodiment, DICOM adapter 3202B may enable sending and receipt of DICOM objects using DICOM protocols. In at least one embodiment, DICOM adapter 3202B may aid in preparation or configuration of DICOM data from PACS server(s) 3304 for use by deployment pipeline 3210A. In at least one embodiment, once DICOM data is processed through DICOM adapter 3202B, pipeline manager 3212 may route data through to deployment pipeline 3210A. In at least one embodiment, DICOM reader 3306 may extract image files and any associated metadata from DICOM data (e.g., raw sinogram data, as illustrated in visualization 3316A). In at least one embodiment, working files that are extracted may be stored in a cache for faster processing by other applications in deployment pipeline 3210A. In at least one embodiment, once DICOM reader 3306 has finished extracting and/or storing data, a signal of completion may be communicated to pipeline manager 3212. In at least one embodiment, pipeline manager 3212 may then initiate or call upon one or more other applications or containers in deployment pipeline 3210A.

In at least one embodiment, CT reconstruction 3308 application and/or container may be executed once data (e.g., raw sinogram data) is available for processing by CT reconstruction 3308 application. In at least one embodiment, CT reconstruction 3308 may read raw sinogram data from a cache, reconstruct an image file out of raw sinogram data (e.g., as illustrated in visualization 3316B), and store resulting image file in a cache. In at least one embodiment, at completion of reconstruction, pipeline manager 3212 may be signaled that reconstruction task is complete. In at least one embodiment, once reconstruction is complete, and a reconstructed image file may be stored in a cache (or other storage device), organ segmentation 3310 application and/or container may be triggered by pipeline manager 3212. In at least one embodiment, organ segmentation 3310 application and/or container may read an image file from a cache, normalize or convert an image file to format suitable for inference (e.g., convert an image file to an input resolution of a machine learning model), and run inference against a normalized image. In at least one embodiment, to run inference on a normalized image, organ segmentation 3310 application and/or container may rely on services 3120, and pipeline manager 3212 and/or application orchestration system 3228 may facilitate use of services 3120 by organ segmentation 3310 application and/or container. For example, organ segmentation 3310 application and/or container may leverage AI services 3218 to perform inference on a normalized image, and AI services 3218 may leverage hardware 3122 (e.g., AI system 3224) to execute AI services 3218. In at least one embodiment, a result of an inference may be a mask file (e.g., as illustrated in visualization 3316C) that may be stored in a cache (or other storage device).

In at least one embodiment, once applications that process DICOM data and/or data extracted from DICOM data have completed processing, a signal may be generated for pipeline manager 3212. In at least one embodiment, pipeline manager 3212 may then execute DICOM writer 3312 to read results from a cache (or other storage device), package results into a DICOM format (e.g., as DICOM output 3314) for use by users at a facility who generated a request. In at least one embodiment, DICOM output 3314 may then be transmitted to DICOM adapter 3202B to prepare DICOM output 3314 for storage on PACS server(s) 3304 (e.g., for viewing by a DICOM viewer at a facility). In at least one embodiment, in response to a request for reconstruction and segmentation, visualizations 3316B and 3316C may be generated and available to a user for diagnoses, research, and/or for other purposes.

Although illustrated as consecutive application in deployment pipeline 3210A, CT reconstruction 3308 and organ segmentation 3310 applications may be processed in parallel in at least one embodiment. In at least one embodiment, where applications do not have dependencies on one another, and data is available for each application (e.g., after DICOM reader 3306 extracts data), applications may be executed at a same time, substantially at a same time, or with some overlap. In at least one embodiment, where two or more applications require similar services 3120, a scheduler of system 3200 may be used to load balance and distribute compute or processing resources between and among various applications. In at least one embodiment, in some embodiments, parallel computing platform 3230 may be used to perform parallel processing for applications to decrease run-time of deployment pipeline 3210A to provide real-time results.

Figure 34A:
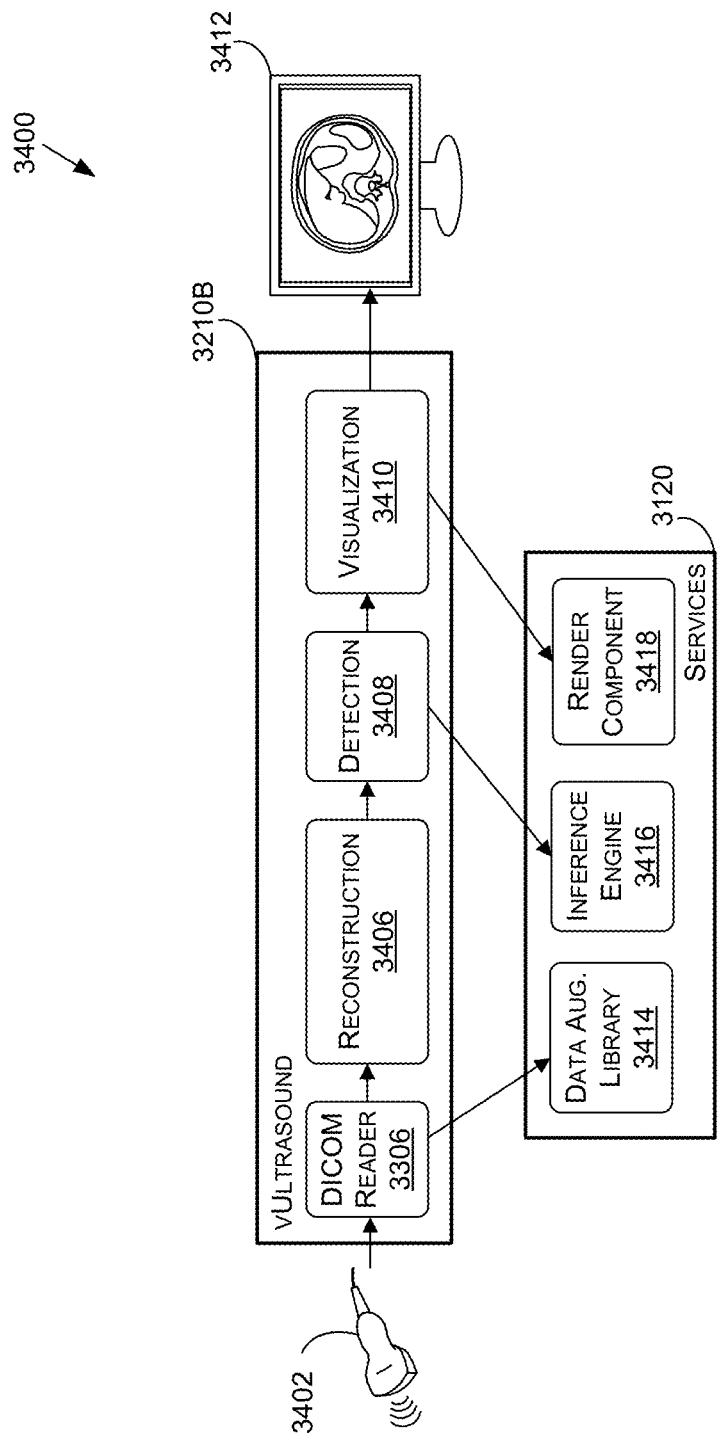
FIG. 34A includes an example data flow diagram of a virtual instrument supporting an ultrasound device, in accordance with at least one embodiment.
Figure 34B:
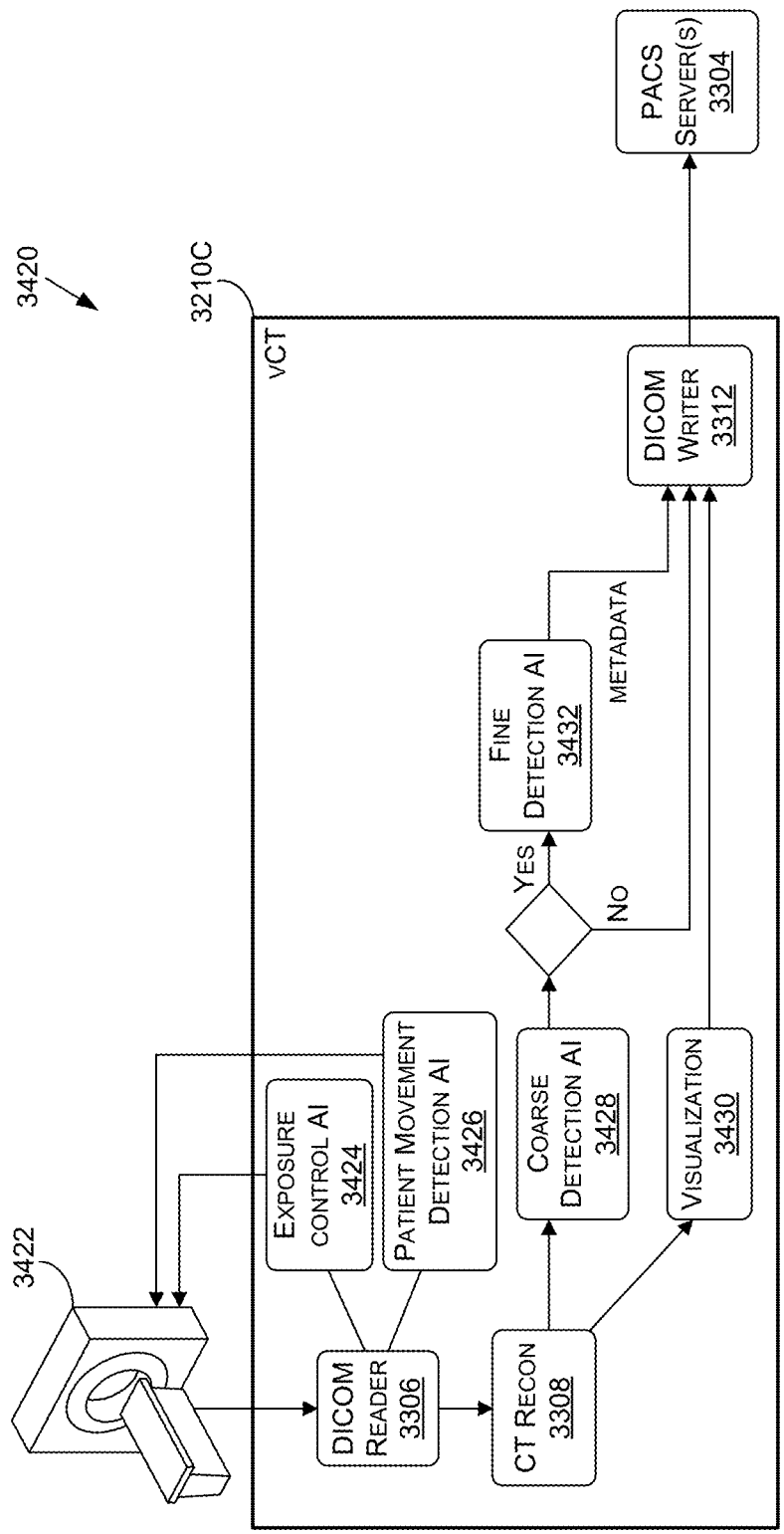
FIG. 34B includes an example data flow diagram of a virtual instrument supporting an CT scanner, in accordance with at least one embodiment.

In at least one embodiment, and with reference to FIGS. 34A-34B, deployment system 3106 may be implemented as one or more virtual instruments to perform different functionalities—such as image processing, segmentation, enhancement, AI, visualization, and inferencing—with imaging devices (e.g., CT scanners, X-ray machines, MRI machines, etc.), sequencing devices, genomics devices, and/or other device types. In at least one embodiment, ystem 3200 may allow for creation and provision of virtual instruments that may include a software-defined deployment pipeline 3210 that may receive raw/unprocessed input data generated by a device(s) and output processed/reconstructed data. In at least one embodiment, deployment pipelines 3210 (e.g., 3210A and 3210B) that represent virtual instruments may implement intelligence into a pipeline, such as by leveraging machine learning models, to provide containerized inference support to a system. In at least one embodiment, virtual instruments may execute any number of containers each including instantiations of application In at least one embodiment, such as where real-time processing is desired, deployment pipelines 3210 representing virtual instruments may be static (e.g., containers and/or applications may be set), while in other examples, container and/or applications for virtual instruments may be selected (e.g., on a per-request basis) from a pool of applications or resources (e.g., within a container registry).

In at least one embodiment, system 3200 may be instantiated or executed as one or more virtual instruments on-premise at a facility in, for example, a computing system deployed next to or otherwise in communication with a radiology machine, an imaging device, and/or another device type at a facility. In at least one embodiment, however, an on-premise installation may be instantiated or executed within a computing system of a device itself (e.g., a computing system integral to an imaging device), in a local datacenter (e.g., a datacenter on-premise), and/or in a cloud-environment (e.g., in cloud 3226). In at least one embodiment, deployment system 3106, operating as a virtual instrument, may be instantiated by a supercomputer or other HPC system in some examples. In at least one embodiment, on-premise installation may allow for high-bandwidth uses (via, for example, higher throughput local communication interfaces, such as RF over Ethernet) for real-time processing. In at least one embodiment, real-time or near real-time processing may be particularly useful where a virtual instrument supports an ultrasound device or other imaging modality where immediate visualizations are expected or required for accurate diagnoses and analyses. In at least one embodiment, a cloud-computing architecture may be capable of dynamic bursting to a cloud computing service provider, or other compute cluster, when local demand exceeds on-premise capacity or capability. In at least one embodiment, a cloud architecture, when implemented, may be tuned for training neural networks or other machine learning models, as described herein with respect to training system 3104. In at least one embodiment, with training pipelines in place, machine learning models may be continuously learn and improve as they process additional data from devices they support. In at least one embodiment, virtual instruments may be continually improved using additional data, new data, existing machine learning models, and/or new or updated machine learning models.

In at least one embodiment, a computing system may include some or all of hardware 3122 described herein, and hardware 3122 may be distributed in any of a number of ways including within a device, as part of a computing device coupled to and located proximate a device, in a local datacenter at a facility, and/or in cloud 3226. In at least one embodiment, because deployment system 3106 and associated applications or containers are created in software (e.g., as discrete containerized instantiations of applications), behavior, operation, and configuration of virtual instruments, as well as outputs generated by virtual instruments, may be modified or customized as desired, without having to change or alter raw output of a device that a virtual instrument supports.

FIG. 34A includes an example data flow diagram of a virtual instrument supporting an ultrasound device, in accordance with at least one embodiment. In at least one embodiment, deployment pipeline 3210B may leverage one or more of services 3120 of system 3200. In at least one embodiment, deployment pipeline 3210B and services 3120 may leverage hardware 3122 of a system either locally or in cloud 3226. In at least one embodiment, although not illustrated, process 3400 may be facilitated by pipeline manager 3212, application orchestration system 3228, and/or parallel computing platform 3230.

In at least one embodiment, process 3400 may include receipt of imaging data from an ultrasound device 3402. In at least one embodiment, imaging data may be stored on PACS server(s) in a DICOM format (or other format, such as RIS, CIS, REST compliant, RPC, raw, etc.), and may be received by system 3200 for processing through deployment pipeline 3210 selected or customized as a virtual instrument (e.g., a virtual ultrasound) for ultrasound device 3402. In at least one embodiment, imaging data may be received directly from an imaging device (e.g., ultrasound device 3402) and processed by a virtual instrument. In at least one embodiment, a transducer or other signal converter communicatively coupled between an imaging device and a virtual instrument may convert signal data generated by an imaging device to image data that may be processed by a virtual instrument. In at least one embodiment, raw data and/or image data may be applied to DICOM reader 3306 to extract data for use by applications or containers of deployment pipeline 3210B. In at least one embodiment, DICOM reader 3306 may leverage data augmentation library 3414 (e.g., NVIDIA's DALI) as a service 3120 (e.g., as one of compute service(s) 3216) for extracting, resizing, rescaling, and/or otherwise preparing data for use by applications or containers.

In at least one embodiment, once data is prepared, a reconstruction 3406 application and/or container may be executed to reconstruct data from ultrasound device 3402 into an image file. In at least one embodiment, after reconstruction 3406, or at a same time as reconstruction 3406, a detection 3408 application and/or container may be executed for anomaly detection, object detection, feature detection, and/or other detection tasks related to data. In at least one embodiment, an image file generated during reconstruction 3406 may be used during detection 3408 to identify anomalies, objects, features, etc. In at least one embodiment, detection 3408 application may leverage an inference engine 3416 (e.g., as one of AI service(s) 3218) to perform inference on data to generate detections. In at least one embodiment, one or more machine learning models (e.g., from training system 3104) may be executed or called by detection 3408 application.

In at least one embodiment, once reconstruction 3406 and/or detection 3408 is/are complete, data output from these application and/or containers may be used to generate visualizations 3410, such as visualization 3412 (e.g., a grayscale output) displayed on a workstation or display terminal. In at least one embodiment, visualization may allow a technician or other user to visualize results of deployment pipeline 3210B with respect to ultrasound device 3402. In at least one embodiment, visualization 3410 may be executed by leveraging a render component 3418 of system 3200 (e.g., one of visualization service(s) 3220). In at least one embodiment, render component 3418 may execute a 2D, OpenGL, or ray-tracing service to generate visualization 3412.

FIG. 34B includes an example data flow diagram of a virtual instrument supporting a CT scanner, in accordance with at least one embodiment. In at least one embodiment, deployment pipeline 3210C may leverage one or more of services 3120 of system 3200. In at least one embodiment, deployment pipeline 3210C and services 3120 may leverage hardware 3122 of a system either locally or in cloud 3226. In at least one embodiment, although not illustrated, process 3420 may be facilitated by pipeline manager 3212, application orchestration system 3228, and/or parallel computing platform 3230.

In at least one embodiment, process 3420 may include CT scanner 3422 generating raw data that may be received by DICOM reader 3306 (e.g., directly, via a PACS server 3304, after processing, etc.). In at least one embodiment, a Virtual CT (instantiated by deployment pipeline 3210C) may include a first, real-time pipeline for monitoring a patient (e.g., patient movement detection AI 3426) and/or for adjusting or optimizing exposure of CT scanner 3422 (e.g., using exposure control AI 3424). In at least one embodiment, one or more of applications (e.g., 3424 and 3426) may leverage a service 3120, such as AI service(s) 3218. In at least one embodiment, outputs of exposure control AI 3424 application (or container) and/or patient movement detection AI 3426 application (or container) may be used as feedback to CT scanner 3422 and/or a technician for adjusting exposure (or other settings of CT scanner 3422) and/or informing a patient to move less.

In at least one embodiment, deployment pipeline 3210C may include a non-real-time pipeline for analyzing data generated by CT scanner 3422. In at least one embodiment, a second pipeline may include CT reconstruction 3308 application and/or container, a coarse detection AI 3428 application and/or container, a fine detection AI 3432 application and/or container (e.g., where certain results are detected by coarse detection AI 3428), a visualization 3430 application and/or container, and a DICOM writer 3312 (and/or other data type writer, such as RIS, CIS, REST compliant, RPC, raw, etc.) application and/or container. In at least one embodiment, raw data generated by CT scanner 3422 may be passed through pipelines of deployment pipeline 3210C (instantiated as a virtual CT instrument) to generate results. In at least one embodiment, results from DICOM writer 3312 may be transmitted for display and/or may be stored on PACS server(s) 3304 for later retrieval, analysis, or display by a technician, practitioner, or other user.

Figure 35A:
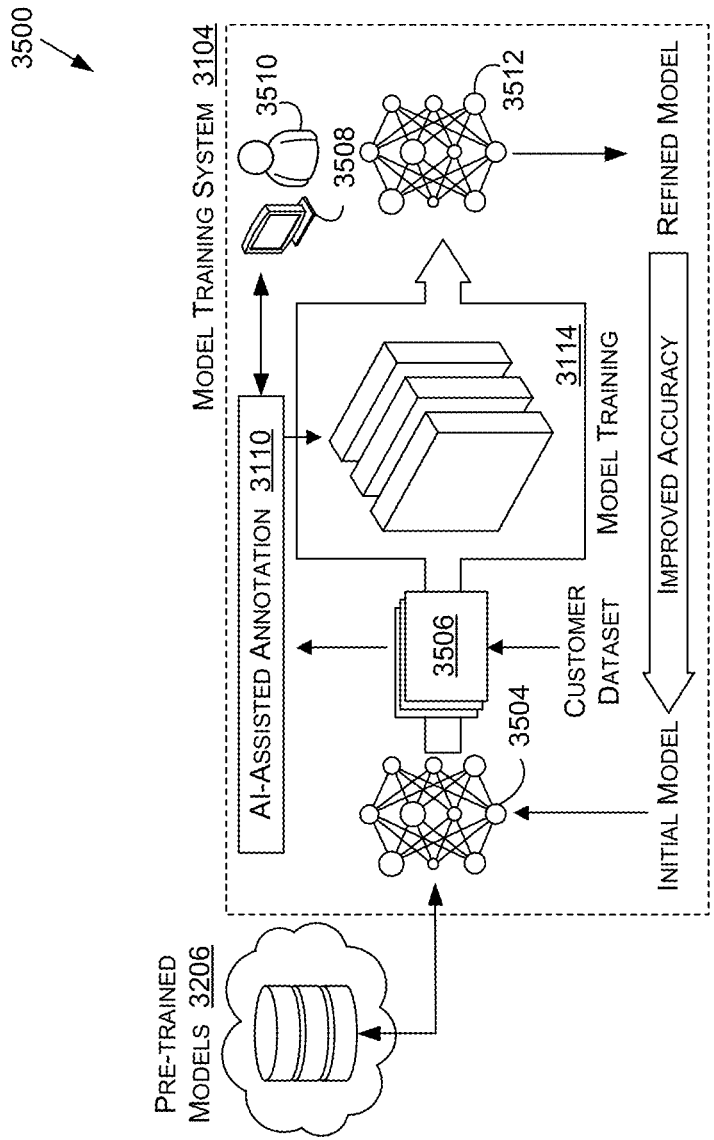
FIG. 35A illustrates a data flow diagram for a process to train a machine learning model, in accordance with at least one embodiment.

FIG. 35A illustrate a data flow diagram for a process 3500 to train, retrain, or update a machine learning model, in accordance with at least one embodiment. In at least one embodiment, process 3500 may be executed using, as a non-limiting example, system 3200 of FIG. 32. In at least one embodiment, process 3500 may leverage services 3120 and/or hardware 3122 of system 3200, as described herein. In at least one embodiment, refined models 3512 generated by process 3500 may be executed by deployment system 3106 for one or more containerized applications in deployment pipelines 3210.

In at least one embodiment, model training 3114 may include retraining or updating an initial model 3504 (e.g., a pre-trained model) using new training data (e.g., new input data, such as customer dataset 3506, and/or new ground truth data associated with input data). In at least one embodiment, to retrain, or update, initial model 3504, output or loss layer(s) of initial model 3504 may be reset, or deleted, and/or replaced with an updated or new output or loss layer(s). In at least one embodiment, initial model 3504 may have previously fine-tuned parameters (e.g., weights and/or biases) that remain from prior training, so training or retraining 3114 may not take as long or require as much processing as training a model from scratch. In at least one embodiment, during model training 3114, by having reset or replaced output or loss layer(s) of initial model 3504, parameters may be updated and re-tuned for a new data set based on loss calculations associated with accuracy of output or loss layer(s) at generating predictions on new, customer dataset 3506 (e.g., image data 3108 of FIG. 31).

In at least one embodiment, pre-trained models 3206 may be stored in a data store, or registry (e.g., model registry 3124 of FIG. 31). In at least one embodiment, pre-trained models 3206 may have been trained, at least in part, at one or more facilities other than a facility executing process 3500. In at least one embodiment, to protect privacy and rights of patients, subjects, or clients of different facilities, pre-trained models 3206 may have been trained, on-premise, using customer or patient data generated on-premise. In at least one embodiment, pre-trained models 3206 may be trained using cloud 3226 and/or other hardware 3122, but confidential, privacy protected patient data may not be transferred to, used by, or accessible to any components of cloud 3226 (or other off premise hardware). In at least one embodiment, where a pre-trained model 3206 is trained at using patient data from more than one facility, pre-trained model 3206 may have been individually trained for each facility prior to being trained on patient or customer data from another facility. In at least one embodiment, such as where a customer or patient data has been released of privacy concerns (e.g., by waiver, for experimental use, etc.), or where a customer or patient data is included in a public data set, a customer or patient data from any number of facilities may be used to train pre-trained model 3206 on-premise and/or off premise, such as in a datacenter or other cloud computing infrastructure.

In at least one embodiment, when selecting applications for use in deployment pipelines 3210, a user may also select machine learning models to be used for specific applications. In at least one embodiment, a user may not have a model for use, so a user may select a pre-trained model 3206 to use with an application. In at least one embodiment, pre-trained model 3206 may not be optimized for generating accurate results on customer dataset 3506 of a facility of a user (e.g., based on patient diversity, demographics, types of medical imaging devices used, etc.). In at least one embodiment, prior to deploying pre-trained model 3206 into deployment pipeline 3210 for use with an application(s), pre-trained model 3206 may be updated, retrained, and/or fine-tuned for use at a respective facility.

In at least one embodiment, a user may select pre-trained model 3206 that is to be updated, retrained, and/or fine-tuned, and pre-trained model 3206 may be referred to as initial model 3504 for training system 3104 within process 3500. In at least one embodiment, customer dataset 3506 (e.g., imaging data, genomics data, sequencing data, or other data types generated by devices at a facility) may be used to perform model training 3114 (which may include, without limitation, transfer learning) on initial model 3504 to generate refined model 3512. In at least one embodiment, ground truth data corresponding to customer dataset 3506 may be generated by training system 3104. In at least one embodiment, ground truth data may be generated, at least in part, by clinicians, scientists, doctors, practitioners, at a facility (e.g., as labeled clinic data 3112 of FIG. 31).

In at least one embodiment, AI-assisted annotation 3110 may be used in some examples to generate ground truth data. In at least one embodiment, AI-assisted annotation 3110 (e.g., implemented using an AI-assisted annotation SDK) may leverage machine learning models (e.g., neural networks) to generate suggested or predicted ground truth data for a customer dataset. In at least one embodiment, user 3510 may use annotation tools within a user interface (a graphical user interface (GUI)) on computing device 3508.

In at least one embodiment, user 3510 may interact with a GUI via computing device 3508 to edit or fine-tune (auto) annotations. In at least one embodiment, a polygon editing feature may be used to move vertices of a polygon to more accurate or fine-tuned locations.

In at least one embodiment, once customer dataset 3506 has associated ground truth data, ground truth data (e.g., from AI-assisted annotation, manual labeling, etc.) may be used by during model training 3114 to generate refined model 3512. In at least one embodiment, customer dataset 3506 may be applied to initial model 3504 any number of times, and ground truth data may be used to update parameters of initial model 3504 until an acceptable level of accuracy is attained for refined model 3512. In at least one embodiment, once refined model 3512 is generated, refined model 3512 may be deployed within one or more deployment pipelines 3210 at a facility for performing one or more processing tasks with respect to medical imaging data.

In at least one embodiment, refined model 3512 may be uploaded to pre-trained models 3206 in model registry 3124 to be selected by another facility. In at least one embodiment, his process may be completed at any number of facilities such that refined model 3512 may be further refined on new datasets any number of times to generate a more universal model.

FIG. 35B is an example illustration of a client-server architecture 3532 to enhance annotation tools with pre-trained annotation models, in accordance with at least one embodiment. In at least one embodiment, AI-assisted annotation tools 3536 may be instantiated based on a client-server architecture 3532. In at least one embodiment, annotation tools 3536 in imaging applications may aid radiologists, for example, identify organs and abnormalities. In at least one embodiment, imaging applications may include software tools that help user 3510 to identify, as a non-limiting example, a few extreme points on a particular organ of interest in raw images 3534 (e.g., in a 3D MRI or CT scan) and receive auto-annotated results for all 2D slices of a particular organ. In at least one embodiment, results may be stored in a data store as training data 3538 and used as (for example and without limitation) ground truth data for training. In at least one embodiment, when computing device 3508 sends extreme points for AI-assisted annotation 3110, a deep learning model, for example, may receive this data as input and return inference results of a segmented organ or abnormality. In at least one embodiment, pre-instantiated annotation tools, such as AI-Assisted Annotation Tool 3536B in FIG. 35B, may be enhanced by making API calls (e.g., API Call 3544) to a server, such as an Annotation Assistant Server 3540 that may include a set of pre-trained models 3542 stored in an annotation model registry, for example. In at least one embodiment, an annotation model registry may store pre-trained models 3542 (e.g., machine learning models, such as deep learning models) that are pre-trained to perform AI-assisted annotation on a particular organ or abnormality. These models may be further updated by using training pipelines 3204. In at least one embodiment, pre-installed annotation tools may be improved over time as new labeled clinic data 3112 is added.

Inference and/or training logic 615 are used to perform inferencing and/or training operations associated with one or more embodiments. In at least one embodiment, this logic can be used with components of these figures to use one or more neural networks to generate one or more ultrasound images of one or more objects based at least in part upon one or more acoustic properties of the one or more objects.

Other variations are within spirit of present disclosure. Thus, while disclosed techniques are susceptible to various modifications and alternative constructions, certain illustrated embodiments thereof are shown in drawings and have been described above in detail. It should be understood, however, that there is no intention to limit disclosure to specific form or forms disclosed, but on contrary, intention is to cover all modifications, alternative constructions, and equivalents falling within spirit and scope of disclosure, as defined in appended claims.

Use of terms "a" and "an" and "the" and similar referents in context of describing disclosed embodiments (especially in context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. Term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within range, unless otherwise indicated herein and each separate value is incorporated into specification as if it were individually recited herein. Use of term "set" (e.g., "a set of items") or "subset," unless otherwise noted or contradicted by context, is to be construed as a nonempty collection comprising one or more members. Further, unless otherwise noted or contradicted by context, term "subset" of a corresponding set does not necessarily denote a proper subset of corresponding set, but subset and corresponding set may be equal.

Conjunctive language, such as phrases of form "at least one of A, B, and C," or "at least one of A, B and C," unless specifically stated otherwise or otherwise clearly contradicted by context, is otherwise understood with context as used in general to present that an item, term, etc., may be either A or B or C, or any nonempty subset of set of A and B and C. For instance, in illustrative example of a set having three members, conjunctive phrases "at least one of A, B, and C" and "at least one of A, B and C" refer to any of following sets: {A}, {B}, {C}, {A, B}, {A, C}, {B, C}, {A, B, C}. Thus, such conjunctive language is not generally intended to imply that certain embodiments require at least one of A, at least one of B, and at least one of C each to be present. In addition, unless otherwise noted or contradicted by context, term "plurality" indicates a state of being plural (e.g., "a plurality of items" indicates multiple items). A plurality is at least two items, but can be more when so indicated either explicitly or by context. Further, unless stated otherwise or otherwise clear from context, phrase "based on" means "based at least in part on" and not "based solely on."

Operations of processes described herein can be performed in any suitable order unless otherwise indicated herein or otherwise clearly contradicted by context. In at least one embodiment, a process such as those processes described herein (or variations and/or combinations thereof) is performed under control of one or more computer systems configured with executable instructions and is implemented as code (e.g., executable instructions, one or more computer programs or one or more applications) executing collectively on one or more processors, by hardware or combinations thereof. In at least one embodiment, code is stored on a computer-readable storage medium, for example, in form of a computer program comprising a plurality of instructions executable by one or more processors. In at least one embodiment, a computer-readable storage medium is a non-transitory computer-readable storage medium that excludes transitory signals (e.g., a propagating transient electric or electromagnetic transmission) but includes non-transitory data storage circuitry (e.g., buffers, cache, and queues) within transceivers of transitory signals. In at least one embodiment, code (e.g., executable code or source code) is stored on a set of one or more non-transitory computer-readable storage media having stored thereon executable instructions (or other memory to store executable instructions) that, when executed (i.e., as a result of being executed) by one or more processors of a computer system, cause computer system to perform operations described herein. A set of non-transitory computer-readable storage media, in at least one embodiment, comprises multiple non-transitory computer-readable storage media and one or more of individual non-transitory storage media of multiple non-transitory computer-readable storage media lack all of code while multiple non-transitory computer-readable storage media collectively store all of code. In at least one embodiment, executable instructions are executed such that different instructions are executed by different processors. For example, a non-transitory computer-readable storage medium stores instructions and a main central processing unit ("CPU") executes some of instructions while a graphics processing unit ("GPU") executes other instructions. In at least one embodiment, different components of a computer system have separate processors and different processors execute different subsets of instructions.

Accordingly, in at least one embodiment, computer systems are configured to implement one or more services that singly or collectively perform operations of processes described herein and such computer systems are configured with applicable hardware and/or software that enable performance of operations. Further, a computer system that implements at least one embodiment of present disclosure is a single device and, in another embodiment, is a distributed computer system comprising multiple devices that operate differently such that distributed computer system performs operations described herein and such that a single device does not perform all operations.

Use of any and all examples, or exemplary language (e.g., "such as") provided herein, is intended merely to better illuminate embodiments of disclosure and does not pose a limitation on scope of disclosure unless otherwise claimed.

No language in specification should be construed as indicating any non-claimed element as essential to practice of disclosure.

All references, including publications, patent applications, and patents, cited herein are hereby incorporated by reference to same extent as if each reference were individually and specifically indicated to be incorporated by reference and were set forth in its entirety herein.

In description and claims, terms "coupled" and "connected," along with their derivatives, may be used. It should be understood that these terms may be not intended as synonyms for each other. Rather, in particular examples, "connected" or "coupled" may be used to indicate that two or more elements are in direct or indirect physical or electrical contact with each other. "Coupled" may also mean that two or more elements are not in direct contact with each other, but yet still co-operate or interact with each other.

Unless specifically stated otherwise, it may be appreciated that throughout specification terms such as "processing," "computing," "calculating," "determining," or like, refer to action and/or processes of a computer or computing system, or similar electronic computing device, that manipulate and/or transform data represented as physical, such as electronic, quantities within computing system's registers and/or memories into other data similarly represented as physical quantities within computing system's memories, registers or other such information storage, transmission or display devices.

In a similar manner, term "processor" may refer to any device or portion of a device that processes electronic data from registers and/or memory and transform that electronic data into other electronic data that may be stored in registers and/or memory. As non-limiting examples, "processor" may be a CPU or a GPU. A "computing platform" may comprise one or more processors. As used herein, "software" processes may include, for example, software and/or hardware entities that perform work over time, such as tasks, threads, and intelligent agents. Also, each process may refer to multiple processes, for carrying out instructions in sequence or in parallel, continuously or intermittently. Terms "system" and "method" are used herein interchangeably insofar as system may embody one or more methods and methods may be considered a system.

In present document, references may be made to obtaining, acquiring, receiving, or inputting analog or digital data into a subsystem, computer system, or computer-implemented machine. Obtaining, acquiring, receiving, or inputting analog and digital data can be accomplished in a variety of ways such as by receiving data as a parameter of a function call or a call to an application programming interface. In some implementations, process of obtaining, acquiring, receiving, or inputting analog or digital data can be accomplished by transferring data via a serial or parallel interface. In another implementation, process of obtaining, acquiring, receiving, or inputting analog or digital data can be accomplished by transferring data via a computer network from providing entity to acquiring entity. References may also be made to providing, outputting, transmitting, sending, or presenting analog or digital data. In various examples, process of providing, outputting, transmitting, sending, or presenting analog or digital data can be accomplished by transferring data as an input or output parameter of a function call, a parameter of an application programming interface or interprocess communication mechanism.

Although discussion above sets forth example implementations of described techniques, other architectures may be used to implement described functionality, and are intended to be within scope of this disclosure. Furthermore, although specific distributions of responsibilities are defined above for purposes of discussion, various functions and responsibilities might be distributed and divided in different ways, depending on circumstances.

Furthermore, although subject matter has been described in language specific to structural features and/or methodological acts, it is to be understood that subject matter claimed in appended claims is not necessarily limited to specific features or acts described. Rather, specific features and acts are disclosed as exemplary forms of implementing the claims.

What is claimed is:

1. A processor, comprising:
one or more circuits to use one or more neural networks to generate one or more ultrasound images of one or more objects based at least in part upon one or more acoustic properties of the one or more objects.

2. The processor of claim 1, wherein the one or more circuits are further to generate, based at least in part upon an annotated image of the one or more objects, one or more acoustic property maps of the one or more acoustic properties to be provided as input to the one or more neural networks.

3. The processor of claim 2, wherein the one or more circuits are further to generate an image based at least in part upon a cross-section taken from the annotated image that comprises an annotated three-dimensional medical image.

4. The processor of claim 3, wherein the one or more circuits are to generate multiple images from different cross-sections of the annotated three-dimensional image and generate corresponding ultrasound images.

5. The processor of claim 3, wherein the one or more acoustic property maps indicate regions of different acoustic property values determined based at least in part upon types of the one or more objects represented in the image.

6. The processor of claim 1, wherein the one or more acoustic properties include at least one of attenuation, density, speed of sound, and non-linear coefficients of a wave equation.

7. A system comprising:
one or more processors to use one or more neural networks to generate one or more ultrasound images of one or more objects based at least in part upon one or more acoustic properties of the one or more objects.

8. The system of claim 7, wherein the one or more processors are further to generate, based at least in part upon an annotated image of the one or more objects, one or more acoustic property maps of the one or more acoustic properties to be provided as input to the one or more neural networks.

9. The system of claim 8, wherein the one or more processors are further to generate an image based at least in part upon a cross-section taken from the annotated image that comprises an annotated three-dimensional medical image.

10. The system of claim 9, wherein the one or more processors are further to generate multiple images from different cross-sections of the annotated three-dimensional image and generate corresponding ultrasound images.

11. The system of claim 9, wherein the one or more acoustic property maps indicate regions of different acoustic property values determined based at least in part upon types of the one or more objects represented in the image.

12. The system of claim 7, wherein the one or more acoustic properties include at least one of attenuation, density, speed of sound, and non-linear coefficients of a wave equation.

13. A method comprising:
using one or more neural networks to generate one or more ultrasound images of one or more objects based at least in part upon one or more acoustic properties of the one or more objects.

14. The method of claim 13, further comprising:
generating, based at least in part upon an annotated image of the one or more objects, one or more acoustic property maps of the one or more acoustic properties to be provided as input to the one or more neural networks.

15. The method of claim 14, further comprising:
generating an image based at least in part upon a cross-section taken from the annotated image that comprises an annotated three-dimensional medical image.

16. The method of claim 15, further comprising:
generating multiple images from different cross-sections of the annotated three-dimensional image and generate corresponding ultrasound images.

17. The method of claim 15, wherein the one or more acoustic property maps indicate regions of different acoustic property values determined based at least in part upon types of the one or more objects represented in the image.

18. The method of claim 13, wherein the one or more acoustic properties include at least one of attenuation, density, speed of sound, and non-linear coefficients of a wave equation.

19. A machine-readable medium having stored thereon a set of instructions, which if performed by one or more processors, cause the one or more processors to at least:
use one or more neural networks to generate one or more ultrasound images of one or more objects based at least in part upon one or more acoustic properties of the one or more objects.

20. The machine-readable medium of claim 19, wherein instructions if performed further cause the one or more processors to:
generate, based at least in part upon an annotated image of the one or more objects, one or more acoustic property maps of the one or more acoustic properties to be provided as input to the one or more neural networks.

21. The machine-readable medium of claim 20, wherein the one or more processors are further to generate an image based at least in part upon a cross-section taken from the annotated image that comprises an annotated three-dimensional medical image.

22. The machine-readable medium of claim 21, wherein the one or more processors are further to generate multiple images from different cross-sections of the annotated three-dimensional image and generate corresponding ultrasound images.

23. The machine-readable medium of claim 21, wherein the one or more acoustic property maps indicate regions of different acoustic property values determined based at least in part upon types of the one or more objects represented in the image.

24. The machine-readable medium of claim 19, wherein the one or more acoustic properties include at least one of attenuation, density, speed of sound, and non-linear coefficients of a wave equation.

25. An ultrasound image generation system, comprising:
one or more processors to use one or more neural networks to generate one or more ultrasound images of one or more objects based at least in part upon one or more acoustic properties of the one or more objects; and
memory for storing network parameters for the one or more neural networks.

26. The ultrasound image generation system of claim 25, wherein the one or more processors are further to generate, based at least in part upon an annotated image of the one or more objects, one or more acoustic property maps of the one or more acoustic properties to be provided as input to the one or more neural networks.

27. The ultrasound image generation system of claim 26, wherein the one or more processors are further to generate an image based at least in part upon a cross-section taken from the annotated image that comprises an annotated three-dimensional medical image.

28. The ultrasound image generation system of claim 27, wherein the one or more processors are further to generate multiple images from different cross-sections of the annotated three-dimensional image and generate corresponding ultrasound images.

29. The ultrasound image generation system of claim 27, wherein the one or more acoustic property maps indicate regions of different acoustic property values determined based at least in part upon types of the one or more objects represented in the image.

30. The ultrasound image generation system of claim 25, wherein the one or more acoustic properties include at least one of attenuation, density, speed of sound, and non-linear coefficients of a wave equation.

* * * * *